(12) United States Patent
Bowman et al.

(10) Patent No.: US 10,907,188 B2
(45) Date of Patent: Feb. 2, 2021

(54) COMPOSITIONS AND METHODS FOR THE PRODUCTION OF COMPOUNDS

(71) Applicant: Warp Drive Bio, Inc., Cambridge, MA (US)

(72) Inventors: Brian R. Bowman, New Rochelle, NY (US); Joshua A. V. Blodgett, Webster Groves, MO (US); Gregory L. Verdine, Boston, MA (US); Daniel C. Gray, Medford, MA (US); Jay P. Morgenstern, Boston, MA (US); Lucy Foulston, Medford, MA (US); Keith Robison, Andover, MA (US)

(73) Assignee: Ginkgo Bioworks, Inc., Boston, MA (US)

(*) Notice: Subject to any disclaimer, the term of this patent is extended or adjusted under 35 U.S.C. 154(b) by 54 days.

(21) Appl. No.: 16/093,074

(22) PCT Filed: Apr. 12, 2017

(86) PCT No.: PCT/US2017/027215
§ 371 (c)(1),
(2) Date: Oct. 11, 2018

(87) PCT Pub. No.: WO2017/180748
PCT Pub. Date: Oct. 19, 2017

(65) Prior Publication Data
US 2019/0136284 A1 May 9, 2019

Related U.S. Application Data

(60) Provisional application No. 62/321,439, filed on Apr. 12, 2016.

(51) Int. Cl.
C12N 1/20 (2006.01)
C12P 35/00 (2006.01)
C07K 14/36 (2006.01)
C12N 15/76 (2006.01)
C12N 15/52 (2006.01)

(52) U.S. Cl.
CPC .............. C12P 35/00 (2013.01); C07K 14/36 (2013.01); C12N 15/52 (2013.01); C12N 15/76 (2013.01)

(58) Field of Classification Search
CPC ..................................................... A61K 48/00
USPC ....................................................... 435/118
See application file for complete search history.

(56) References Cited

U.S. PATENT DOCUMENTS

| 6,183,965 | B1 | 2/2001 | Verdine et al. |
| 6,372,712 | B1 | 4/2002 | Briesewitz et al. |
| 6,686,454 | B1 | 2/2004 | Yatscoff et al. |
| 6,713,607 | B2 | 3/2004 | Caggiano et al. |
| 7,396,660 | B2 | 7/2008 | Huang et al. |
| 7,851,183 | B2 | 12/2010 | Zotchev et al. |
| 8,664,186 | B2 * | 3/2014 | Aigle ..................... C12N 15/52 514/31 |
| 9,250,237 | B2 | 2/2016 | Liu et al. |
| 9,260,484 | B2 | 2/2016 | Briesewitz et al. |
| 9,428,845 | B1 | 8/2016 | Verdine et al. |
| 9,989,535 | B2 | 6/2018 | Verdine et al. |
| 10,039,839 | B2 | 8/2018 | Verdine et al. |
| 10,466,249 | B2 | 11/2019 | Verdine et al. |
| 2002/0110874 | A1 | 8/2002 | Khosla et al. |
| 2002/0147133 | A1 | 10/2002 | Briesewitz et al. |
| 2003/0153053 | A1 | 8/2003 | Reid |
| 2003/0175901 | A1 | 9/2003 | Reeves et al. |
| 2004/0087496 | A1 | 5/2004 | Kim et al. |
| 2004/0157768 | A1 | 8/2004 | Or et al. |
| 2005/0233431 | A1 | 10/2005 | Ashley et al. |
| 2007/0203168 | A1 | 8/2007 | Zhao |
| 2007/0218502 | A1 | 9/2007 | Hahn et al. |
| 2011/0117606 | A1 | 5/2011 | Jorgensen et al. |
| 2012/0208720 | A1 | 8/2012 | Kashiwagi et al. |
| 2012/0270800 | A1 | 10/2012 | Verdine et al. |
| 2013/0072439 | A1 | 3/2013 | Nash et al. |
| 2014/0073581 | A1 | 3/2014 | Liu et al. |
| 2014/0316104 | A1 | 10/2014 | Fischer et al. |
| 2015/0250896 | A1 | 9/2015 | Zhao |
| 2015/0307855 | A1 | 10/2015 | Yuzawa et al. |
| 2016/0199506 | A1 | 7/2016 | Verdine et al. |
| 2016/0341719 | A1 | 11/2016 | Verdine et al. |

FOREIGN PATENT DOCUMENTS

| EP | 0393934 A1 | 10/1990 |
| EP | 0562853 A1 | 9/1993 |
| EP | 1079859 B1 | 7/2010 |
| KR | 10-2009-0041971 A | 4/2009 |
| WO | WO-86/02080 A1 | 4/1986 |
| WO | WO-95/32294 A1 | 11/1995 |
| WO | WO-96/020216 A1 | 7/1996 |
| WO | WO-98/01546 A2 | 1/1998 |

(Continued)

OTHER PUBLICATIONS

U.S. Appl. No. 61/418,038, Johns Hopkins University.
"Substructure Search Report on Specifically Substituted Macrocycles—Substances Only", prepared by Science IP, dated Dec. 17, 2014 (6177 pages).
Allain et al., "Cyclophilin B mediates cyclosporin A incorporation in human blood T-lymphocytes through the specific binding of complexed drug to the cell surface," Biochem J. 317 (Pt 2):565-70 (1996).

(Continued)

Primary Examiner — Tekchand Saidha
(74) Attorney, Agent, or Firm — Clark & Elbing LLP

(57) ABSTRACT

The present disclosure provides nucleic acids encoding a Large ATP-binding regulator of the LuxR family (LAL) of transcription factors, vectors and host cells including such nucleic acids, and methods for producing compounds (e.g., polyketides or β-lactam compounds) with such nucleic acids, vectors, and/or host cells.

20 Claims, 22 Drawing Sheets
Specification includes a Sequence Listing.

(56) References Cited

FOREIGN PATENT DOCUMENTS

| WO | WO-98/07743 | A1 | 2/1998 |
|---|---|---|---|
| WO | WO-98/12217 | A1 | 3/1998 |
| WO | WO-99/61055 | A1 | 12/1999 |
| WO | WO-00/47724 | A2 | 8/2000 |
| WO | WO-01/36460 | A2 | 5/2001 |
| WO | WO-01/36612 | A1 | 5/2001 |
| WO | WO-01/90070 | A2 | 11/2001 |
| WO | WO-2008/069824 | A2 | 6/2008 |
| WO | WO-2010/031185 | A1 | 3/2010 |
| WO | WO-2010/034243 | A1 | 4/2010 |
| WO | WO-2010/088573 | A1 | 8/2010 |
| WO | WO-2012/075048 | A2 | 6/2012 |
| WO | WO-2012/174489 | A2 | 12/2012 |
| WO | WO-2014/009774 | A1 | 1/2014 |
| WO | WO-2014/187959 | A2 | 11/2014 |
| WO | WO-2015/132784 | A1 | 9/2015 |
| WO | WO-2016/112279 | A1 | 7/2016 |
| WO | WO-2016/112295 | A1 | 7/2016 |
| WO | WO-2016/160362 | A1 | 10/2016 |
| WO | WO-2017/059207 | A1 | 4/2017 |
| WO | WO-2018/081592 | A2 | 5/2018 |

OTHER PUBLICATIONS

Andrei et al., "Stabilization of protein-protein interactions in drug discovery," Expert Opin Drug Discov. 12(9):925-40 (2017) (17 pages).

Antunes et al., "A mutational analysis defines Vibrio fischeri LuxR binding sites," J Bacteriol. 190(13):4392-7 (2008).

Archibald et al., "Discovery and Evaluation of Potent, Cysteine-based alpha4beta1 Integrin Antagonists," Bioorg Med Chem Lett. 10(9):993-995 (2000).

Banaszynski et al., "Characterization of the FKBP.rapamycin.FRB ternary complex," J Am Chem Soc. 127(13):4715-21 (2005).

Bayle et al., "Rapamycin analogs with differential binding specificity permit orthogonal control of protein activity," Chem Biol. 13(1):99-107 (2006).

Benjamin et al., "Rapamycin passes the torch: a new generation of mTOR inhibitors," Nat Rev Drug Discov. 10(11):868-80 (2011).

Bhuyan et al., "Antioxidant activity of peptide-based angiotensin converting enzyme inhibitors," Org. Biomol. Chem. 10(11):2237-47 (2012).

Blodgett et al., "Unusual transformations in the biosynthesis of the antibiotic phosphinothricin tripeptide," Nat Chem Biol. 3(8):480-5 (2007).

Briesewitz et al., "Affinity modulation of small-molecule ligands by borrowing endogenous protein surfaces," Proc Natl Acad Sci U.S.A. 96(5):1953-8 (1999).

Bruce, "In vivo protein complex topologies: sights through a cross-linking lens," Proteomics. 12(10):1565-75 (2012).

Burgess et al., "Controlled translocation of palladium(II) within a 22 ring atom macrocyclic ligand," Dalton Trans. 43(45):17006-16 (2014).

Chaurasia et al., "Molecular insights into the stabilization of protein-protein interactions with small molecule: The FKBP12-rapamycin-FRB case study," Chem Phys Lett. 587:68-74 (2013).

Che et al., "Inducing protein-protein interactions with molecular glues," Bioorganic & Medicinal Chemistry Letters (2018).

Chevalier et al., "Straightforward synthesis of bioconjugatable azo dyes. Part 1: Black Hole Quencher-1 (BHQ-1) scaffold," Tetrahedron Lett. 55(50):6759-63 (2014).

Findlay et al., "The structure of demethoxyrapamycin," Can J Chem. 60:2046-7 (1982).

Guerra et al., "LAL regulators SCO0877 and SCO7173 as pleiotropic modulators of phosphate starvation response and actinorhodin biosynthesis in *Streptomyces coelicolor*," PLoS One. 7(2):e31475 (2012) (11 pages).

Horton et al., "Engineering hybrid genes without the use of restriction enzymes: gene splicing by overlap extension," Gene. 77(1):61-8 (1989).

Hosted et al., "Use of rpsL for dominance selection and gene replacement in *Streptomyces roseosporus*," J Bacteriol. 179(1):180-6 (1997).

Huang et al., "Enhanced rapamycin production in *Streptomyces hygroscopicus* by integrative expression of aveR, a LAL family transcriptional regulator," World J Microbiol Biotechnol. 27:2103-9 (2011).

Hubler et al., "Synthetic routes to NEtXaa4-cyclosporin A derivatives as potential anti-HIV I drugs," Tetrahedron Lett. 41:7193-6 (2000).

International Preliminary Report on Patentability for International Application No. PCT/US2017/027215, dated Oct. 25, 2018 (7 pages).

International Search Report and Written Opinion for International Application No. PCT/US2017/027215, dated Jul. 10, 2017 (13 pages).

Ishizawa et al., "TRAP display: a high-speed selection method for the generation of functional polypeptides," J Am Chem. 135(14):5433-40 (2013).

Kawakami et al., "In vitro selection of multiple libraries created by genetic code reprogramming to discover macrocyclic peptides that antagonize VEGFR2 activity in living cells," ACS Chem Biol. 8(6):1205-14 (2013).

Kendrew et al., "Recombinant strains for the enhanced production of bioengineered rapalogs," Metab Eng. 15:167-73 (2013).

Kuramochi et al., "Idenitifcation of Small Molecule Binding Molecules by Affinity Purification Using a Specific Ligand Immobilized on PEGA Resin," Bioconjug. Chem. 19(12):2417-26 (2008).

Laureti et al., "Identification of a bioactive 51-membered macrolide complex by activation of a silent polyketide synthase in *Streptomyces ambofaciens*," Proc Natl Acad Sci USA. 108(15):6258-63 (2011).

Leskiw et al., "TTA codons in some genes prevent their expression in a class of developmental, antibiotic-negative, *Streptomyces* mutants," Proc Natl Acad Sci USA. 88(6):2461-5 (1991).

Li et al., "A simple and efficient route to the FKBP-binding domain from rapamycin," available in PMC Sep. 28, 2012, published in final edited form as: Tetrahedron Lett. 52(39):5070-2 (2011) (7 pages).

Luengo et al., "Structure-activity studies of rapamycin analogs: evidence that the C-7 methoxy group is part of the effector domain and positioned at the FKBP12-FRAP interface," Chem Biol. 2(7):471-81 (1995).

Meyer et al., "Selective palladation of a large (32 ring atom) macrocyclic ligand at a bis(N-heterocyclic carbene) coordination pocket through transmetallation of the corresponding mercury(II) derivative," Dalton Trans. 41(46):14059-67 (2012).

Ochi et al., "New strategies for drug discovery: activation of silent or weakly expressed microbial gene clusters," Appl Microbiol Biotechnol. 97(1):87-98 (2013).

Papageorgiou et al., "Improved binding affinity for cyclophilin A by a cyclosporin derivative singly modified at its effector domain," J Med Chem. 37(22):3674-6 (1994).

Pfeifer et al., "Biosynthesis of complex polyketides in a metabolically engineered strain of *E. coli*," Science 291(5509):1790-2 (2001).

Ranganathan et al., "Knowledge-based design of bimodular and trimodular polyketide synthases based on domain and module swaps: a route to simple statin analogues," Chem Biol. 6(10):731-41 (1999).

Revill et al., "Genetically engineered analogs of ascomycin for nerve regeneration," J Pharmacol Exp Ther. 302(3):1278-85 (2002).

Ruan et al., "Binding of rapamycin analogs to calcium channels and FKBP52 contributes to their neuroprotective activities," Proc Natl Acad Sci U.S.A. 105(1):33-8 (2008).

Schwecke et al., "The biosynthetic gene cluster for the polyketide immunosuppressant rapamycin," Proc Natl Acad Sci USA. 92(17):7839-43 (1995).

Sieber et al., "Novel inhibitors of the calcineurin/NFATc hub—alternatives to CsA and FK506?," Cell Commun Signal. 7:25 (2009) (19 pages).

STN record of WO 2014/009774, available online Jan. 16, 2014 (4 pages).

(56) References Cited

OTHER PUBLICATIONS

STN record of WO 98/12217, available online Mar. 26, 1998 (6 pages).
Sweeney et al., "From chemical tools to clinical medicines: non-immunosuppressive cyclophilin inhibitors derived from the cyclosporin and sanglifehrin scaffolds," J Med Chem. 57(17):7145-59 (2014) (63 pages).
Takakusagi et al., "Efficient one-cycle affinity selection of binding proteins or peptides specific for a small-molecule using a T7 phage display pool," Bioorg. Med. Chem. 16(22):9837-46 (2008).
UniProtKB Accession No. A0A061A6I8, Sep. 3, 2014, available <http://www.uniprot.org/uniprot/A0A061A6I8>, (12 pages).
UniProtKB Accession No. Q54296, Nov. 1, 1996, available <http://www.uniprot.org/uniprot/Q54296>, (12 pages).
UniProtKB Accession No. Q54297, Nov. 1, 1996, available <https://www.uniprot.org/uniprot/Q54297.txt>, (3 pages).
Vignot et al., "mTOR-targeted therapy of cancer with rapamycin derivatives," Ann Oncol. 16(4):525-37 (2005).
Wagner et al., "New naturally occurring amino acids," Angew Chem Int Ed Engl. 22:816-28 (1983).
Wang et al., "Thermodynamic analysis of cyclosporin a binding to cyclophilin a in a lung tumor tissue lysate," Anal Chem. 76(15):4343-8 (2004).
Wilson et al., "Comparative X-ray structures of the major binding protein for the immunosuppressant FK506 (tacrolimus) in unliganded form and in complex with FK506 and rapamycin," Acta Cryst. D51:511-21 (1995).
Wright et al., "Multivalent binding in the design of bioactive compounds," Curr Org Chem. 5(11):1107-31 (2001).
Wu et al., "Creating diverse target-binding surfaces on FKBP12: synthesis and evaluation of a rapamycin analogue library," available in PMC Sep. 12, 2012, published in final edited form as: ACS Comb Sci. 13(5):486-95 (2011) (22 pages).
Wu et al., "Inhibition of ras-effector interactions by cyclic peptides," Med Chem Commun. 4(2):378-82 (2013).
Aebi et al., "Synthesis, conformation, and immunosuppressive activities of three analogues of cyclosporin A modified in the 1-position," J Med Chem. 33(3):999-1009 (1990).
Eberle et al., "Preparation of Functionalized Ethers of Cyclosporin A," Tetrahedron Lett. 35(35):6477-6480 (1994).
Lee et al., "Current implications of cyclophilins in human cancers," J Exp Clin Cancer Res. 29(1):97 (2010) (6 pages).
Majumder et al., "Interaction of aryl hydrocarbon receptor-interacting protein-like 1 with the farnesyl moiety," J Biol Chem. 288(29):21320-8 (2013).
Sun et al., "Design and structure-based study of new potential FKBP12 inhibitors," Biophys J. 85(5):3194-201 (2003).
"*Streptomyces iranensis* regulatory protein LuxR," EBI Database Accession No. CDR13506 (2014) (2 pages).
"*Streptomyces rapamycinicus* NRRL 5491 hypothetical protein," EBI Database Accession No. AGP59507 (2014) (2 pages).
Baranasic et al., "Draft Genome Sequence of *Streptomyces rapamycinicus* Strain NRRL 5491, the Producer of the Immunosuppressant Rapamycin," Genome Announc. 1(4):e000581-13 (2013) (2 pages).

Extended European Search Report for European Patent Application No. 1778058.5, dated Aug. 22, 2019 (15 pages).
He et al., "The LuxR family members GdmRI and GdmRII are positive regulators of geldanamycin biosynthesis in *Streptomyces hygroscopicus* 17997," Arch Microbiol. 189(5):501-10 (2008).
Horn et al., "Draft Genome Sequence of *Streptomyces iranensis*," Genome Announc. 2(4):e00616-14 (2014) (2 Pages).
Laureti et al., Supporting Material for "Identification of a bioactive 51-membered macrolide complex by activation of a silent polyketide synthase in *Streptomyces ambofaciens*," Proc Natl Acad Sci U.S.A. 108(15):6258-63 (2011), accessed via <https://www.pnas.org/content/suppl/2011/03/24/1019077108.DCSupplemental> (41 pages).
Mo et al., "Interspecies Complementation of the LuxR Family Pathway-Specific Regulator Involved in Macrolide Biosynthesis," J Microbiol Biotechnol. 26(1):66-71 (2016).
"SMART™ Drugs: Engineering Nature's Solution to the Undruggable Target Challenge," WarpDrive Bio, 2016 (31 pages).
Ding et al. "Insights into Bacterial 6-Methylsalicylic Acid Synthase and Its Engineering to Orsellinic Acid Synthase for Spirotetronate Generation," Chem Biol. 17(5):495-503 (2010).
Garg et al. "Elucidation of the Cryptic Epimerase Activity of Redox-Inactive Ketoreductase Domains from Modular Polyketide Synthases by Tandem Equilibrium Isotope Exchange," J. Am. Chem. Soc. 136(29):10190-10193 (2014).
Murphy et al. "Isolation and characterisation of amphotericin B analogues and truncated polyketide intermediates produced by genetic engineering of *Streptomyces nodosus*," Org Biomol Chem. 8(16):3758-70 (2010).
Supplementary Partial European Search Report for European Patent Application No. 17865512.2, dated May 7, 2020 (20 pages).
Power et al. "Engineered Synthesis of 7-Oxo- and 15-Deoxy-15-Oxo-Amphotericins: Insights into Structure-Activity Relationships in Polyene Antibiotics," Chem Biol. 15:78-86 (2008).
Reid et al. "A model of structure and catalysis for ketoreductase domains in modular polyketide synthases," Biochemistry. 42(1):72-79 (2003).
Tang et al. "Generation of New Epothilones by Genetic Engineering of a Polyketide Synthase in *Myxococcus xanthus*," J Antibiot (Tokyo). 58(3):178-184 (2005).
Weissman, "Genetic engineering of modular PKSs: from combinatorial biosynthesis to synthetic biology," Nat Prod Rep. 33(2):203-230 (2016).
Weissman et al., "Combinatorial biosynthesis of reduced polyketides," Nat Rev Microbiol 3(12):925-36 (2005).
Hong et al., "Evidence for an iterative module in chain elongation on the azalomycin polyketide synthase," Beilstein J Org Chem 12:2164-2172 (2016).
UniProtKB Accession No. Q54296, "Polyketide synthase," <https://www.uniprot.org/uniprot/A0A61A618.txt?version=14>, retrieved May 29, 2020 (12 pages).
Supplementary Partial European Search Report for European Application No. 17863519.9, dated Jun. 15, 2020 (16 pages).
De Schrijver et al., "A subfamily of MalT-related ATP-dependent regulators in the LuxR family," Microbiology. 145(6):1287-8 (1999).

* cited by examiner

FIG. 1

A)
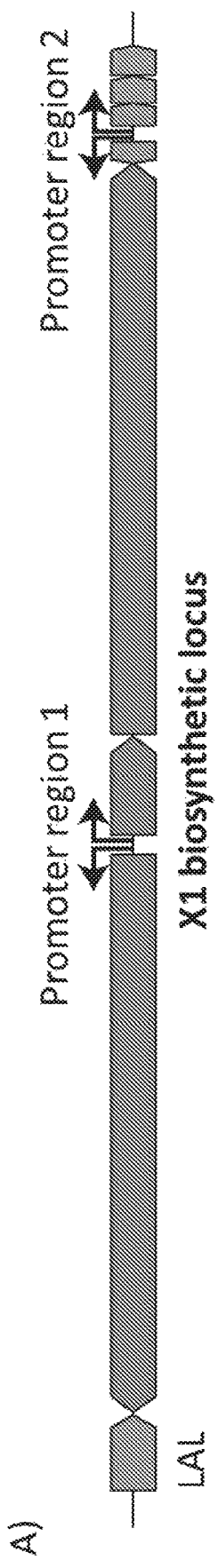

Promoter region 1 — Promoter region 2
LAL — X1 biosynthetic locus

B) Conserved putative LAL binding domains extracted from FK cluster promoter regions

```
SEQ ID NO: 38  S12intergenicPIPrt    TG--GCCGGAAACCTAGGGGGTTGCGTGGAAAGCACCGGGGTGTTCGCT   169
SEQ ID NO: 39  S22intergenicPIPrt    TG--GCCGGAAACCTAGGGGGTTGCGTGGAAAGCACCGGCGGTGTTCGCT  169
SEQ ID NO: 40  S9intergenicPIPrt     AG--GCAGGACGTCTAGGGGGTTGCGTGGACTGCGCCTGAGGGTGTCTTCT 218
SEQ ID NO: 41  S18intergenicPIPrt    AG--GCAGGAAGCCTAGGGGGTTGCGTGGACTGCGACCTGGGTGTCTTCT  227
SEQ ID NO: 42  S1intergenicPIPrt     AG--GTACGACACCTAGGGGGTTGCGTGGCTGCGACCC-GGTGTCT-GC   145
SEQ ID NO: 43  S21intergenicPIPrt    AG--CTCGGCCCCCTAGGGGGTTGCGCCCGCTGAGGCG-GAGGTGTTTGGC 246
SEQ ID NO: 44  FK506intergenicPIPrt  TG--TTGCCCATCTAGGGGGTTGCACGAATAACGTC----ACACGTACT   217
SEQ ID NO: 45  Stacrolimicus         TG--TCATATGTCTAGGGGGTTGCACGAATACCGTC----GGCGTACT    170
SEQ ID NO: 46  FK520intergenicPIPrt  GG--ACGTTCATCTAGGGGGTTGCACGCATACCGCC----GTCGTAAT    170
SEQ ID NO: 47  S12-promoter region 2 GGCGGCCTGT-TCTAGGGGGTTGCGGGGAGTG--------GCCGGCACA   174
```

C) Phage-integrating constitutive LAL expression scheme

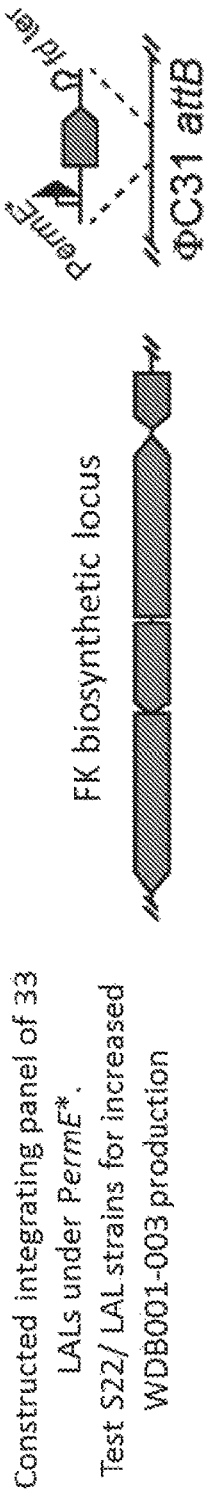

FK biosynthetic locus

Constructed integrating panel of 33
LALs under *PermE**.
Test S22/LAL strains for increased
WDB001-003 production

FIG. 2

Helix-Turn-Helix Motif

Alignment of all WDB FK LALs

Designed query:
SEQ ID NO: 54
>s9-rap
LTDAERRVASLAAGGQTNRVTADQLFVTASTVEQHLTNVERKLGV
**::* *.: ** * : :******** :**.*

* = 100% conserved in FK LALs
: = Strongly similar residues
. = Weakly similar residues Search highpass using this query

SEQUENCE LISTING

<160> NUMBER OF SEQ ID NOS: 112

<210> SEQ ID NO 1
<211> LENGTH: 914
<212> TYPE: PRT
<213> ORGANISM: Streptomyces hygroscopicus

<400> SEQUENCE: 1

Met Pro Ala Val Glu Ser Tyr Glu Leu Asp Ala Arg Asp Asp Glu Leu
1               5                   10                  15

Arg Arg Leu Glu Glu Ala Val Gly Gln Ala Gly Asn Gly Arg Gly Val
                20                  25                  30

Val Val Thr Ile Thr Gly Pro Ile Ala Cys Gly Lys Thr Glu Leu Leu
            35                  40                  45

Asp Ala Ala Ala Ala Lys Ser Asp Ala Ile Thr Leu Arg Ala Val Cys
        50                  55                  60

Ser Glu Glu Glu Arg Ala Leu Pro Tyr Ala Leu Ile Gly Gln Leu Ile
65                  70                  75                  80

Asp Asn Pro Ala Val Ala Ser Gln Leu Pro Asp Pro Val Ser Met Ala
                85                  90                  95

```
Leu Pro Gly Glu His Leu Ser Pro Glu Ala Glu Asn Arg Leu Arg Gly
            100                 105                 110

Asp Leu Thr Arg Thr Leu Leu Ala Leu Ala Ala Glu Arg Pro Val Leu
            115                 120                 125

Ile Gly Ile Asp Asp Met His His Ala Asp Thr Ala Ser Leu Asn Cys
            130                 135                 140

Leu Leu His Leu Ala Arg Arg Val Gly Pro Ala Arg Ile Ala Met Val
145                 150                 155                 160

Leu Thr Glu Leu Arg Arg Leu Thr Pro Ala His Ser Gln Phe His Ala
                165                 170                 175

Glu Leu Leu Ser Leu Gly His His Arg Glu Ile Ala Leu Arg Pro Leu
            180                 185                 190

Gly Pro Lys His Ile Ala Glu Leu Ala Arg Ala Gly Leu Gly Pro Asp
            195                 200                 205

Val Asp Glu Asp Val Leu Thr Gly Leu Tyr Arg Ala Thr Gly Gly Asn
            210                 215                 220

Leu Asn Leu Gly His Gly Leu Ile Lys Asp Val Arg Glu Ala Trp Ala
225                 230                 235                 240

Thr Gly Gly Thr Gly Ile Asn Ala Gly Arg Ala Tyr Arg Leu Ala Tyr
                245                 250                 255

Leu Gly Ser Leu Tyr Arg Cys Gly Pro Val Pro Leu Arg Val Ala Arg
            260                 265                 270

Val Ala Ala Val Leu Gly Gln Ser Ala Asn Thr Thr Leu Val Arg Trp
            275                 280                 285

Ile Ser Gly Leu Asn Ala Asp Ala Val Gly Glu Ala Thr Glu Ile Leu
            290                 295                 300

Thr Glu Gly Gly Leu Leu His Asp Leu Arg Phe Pro His Pro Ala Ala
305                 310                 315                 320

Arg Ser Val Val Leu Asn Asp Leu Ser Ala Arg Glu Arg Arg Arg Leu
                325                 330                 335

His Arg Ser Ala Leu Glu Val Leu Asp Asp Val Pro Val Glu Val Val
            340                 345                 350

Ala His His Gln Ala Gly Ala Gly Phe Ile His Gly Pro Lys Ala Ala
            355                 360                 365

Glu Ile Phe Ala Lys Ala Gly Gln Glu Leu His Val Arg Gly Glu Leu
            370                 375                 380

Asp Ala Ala Ser Asp Tyr Leu Gln Leu Ala His His Ala Ser Asp Asp
385                 390                 395                 400

Ala Val Thr Arg Ala Ala Leu Arg Val Glu Ala Val Ala Ile Glu Arg
                405                 410                 415

Arg Arg Asn Pro Leu Ala Ser Ser Arg His Leu Asp Glu Leu Thr Val
            420                 425                 430

Ala Ala Arg Ala Gly Leu Leu Ser Leu Glu His Ala Ala Leu Met Ile
            435                 440                 445

Arg Trp Leu Ala Leu Gly Gly Arg Ser Gly Glu Ala Ala Glu Val Leu
            450                 455                 460

Ala Ala Gln Arg Pro Arg Ala Val Thr Asp Gln Asp Arg Ala His Leu
465                 470                 475                 480

Arg Ala Ala Glu Val Ser Leu Ala Leu Val Ser Pro Gly Ala Ser Gly
                485                 490                 495

Val Ser Pro Gly Ala Ser Gly Pro Asp Arg Arg Pro Arg Pro Leu Pro
            500                 505                 510
```

```
Pro Asp Glu Leu Ala Asn Leu Pro Lys Ala Ala Arg Leu Cys Ala Ile
        515                 520                 525

Ala Asp Asn Ala Val Ile Ser Ala Leu His Gly Arg Pro Glu Leu Ala
530                 535                 540

Ser Ala Glu Ala Glu Asn Val Leu Lys Gln Ala Asp Ser Ala Ala Asp
545                 550                 555                 560

Gly Ala Thr Ala Leu Ser Ala Leu Thr Ala Leu Leu Tyr Ala Glu Asn
                565                 570                 575

Thr Asp Thr Ala Gln Leu Trp Ala Asp Lys Leu Val Ser Glu Thr Gly
                580                 585                 590

Ala Ser Asn Glu Glu Gly Ala Gly Tyr Ala Gly Pro Arg Ala Glu
                595                 600                 605

Thr Ala Leu Arg Arg Gly Asp Leu Ala Ala Val Glu Ala Gly Ser
                610                 615                 620

Ala Ile Leu Asp His Arg Gly Ser Leu Leu Gly Ile Thr Ala Ala
625                 630                 635                 640

Leu Pro Leu Ser Ser Ala Val Ala Ala Ile Arg Leu Gly Glu Thr
                645                 650                 655

Glu Arg Ala Glu Lys Trp Leu Ala Glu Pro Leu Pro Glu Ala Ile Arg
                660                 665                 670

Asp Ser Leu Phe Gly Leu His Leu Leu Ser Ala Arg Gly Gln Tyr Cys
                675                 680                 685

Leu Ala Thr Gly Arg His Glu Ser Ala Tyr Thr Ala Phe Arg Thr Cys
                690                 695                 700

Gly Glu Arg Met Arg Asn Trp Gly Val Asp Val Pro Gly Leu Ser Leu
705                 710                 715                 720

Trp Arg Val Asp Ala Ala Glu Ala Leu Leu His Gly Arg Asp Arg Asp
                725                 730                 735

Glu Gly Arg Arg Leu Ile Asp Glu Gln Leu Thr His Ala Met Gly Pro
                740                 745                 750

Arg Ser Arg Ala Leu Thr Leu Arg Val Gln Ala Ala Tyr Ser Pro Gln
                755                 760                 765

Ala Gln Arg Val Asp Leu Leu Glu Gly Ala Ala Asp Leu Leu Leu Ser
                770                 775                 780

Cys Asn Asp Gln Tyr Glu Arg Ala Arg Val Leu Ala Asp Leu Ser Glu
785                 790                 795                 800

Ala Phe Ser Ala Leu Arg His His Ser Arg Ala Arg Gly Leu Leu Arg
                805                 810                 815

Gln Ala Arg His Leu Ala Ala Gln Cys Gly Ala Thr Pro Leu Leu Arg
                820                 825                 830

Arg Leu Gly Ala Lys Pro Gly Gly Pro Gly Trp Leu Glu Glu Ser Gly
                835                 840                 845

Leu Pro Gln Arg Ile Lys Ser Leu Thr Asp Ala Glu Arg Arg Val Ala
850                 855                 860

Ser Leu Ala Ala Gly Gly Gln Thr Asn Arg Val Ile Ala Asp Gln Leu
865                 870                 875                 880

Phe Val Thr Ala Ser Thr Val Glu Gln His Leu Thr Asn Val Phe Arg
                885                 890                 895

Lys Leu Gly Val Lys Gly Arg Gln His Leu Pro Ala Glu Leu Ala Asn
                900                 905                 910

Ala Glu

<210> SEQ ID NO 2
```

```
<211> LENGTH: 12
<212> TYPE: DNA
<213> ORGANISM: Artificial Sequence
<220> FEATURE:
<223> OTHER INFORMATION: synthetic construct

<400> SEQUENCE: 2 ctaggggggtt gc                                                           12

<210> SEQ ID NO 3
<211> LENGTH: 6
<212> TYPE: DNA
<213> ORGANISM: Artificial Sequence
<220> FEATURE:
<223> OTHER INFORMATION: synthetic construct

<400> SEQUENCE: 3 gggggt                                                                    6

<210> SEQ ID NO 4
<211> LENGTH: 2685
<212> TYPE: DNA
<213> ORGANISM: Streptomyces hygroscopicus

<400> SEQUENCE: 4
atgcctgccg tggagtgcta tgaactggac gcccgcgatg acgagctcag aaaactggag        60
gaggttgtga ccgggcgggc caacggccgg ggtgtggtgg tcaccatcac cggaccgatc       120
gcctgcggca agaccgaact gctcgacgca gccgccgcga aggccgacgc catcacgtta       180
cgagcggtct gctccgcgga ggaacaggca ctcccgtacg ccctgatcgg cagctcatc        240
gacaacccgg cgctcgcctc ccacgcgctg agccggcct gcccgaccct ccggggcgag       300
cacctgtcgc cggaggccga gaaccggctg cgcagcgacc tcacccgtac cctgctggcg       360
ctcgccgccg aacggccggt gctgatcggc atcgacgagt cacacgcgaa cgctttgtgt       420
ctgctccacc tggcccgaag ggtcggctcg gcccggatcg ccatggtcct caccgagttg       480
cgccggctca ccccggccca ctcacagttc caggccgagc tgctcagcct ggggcaccac       540
cgcgagatcg cgctgcgccc gctcagcccg aagcacaccg ccgagctggt ccgcgccggt       600
ctcggtcccg acgtcgacga ggacgtgctc acggggttgt accgggcgac cggcggcaac       660
ctgaacctca cccgcggact gatcaacgat gtgcgggagg cctgggagac gggagggacg       720
ggcatcagcg cgggccgcgc gtaccggctg gcataccctcg gttccctcta ccgctgcggc       780
ccggtcccgt tgcgggtcgc acgggtggcc gccgtgctgg ccagagcgc caacaccacc       840
ctggtgcgct ggatcagcgg gctcaacgcg gacgcggtgg gcgaggcaac cgagatcctc       900
accgaaggcg gcctgctgca cgacctgcgg ttcccgcacc cggcggcccg ttcggtggta       960
ctcaacgaca tgtccgccca ggaacgacgc cgcctgcacc ggtccgctct ggaagtgctg      1020
gacgacgtgc ccgtggaagt ggtcgcgcac caccaggtcg cgccggtct cctgcacggc      1080
ccgaaggccg ccgagatatt cgccaaggcc ggccaggagc tgcatgtgcg cggcgagttg      1140
gacaccgcgt ccgactatct gcaactggcc caccaggcct ccgacgacgc cgtcaccggg      1200
atgcgggccg aggccgtggc gatcgagcgc gccgcaacc cgctggcctc gagccggcac      1260
ctcgacgagc tgaccgtcgt cgcccgtgcc gggctgctct tccccgagca cggcgcgctg      1320
atgatccgct ggctgggcgt cggcgggcgg tccggcgagg cagccgggct gctggcctcg      1380
cagcgccccc gtgcggtcac cgaccaggac aggggcccata tgcggggccgc cgaggtatcg      1440
ctcgcgctgg tcagcccccgg cacgtccggc ccggaccggc ggccgcgtcc gctcacgccg      1500
```

```
gatgagctcg cgaacctgcc gaaggcggcc cggctctgcg cgatcgccga caatgccgtc   1560
atgtcggccc tgcgcggtcg tcccgagctc gccgcgccg aggcggagaa cgtcctgcag   1620
cacgccgact cggcggcggc cggcaccacc gccctcgccg cgctgaccgc cttgctgtac   1680
gcggagaaca ccgacaccgc tcagctctgg gccgacaagc tggtctccga gaccggggcg   1740
tcgaacgagg aggaggcggg ctacgcgggg ccgcgcgccg aagccgcgtt gcgtcgcggc   1800
gacctggccg cggcggtcga ggcaggcagc accgttctgg accaccggcg gctctcgacg   1860
ctcggcatca ccgccgcgct accgctgagc agcgcggtgg ccgccgccat ccggctgggc   1920
gagaccgagc gggcggagaa gtggctcgcc cagccgctgc cgcaggccat ccaggacggc   1980
ctgttcggcc tgcacctgct ctcggcgcgc ggccagtaca gcctcgccac gggccagcac   2040
gagtcggcgt acacgcgtt tcgcacctgc ggggaacgta tgcggaactg gggcgttgac   2100
gtgccgggtc tgtccctgtg gcgcgtcgac gccgccgagg cgctgctgca cggccgcgac   2160
cgggacgagg ccgacggct cgtcgacgag caactcaccc gtgcgatggg accccgttcc   2220
cgcgccttga cgctgcgggt gcaggcggcg tacagcccgc cggcgaagcg ggtcgacctg   2280
ctcgatgaag cggccgacct gctgctctcc tgcaacgacc agtacgagcg ggcacggtg   2340 ctcgccgacc tgagcgagac gttcagcgcg ctccggcacc acagccgggc gcggggactg   2400
cttcggcagg cccggcacct ggccgcccag cgcggcgcga taccgctgct cgccgactc   2460 ggggccaagc ccgaggccc cggctggctg gaggaatccg gcctgccgca gcggatcaag   2520
tcgctgaccg acgcggagcg gcgggtggcg tcgctggccg ccggcggaca gaccaaccgc   2580
gtgatcgccg accagctctt cgtcacggcc agcacggtgg agcagcacct cacggacgtc   2640
tccactgggt caaggccgcc agcacctgcc gccgaactcg tctag              2685
```

<210> SEQ ID NO 5
<211> LENGTH: 2685
<212> TYPE: DNA
<213> ORGANISM: Streptomyces hygroscopicus

<400> SEQUENCE: 5

```
atgcctgccg tggagtgcta tgaactggac gcccgcgatg acgagctcag aaaactggag     60
gaggttgtga ccgggcgggc caacggccgg ggtgtggtgg tcaccatcac cggaccgatc    120
gcctgcggca agaccgaact gctcgacgca ccgccgcga aggccgacgc catcacgctg    180
cgagcggtct gctccgcgga ggaacaggca ctcccgtacg ccctgatcgg cagctcatc    240 gacaacccgg cgctcgcctc ccacgcgctg agccggcct gccgaccct ccggggcgag    300 cacctgtcgc cggaggccga gaaccggctg cgcagcgacc tcacccgtac cctgctggcg    360
ctcgccgccg aacggccggt gctgatcggc atcgacgagt cacacgcgaa cgctttgtgt    420
ctgctccacc tggcccgaag ggtcggctcg cccggatcg ccatggtcct caccgagttg    480
cgccggctca ccccggccca ctcacagttc caggccgagc tgctcagcct ggggcaccac    540
cgcgagatcg cgctgcgccc gctcagcccg aagcacaccg ccgagctggt ccgcgccggt    600
ctcggtcccg acgtcgacga ggacgtgctc acggggttgt accgggcgac cggcggcaac    660
ctgaacctca cccgcggact gatcaacgat gtgcgggagg cctgggagac ggggagggacg    720 ggcatcagcg cgggccgcgc gtaccggctg gcatacctcg gttccctcta ccgctgcggc    780
ccggtcccgt tgcgggtcgc acgggtggcc ccgtgctgg gccagagcgc caacaccacc    840
ctggtgcgct ggatcagcgg gctcaacgcg gacgcggtgg gcgaggcaac cgagatcctc    900
```

```
accgaaggcg gcctgctgca cgacctgcgg ttcccgcacc cggcggcccg ttcggtggta    960
ctcaacgaca tgtccgccca ggaacgacgc cgcctgcacc ggtccgctct ggaagtgctg   1020
gacgacgtgc ccgtggaagt ggtcgcgcac caccaggtcg gcgccggtct cctgcacggc   1080
ccgaaggccg ccgagatatt cgccaaggcc ggccaggagc tgcatgtgcg cggcgagttg   1140
gacaccgcgt ccgactatct gcaactggcc caccaggcct ccgacgacgc cgtcaccggg   1200
atgcgggccg aggccgtggc gatcgagcgc cgccgcaacc cgctggcctc gagcggcac    1260
ctcgacgagc tgaccgtcgt cgcccgtgcc gggctgctct tccccgagca cacggcgctg   1320
atgatccgct ggctgggcgt cggcgggcgg tccggcgagg cagccgggct gctggcctcg   1380
cagcgccccc gtgcggtcac cgaccaggac agggcccata tgcgggccgc cgaggtatcg   1440
ctcgcgctgg tcagccccgg cacgtccggc ccgaccggc ggccgcgtcc gctcacgccg    1500
gatgagctcg cgaacctgcc gaaggcggcc cggctctgcg cgatcgccga caatgccgtc   1560
atgtcggccc tgcgcggtcg tcccgagctc gccgcggccg aggcggagaa cgtcctgcag   1620
cacgccgact cggcggcggc cggcaccacc gccctcgccg cgctgaccgc cttgctgtac   1680
gcggagaaca ccgacaccgc tcagctctgg gccgacaagc tggtctccga accggggcg    1740
tcgaacgagg aggaggcggg ctacgcgggg ccgcgcgccg aagccgcgtt gcgtcgcggc   1800
gacctggccg gcggcgtcga ggcaggcagc accgttctgg accaccggcg gctctcgacg   1860
ctcggcatca ccgccgcgct accgctgagc agcgcggtgg ccgccgccat ccggctgggc   1920
gagaccgagc gggcggagaa gtggctcgcc cagccgctgc cgcaggccat ccaggacggc   1980
ctgttcggcc tgcacctgct ctcggcgcgc ggccagtaca gcctcgccac gggccagcac   2040
gagtcggcgt acacggcgtt tcgcacctgc ggggaacgta tgcggaactg gggcgttgac   2100
gtgccgggtc tgtccctgtg gcgcgtcgac ccgccgagg cgctgctgca cggccgcgac   2160
cgggacgagg gccgacggct cgtcgacgag caactcaccc gtgcgatggg accccgttcc   2220
cgcgccttga cgctgcgggt gcaggcggcg tacagcccgc cggcgaagcg ggtcgacctg   2280
ctcgatgaag cggccgacct gctgctctcc tgcaacgacc agtacgagcg ggcacgggtg   2340
ctcgccgacc tgagcgagac gttcagcgcg ctccggcacc acagccgggc gcggggactg   2400
cttcggcagg cccggcacct ggccgcccag cgcggcgcga taccgctgct gcgccgactc   2460
ggggccaagc ccgaggccc cggctggctg gaggaatccg gcctgccgca gcggatcaag   2520
tcgctgaccg acgcggagcg gcgggtggcg tcgctggccg ccggcggaca gaccaaccgc   2580
gtgatcgccg accagctctt cgtcacggcc agcacggtgg agcagcacct cacggacgtc   2640
tccactgggt caaggccgcc agcacctgcc gccgaactcg tctag                    2685

<210> SEQ ID NO 6
<211> LENGTH: 2772
<212> TYPE: DNA
<213> ORGANISM: Streptomyces kanamyceticus

<400> SEQUENCE: 6
gtggttcctg aagtgcgagc agcccccgac gaactgatcg cccgcgatga cgagctgagc     60
cgcctccaac gggcactcac cagggcgggg agcggaaggg gcggcgtcgt cgccatcacc    120
gggcccatcg ccagcggaaa gacggcgctg ctcgacgccg gagcggccaa gtccggcttc    180
gtcgcactcc gtcggtgtg ctcctgggaa gagcgcactc tgccgtacgg gatgctgggc    240
cagctcttcg accatcccga actggccgcc caggcgccgg accttgccca cttcacggct    300
tcgtgcgaga gccctcaggc cggtaccgac aaccgcctgc gggccgagtt cacccgcacc    360
```

| | | | | | |
|---|---|---|---|---|---|
| ctgctggcgc | tcgccgcgga | ctggcccgtc | ctgatcggca | tcgacgacgt | gcaccacgcc | 420 |
| gacgcggaat | cactgcgctg | tctgctccac | ctcgcccgcc | gcatcggccc | ggcccgcatc | 480 |
| gcggtcgtac | tgaccgagct | gcgcagaccg | acgcccgccg | actcccgctt | ccaggcggaa | 540 |
| ctgctgagcc | tgcgctccta | ccaggagatc | gcgctcagac | cgctcaccga | ggcgcagacc | 600 |
| ggcgaactcg | tacgtcggca | cctcggcgcg | gagacccacg | aggacgtctc | cgccgatacg | 660 |
| ttccgggcga | ccggcgggaa | cctgctcctc | gggcacggtt | tgatcaatga | catccgggag | 720 |
| gcgcggacag | cgggacggcc | ggggtcgtc | gcggggcggg | cgtaccggct | cgcgtacctc | 780 |
| agctcgctct | accgctgcgg | cccgagcgcg | ctgcgtgtcg | cccgggcgtc | cgccgtgctc | 840 |
| ggcgcgagcg | ccgaagccgt | gctcgtccag | cggatgaccg | gactgaacaa | ggacgcggtc | 900 |
| gaacaggtct | atgagcagct | gaacgaggga | cggctgctgc | agggcgagcg | gtttccgcac | 960 |
| ccggcggccc | gctccatcgt | ccttgacgac | ctgtcggccc | tggaacgcag | aaacctgcac | 1020 |
| gagtcggcgc | tggagctgct | gcgggaccac | ggcgtggccg | gcaacgtgct | cgcccgccac | 1080 |
| cagatcggcg | ccggccgggt | gcacggcgag | gaggccgtcg | agctgttcac | cggggccgca | 1140 |
| cgggagcacc | acctgcgcgg | tgaactggac | gacgcggccg | gataccTgga | actcgcccac | 1200 |
| cgtgcctccg | acgaccccgt | cacgcgcgcc | gcactacgcg | tcggcgccgc | cgcgatcgag | 1260 |
| cgcctctgca | atccggtacg | ggcaggccgg | catctgcccg | agctgctcac | cgcgtcgcgc | 1320 |
| gcgggactgc | tctccagcga | gcacgccgtg | tcgctcgccg | actggctggc | gatgggcggg | 1380 |
| cgcccggggcg | aggcggccga | ggtcctcgcg | acgcagcgtc | ccgcggccga | cagcgagcag | 1440 |
| caccgcgcac | tcctgcgcag | cggcgagttg | tccctcgcgc | tggtccaccc | cggcgcgtgg | 1500 |
| gatccgttgc | gccggaccga | tcggttcgcc | gcgggcgggc | tcggctcgct | tcccggaccc | 1560 |
| gcccggcacc | gcgcggtcgc | cgaccaagcc | gtcatcgcgg | cgctgcgtgg | acgtctcgac | 1620 |
| cgggcggacg | ccaacgcgga | gagcgttctc | cagcacaccg | acgccacggc | ggaccggacc | 1680 |
| acggccatca | tggcgttgct | ggccctgctc | tacgcggaga | acaccgatgc | tgtccagttc | 1740 |
| tgggtcgaca | aactggccgg | tgacgagggc | accaggacac | cggccgacga | ggcggtccac | 1800 |
| gcggggttca | acgccgagat | cgcgctgcgc | cgcggcgact | tgatgagagc | cgtcgagtac | 1860 |
| ggcgaggcag | cgctcggcca | ccggcacctg | cccacctggg | gaatggccgc | cgctctgccg | 1920 |
| ctgagcagca | ccgtggttgc | cgcgatccgg | ctcggcgacc | tcgacagggc | cgagcggtgg | 1980 |
| ctcgccgagc | cgctgccgca | gcagacgccg | gagagcctct | cgggctgca | cctgctctgg | 2040 |
| gcccgcgggc | agcaccacct | cgcgaccggg | cggcacgggg | cggcgtacac | ggcgttcagg | 2100 |
| gaatgcggcg | agcggatgcg | gcggtgggcc | gtcgacgtgc | cgggcctggc | cctgtggcgg | 2160 |
| gtcgacgccg | ccgaatcgct | gctgctgctc | ggccgtgacc | gtgccgaagg | actgcggctc | 2220 |
| gtctccgagc | agctgtcccg | gccgatgcgc | cctcgcgcgc | gcgtgcagac | gttacgggta | 2280 |
| caggcggcct | acagtccgcc | gccccaacgg | atcgacctgc | tcgaagaggc | cgccgacctg | 2340 |
| ctggtcacct | gcaacgacca | gtacgaactg | gcaaacgtac | tcagcgactt | ggcagaggcc | 2400 |
| tccagcatgg | tccggcagca | cagcagggcg | cggggtctgc | tccgccgggc | acggcacctc | 2460 |
| gccacccagt | gcgcgccgt | gccgctcctg | cggcggctcg | gcgcggaacc | ctcggacatc | 2520 |
| ggcggagcct | gggacgcgac | gctgggacag | cggatcgcgt | cactgacgga | gtcggagcgg | 2580 |
| cgggtggccg | cgctcgccgc | ggtcgggcgt | acgaacaggg | agatcgccga | gcagctgttc | 2640 |
| gtcacggcca | gcacggtgga | acagcacctc | acgaacgtgt | tccgcaaact | ggcggtgaag | 2700 |

| | |
|---|---:|
| ggccgccagc agcttccgaa ggaactggcc gacgtcggcg agccggcgga ccgcgaccgc | 2760 |
| cggtgcgggt ag | 2772 |

<210> SEQ ID NO 7
<211> LENGTH: 2772
<212> TYPE: DNA
<213> ORGANISM: Streptomyces kanamyceticus

<400> SEQUENCE: 7

| | |
|---|---:|
| atggttcctg aagtgcgagc agcccccgac gaactgatcg cccgcgatga cgagctgagc | 60 |
| cgcctccaac gggcactcac cagggcgggg agcggaaggg gcggcgtcgt cgccatcacc | 120 |
| gggcccatcg ccagcggaaa gacggcgctg ctcgacgccg agcggccaa gtccggcttc | 180 |
| gtcgcactcc gtgcggtgtg ctcctgggaa gagcgcactc tgccgtacgg gatgctgggc | 240 |
| cagctcttcg accatcccga actggccgcc caggcgccgg accttgccca cttcacggct | 300 |
| tcgtgcgaga gccctcaggc cggtaccgac aaccgcctgc gggccgagtt caccgcacc | 360 |
| ctgctggcgc tcgccgcgga ctggcccgtc ctgatcggca tcgacgacgt gcaccacgcc | 420 |
| gacgcggaat cactgcgctg tctgctccac ctcgcccgcc gcatcggccc ggcccgcatc | 480 |
| gcggtcgtac tgaccgagct gcgcagaccg acgcccgccg actcccgctt ccaggcggaa | 540 |
| ctgctgagcc tgcgctccta ccaggagatc gcgctcagac cgctcaccga ggcgcagacc | 600 |
| ggcgaactcg tacgtcggca cctggccgcg gagacccacg aggacgtctc cgccgatacg | 660 |
| ttccgggcga ccggcgggaa cctgctcctc gggcacggtt tgatcaatga catccgggag | 720 |
| gcgcggacag cgggacggcc ggggtcgtc gggggcggg cgtaccggct cgcgtacctc | 780 |
| agctcgctct accgctgcgg cccgagcgcg ctgcgtgtcg cccgggcgtc cgccgtgctc | 840 |
| ggcgcgagcg ccgaagccgt gctcgtccag cggatgaccg gactgaacaa ggacgcggtc | 900 |
| gaacaggtct atgagcagct gaacgaggga cggctgctgc agggcgagcg gtttccgcac | 960 |
| ccggcggccc gctccatcgt ccttgacgac ctgtcggccc tggaacgcag aaacctgcac | 1020 |
| gagtcggcgc tggagctgct gcgggaccac ggcgtggccg caacgtgct cgcccgccac | 1080 |
| cagatcggcg ccgccgggt gcacggcgag gaggccgtcg agctgttcac cggggccgca | 1140 |
| cgggagcacc acctgcgcgg tgaactggac gacgcggccg gataccctgga actcgcccac | 1200 |
| cgtgcctccg acgaccccgt cacgcgcgcc gcactacgcg tcggcgccgc cgcgatcgag | 1260 |
| cgcctctgca atccggtacg ggcaggccgg catctgcccg agctgctcac cgcgtcgcgc | 1320 |
| gcgggactgc tctccagcga gcacgccgtg tcgctcgccg actggctggc gatgggcggg | 1380 |
| cgggcgggcg aggcggccga ggtcctcgcg acgcagcgtc ccgcggccga cagcgagcag | 1440 |
| caccgcgcac tcctgcgcag cggcgagttg tccctcgcgc tggtccaccc cggcgcgtgg | 1500 |
| gatccgttgc gccggaccga tcggttcgcc gcgggcgggc tcggctcgct tcccggaccc | 1560 |
| gcccggcacc gcgcggtcgc cgaccaagcc gtcatcgcgg cgctgcgtgg acgtctcgac | 1620 |
| cgggcggacg ccaacgcgga gagcgttctc cagcacaccg acgccacggc ggaccggacc | 1680 |
| acggccatca tggcgttgct ggccctgctc tacgcggaga acaccgatgc tgtccagttc | 1740 |
| tgggtcgaca aactggccgg tgacgagggc accaggacac cggccgacga ggcggtccac | 1800 |
| gcggggttca acgccgagat cgcgctgcgc cgcggcgact tgatgagagc cgtcgagtac | 1860 |
| ggcgaggcag cgctcggcca ccggcacctg cccacctggg aatggccgc cgctctgccg | 1920 |
| ctgagcagca ccgtggttgc cgcgatccgg ctcggcgacc tcgacagggc cgagcggtgg | 1980 |
| ctcgccgagc cgctgccgca gcagacgccg gagagcctct tcgggctgca cctgctctgg | 2040 |

```
gcccgcgggc agcaccacct cgcgaccggg cggcacgggg cggcgtacac ggcgttcagg    2100
gaatgcggcg agcggatgcg gcggtgggcc gtcgacgtgc cgggcctggc cctgtggcgg    2160
gtcgacgccg ccgaatcgct gctgctgctc ggccgtgacc gtgccgaagg actgcggctc    2220
gtctccgagc agctgtcccg gccgatgcgc cctcgcgcgc cgtgcagac gctgcgggta    2280 caggcggcct acagtccgcc gccccaacgg atcgacctgc tcgaagaggc cgccgacctg    2340
ctggtcacct gcaacgacca gtacgaactg caaacgtac tcagcgactt ggcagaggcc    2400
tccagcatgg tccggcagca cagcagggcg cggggtctgc tccgccgggc acggcacctc    2460
gccacccagt gcggcgccgt gccgctcctg cggcggctcg gcgcggaacc ctcggacatc    2520
ggcggagcct gggacgcgac gctgggacag cggatcgcgt cactgacgga gtcggagcgg    2580
cgggtggccg cgctcgccgc ggtcgggcgt acgaacaggg agatcgccga gcagctgttc    2640
gtcacggcca gcacggtgga acagcacctc acgaacgtgt ccgcaaaact ggcggtgaag    2700
ggccgccagc agcttccgaa ggaactggcc gacgtcggcg agccggcgga ccgcgaccgc    2760
cggtgcgggt ag                                                         2772

<210> SEQ ID NO 8
<211> LENGTH: 2742
<212> TYPE: DNA
<213> ORGANISM: Streptomyces ascomyceticus

<400> SEQUENCE: 8
gtgatagcgc gcttatctcc cccagacctg atcgcccgcg atgacgagtt cggttccctc      60
caccgggcgc tcacccgagc gggggggcggg cggggcgtcg tcgccgccgt caccgggccg     120
atcgcctgcg gcaagaccga actcctcgac gccgccgcgg ccaaggccgg cttcgtcacc     180
cttcgcgcgg tgtgctccat ggaggagcgg gccctgccgt acggcatgct cggccagctc     240
ctcgaccagc ccgagctggc cgcccggaca ccggagctgg tccggctgac ggcatcgtgc     300
gaaaacctgc cggccgacgt cgacaaccgc ctggggaccg aactcacccg cacggtgctg     360
acgctcgccg cggagcggcc cgtactgatc ggcatcgacg acgtgcacca cgccgacgcg     420
ccgtcgctgc gctgcctgct ccacctcgcg cgccgcatca gccgggcccg tgtcgccatc     480
gtgctgaccg agctgctccg gccgacgccc gcccactccc aattccgggc ggcactgctg     540
agtctgcgcc actaccagga gatcgcgctg cgcccgctca ccgaggcgca gaccaccgaa     600
ctcgtgcgcc ggcacctcgg ccaggacgcg cacgacgacg tggtggccca ggcgttccgg     660
gcgaccggcg gcaacctgct cctcggccac ggcctgatcg acgacatccg ggaggcacgg     720
acacggacct cagggtgcct ggaagtggtc gcggggcggg cgtaccggct cgcctacctc     780
gggtcgctct atcgttgcgg cccggccgcg ctgagcgtcg cccgagcttc cgccgtgctc     840
ggcgagagtg tcgaactcac cctcgtccag cggatgaccg gcctcgacac cgaggcggtc     900
gagcaggccc acgaacagct ggtcgagggg cggctgctgc gggaagggcg gttcccgcac     960
cccgcggccc gctccgtcgt actcgacgac ctctccgccg ccgagcggcg tggcctgcac    1020
gagctggcgc tggaactgct gcgggaccgc ggcgtggcca gcaaggtgct cgcccgccac    1080
cagatgggta ccggccgggt gcacggcgcc gaggtcgccg gctgttcac cgacgccgcg    1140 cgcgagcacc acctgcgcgg cgagctcgac gaggccgtca cctacctgga gttcgcctac    1200
cgggcctccg acgaccccgc cgtccacgcc gcactgcgcg tcgacaccgc cgccatcgag    1260
cggctctgcg atcccgccag atccggccgg catgtgcccg agctgctcac cgcgtcgcgg    1320
```

```
gaacggctcc tctccagcga gcacgccgtg tcgctcgcct gctggctggc gatggacggg    1380
cggccgggcg aggccgccga ggtcctggcg gcccagcgct ccgccgcccc gagcgagcag    1440
ggccgggcgc acctgcgcgt cgcggacctg tccctcgcgc tgatctatcc cggcgcggcc    1500
gatccgccgc gtccggccga tccgccggcc gaggacgagg tcgcctcgtt ttccggagcc    1560
gtccggcacc gcgccgtcgc cgacaaggcc ctgagcaacg cgctgcgcgg ctggtccgaa    1620
caggccgagg ccaaagccga gtacgtgctc cagcactccc gggtcacgac ggaccggacc    1680
acgaccatga tggcgttgct ggccctgctc tacgccgagg acaccgatgc cgtccagtcc    1740
tgggtcgaca gctggccgg tgacgacaac atgcggaccc cggccgacga ggcggtccac    1800
gcggggttcc gcgccgaggc cgcgctgcgc cgcggcgacc tgaccgccgc cgtcgaatgc    1860
ggcgaggccg cgctcgcccc ccgggtcgtg ccctcctggg ggatggccgc cgcattgccg    1920
ctgagcagca ccgtggccgc cgcgatccga ctgggcgacc tggaccgggc ggagcggtgg    1980
ctcgccgagc cgttgccgga ggagacctcc gacagcctct tcggactgca catggtctgg    2040
gccgtgggc aacaccatct cgcggccggg cggtaccggg cggcgtacaa cgcgttccgg    2100
gactgcgggg agcggatgcg acgctggtcc gtcgacgtgc cgggcctggc cctgtggcgg    2160
gtcgacgccg ccgaagcgct tctgctgctc ggccgcggcc gtgacgaggg gctgaggctc    2220
atctccgagc agctgtcccg gccgatgggg tcccgggcgc gggtgatgac gctgcgggtg    2280
caggcggcct acagtccgcc ggccaagcgg atcgaactgc tcgacgaggc cgccgatctg    2340
ctcatcatgt gccgcgacca gtacgagctg gcccgcgtcc tcgccgacat gggcgaagcg    2400
tgcggcatgc tccggcggca cagccgtgcg cggggactgt ccgccgcgc acggcacctc    2460
gcgacccagt gcggagccgt gccgctcctc cggcggctcg gtggggagtc ctcggacgcg    2520
gacggcaccc aggacgtgac gccggcgcag cggatcacat cgctgaccga ggcggagcgg    2580
cgggtggcgt cgcacgccgc ggtcgggcgc accaacaagg agatcgccag ccagctgttc    2640
gtcacctcca gcacggtgga acagcacctc accaacgtgt ccgcaagct gggggtgaag    2700
ggccgtcagc aactgcccaa ggaactgtcc gacgccggct ga                      2742
```

<210> SEQ ID NO 9
<211> LENGTH: 2742
<212> TYPE: DNA
<213> ORGANISM: Streptomyces ascomyceticus

<400> SEQUENCE: 9

```
atgatagcgc gcctgtctcc cccagacctg atcgcccgcg atgacgagtt cggttccctc      60
caccgggcgc tcacccgagc gggggcggg cggggcgtcg tcgccgccgt caccgggccg     120
atcgcctgcg gcaagaccga actcctcgac gccgccgcgg ccaaggccgg cttcgtcacc     180
cttcgcgcgg tgtgctccat ggaggagcgg gccctgccgt acggcatgct cggccagctc     240
ctcgaccagc ccgagctggc cgcccggaca ccggagctgg tccggctgac ggcatcgtgc     300
gaaaacctgc cggccgacgt cgacaaccgc ctggggaccg aactcacccg cacggtgctg     360
acgctcgccg cggagcggcc cgtactgatc ggcatcgacg acgtgcacca cgccgacgcg     420
ccgtcgctgc gctgcctgct ccacctcgcg cgccgcatca gccgggcccg tgtcgccatc     480
gtgctgaccg agctgctccg gccgacgccc gcccactccc aattccgggc ggcactgctg     540
agtctgcgcc actaccagga gatcgcgctg cgcccgctca ccgaggcgca gaccaccgaa     600
ctcgtgcgcc ggcacctcgg ccaggacgcg cacgacgacg tggtgcccca ggcgttccgg     660
gcgaccggcg gcaacctgct cctcggccac ggcctgatcg acgacatccg ggaggcacgg     720
```

| | |
|---|---|
| acacggacct cagggtgcct ggaagtggtc gcggggcggg cgtaccggct cgcctacctc | 780 |
| gggtcgctct atcgttgcgg cccggccgcg ctgagcgtcg cccgagcttc cgccgtgctc | 840 |
| ggcgagagtg tcgaactcac cctcgtccag cggatgaccg gcctcgacac cgaggcggtc | 900 |
| gagcaggccc acgaacagct ggtcgagggg cggctgctgc gggaagggcg gttcccgcac | 960 |
| cccgcggccc gctccgtcgt actcgacgac ctctccgccg ccgagcggcg tggcctgcac | 1020 |
| gagctggcgc tggaactgct gcgggaccgc ggcgtggcca gcaaggtgct cgcccgccac | 1080 |
| cagatgggta ccggccgggt gcacggcgcc gaggtcgccg ggctgttcac cgacgccgcg | 1140 |
| cgcgagcacc acctgcgcgg cgagctcgac gaggccgtca cctacctgga gttcgcctac | 1200 |
| cgggcctccg acgacccgc cgtccacgcc gcactgcgcg tcgacaccgc cgccatcgag | 1260 |
| cggctctgcg atcccgccag atccggccgg catgtgcccg agctgctcac cgcgtcgcgg | 1320 |
| gaacggctcc tctccagcga gcacgccgtg tcgctcgcct gctggctggc gatggacggg | 1380 |
| cggccggggcg aggccgccga ggtcctggcg gcccagcgct ccgccgcccc gagcgagcag | 1440 |
| ggccgggcgc acctgcgcgt cgcggacctg tccctcgcgc tgatctatcc cggcgcggcc | 1500 |
| gatccgccgc gtccggccga tccgccggcc gaggacgagg tcgcctcgtt ttccggagcc | 1560 |
| gtccggcacc gcgccgtcgc cgacaaggcc ctgagcaacg cgctgcgcgg ctggtccgaa | 1620 |
| caggccgagg ccaaagccga gtacgtgctc cagcactccc gggtcacgac ggaccggacc | 1680 |
| acgaccatga tggcgttgct ggccctgctc tacgccgagg acaccgatgc cgtccagtcc | 1740 |
| tgggtcgaca gctggccgg tgacgacaac atgcggaccc cggccgacga ggcggtccac | 1800 |
| gcggggttcc gcgccgaggc cgcgctgcgc cgcggcgacc tgaccgccgc cgtcgaatgc | 1860 |
| ggcgaggccg cgctcgcccc ccgggtcgtg ccctcctggg ggatggccgc cgcattgccg | 1920 |
| ctgagcagca ccgtggccgc cgcgatccga ctgggcgacc tggaccgggc ggagcggtgg | 1980 |
| ctcgccgagc cgttgccgga ggagacctcc gacagcctct tcggactgca catggtctgg | 2040 |
| gcccgtgggc aacaccatct cgcggccggg cggtaccggg cggcgtacaa cgcgttccgg | 2100 |
| gactgcgggg agcggatgcg acgctggtcc gtcgacgtgc cgggcctggc cctgtggcgg | 2160 |
| gtcgacgccg ccgaagcgct tctgctgctc ggccgcggcc gtgacgaggg gctgaggctc | 2220 |
| atctccgagc agctgtcccg gccgatgggg tcccgggcgc gggtgatgac gctgcgggtg | 2280 |
| caggcggcct acagtccgcc ggccaagcgg atcgaactgc tcgacgaggc cgccgatctg | 2340 |
| ctcatcatgt gccgcgacca gtacgagctg gcccgcgtcc tcgccgacat gggcgaagcg | 2400 |
| tgcggcatgc tccggcggca cagccgtgcg cggggactgt tccgccgcgc acggcacctc | 2460 |
| gcgacccagt gcggagccgt gccgctcctc cggcggctcg gtggggagtc ctcggacgcg | 2520 |
| gacggcaccc aggacgtgac gccggcgcag cggatcacat cgctgaccga gcggagcgg | 2580 |
| cgggtggcgt cgcacgccgc ggtcgggcgc accaacaagg agatcgccag ccagctgttc | 2640 |
| gtcacctcca gcacggtgga acagcacctc accaacgtgt ccgcaagct ggggggtgaag | 2700 |
| ggccgtcagc aactgcccaa ggaactgtcc gacgccggct ga | 2742 |

<210> SEQ ID NO 10
<211> LENGTH: 2706
<212> TYPE: DNA
<213> ORGANISM: Micromonospora sp. S92-306401

<400> SEQUENCE: 10

| | |
|---|---|
| gtggagtttt acgacctggt cgcccgcgat gacgagctca gaaggttgga ccaggccctc | 60 |

```
ggccgcgccg ccggcggacg gggtgtcgtg gtcaccgtca ccggaccggt cggctgcggc      120
aagaccgaac tgctggacgc ggccgcggcc gaggaggaat tcatcacgtt gcgtgcggtc      180
tgctcggccg aggagcgggc cctgccgtac gccgtgatcg gccaactcct cgaccatccc      240
gtactctccg cacgcgcgcc cgacctggcc tgcgtgacgg ctccgggccg gacgctgccg      300
gccgacaccg agaaccgcct gcgccgcgac ctcacccggg ccctgctggc cctggcctcc      360
gaacgaccgg ttctgatctg catcgacgac gtgcaccagg ccgacaccgc ctcgctgaac      420
tgcctgctgc acctggcccg gcgggtcgcc tcggcccgga tcgccatgat cctcaccgag      480
ttgcgccggc tcaccccggc tcactccggg ttcgaggcgg aactgctcag cctgcggcac      540
cgccacgaga tcgcgctgcg tcccctcggc ccggccgaca ccgccgaact ggcccgcgcc      600
cggctcggcg ccggcgtcac cgccgacgag ctggcccagg tccacgaggc caccagcggg      660
aaccccaacc tggtcggagg cctggtcaac gacgtgcgag aggcctgggc ggccggtggc      720
acgggcattg cggcggggcg ggcgtaccgg ctggcgtacc tcagctccgt gtaccgctgt      780
ggtccggtcc cgttgcggat cgcccaggcg gcggcggtgc tgggtcccag cgccaccgtc      840
acgctggtgc gccggatcag cgggctcgac gccgagacgg tggacgaggc gaccgcgatc      900
ctcaccgagg gcggcctgct ccgggaccac cggttcccgc atccggcggc ccgctcggtc      960
gtactcgacg acatgtccgc gcaggaacgc cgccgcctgc accggtccac gctggacgtg     1020
ctggacggcg tacccgtcga cgtgctcgcg caccaccagg ccggcgccgg tctgctgcac     1080
ggcccgcagg cggccgagat gttcgcccgg gccagccagg agctgcgggt acgcggcgag     1140
ctggacgccg cgaccgagta cctgcaactg gcctaccggg cctccgacga cgccggcgcc     1200
cgggccgccc tgcaggtgga gaccgtggcc ggcgagcgcc gccgcaaccc gctggccgcc     1260
agccggcacc tggacgagct ggccgccgcc gcccgggccg gcctgctgtc ggccgagcac     1320
gccgccctgg tcgtgcactg gctggccgac gccggacgac ccggcgaggc cgccgaggtg     1380
ctggcgctga gcgggcgct ggccgtcacc gaccacgacc gggcccgcct gcgggcggcc     1440
gaggtgtcgc tcgcgctgtt ccaccccggc gtccccggtt cggacccgcg gccccctcgcg     1500 ccggaggagc tcgcgagcct gtccctgtcg gcccggcacg tgtgaccgc cgacaacgcg     1560 gtgctggcgg cgctgcgcgg ccgtcccgag tcggccgccg ccgaggcgga gaacgtgctg     1620
cgcaacgccg acgccgccgc gtccggcccg accgccctgg ccgcgctgac ggccctgctc     1680
tacgccgaga acaccgacgc cgcccagctc tgggcggaca gctggccgc gggcatcggg     1740 gcggggggagg gggaggccgg ctacgcgggg ccgcggaccg tggccgccct gcgtcgcggc     1800
gacctgacca ccgcggtcca gcggccggc gcggtcctgg accgcggccg gccgtcgtcg     1860
ctcggcatca ccgccgtgtt gccgttgagc ggcgcggtcg ccgccgcgat ccggctgggc     1920
gagctcgagc gggccgagaa gtggctggcc gagccgctgc ccgaagccgt ccacgacagc     1980
ctgttcggcc tgcacctgct gatgcgcgcg ggccgctaca gcctcgcggt gggcggcac     2040 gaggcggcgt acgccgcgtt ccgggactgc ggtgaacgga tgcgcggtg gacgtcgac     2100 gtgcccgggc tggccctgtg gcgggtggac gcggccgagg cgctgctgcc cggcgatgac     2160
cgggcggagg ccggcggct gatcgacgag cagctcaccc ggcgatggg gccccggtca     2220 cgagccctga ccctgcgggt acgagcggcc tacgccccgc cggcgaaacg gatcgacctg     2280
ctcgacgaag cggccgacct gctgctctcc agcaacgacc agtacgagcg ggcacgggtg     2340
ctggccgacc tgagcgaggc gttcagcgcg ctccggcaga acggcgggc gcgcggcatc     2400 ctgcggcagg cccggcacct ggccgcccag tgcggggcgg tccccctgct gcgccggctg     2460
```

```
ggcgtcaagg ccggccggtc cggtcggctc ggccggccgc cgcagggaat ccgctccctg    2520
accgaggccg agcgccgggt ggccacgctg ccgccgccg  ggcagaccaa ccgggagatc    2580
gccgaccagc tcttcgtcac cgccagcacg tcgagcagc  acctcaccaa cgtgttccgc    2640
aagctcggcg tgaagggccg ccagcaattg ccggccgagc tggccgacct gcggccgccg    2700
ggctga                                                               2706
```

<210> SEQ ID NO 11
<211> LENGTH: 2706
<212> TYPE: DNA
<213> ORGANISM: Micromonospora sp. S92-306401

<400> SEQUENCE: 11

```
atggagtttt cgacctggt  cgcccgcgat gacgagctca gaaggttgga ccaggccctc      60
ggccgcgccg ccggcggacg gggtgtcgtg gtcaccgtca ccggaccggt cggctgcggc     120
aagaccgaac tgctggacgc ggccgcggcc gaggaggaat tcatcacgtt gcgtgcggtc     180
tgctcggccg aggagcgggc cctgccgtac gccgtgatcg ccaactcctc gaccatccc     240 gtactctccg cacgcgcgcc cgacctggcc tgcgtgacgg ctccgggccg gacgctgccg     300
gccgacaccg agaaccgcct cgccgcgac  ctcacccggg ccctgctggc cctggcctcc     360
gaacgaccgg ttctgatctg catcgacgac gtgcaccagg ccgacaccgc ctcgctgaac     420
tgcctgctgc acctggcccg gcgggtcgcc tcggcccgga tcgccatgat cctcaccgag     480
ttgcgccggc tcaccccggc tcactcccgg ttcgaggcgg aactgctcag cctgcggcac     540
cgccacgaga tcgcgctgcg tcccctcggc ccggccgaca ccgccgaact ggcccgcgcc     600
cggctcggcg ccggcgtcac cgccgacgag ctggcccagg tccacgaggc caccagcggg     660
aaccccaacc tggtcggagg cctggtcaac gacgtgcgag aggcctgggc ggccggtggc     720
acgggcattg cggcggggcg ggcgtaccgg ctggcgtacc tcagctccgt gtaccgctgt     780
ggtccggtcc cgttgcggat cgcccaggcg gcggcggtgc tgggtcccag cgccaccgtc     840
acgctggtgc gccggatcag cgggctcgac gccgagacgg tggacgaggc gaccgcgatc     900
ctcaccgagg gcggcctgct ccgggaccac cggttcccgc atccggcggc ccgctcggtc     960
gtactcgacg acatgtccgc gcaggaacgc cgccgcctgc accggtccac gctggacgtg    1020
ctggacggcg tacccgtcga cgtgctcgcg caccaccagg ccggcgccgg tctgctgcac    1080
ggcccgcagg cggccgagat gttcgcccgg gccagccagg agctgcgggt acgcggcgag    1140
ctggacgccg cgaccgagta cctgcaactg gcctaccggg cctccgacga cgccggcgcc    1200
cgggccgccc tgcaggtgga gaccgtggcc ggcgagcgcc gccgcaaccc gctggccgcc    1260
agccggcacc tggacgagct ggccgccgcc gcccgggccg gctgctgtc  ggccgagcac    1320 gccgccctgg tcgtgcactg gctggccgac gccggacgac ccgcgaggc  cgccgaggtg    1380 ctggcgctgc agcgggcgct ggccgtcacc gaccacgacc gggcccgcct gcgggcggcc    1440
gaggtgtcgc tcgcgctgtt ccaccccggc gtccccggtt cggacccgcg gcccctcgcg    1500
ccggaggagc tcgcgagcct gtccctgtcg gccggcacg  tgtgaccgc  cgacaacgcg    1560 gtgctggcgg cgctgcgcgg ccgtcccgag tcggccgccg ccgaggcgga aacgtgctg     1620 cgcaacgccg acgccgccgc gtccggcccg accgcctgg  ccgcgctgac ggccctgctc    1680
tacgccgaga acaccgacgc cgcccagctc tgggcggaca agctggccgc gggcatcggg    1740 gcggggagg  gggaggccgg ctacgcgggg ccgcggaccg tggccgccct gcgtcgcggc    1800
```

```
gacctgacca ccgcggtcca ggcggccggc gcggtcctgg accgcggccg gccgtcgtcg    1860
ctcggcatca ccgccgtgtt gccgttgagc ggcgcggtcg ccgccgcgat ccggctgggc    1920
gagctcgagc gggccgagaa gtggctggcc gagccgctgc ccgaagccgt ccacgacagc    1980
ctgttcggcc tgcacctgct gatgcgcggg gccgctaca gcctcgcggt gggccggcac     2040
gaggcggcgt acgccgcgtt ccgggactgc ggtgaacgga tgcgccggtg ggacgtcgac    2100
gtgcccgggc tggccctgtg gcgggtggac gcggccgagg cgctgctgcc cggcgatgac    2160
cgggcggagg gccggcggct gatcgacgag cagctcaccc ggccgatggg gccccggtca    2220
cgagccctga ccctgcgggt acgagcggcc tacgccccgc cggcgaaacg gatcgacctg    2280
ctcgacgaag cggccgacct gctgctctcc agcaacgacc agtacgagcg ggcacgggtg    2340
ctggccgacc tgagcgaggc gttcagcgcg ctccggcaga acggccgggc gcgcggcatc    2400
ctgcggcagg cccggcacct ggccgcccag tgcggggcgg tccccctgct gcgccggctg    2460
ggcgtcaagg ccggccggtc cggtcggctc ggccggccgc cgcagggaat ccgctccctg    2520
accgaggccg agcgccgggt ggccacgctg ccgccgccgc ggcagaccaa ccgggagatc    2580
gccgaccagc tcttcgtcac cgccagcacg gtcgagcagc acctcaccaa cgtgttccgc    2640
aagctcggcg tgaagggccg ccagcaattg ccggccgagc tggccgacct gcggccgccg    2700
ggctga                                                              2706
```

<210> SEQ ID NO 12
<211> LENGTH: 2616
<212> TYPE: DNA
<213> ORGANISM: Streptomyces violaceusniger

<400> SEQUENCE: 12

```
gtggtcaccg tcaccggccc aatcgcctgc ggcaagacag aactgcttga cgcggctgcc      60
gcgaaggctg aggccatcat tctgcgcgcg gtctgcgcgc cagaagagcg ggctatgccg     120
tacgccatga tcgggcagct catcgacgac ccggcgctcg cgcatcgggc gccggggctg     180
gctgatcgga tagcccaggg cgggcagctg tcgctgaggg ccgagaaccg actgcgcagg     240
gatctcaccc gtgccctgct ggcgcttgcc gtcgaccggc tgtgctgat cggcgtcgac      300 gatgtgcatc acgccgacac cgcctctttg aactgtctgc tgcatttggc gcgccgggtc    360
cgtccggccc ggatatccat gatcttcacc gagttgcgca gcctcacccc tactcagtca    420
cggttcaagg cggagctgct cagcctgccg taccaccacg agatcgcgct gcgtccgttc    480
ggaccggagc aatcggcgga gctggcccgc gccgccttcg gcccgggcct cgccgaggat   540
gtgctcgtgg ggttgtataa aacgaccagg ggcaatctga gtctcagccg tggactgatc    600
agcgatgtgc gggaggccct ggccaacgga gagagcgcct tcgaggcggg ccgcgcgttc    660
cggctggcgt acctcggctc gctctaccgc tgtggcccgg tcgcgctgcg ggtcgcccga    720
gtggctgccg tgctgggccc gagcgccacc accacgctgg tgcgccgtct aagcgggctc    780
agcgcggaga cgatagaccg ggcaaccaag atcctcaccg agggcgggct gctgctcgac    840
cagcagttcc cgcacccggc cgcccgctcg gtggtgcttg atgacatgtc cgcccaggaa    900
cgacgcggcc tgcacactct cgccctggaa ctgctggacg aggcgccggt tgaagtgctc    960
gcgcaccacc aggtcggcgc cggtctcata cacgggccca aggctgcgga gatgttcgcc    1020
aaggccggca aggctctggt cgtacgcaac gagttgggcg acgcggcaga ataccctgcaa   1080 ctggctcacc gggcctccga cgatgtctcc accggggccg ccttacgggt cgaggccgtg   1140
gcgatcgagc gccgccgcaa tccgctggcc tccagtcggc acatggacga gctgagcgcc   1200
```

```
gccggccgcg ccggtctgct ttcccccaag catgcggcgc tggccgtctt ctggctggcc    1260
gacggcgggc gatccggcga ggcagccgag gtgctggcgt cggaacgccc gctagcgacc    1320
accgatcaga accgggccca cttgcgattt gtcgaggtga ctctcgcgct gttctctccc    1380
ggcgccttcg gatcggaccg gcgcccacct ccgctgacgc cggacgaact cgccagcctg    1440
ccgaaggcgg cctggcaatg cgcggtcgcc gacaacgcgg ccatgaccgc cttgcacggt    1500
catccagaac ttgccaccgc tcaggcgaaa acagttctgc ggcaggctga ttcggcagcc    1560
gacgcgatcc ccgccgcgct gatcgccctg ttgtacgcgg agaacaccga gtccgctcat    1620
atctgggcca caagctggg cagcacgaat ggcggggtat cgaacgaggc ggaagcgggc    1680
tacgccggcc cgtgcgccga gatcgccctg cggcgcggcg acctggccac ggcgttcgag    1740
gctggtagca ccgtcctgga cgaccggtcg ctgccgtcgc tcggcatcac cgccgcattg    1800
ctgttgagca gcaagacggc cgccgctgtc cggctgggcg aactcgagcg tgcggagaag    1860
ctgctcgccg agccgcttcc gaacggcgtc caggacagcc ttttcggtct gcacctgctc    1920
tcggcatacg gccagtacag cctcgcgatg ggccgatatg aatcggctct ccgggcgttt    1980
cacacctgcg gagaacgtat gcgcagctgg gatgttgacg tgcctggtct ggccctgtgg    2040
cgtgtcgacg ccgccgaggc gctgctcagc ctcgaccgga acgagggcca gcggctcatc    2100
gacgaacaac tcacccgtcc gatggggcct cgttcccgcg cgttaacgct gcggatcaag    2160
gcggcatacc tcccgcggac gaagcggatc cccctgctcc atgaggcggc cgagctgctg    2220
ctcccctgcc ccgacccgta cgagcaagcg cgggtgctcg ccgatctggg cgacacgctc    2280
agcgcgctca gacgctatag ccggggcgcgg ggagttctcc ggcaggctcg tcacctggcc    2340
gcccagtgcg gtgctgtccc gctgctgcgc aggctcgggg gcgagcccgg ccggatcgac    2400
gacgccggcc tgccgcagcg gagcacatcg ttgaccgatg cggagcggcg ggtggcggcg    2460
ctggccgcgg ccgacagac caaccgggag atcgccaaac agctgttcgt cacgccaggc    2520
acagtggaac agcacctcac aagcgtcttc cgcaaactgg gggtcaaggg tcgcaagcag    2580
ctgccgaccg cgctggccga cgtggaacag acctga                              2616

<210> SEQ ID NO 13
<211> LENGTH: 2721
<212> TYPE: DNA
<213> ORGANISM: Streptomyces violaceusniger

<400> SEQUENCE: 13
atgtatagcg gtacctgccg tgaaggatac gaactcgtcg cacgcgagga cgaactcggc      60
attctacaga ggtctctgga caagcgagc agcggccagg gcgtcgtggt caccgtcacc     120
ggcccaatcg cctgcggcaa gacagaactg cttgacgcgg ctgccgcgaa ggctgaggcc     180
atcattctgc gcgcggtctg cgcgccagaa gagcgggcta tgccgtacgc catgatcggg     240
cagctcatcg acgacccggc gctcgcgcat cgggcgccgg ggctggctga tcggatagcc     300
cagggcgggc agctgtcgct gagggccgag aaccgactgc gcaggatctc acccgtgcc     360 ctgctggcgc ttgccgtcga ccggcctgtg ctgatcggcg tcgacgatgt gcatcacgcc     420
gacaccgcct ctttgaactg tctgctgcat ttggcgcgcc gggtccgtcc ggcccggata     480
tccatgatct tcaccgagtt gcgcagcctc accctactc agtcacggtt caaggcggag     540
ctgctcagcc tgccgtacca ccacgagatc gcgctgcgtc cgttcggacc ggagcaatcg     600
gcggagctgg cccgcgccgc cttcggcccg ggcctcgccg aggatgtgct cgtggggttg     660
```

```
tataaaacga ccaggggcaa tctgagtctc agccgtggac tgatcagcga tgtgcgggag      720
gccctggcca acgagagag cgccttcgag gcgggccgcg cgttccggct ggcgtacctc      780
ggctcgctct accgctgtgg cccggtcgcg ctgcgggtcg cccgagtggc tgccgtgctg      840
ggcccgagcg ccaccaccac gctggtgcgc cgtctaagcg ggctcagcgc ggagacgata      900 gacccgggcaa ccaagatcct caccgagggc gggctgctgc tcgaccagca gttcccgcac      960
ccggccgccc gctcggtggt gcttgatgac atgtccgccc aggaacgacg cggcctgcac     1020
actctcgccc tggaactgct ggacgaggcg ccggttgaag tgctcgcgca ccaccaggtc     1080
ggcgccggtc tcatacacgg gcccaaggct gcggagatgt tcgccaaggc cggcaaggct     1140
ctggtcgtac gcaacgagtt gggcgacgcg gcagaatacc tgcaactggc tcaccgggcc     1200
tccgacgatg tctccacccg ggccgccctg cgggtcgagg ccgtggcgat cgagcgccgc     1260
cgcaatccgc tggcctccag tcggcacatg gacgagctga gcgccgccgg ccgcgccggt     1320
ctgcttcccc ccaagcatgc ggcgctggcc gtcttctggc tggccgacgg cgggcgatcc     1380
ggcgaggcag ccgaggtgct ggcgtcggaa cgcccgctag cgaccaccga tcagaaccgg     1440
gcccacttgc gatttgtcga ggtgactctc gcgctgttct ctcccggcgc cttcggatcg     1500
gaccggcgcc cacctccgct gacgccggac gaactcgcca gcctgccgaa ggcggcctgg     1560
caatgcgcgg tcgccgacaa cgcggccatg accgccttgc acggtcatcc agaacttgcc     1620
accgctcagg cggaaacagt tctgcggcag gctgattcgg cagccgacgc gatccccgcc     1680
gcgctgatcg ccctgttgta cgcggagaac accgagtccg ctcatatctg ggccgacaag     1740
ctgggcagca cgaatggcgg ggtatcgaac gaggcggaag cgggctacgc cggcccgtgc     1800
gccgagatcg ccctgcggcg cggcgacctg ccacggcgt tcgaggctgg tagcaccgtc     1860
ctggacgacc ggtcgctgcc gtcgctcggc atcaccgccg cattgctgtt gagcagcaag     1920
acggccgccg ctgtccggct gggcgaactc gagcgtgcgg agaagctgct cgccgagccg     1980
cttccgaacg gcgtccagga cagccttttc ggtctgcacc tgctctcggc atacggccag     2040
tacagcctcg cgatgggccg atatgaatcg gctctccggg cgtttcacac ctgcggagaa     2100
cgtatgcgca gctgggatgt tgacgtgcct ggtctgcccc tgtggcgtgt cgacgccgcc     2160
gaggcgctgc tcagcctcga ccggaacgag ggccagcggc tcatcgacga caactcacc      2220 cgtccgatgg ggcctcgttc ccgcgcgctg acgctgcgga tcaaggcggc atacctcccg     2280
cggacgaagc ggatccccct gctccatgag gcggccgagc tgctgctccc ctgccccgac     2340
ccgtacgagc aagcgcgggt gctcgccgat ctgggcgaca cgctcagcgc gctcagacgc     2400
tatagccggg cgcggggagt tctccggcag gctcgtcacc tggccgccca gtgcggtgct     2460
gtcccgctgc tgcgcaggct cggggggcgag cccggccgga tcgacgacgc cggcctgccg     2520
cagcggagca catcgttgac cgatgcggag cggcggtgg cggcgctggc cgcggccgga     2580
cagaccaacc gggagatcgc caaacagctg ttcgtcacgg ccagcacagt ggaacagcac     2640
ctcacaagcg tcttccgcaa actggggtc aagggtcgca agcagctgcc gaccgcgctg     2700
gccgacgtgg aacagacctg a                                              2721
```

<210> SEQ ID NO 14
<211> LENGTH: 2745
<212> TYPE: DNA
<213> ORGANISM: Streptomyces hygroscopicus

<400> SEQUENCE: 14

```
atgcctgccg tggagagcta tgaactggac gcccgcgatg acgagctcag aagactggag      60
```

-continued

```
gaggcggtag gccaggcggg caacggccgg ggtgtggtgg tcaccatcac cgggccgatc      120
gcctgcggca agaccgaact gctcgacgcg ccgccgcga agagcgacgc catcacatta      180
cgtgcggtct gctccgagga ggaacgggcc ctcccgtacg ccctgatcgg gcagctcatc      240
gacaacccgg cggtcgcctc ccagctgccg gatccggtct ccatggccct cccgggcgag      300
cacctgtcgc cggaggccga gaacggctg cgcggcgacc tcacccgtac cctgctggcg      360
ctcgccgccg aacggccggt gctgatcggc atcgacgaca tgcaccacgc cgacaccgcc      420
tctttgaact gcctgctcca cctggcccgg agggtcggcc cggcccggat cgccatggtc      480
ctcaccgagc tgcgccggct cacccccgcc cactcccagt tccacgccga gctgctcagc      540
ctggggcacc accgcgagat cgcgctgcgc ccgctcggcc cgaagcacat cgccgagctg      600
gcccgcgccg gcctcggtcc cgatgtcgac gaggacgtgc tcacgggggtt gtaccgggcg      660 accggcggca acctgaacct cggccacgga ctgatcaagg atgtgcggga ggcctgggcg      720
acgggcggga cgggcatcaa cgcgggccgc gcgtaccggc tggcgtacct cggttccctc      780
taccgctgcg gcccggtccc gttgcgggtc gcacgggtgg ccgccgtgct gggccagagc      840
gccaacacca ccctggtgcg ctggatcagc gggctcaacg cggacgcggt gggcgaggcg      900
accgagatcc tcaccgaggg cggcctgctg cacgacctgc ggttcccgca tccggcggcc      960
cgttcggtcg tactcaacga cctgtccgcc cgggaacgcc gccgactgca ccggtccgct      1020
ctggaagtgc tggatgacgt acccgttgaa gtggtcgcgc accaccaggc cggtgccggt      1080
ttcatccacg gtcccaaggc cgccgagatc ttcgccaagg ccggccagga gctgcatgtg      1140
cgcggcgagc tggacgccgc gtccgactat ctgcaactgg cccaccacgc ctccgacgac      1200
gccgtcaccc gggccgcgct gcgggtcgag gccgtggcga tcgagcgccg ccgcaacccg      1260
ctggcctcca gccgccacct cgacgagctg accgtcgccg cccgtgccgg tctgctctcc      1320
ctcgagcacg ccgcgctgat gatccgctgg ctggctctcg gcgggcggtc cggcgaggcg      1380
gccgaggtgc tggccgcgca cgcccgcgt gcggtcaccg accaggacag ggcccacctg      1440
cgggccgccg aggtatcgct ggcgctggtc agcccgggcg cgtccggcgt cagcccgggt      1500
gcgtccggcc cggatcggcg gccgcgtccg ctcccgccgg atgagctcgc gaacctgccg      1560
aaggcggccc ggctttgtgc gatcgccgac aacgccgtca tatcggccct gcacggtcgt      1620
cccgagcttg cctcggccga ggcggagaac gtcctgaagc aggctgactc ggcggcggac      1680
ggcgccaccg ccctctccgc gctgacggcc ttgctgtacg cggagaacac cgacaccgct      1740
cagctctggg ccgacaagct cgtctccgag accggggcgt cgaacgagga ggaaggcgcg      1800
ggctacgcgg ggccgcgcgc cgagaccgcg ttgcgccgcg cgacctggc cgcggcggtc      1860 gaggcgggca cgccattct ggaccaccgg cggggtcgt tgctcggcat caccgccgcg      1920
ctaccgctga gcagcgcggt agccgccgcc atccggctgg gcgagaccga gcgggcggag      1980
aagtggctcg ccgagccgct gccggaggcc attcgggaca gcctgttcgg gctgcacctg      2040
ctctcggcgc gcggccagta ctgcctcgcg acgggccggc acgagtcggc gtacacggcg      2100
ttccgcacct gcggggaacg gatgcggaac tggggcgtcg acgtgccggg tctgtccctg      2160
tggcgcgtcg acgccgccga ggcgctgctg cacggccgcg accgggacga gggccgacgg      2220
ctcatcgacg agcagctcac ccatgcgatg ggaccccgtt ccgcgctttt gacgctgcgg      2280
gtgcaggcgg cgtacagccc gcaggcgcag cgggtcgacc tgctcgaaga ggcggccgac      2340
ctgctgctct cctgcaacga ccagtacgag cgggcgcggg tgctcgccga tctgagcgag      2400
```

```
gcgttcagcg cgctcaggca ccacagccgg gcgcggggac tgctccggca ggcccggcac   2460
ctggccgccc agtgcggcgc gaccccgctg ctgcgccggc tcggggccaa gcccggaggc   2520
cccggctggc tggaggaatc cggcctgccg cagcggatca agtcgctgac cgacgcggag   2580
cggcgggtgg cgtcgctggc cgccggcggc cagaccaacc gcgtgatcgc cgaccagctc   2640
ttcgtcacgg ccagcacggt ggagcagcac ctcacgaacg tcttccgcaa gctgggcgtc   2700
aagggccgcc agcacctgcc ggccgaactc gccaacgcgg aatag                   2745
```

<210> SEQ ID NO 15
<211> LENGTH: 2745
<212> TYPE: DNA
<213> ORGANISM: Streptomyces hygroscopicus

<400> SEQUENCE: 15

```
atgcctgccg tggagagcta tgaactggac gcccgcgatg acgagctcag aagactggag     60
gaggcggtag gccaggcggg caacggccgg ggtgtggtgg tcaccatcac cgggccgatc    120
gcctgcggca agaccgaact gctcgacgcg ccgccgcga agagcgacgc catcacactg    180
cgtgcggtct gctccgagga ggaacgggcc ctcccgtacg ccctgatcgg gcagctcatc    240
gacaacccgg cggtcgcctc ccagctgccg gatccggtct ccatggccct cccggggcgag   300 cacctgtcgc cggaggccga gaaccggctg cgcggcgacc tcacccgtac cctgctggcg    360
ctcgccgccc aacggccggt gctgatcggc atcgacgaca tgcaccacgc cgacaccgcc    420
tctttgaact gcctgctcca cctggcccgg agggtcggcc cggcccggat cgccatggtc    480
ctcaccgagc tgccgccggct cacccccgcc cactcccagt ccacgccga gctgctcagc    540 ctggggcacc accgcgagat cgcgctgcgc ccgctcggcc gaagcacat cgccgagctg    600 gcccgcgccg gcctcggtcc cgatgtcgac gaggacgtgc tcacgggggtt gtaccggggcg   660 accggcggca acctgaacct cggccacgga ctgatcaagg atgtgcggga ggcctgggcg    720
acgggcggga cgggcatcaa cgcgggccgc gcgtaccggc tggcgtacct cggttccctc    780
taccgctgcg gcccggtccc gttgcgggtc gcacggggtgg ccgccgtgct gggccagagc    840
gccaacacca cctggtgcg ctggatcagc gggctcaacg cggacgcggt gggcgaggcg    900
accgagatcc tcaccgaggg cggcctgctg cacgacctgc ggttcccgca tccggcggcc    960
cgttcggtcg tactcaacga cctgtccgcc cgggaacgcc gccgactgca ccggtccgct    1020
ctggaagtgc tggatgacgt acccgttgaa gtggtcgcgc accaccaggc cggtgccggt    1080
ttcatccacg gtccccaaggc cgccgagatc ttcgccaagg ccggcagga gctgcatgtg    1140 cgcggcgagc tggacgccgc gtccgactat ctgcaactgg cccaccacgc ctccgacgac    1200
gccgtcaccc gggccgcgct gcgggtcgag gccgtggcga tcgagcgccg ccgcaacccg    1260
ctggcctcca gccgccacct cgacgagctg accgtcgccg cccgtgccgg tctgctctcc    1320
ctcgagcacg ccgcgctgat gatccgctgg ctggctctcg gcgggcggtc cggcgaggcg    1380
gccgaggtgc tggccgcgca cgccccgcgt cggtcaccg accaggacag ggcccacctg    1440
cgggccgccg aggtatcgct ggcgctggtc agcccgggcg cgtccggcgt cagcccgggt    1500
gcgtccggcc cggatcggcg gccgcgtccg ctcccgccgg atgagctcgc gaacctgccg    1560
aaggcggccc ggctttgtgc gatcgccgac aacgccgtca tatcggccct gcacggtcgt    1620
cccgagcttg cctcggccga ggcggagaac gtcctgaagc aggctgactc ggcggcggac    1680
ggcgccaccg ccctctccgc gctgacggcc ttgctgtacg cggagaacac cgacaccgct    1740
cagctctggg ccgacaagct cgtctccgag accggggcgt cgaacgagga ggaaggcgcg    1800
```

```
ggctacgcgg ggccgcgcgc cgagaccgcg ttgcgccgcg gcgacctggc cgcggcggtc    1860
gaggcgggca gcgccattct ggaccaccgg cgggggtcgt tgctcggcat caccgccgcg    1920
ctaccgctga gcagcgcggt agccgccgcc atccggctgg gcgagaccga gcgggcggag    1980
aagtggctcg ccgagccgct gccggaggcc attcgggaca gcctgttcgg gctgcacctg    2040
ctctcggcgc gcggccagta ctgcctcgcg acgggccggc acgagtcggc gtacacggcg    2100
ttccgcacct gcggggaacg gatgcggaac tggggcgtcg acgtgccggg tctgtccctg    2160
tggcgcgtcg acgccgccga ggcgctgctg cacggccgcg accgggacga gggccgacgg    2220
ctcatcgacg agcagctcac ccatgcgatg gacccccgtt ccgcgctttt gacgctgcgg    2280
gtgcaggcgg cgtacagccc gcaggcgcag cgggtcgacc tgctcgaaga ggcggccgac    2340
ctgctgctct cctgcaacga ccagtacgag cgggcgcggg tgctcgccga tctgagcgag    2400
gcgttcagcg cgctcaggca ccacagccgg gcgcggggac tgctccggca ggcccggcac    2460
ctggccgccc agtgcggcgc gaccccgctg ctgcgccggc tcggggccaa gcccggaggc    2520
cccggctggc tggaggaatc cggcctgccg cagcggatca agtcgctgac cgacgcggag    2580
cggcgggtgg cgtcgctggc cgccggcggc cagaccaacc gcgtgatcgc cgaccagctc    2640
ttcgtcacgg ccagcacggt ggagcagcac ctcacgaacg tcttccgcaa gctgggcgtc    2700
aagggccgcc agcacctgcc ggccgaactc gccaacgcgg aatag                    2745
```

<210> SEQ ID NO 16  
<211> LENGTH: 2619  
<212> TYPE: DNA  
<213> ORGANISM: Actinoplanes sp. N01-109

<400> SEQUENCE: 16

```
gtgaagcgca acgatctggt tgcccgcgat ggcgagctca ggtggatgca agagattctc      60
agtcaggcga gcgagggccg gggggccgtg gtcaccatca cggggggcgat cgcctgtggc    120 aagacggtgc tgctggacgc cgcggcagcc agtcaagacg tgatccaact gcgtgcggtc    180
tgctcggcgg aggagcagga gctgccgtac gcgatggtcg acaactact cgacaatccg     240 gtgctcgccg cgcgagtgcc ggccctgggc aacctggctg cggcgggcga gcggctgctg    300
ccgggcaccg agaacaggat ccggcgggag ctcacccgca ccctgctggc tctcgccgac    360
gaacgaccgg tgctgatcgg cgtcgacgac atgcaccatg cggaccccgc ctcgctggac    420
tgcctgctgc acctggcccg gcgggtcggc ccggcccgca tcgcgatcgt tctgaccgag    480
ttgcgccggc tcaccccggc tcactcgcgc ttccagtccg agctgctcag cctgcggtac    540
caccacgaga tcgggttgca gccgctcacc gcggagcaca ccgccgacct ggcccgcgtc    600
ggcctcggtg ccgaggtcga cgacgacgtg ctcaccgagc tctacgaggc gaccggcggc    660
aacccgagtc tgtgctgcgg cctgatcagg gacgtgcggc aggactggga ggccggggtc    720
accggtatcc acgtcggccg ggcgtaccgg ctggcctatc tcagttcgct ctaccgctgc    780
ggcccggcgg cgctgcggac cgcccgcgcg gccgcggtgc tgggcgacag cgccgacgcc    840
tgcctgatcc gccgggtcag cggcctcggt acgaggccg tgggccaggc gatccagcag    900
ctcaccgagg gcggcctgct gcgtgaccag cagttcccgc acccggcggc cgctcggtc     960 gtgctcgacg acatgtccgc gcaggaacgc cacgcgatgt atcgcagcgc ccgggaggca   1020
gccgccgaag tcaggccgca ccccggcacc ccgggcgagc gcggggcggc tacgcgtac    1080 gccgggtgtg gtgagcaagc cggtgactac ccggagccgg ccggccgggc ctgcgtggac    1140
```

| | |
|---|---|
| ggtgccggtc cggccgagta ctgcggcgac ccgcacggcg ccgacgacga cccggacgag | 1200 |
| ctggtcgccg cgctgggcgg gctgctgccg agccggctcg tggcgatgaa gatccggcgc | 1260 |
| ctggcggtgg ccgggcgccc cggggcggct gccgagctgc tgacctcgca gcggttgcac | 1320 |
| gcggtgacca gcgaggaccg ggccagcctg cgggccgccg aggtggcgct cgccacgctg | 1380 |
| tggccgggtg cgaccggccc ggaccggcat ccgctcacgg agcaggaggc ggcgagcctg | 1440 |
| ccggagggtc cgcgcctgct cgctgccgcc gacgatgccg tcggggccgc cctgcgcggt | 1500 |
| cgcgccgagt acgccgcggc cgaggcggag aacgtcctgc ggcacgccga tccggcagcc | 1560 |
| ggtggtgacg cctacgccgc catgatcgcc ctgctgtaca cggagcaccc cgagaacgtg | 1620 |
| ctgttctggg ccgacaagct cgacgcgggc cgccccgacg aggagaccag ttatcccggg | 1680 |
| ctgcgggccg agaccgcggt gcggctcggt gacctggaaa cggcgatgga gctgggccgc | 1740 |
| acggtgctgg accagcggcg gctgccgtcc ctgggtgtcg ccgcgggcct gctcctgggc | 1800 |
| ggcgcggtga cggccgccat ccggctcggc gacctcgacc gggcggagaa gtggctcgcc | 1860 |
| gagccgatcc ccgacgccat ccgtaccagc ctctacggcc tgcacgtgct ggccgcgcgg | 1920 |
| ggccggctcg acctggccgc gggccgctac gaggcggcgt acacggcgtt ccggctgtgt | 1980 |
| ggcgagcgga tggcaggctg ggatgccgat gtctccgggc tggcgctgtg gcgcgtcgac | 2040 |
| gccgccgagg ccctgctgtc cgcgggcatc cgcccggacg agggccgcaa gctcatcgac | 2100 |
| gaccagctca cccgtgagat gggggcccgc tcccggcgc tgacgctgcg ggcgcaagcg | 2160 |
| gcgtacagcc tgccggtgca ccgggtgggc ctgctcgacg aggcggccgg cctgctgctc | 2220 |
| gcctgccatg acgggtacga gcgggcgcgg gtgctcgcgg acctggggga cccctgcgc | 2280 |
| acgctgcggc acaccgacgc ggcccagcgg gtgctccggc aggccgagca ggcggccgcg | 2340 |
| cggtgcgggt cggtcccgct gctgcggcgg ctcggggccg aacccgtacg catcggcacc | 2400 |
| cggcgtggtg aacccggcct gccgcagcgg atcaggctgc tgaccgatgc cgagcggcgg | 2460 |
| gttgccgcga tggccgccgc cgggcagacc aaccgggaga tcgccggtcg gctcttcgtc | 2520 |
| acggccagca cggtggagca gcacctgacc agcgtcttcc gcaagctggg cgtcaagggc | 2580 |
| cgccggttcc tgccgaccga gctcgcccaa gccgtctga | 2619 |

<210> SEQ ID NO 17
<211> LENGTH: 2628
<212> TYPE: DNA
<213> ORGANISM: Actinoplanes sp. N01-109

<400> SEQUENCE: 17

| | |
|---|---|
| atgcctgccg tgaagcgcaa cgatctggtt gcccgcgatg gcgagctcag gtggatgcaa | 60 |
| gagattctca gtcaggcgag cgagggccgg ggggccgtgg tcaccatcac gggggcgatc | 120 |
| gcctgtggca agacggtgct gctggacgcc gcggcagcca gtcaagacgt gatccaactg | 180 |
| cgtgcggtct gctcggcgga ggagcaggag ctgccgtacg cgatggtcgg acaactactc | 240 |
| gacaatccgg tgctcgccgc gcgagtgccg ggccctggca acctggctgc ggcgggcgag | 300 |
| cggctgctgc cgggcaccga gaacaggatc cggcgggagc tcacccgcac cctgctggct | 360 |
| ctcgccgacg aacgaccggt gctgatcggc gtcgacgaca tgcaccatgc ggaccccgcc | 420 |
| tcgctggact gcctgctgca cctggcccgg cgggtcggcc cggcccgcat cgcgatcgtt | 480 |
| ctgaccgagt tgcgccggct caccccggct cactcgcgct tccagtccga gctgctcagc | 540 |
| ctgcggtacc accacgagat cggggttcag ccgtcaccg cggagcacac cgccgacctg | 600 |
| gcccgcgtcg gcctcggtgc cgaggtcgac gacgacgtgc tcaccgagct ctacgaggcg | 660 |

```
accggcggca acccgagtct gtgctgcggc ctgatcaggg acgtgcggca ggactgggag      720
gccggggtca ccggtatcca cgtcggccgg gcgtaccggg tggcctatct cagttcgctc      780
taccgctgcg gcccggcggc gctgcggacc gcccgcgcgg ccgcggtgct gggcgacagc      840
gccgacgcct gcctgatccg ccgggtcagc ggcctcggta cggaggccgt gggccaggcg      900
atccagcagc tcaccgaggg cggcctgctg cgtgaccagc agttcccgca cccggcggcc      960
cgctcggtcg tgctcgacga catgtccgcg caggaacgcc acgcgatgta tcgcagcgcc     1020
cgggaggcag ccgccgaagg tcaggccgac cccggcaccc cgggcgagcc gcgggcggct     1080
acggcgtacg ccgggtgtgg tgagcaagcc ggtgactacc cggagccggc cggccgggcc     1140
tgcgtggacg gtgccggtcc ggccgagtac tgcggcgacc cgcacggcgc cgacgacgac     1200
ccggacgagc tggtcgccgc gctgggcggg ctgctgccga gccggctcgt ggcgatgaag     1260
atccggcgcc tggcggtggc cgggcgcccc ggggcggctg ccgagctgct gacctcgcag     1320
cggttgcacg cggtgaccag cgaggaccgg gccagcctgc gggccgccga ggtggcgctc     1380
gccacgctgt ggccgggtgc gaccggcccg gaccggcatc cgctcacgga gcaggaggcg     1440
gcgagcctgc cggagggtcc gcgcctgctc gctgccgccg acgatgccgt cggggccgcc     1500
ctgcgcggtc gcgccgagta cgccgcggcc gaggcggaga acgtcctgcg gcacgccgat     1560
ccggcagccg gtggtgacgc ctacgccgcc atgatcgccc tgctgtacac ggagcacccc     1620
gagaacgtgc tgttctgggc cgacaagctc gacgcgggcc gccccgacga ggagaccagt     1680
tatcccgggc tgcgggccga gaccgcggtg cggctcggtg acctggaaac ggcgatggag     1740
ctgggccgca cggtgctgga ccagcggcgg ctgccgtccc tgggtgtcgc cgcgggcctg     1800
ctcctgggcg gcgcggtgac ggccgccatc cggctcggcg acctcgaccg gcggagaag      1860
tggctcgccg agccgatccc cgacgccatc cgtaccagcc tctacggcct gcacgtgctg     1920
gccgcgcggg gccggctcga cctgccgcg ggccgctacg aggcggcgta cacggcgttc      1980
cggctgtgtg gcgagcggat ggcaggctgg gatgccgatg tctccgggct ggcgctgtgg     2040
cgcgtcgacg ccgccgaggc cctgctgtcc gcgggcatcc gcccggacga gggccgcaag     2100
ctcatcgacg accagctcac ccgtgagatg ggggcccgct cccgggcgct gacgctgcgg     2160
gcgcaagcgg cgtacagcct gccggtgcac cgggtgggcc tgctcgacga ggcggccggc     2220
ctgctgctcg cctgccatga cgggtacgag cgggcgcggg tgctcgcgga cctggggag      2280
accctgcgca cgctgcggca caccgacgcg gcccagcggg tgctccggca ggccgagcag     2340
gcggccgcgc ggtgcgggtc ggtcccgctg ctgcggcggc tcggggccga accgtacgc      2400
atcggcaccc ggcgtggtga acccggcctg ccgcagcgga tcaggctgct gaccgatgcc     2460
gagcggcggg ttgccgcgat ggccgccgcc ggcagacca accgggagat cgccggtcgg      2520
ctcttcgtca cggccagcac ggtggagcag cacctgacca gcgtcttccg caagctgggc     2580
gtcaagggcc gccggttcct gccgaccgag ctcgcccaag ccgtctga                  2628
```

<210> SEQ ID NO 18
<211> LENGTH: 2616
<212> TYPE: DNA
<213> ORGANISM: Streptomyces malaysiensis

<400> SEQUENCE: 18

```
gtggtcaccg tcaccggccc aatcgcctgc ggcaagacag aactgcttga cgcggctgcc       60
gcgaaggctg aggccatcat tctgcgcgcg gtctgcgcgc cagaagagcg ggctatgccg      120
```

-continued

```
tacgccatga tcgggcagct catcgacgac ccggcgctcg cgcatcgggc gccggggctg      180
gctgatcgga tagcccaggg cgggcagctg tcgctgaggg ccgagaaccg actgcgcagg      240
gatctcaccc gtgccctgct ggcgcttgcc gtggaccggc ctgtgctgat cggcgtcgac      300
gatgtgcatc acgccgacac cgcctctttg aactgtctgc tgcatttggc ccgccgggtc      360
cgtccggccc ggatatccat gatcttcacc gagttgcgca gcctcacccc tactcagtca      420
cggttcaagg cggagctgct cagcctgcca taccaccacg atcgcgct gcgtccattc        480
ggaccggagc aatcggcgga gctggctcgc gccgccttcg gcccgggcct cgccgaggat     540
gtgctcgcgg ggttgtataa aacgaccagg ggcaatctga gtctcagccg tggactgatc     600
agcgatgtgc gggaggccct ggccaacgga gagagcgctt cgaggcggg ccgcgcgttc      660
cggctggcgt acctcagctc gctctaccgc tgtggcccgg tcgcgctgcg ggtcgcccga     720
gtggctgccg tgctgggccc aagcgccacc accacgctgg tgcgccggct aagcgggctc    780
agcgcggaga cgatagaccg ggcaaccaag atcctcactg agggcgggct gctgctcgac    840
cagcagttcc cgcacccggc cgcccgctcg gtggtgctcg atgacatgtc cgcccaggaa    900
cgacgcagcc tgcacactct cgccctggaa ctgctggacg aggcgccggt tgaagtgctc    960
gcgcaccacc aggtcggcgc cggtctcata cacgggccca aggctgcgga gatgttcgcc   1020
aaggccggca aggctctggt cgtacgcaac gagttgggcg acgcggccga atacctgcaa   1080
ctggctcacg gggcctccga cgatgtctcc acccgggccg ccttacgggt cgaggccgtg   1140
gccatcgagc gccgccgcaa tccgctggcc tccagtcggc acatggacga actgagcgcc   1200
gccggccgcg ccggtctgct ttcccccaag catgcgcgcg tggccgtctt ctggctagcc    1260
gacggcgggc gatccggcga ggcagccgaa gtgctggcgt cggaacgccc gctcgcgacc    1320
accgatcaga accgggccca cctgcgattt gtcgaggtga ctctcgcgct gttctctccc    1380
ggcgccttcg gatcggaccg gcgcccacct ccgctgacgc cggacgaact cgccagcctg   1440
ccgaaggcgg cctggcaatg cgcggtcgcc gacaacgcgg ccatgaccgc cttgcacggc    1500
catccagaac ttgccaccgc tcaggcggaa acagttctgc ggcaggctga ttcggcagcc    1560
gacgcgatcc ccgccgcgct gatcgccctg ttgtacgcgg agaacaccga gtccgctcat   1620
atctgggccg acaagctggg cagcacgaat gccggggtat cgaacgaggc ggaagcgggc   1680
tacgccggcc cgtgcgccga gatcgccctg cggcgcggcg acctggccac ggcgttcgag   1740
gctggtagcg ccgtcctgga cgaccggtcg ctgccgtcgc tcggcatcac cgccgcattg   1800
ctgttgagca gcaagacggc cgccgctgtc cggctgggcg aactcgagcg tgcggagaag   1860
ctgctcgccg agccgcttcc gaacggcgtc caggacagcc ttttcggtct gcacctgctc   1920
tcggcgtacg gccagtacag cctcgcgatg ggccgatatg aatcagctca ccgggcgttt   1980
cgcacctgcg gagaacgtat gcgcagctgg gatgttgacg tgcctggtct ggccctgtgg   2040
cgtgtcgacg ccgccgaggc gctgctcagc ctcgaccgga acgagggcca gcggctcatc   2100
gacgaacaac tcacccgtcc gatggggcct cgttcccacg cgttaacgct gcggatcaag   2160
gcggcatacc tcccgcggac gaagcggatc cccctgctcc atgaggcggc cgagctgctg   2220
ctccccctgcc ccgacccgta cgagcaagcg cgggtgctcg ccgatctggg cgacacgctc   2280
agcgcgctca gacgctatag ccgggcgcgg ggagttctcc ggcaggctcg tcacctggcc   2340
acccagtgcg gtgctgtccc gctgctgcgc aggctcgggg gcgagccggg ccggatcgac   2400
gacgccggcc tgccgcagcg gagcacatcg ttgaccgatg cggagcggcg ggtggcggcg   2460
ctggccgcgg ccggacagac caaccgggag atcgccgaac agctgttcgt cacggccagc   2520
```

```
acagtggaac agcacctcac aagcgtcttc cgcaagctgg gcgtcaaggg ccgcaagcag    2580
ctgccgaccg cgctggccga cgtggaacag acctga                             2616

<210> SEQ ID NO 19
<211> LENGTH: 2721
<212> TYPE: DNA
<213> ORGANISM: Streptomyces malaysiensis

<400> SEQUENCE: 19
atgtatagcg gtacctgccg tgaaggatac gaactcgtcg cacgcgagga cgaactcggt      60
attctacaga ggtctctgga acaagcgagc agcggccagg cgtcgtggt caccgtcacc     120 ggcccaatcg cctgcggcaa gacagaactg cttgacgcgg ctgccgcgaa ggctgaggcc     180
atcattctgc gcgcggtctg cgcgccagaa gagcgggcta tgccgtacgc catgatcggg     240
cagctcatcg acgacccggc gctcgcgcat cgggcgccgg ggctggctga tcggatagcc     300
cagggcgggc agctgtcgct gagggccgag aaccgactgc gcagggatct cacccgtgcc     360
ctgctggcgc ttgccgtgga ccggcctgtg ctgatcggcg tcgacgatgt gcatcacgcc     420
gacaccgcct ctttgaactg tctgctgcat ttggcccgcc gggtccgtcc ggcccggata     480
tccatgatct tcaccgagtt gcgcagcctc acccctactc agtcacggtt caaggcggag     540
ctgctcagcg tgccatacca ccacgagatc gcgctgcgtc cattcggacc ggagcaatcg     600
gcggagctgg ctcgcgccgc cttcggcccg ggcctcgccg aggatgtgct cgcggggttg     660
tataaaacga ccaggggcaa tctgagtctc agccgtggac tgatcagcga tgtgcgggag     720
gccctggcca acggagagag cgcttcgag gcgggccgcg cgttccggct ggcgtacctc     780
agctcgctct accgctgtgg cccggtcgcg ctgcgggtcg cccgagtggc tgccgtgctg     840
ggcccaagcg ccaccaccac gctggtgcgc cggctaagcg ggctcagcgc ggagacgata     900
gaccgggcaa ccaagatcct cactgagggc gggctgctgc tcgaccagca gttcccgcac     960
ccggccgccc gctcggtggt gctcgatgac atgtccgccc aggaacgacg cagcctgcac    1020
actctcgccc tggaactgct ggacgaggcg ccggttgaag tgctcgcgca ccaccaggtc    1080
ggcgccggtc tcatacacgg gcccaaggct gcggagatgt tcgccaaggc cggcaaggct    1140
ctggtcgtac gcaacgagtt gggcgacgcg gccgaatacc tgcaactggc tcaccgggcc    1200
tccgacgatg tctccacccg gccgccctg cgggtcgagg ccgtggccat cgagcgccgc    1260
cgcaatccgc tggcctccag tcggcacatg gacgaactga gcgccgccgg ccgcgccggt    1320
ctgctttccc ccaagcatgc ggcgctggcc gtcttctggc tagccgacgg cgggcgatcc    1380
ggcgaggcag ccgaagtgct ggcgtcggaa cgcccgctcg cgaccaccga tcagaaccgg    1440
gcccacctgc gatttgtcga ggtgactctc cgctgttct ctcccggcgc cttcggatcg    1500
gaccggcgcc cacctccgct gacgccggac gaactcgcca gcctgccgaa ggcggcctgg    1560
caatgcgcgc tcgccgacaa cgcggccatg accgccttgc acggccatcc agaacttgcc    1620
accgctcagg cggaaacagt tctgcggcag gctgattcgg cagccgacgc gatccccgcc    1680
gcgctgatcg ccctgttgta cgcggagaac accgagtccg ctcatatctg ggccgacaag    1740
ctgggcagca cgaatgccgg ggtatcgaac gaggcggaag cgggctacgc cggcccgtgc    1800
gccgagatcg ccctgcgcgcg cggcgacctg ccacggcgt tcgaggctgg tagcgccgtc    1860
ctggacgacc ggtcgctgcc gtcgctcggc atcaccgccg cattgctgtt gagcagcaag    1920
acggccgccg ctgtccggct gggcgaactc gagcgtgcgg agaagctgct cgccgagccg    1980
```

|          |          |          |          |          |      |
|----------|----------|----------|----------|----------|------|
| cttccgaacg | gcgtccagga | cagccttttc | ggtctgcacc | tgctctcggc gtacggccag | 2040 |
| tacagcctcg | cgatgggccg | atatgaatca | gctcaccggg | cgtttcgcac ctgcggagaa | 2100 |
| cgtatgcgca | gctgggatgt | tgacgtgcct | ggtctggccc | tgtggcgtgt cgacgccgcc | 2160 |
| gaggcgctgc | tcagcctcga | ccggaacgag | ggccagcggc | tcatcgacga acaactcacc | 2220 |
| cgtccgatgg | ggcctcgttc | ccacgcgctg | acgctgcgga | tcaaggcggc ataccteccg | 2280 |
| cggacgaagc | ggatccccct | gctccatgag | gcggccgagc | tgctgctccc ctgcccegac | 2340 |
| ccgtacgagc | aagcgcgggt | gctcgccgat | ctgggcgaca | cgctcagcgc gctcagacgc | 2400 |
| tatagccggg | cgcggggagt | tctccggcag | gctcgtcacc | tggccaccca gtgcggtgct | 2460 |
| gtcccgctgc | tgcgcaggct | cggggggcgag | cccggccgga | tcgacgacgc cggcctgccg | 2520 |
| cagcggagca | catcgttgac | cgatgcgag | cggcgggtgg | cggcgctggc cgcggccgga | 2580 |
| cagaccaacc | gggagatcgc | cgaacagctg | ttcgtcacgg | ccagcacagt ggaacagcac | 2640 |
| ctcacaagcg | tcttccgcaa | gctgggcgtc | aagggccgca | agcagctgcc gaccgcgctg | 2700 |
| gccgacgtgg | aacagacctg | a |  |  | 2721 |

<210> SEQ ID NO 20
<211> LENGTH: 2715
<212> TYPE: DNA
<213> ORGANISM: Streptomyces violaceusniger

<400> SEQUENCE: 20

|          |          |          |          |          |      |
|----------|----------|----------|----------|----------|------|
| gtgtatagcg | gtacctgccg | tgaaggatac | gaactcgtcg | cccgcgagga cgaactcggc | 60 |
| attctgcaga | ggtctctgga | agaagcaggc | agcggccagg | gcgccgtggt caccgtcacc | 120 |
| ggcccgatcg | cctgcggcaa | gacagaactg | cttgacgcgg | ctgccgcgaa ggctgacgcc | 180 |
| atcattctgc | gcgcggtctg | cgcgcccgaa | gagcgcgcta | tgccgtacgc catgatcggg | 240 |
| cagctcatcg | acgacccggc | gctcgcgcat | cgggcgccgg | agctggctga tcggatagcc | 300 |
| cagggcgggc | atctgtcgct | gagggccgag | aaccgactgc | gcaggatct cacccgtgcc | 360 |
| ctgctggcgc | ttgccgtcga | ccggcctgtg | ctgatcggcg | tcgacgatgt gcatcacgcc | 420 |
| gacaccgcct | ctttgaactg | tctgctgcat | ttagcccgcc | gggtccgtcc ggcccggata | 480 |
| tccatgatct | tcaccgagtt | gcgcagcctc | accctactc | agtcacgatt caaggcggag | 540 |
| ctgctcagcc | tgccgtacca | ccacgagatc | gcgctgcgtc | cactcggacc ggagcaatcg | 600 |
| gcggagctgg | cccacgccgc | cttcggcccg | ggcctcgccg | aggatgtgct cgcggggttg | 660 |
| tatgggatga | ccaggggcaa | cctgagtctc | agccgtggac | tgatcagcga tgtgcgggag | 720 |
| gcccaggcca | acggagagag | cgctttcgag | gtgggccgcg | cgttccggct ggcgtacctc | 780 |
| agctcgctct | accgctgtgg | cccgatcgcg | ctgcgggtcg | cccgagtggc tgccgtgctg | 840 |
| ggcccaagcg | ccaccaccac | gctggtgcgc | cgtctaagcg | ggctcagcgc ggagacgata | 900 |
| gaccgggcaa | ccaagatcct | cactgagggc | gggctgctgc | tcgaccacca gttcccgcac | 960 |
| ccggccgccc | gctcggtggt | gctcgatgac | atgtccgccc | aggaacgacg cagcctgcac | 1020 |
| actctcgccc | tggaactgct | ggacgaggcg | ccggttgaag | tgctcgcgca ccaccaggtc | 1080 |
| ggcgccggtc | tcatacacgg | gcccaaggct | gcggagatat | cgccagggc tggcaggct | 1140 |
| ctggttgtac | gcaacgagtt | gggcgacgcg | gccgaatacc | tgcaactggc tcaccgagcc | 1200 |
| tccgacgatg | tctccacccg | ggccgcctta | cgggtcgagg | ccgtggcaat cgagcgccgc | 1260 |
| cgcaatccgc | tggcctccag | tcgtcacatg | gacgagctga | gcgccgccgg ccgcgccggt | 1320 |
| ctgctttccc | ccaagcatgc | agcgctggct | gtcttctggc | tggccgacgg cgggcgatcc | 1380 |

```
ggcgaggcag ccgaggtgct ggcgtcggaa cacccgctcg cgaccaccga tcagaaccga    1440
gcacacctgc gatttgccga ggtgactctc gcgctgttct gtcccggcgc cttcgggtcg    1500
gaccggcgcc cacctccgct ggcgccggac gagctcgcca gcttgccgaa ggcggcctgg    1560
caatgcgcgg tcgccgacaa cgcggtcatg acagcgttgc atgctcatcc agaacttgcc    1620
accgctcagg cggaaacagt tctgcggcag gctgattcgg cagccgacgc aatccccgcc    1680
gcactgatcg ccctgttgta cgcagagaac accgagtccg ctcagatctg gccgacaag    1740 ctgggcagca ccaatgccgg ggtatcgaac gaggcggaag cgggctacgc cggcccgtgc    1800
gccgagatcg ccctgcggcg cggcgacctg gccacgcgt tcgaggctgg tggcaccgtc     1860
ctggacgacc ggccgctgcc gtcgctcggc atcaccgccg cattgctgtt gagcagcaag    1920
acggcagccg ctgtccgcct gggcgaactc gagcgtgcgg agaagctgct cgctgagccg    1980
cttccgaacg gtgtccagga cagccttttc ggtctgcacc tgctctcggc gcacggccag    2040
tacagcctcg cgatgggccg atatgaatcg gctcaccggg cgtttcacac ctgcggagaa    2100
cgtatgcgca gctggggtgt tgacgtgcct ggtctagccc tgtggcgtgt cgacgccgcc    2160
gaggcactgc tcagcctcga ccggaacgag ggccagcggc tcatcgacga acaactcgcc    2220
cgtccgatgg gacctcgttc ccgcgcatta acgctgcgga tcaaggcggc atacctcccg    2280
cggacgaagc ggatccccct gctccatgag gcagctgagc tgctgctctc ctgccccgac    2340
ccgtacgagc aagcgcgggt gctcgccgat ctgggcgaca cgctcagcgc gctcagacgc    2400
tatagccggg cgcggggagt tctccggcag gctcgtcacc tggccaccca gtgcggtgct    2460
gtcccgctgc tgcgccgact cggggcgag cccgccgga tcgacgacgc cggcctgccg     2520
cagcggagca catcgttgac cgatgcggag cggcgggtgt cggccctggc gcggccgga    2580 cagaccaacc gggagatcgc caaacagcta ttcgtcacgg ccagcaccgt ggaacagcac    2640
ctcacaagcg tcttccgcaa gctgggcgtt aagggccgca ggcagctacc gaccgcgctg    2700
gccgacgtgg aatag                                                    2715
```

<210> SEQ ID NO 21
<211> LENGTH: 2715
<212> TYPE: DNA
<213> ORGANISM: Streptomyces violaceusniger

<400> SEQUENCE: 21

```
atgtatagcg gtacctgccg tgaaggatac gaactcgtcg cccgcgagga cgaactcggc      60
attctgcaga ggtctctgga agaagcaggc agcggccagg gcgccgtggt caccgtcacc     120
ggcccgatcg cctgcggcaa gacagaactg cttgacgcgg ctgccgcgaa ggctgacgcc     180
atcattctgc gcgcggtctg cgcgcccgaa gagcgcgcta tgccgtacgc catgatcggg     240
cagctcatcg acgacccggc gctcgcgcat cgggcgccgg agctggctga tcggatagcc     300
cagggcgggg atctgtcgct gagggccgag aaccgactgc gcaggatct cacccgtgcc     360 ctgctggcgc ttgccgtcga ccggcctgtg ctgatcggcg tcgacgatgt gcatcacgcc    420
gacaccgcct ctttgaactg tctgctgcat ctggcccgcc gggtccgtcc ggcccggata    480
tccatgatct tcaccgagtt gcgcagcctc acccctactc agtcacgatt caaggcggag    540
ctgctcagcc tgccgtacca ccacgagatc gcgctgcgtc cactcggacc ggagcaatcg    600
gcggagctgg cccacgccgc cttcggcccg ggctcgcccg aggatgtgct cgcggggttg    660
tatgggatga ccaggggcaa cctgagtctc agccgtggac tgatcagcga tgtgcgggag    720
```

```
gcccaggcca acggagagag cgctttcgag gtgggccgcg cgttccggct ggcgtacctc    780
agctcgctct accgctgtgg cccgatcgcg ctgcgggtcg cccgagtggc tgccgtgctg    840
ggcccaagcg ccaccaccac gctggtgcgc cgtctaagcg ggctcagcgc ggagacgata    900
gaccgggcaa ccaagatcct cactgagggc gggctgctgc tcgaccacca gttcccgcac    960
ccggccgccc gctcggtggt gctcgatgac atgtccgccc aggaacgacg cagcctgcac   1020
actctcgccc tggaactgct ggacgaggcg ccggttgaag tgctcgcgca ccaccaggtc   1080
ggcgccggtc tcatacacgg gcccaaggct gcggagatat cgccagggc tggccaggct    1140
ctggttgtac gcaacgagtt gggcgacgcg gccgaatacc tgcaactggc tcaccgagcc   1200
tccgacgatg tctccacccg ggccgccctg cgggtcgagg ccgtggcaat cgagcgccgc   1260
cgcaatccgc tggcctccag tcgtcacatg gacgagctga gcgccgccgg ccgcgccggt   1320
ctgctttccc ccaagcatgc agcgctggct gtcttctggc tggccgacgg cgggcgatcc   1380
ggcgaggcag ccgaggtgct ggcgtcggaa caccgctcg cgaccaccga tcagaaccga    1440
gcacacctgc gatttgccga ggtgactctc gcgctgttct gtcccggcgc cttcgggtcg   1500
gaccggcgcc cacctccgct ggcgccggac gagctcgcca gcttgccgaa ggcggcctgg   1560
caatcgcgcg tcgccgacaa cgcggtcatg acagcgttga atgctcatcc agaacttgcc   1620
accgctcagg cggaaacagt tctgcggcag gctgattcgg cagccgacgc aatccccgcc   1680
gcactgatcg ccctgttgta cgcagagaac accgagtccg ctcagatctg ggccgacaag   1740
ctgggcagca ccaatgccgg ggtatcgaac gaggcggaag cgggctacgc cggcccgtgc   1800
gccgagatcg ccctgcggcg cggcgacctg gccacgcgt tcgaggctgg tggcaccgtc    1860
ctggacgacc ggccgctgcc gtcgctcggc atcaccgccg cattgctgtt gagcagcaag   1920
acggcagccg ctgtccgcct gggcgaactc gagcgtgcgg agaagctgct cgctgagccg   1980
cttccgaacg gtgtccagga cagccttttc ggtctgcacc tgctctcggc gcacggccag   2040
tacagcctcg cgatgggccg atatgaatcg gctcaccggg cgtttcacac ctgcggagaa   2100
cgtatgcgca gctggggtgt tgacgtgcct ggtctagccc tgtggcgtgt cgacgccgcc   2160
gaggcactgc tcagcctcga ccggaacgag gccagcggc tcatcgacga caactcgcc    2220
cgtccgatgg gacctcgttc ccgcgcactg acgctgcgga tcaaggcggc atacctcccg   2280
cggacgaagc ggatccccct gctccatgag gcagctgagc tgctgctctc ctgccccgac   2340
ccgtacgagc aagcgcgggt gctcgccgat ctgggcgaca cgctcagcgc gctcagacgc   2400
tatagccggg cgcggggagt tctccggcag gctcgtcacc tggccaccca gtgcggtgct   2460
gtcccgctgc tgcgccgact cgggggcgag cccgccgga tcgacgacgc cggcctgccg    2520
cagcggagca catcgttgac cgatgcggag cggcgggtgt cggccctggc gcggccgga    2580
cagaccaacc gggagatcgc caaacagcta ttcgtcacgg ccagcaccgt ggaacagcac   2640
ctcacaagcg tcttccgcaa gctgggcgtt aagggccgca gcagctacc gaccgcgctg    2700
gccgacgtgg aatag                                                   2715

<210> SEQ ID NO 22
<211> LENGTH: 2721
<212> TYPE: DNA
<213> ORGANISM: Streptomyces Sp. NRRL F-4729

<400> SEQUENCE: 22
gtgtatagcg gtacctgccg tgaaggatac gaactcgtcg cacgcgagga cgaactcggc     60
attctacaga ggtctctgga acaagcgagc agcggccagg gcgtcgtggt caccgtcacc    120
```

```
ggcccaatcg cctgcggcaa gacagaactg cttgacgcgg ctgccgcgaa ggctgaggcc      180
atcattctgc gcgcggtctg cgcgcccgaa gagcgggcta tgccgtacgc catgatcggg      240
cagctcatcg acgacccggc gctcgcgcat cgggcgccgg ggctggctga tcggatagcc      300
cagggcgggc agctgtcgct gagggccgag aaccgactgc gcaggatct cacccgtgcc       360 ctgctggcgc ttgccgtgca ccggcctgtg ctgatcggcg tcgatgatgt gcatcacgcc      420
gacaccgcct ctttgaactg tctgctgcat ttggcgcgcc gggtccgtcc ggcccggata      480
tccatgatct tcaccgagtt gcgcagcctc acccctactc agtcacgatt caaggcggag      540
ctgctcagcc tgccgtacca ccacgagatc gcgctgcgtc cattcggacc ggagcaatcg      600
gcggagctgg ctcgcgccgc cttcggcccg ggcctcgccg aggatgtgct cgcggggttg      660
tataaaacga ccaggggcaa tctgagtctc agccgtggac tgatcagcga tgtgcgggag      720
gccctggcca acggagagag cgctttcgag gcgggccgcg cgttccggct ggcgtacctc      780
agctcgctct accgctgtgg cccggtcgcg ctgcgggtcg cccgagtggc tgccgtgctg      840
ggcccaagcg ccaccaccac gctggtgcgc cggctaagcg ggctcagcgc ggagacgata      900
gaccgggcaa ccaagatcct caccgagggc gggctgctgc tcgaccagca gtttccgcac      960
ccggccgccc gctcggtggt gctcgatgac atgtccgccc aggaacgacg cggcctgcac     1020
actctcgccc tggaactgct ggacgaggcg ccggttgaag tgctcgcgca ccaccaggtc     1080
ggcgccggtc tcatacacgg gcccaaggct gcggagatgt tcgccaaggc cggcaaggct     1140
ctggtcgtac gcaacgagtt gggcgacgcg gccgaatacc tgcaactggc tcaccggggcc    1200 tccgacgatg tctccacccg ggccgcctta cgggtcgagg ccgtggcgat cgagcgccgc     1260
cgcaatccgc tggcctccag tcggcacatg gacgagctga gcgccgccgg ccgcgccggt     1320
ctgctttccc ccaagcatgc ggcgctggcc gtcttctggc tggccgacgg cgggcgatcc     1380
ggcgaggcag cccaggtgct ggcgtcggaa cgcccgctcg cgaccaccga tcagaaccgg     1440
gcccacctgc gatttgtcga ggtgactctc gcgctgttct ctcccggcgc cttcggatcg     1500
gaccggcgcc cacctccgct gacgccggac gaactcgcca gcctgccgaa ggcggcctgg     1560
caatgcgcgg tcgccgacaa cgcggccatg accgccttgc acggccatcc agaacttgcc     1620
accgctcagg cggaaacagt tctgcggcag gctgattcgg cagccgacgc gatccccgcc     1680
gcgctgatcg ccctgttgta cgcggagaac accgagtccg ctcatatctg ggccgacaag     1740
ctgggcagca tgaatgccgg ggtatcgaac gaggcggaag cgggctacgc cggcccgtgc     1800
gccgagatcg ccctgcggcg cggcgacctg gccacggcgt tcgaggctgg tagcaccgtc     1860
ctggacgacc ggtcactgcc gtcgctcggc atcaccgccg cattgctgtt gagcagcaag     1920
acggccgccc ctgtccggct gggcgaactc gagcgtgcgg agaagctgct cgccgagccg     1980
cttccgaacg gcgtccagga cagccttttc ggtctgcacc tgctctcggc gtacggccag     2040
tacagcctcg cgatgggccg atatgaatcg gctcaccggg cgtttcgcac ctgcggagaa     2100
cgtatgcgca gctgggatgt tgacgtgcct ggtctggccc tgtggcgtgt cgacgccgcc     2160
gaggcgctgc tcagcctcga ccggaacgag ggccagcggc tcatcgacga acaactcacc     2220
cgtccgatgg gacctcgttc ccgcgcgtta acgctgcgga tcaaggcggc atacctcccg     2280
cggacgaagc ggatccccct gctccatgag gcggccgagc tgctgctccc ctgccccgac     2340
ccgtacgagc aagcgcgggt gctcgccgat ctgggcgaca cgctcagcgc gctcagacgc     2400
tatagccggg cgcggggagt tctccggcag gctcgtcacc tggccaccca gtgcggtgct     2460
```

-continued

```
gtcccgctgc tgcgccgact cggggcgag cccggccgga tcgacgacgc cggcctgccg    2520
cagcggagca catcgttgac cgatgcgag cggcgggtgg cggcgctggc cgcggccgga    2580
cagaccaacc gggagatcgc cgaacagctg ttcgtcacgg ccagcacagt ggaacagcac    2640
ctcacaagcg tcttccgcaa gctgggcgtc aagggccgca agcagctgcc gaccgcgctg    2700
gccgacgtgg aacagacctg a                                              2721
```

<210> SEQ ID NO 23
<211> LENGTH: 2721
<212> TYPE: DNA
<213> ORGANISM: Streptomyces Sp. NRRL F-4729

<400> SEQUENCE: 23

```
atgtatagcg gtacctgccg tgaaggatac gaactcgtcg cacgcgagga cgaactcggc     60
attctacaga ggtctctgga acaagcgagc agcggccagg gcgtcgtggt caccgtcacc    120
ggcccaatcg cctgcggcaa gacagaactg cttgacgcgg ctgccgcgaa ggctgaggcc    180
atcattctgc gcgcggtctg cgcgcccgaa gagcgggcta tgccgtacgc catgatcggg    240
cagctcatcg acgacccggc gctcgcgcat cgggcgccgg gctggctga tcggatagcc    300 cagggcgggc agctgtcgct gagggccgag aaccgactgc gcaggatct cacccgtgcc    360 ctgctggcgc ttgccgtgca ccggcctgtg ctgatcggcg tcgatgatgt gcatcacgcc    420
gacaccgcct ctttgaactg tctgctgcat ttggcgcgcc gggtccgtcc ggcccggata    480
tccatgatct tcaccgagtt gcgcagcctc acccctactc agtcacgatt caaggcggag    540
ctgctcagcc tgccgtacca ccacgagatc gcgctgcgtc cattcggacc ggagcaatcg    600
gcggagctgg ctcgcgccgc cttcggcccg ggcctcgccg aggatgtgct cgcggggttg    660
tataaaacga ccaggggcaa tctgagtctc agccgtggac tgatcagcga tgtgcgggag    720
gccctggcca acggagagag cgcttttcgag gcgggccgcg cgttccggct ggcgtacctc    780
agctcgctct accgctgtgg cccggtcgcg ctgcgggtcg cccgagtggc tgccgtgctg    840
ggcccaagcg ccaccaccac gctggtgcgc cggctaagcg ggctcagcgc ggagacgata    900
gaccgggcaa ccaagatcct caccgagggc gggctgctgc tcgaccagca gtttccgcac    960
ccggccgccc gctcggtggt gctcgatgac atgtccgccc aggaacgacg cggcctgcac   1020
actctcgccc tggaactgct ggacgaggcg ccggttgaag tgctcgcgca ccaccaggtc   1080
ggcgccggtc tcatacacgg gcccaaggct gcggagatgt tcgccaaggc cggcaaggct   1140
ctggtcgtac gcaacgagtt gggcgacgcg ccgaatacc tgcaactggc tcaccggggcc   1200 tccgacgatg tctccacccg gccgccctg cgggtcgagg ccgtggcgat cgagcgccgc   1260
cgcaatccgc tggcctccag tcggcacatg gacgagctga gcgccgccgg ccgcgccggt   1320 ctgcttttccc ccaagcatgc ggcgctggcc gtcttctggc tggccgacgg cgggcgatcc   1380
ggcgaggcag cccaggtgct ggcgtcggaa cgcccgctcg cgaccaccga tcagaaccgg   1440
gcccacctgc gatttgtcga ggtgactctc cgctgttct ctcccggcgc cttcggatcg    1500
gaccggcgcc cacctccgct gacgccggac gaactcgcca gcctgccgaa ggcggcctgg   1560
caatgcgcgc tcgccgacaa cgcggccatg accgccttgc acggccatcc agaacttgcc   1620
accgctcagg cggaaacagt tctgcggcag gctgattcgg cagccgacgc gatccccgcc   1680
gcgctgatcg ccctgttgta cgcggagaac accgagtccg ctcatatctg ggccgacaag   1740
ctgggcagca tgaatgccgg ggtatcgaac gaggcggaag cgggctacgc cggcccgtgc   1800
gccgagatcg ccctgcgcg cggcgacctg gccacggcgt tcgaggctgg tagcaccgtc   1860
```

```
ctggacgacc ggtcactgcc gtcgctcggc atcaccgccg cattgctgtt gagcagcaag    1920
acggccgccg ctgtccggct gggcgaactc gagcgtgcgg agaagctgct cgccgagccg    1980
cttccgaacg gcgtccagga cagccttttc ggtctgcacc tgctctcggc gtacggccag    2040
tacagcctcg cgatgggccg atatgaatcg gctcaccggg cgtttcgcac ctgcggagaa    2100
cgtatgcgca gctgggatgt tgacgtgcct ggtctggccc tgtggcgtgt cgacgccgcc    2160
gaggcgctgc tcagcctcga ccggaacgag gccagcggc tcatcgacga caactcacc     2220 cgtccgatgg gacctcgttc ccgcgcgctg acgctgcgga tcaaggcggc atacctcccg    2280
cggacgaagc ggatccccct gctccatgag gcggccgagc tgctgctccc ctgccccgac    2340
ccgtacgagc aagcgcgggt gctcgccgat ctgggcgaca cgctcagcgc gctcagacgc    2400
tatagccggg cgcggggagt tctccggcag gctcgtcacc tggccaccca gtgcggtgct    2460
gtcccgctgc tgcgccgact cggggggcgag cccgccgga tcgacgacgc cggcctgccg    2520
cagcggagca catcgttgac cgatgcggag cggcgggtgg cggcgctggc cgcggccgga    2580
cagaccaacc gggagatcgc cgaacagctg ttcgtcacgg ccagcacagt ggaacagcac    2640
ctcacaagcg tcttccgcaa gctgggcgtc aagggccgca agcagctgcc gaccgcgctg    2700
gccgacgtgg aacagacctg a                                              2721

<210> SEQ ID NO 24
<211> LENGTH: 2715
<212> TYPE: DNA
<213> ORGANISM: Streptomyces filamentosus

<400> SEQUENCE: 24
gtgcgagcta ttaatgcgtc cgacaccggt cctgaactgg tcgcccgcga agacgaactg      60
ggacgtgtac gaagtgccct gaaccgagcg aacggcggcc aaggtgtcct gatctccatt    120
accggtccga tcgcctgcgg caagaccgaa ctgcttgagg ctgccgcctc ggaagttgac    180
gccatcactc tgcgcgcggt ctgtgccgcc gaggaacggg cgatacctta tgccctgatc    240
gggcagctta tcgacaaccc cgcgctcggc attccggttc cggatccggc cggcctgacc    300
gcccagggcg gacgactgtc atcgagcgcc gagaaccgac tgcgtcgcga cctcacccgt    360
gccctgctga cgctcgccac cgaccggctg gtgctgatct gtgtcgatga cgtgcagcac    420
gccgacaacg cctcgttgag ctgccttctg tatctggccc gacggcttgt cccggctcga    480
atcgctctgg tattcaccga gttgcgagtc ctcacctcgt ctcagttacg gttcaacgcg    540
gagctgctca gcttgcggaa ccactgcgag atcgcgctgc gcccactcgg cccgggggcat    600 gcggccgagc tggcccgcgc caccctcggc cccggcctct ccgacgaaac actcacggag    660
ctgtaccggg tgaccggagg caacctgagt ctcagccgcg gctgatcga cgatgtgcgg    720 gacgcctggg cacgagggga acgggcgtc caggtgggcc gggcgttccg gctggcctac    780
ctcggttccc tccaccgctg tggtccgctg gcgttgcggg tcgcccgcgt agccgccgta    840
ctgggcccga gcgccaccag cgtcctggtg cgccggatca gtgggctcag cgcggaggcc    900
atggcccagg cgaccgatat cctcgctgac ggcggcctcc tgcgcgacca gcggttcaca    960
catccagcgg cccgctcggt ggtgctcgac gacatgtccg ccgaggaacg acgcagcgtg   1020
cacagcctcg ccctggaact gctggacgag gcaccggccg agatgctcgc gcaccaccgg   1080 gtcgcgccg gtctcgtgca cgggccgaag gccgcggaga cattcaccgg ggccggccgg   1140
gcactggccg ttcgcggcat gctgggcgag gcagccgact acctgcaact ggcgtaccgg   1200
```

```
gcctccggcg acgccgctac caaggccgcg atacgcgtcg agtccgtggc ggtcgagcgc    1260
cgacgcaatc cgctggtcgt cagtcgccat tgggacgagc tgagcgtcgc ggcccgcgcc    1320
ggtctgctct cctgcgagca cgtgtccagg acggcccgct ggctgaccgt cggtgggcgg    1380
cccggcgagg cggccagggt gctggcgtcg caacaccgac gggtcgtcac cgatcaggac    1440
cgggcccacc tgcgggtcgc cgagttctcg ctcgcgctgc tgtaccccgg tacgtccggc    1500
tcggaccggc gcccgcaccc gctcacgtcg gacgaactcg cggccctacc gactgcgacc    1560
agacactgcg cgatcgccga taacgctgtc atggctgcct tgcgtggtca tccggagctt    1620
gccaccgccg aggcagaagc cgttctgcag caagccgacg cggcggacgg cgctgctctc    1680
accgcgctga tggccctgct gtacgcggag agcatcgagg tcgctgaagt ctgggcggac    1740
aagctggcgg cagaggccgg agcatcgaac gggcaggacg cggagtacgc cggtatacgc    1800
gccgaaatcg ccctgcggcg cggcgatctg accgcggccg tcgagaccgc cggcatggtc    1860
ctggacggcc ggccgctgcc gtcgctcgac atcaccgcca cgttgctgtt ggccggcagg    1920
gcgtccgtcg ccgtccggct gggcgaactc gaccacgcgg aggagctgtt cgccgcgccg    1980
ccggaggacg ccttccagga cagcctcttc ggtctgcatc tgctctcggc gcacggccag    2040
tacagcctcg cgacaggccg gcccgagtcg gcataccggg cctttcgtgc ctgcggcgaa    2100
cgtatgcgcg attggggctt cgacgcgccc ggtgtggccc tgtggcgcgt cggcgccgcc    2160
gaggcgctgc tcggcctcga ccggaacgag ggccgacggc tcatcgacga acagctgagc    2220
cggacgatgg cccccccggtc ccacgcgttg acgctgcgga taaaagcggc gtacatgccg    2280
gagccgaagc gggtcgacct gctctacgaa gcggctgagc tgctgctctc ctgccgggac    2340
cagtatgagc gagcgcgggt gctcgccgat ctgggcgagg cgctcagcgc gctcgggaac    2400
taccggcagg cgcgaggtgt gctccggcag gctcggcatc tggccatgcg aaccggcgcg    2460
gacccgctgc tgcgccggct cggaatcagg cccggccggc aggacgaccc cgacccgcag    2520
ccgcggagca gatcgctgac caacgctgag cggcgtgcgg cgtcgctggc cgcgaccgga    2580
ctgaccaacc gggagatcgc cgaccggctc ttcgtcaccg ccagcaccgt ggagcagcac    2640
ctcaccaacg tcttccgcaa gctgggcgtc aagggccgca agcagctgcc ggccgagttg    2700
gacgacatgg aatag                                                    2715
```

<210> SEQ ID NO 25
<211> LENGTH: 2715
<212> TYPE: DNA
<213> ORGANISM: Streptomyces filamentosus

<400> SEQUENCE: 25

```
atgcgagcta ttaatgcgtc cgacaccggt cctgaactgg tcgcccgcga agacgaactg     60
ggacgtgtac gaagtgccct gaaccgagcg aacggcggcc aaggtgtcct gatctccatt    120
accggtccga tcgcctgcgg caagaccgaa ctgcttgagg ctgccgcctc ggaagttgac    180
gccatcactc tgcgcgcggt ctgtgccgcc gaggaacggc cgataccctta tgccctgatc    240 gggcagctta tcgacaaccc cgcgctcggc attccggttc cggatccggc cggcctgacc    300
gcccagggcg gacgactgtc atcgagcgcc gagaaccgac tgcgtcgcga cctcacccgt    360
gccctgctga cgctcgccac cgaccggctg gtgctgatct gtgtcgatga cgtgcagcac    420
gccgacaacg cctcgttgag ctgccttctg tatctggccc gacggcttgt cccggctcga    480
atcgctctgg tattcaccga gttgcgagtc ctcacctcgt ctcagctgcg gttcaacgcg    540
gagctgctca gcttgcggaa ccactgcgag atcgcgctgc gcccactcgg cccggggcat    600
```

```
gcggccgagc tggcccgcgc caccctcggc cccggcctct ccgacgaaac actcacggag    660
ctgtaccggg tgaccggagg caacctgagt ctcagccgcg ggctgatcga cgatgtgcgg    720
gacgcctggg cacgagggga aacgggcgtc caggtgggcc gggcgttccg gctggcctac    780
ctcggttccc tccaccgctg tggtccgctg gcgttgcggg tcgcccgcgt agccgccgta    840
ctgggcccga gcgccaccag cgtcctggtg cgccggatca gtgggctcag cgcggaggcc    900
atggcccagc cgaccgatat cctcgctgac ggcggcctcc tgcgcgacca gcggttcaca    960
catccagcgg cccgctcggt ggtgctcgac gacatgtccg ccgaggaacg acgcagcgtg   1020
cacagcctcg ccctggaact gctggacgag gcaccggccg agatgctcgc gcaccaccgg   1080
gtcggcgccg gtctcgtgca cgggccgaag gccgcggaga cattcaccgg ggccggccgg   1140
gcactggccg ttcgcggcat gctgggcgag gcagccgact acctgcaact ggcgtaccgg   1200
gcctccggcg acgccgctac caaggccgcg atacgcgtcg agtccgtggc ggtcgagcgc   1260
cgacgcaatc cgctggtcgt cagtcgccat tgggacgagc tgagcgtcgc ggcccgcgcc   1320
ggtctgctct cctgcgagca cgtgtccagg acggcccgct ggctgaccgt cggtgggcgg   1380
cccggcgagg cggccagggt gctggcgtcg caacaccgac gggtcgtcac cgatcaggac   1440
cgggcccacc tgcgggtcgc cgagttctcg ctcgcgctgc tgtaccccgg tacgtccggc   1500
tcggaccggc gcccgcaccc gctcacgtcg gacgaactcg cggccctacc gactgcgacc   1560
agacactgcg cgatcgccga taacgctgtc atggctgcct tgcgtggtca tccggagctt   1620
gccaccgccg aggcagaagc cgttctgcag caagccgacg cggcggacgg cgctgctctc   1680
accgcgctga tggccctgct gtacgcggag agcatcgagg tcgctgaagt ctgggcggac   1740
aagctggcgg cagaggccgg agcatcgaac gggcaggacg cggagtacgc cggtatacgc   1800
gccgaaatcg ccctgcggcg cggcgatctg accgcggccg tcgagaccgc cggcatggtc   1860
ctggacggcc ggccgctgcc gtcgctcgac atcaccgcca cgttgctgtt ggccggcagg   1920
gcgtccgtcg ccgtccggct gggcgaactc gaccacgcgg aggagctgtt cgcccgcgcc   1980
ccggaggacg ccttccagga cagcctcttc ggtctgcatc tgctctcggc gcacggccag   2040
tacagcctcg cgacaggccg gcccgagtcg gcataccggg cctttcgtgc ctgcggcgaa   2100
cgtatgcgcg attggggctt cgacgcgccc ggtgtggccc tgtggcgcgt cggcgccgcc   2160
gaggcgctgc tcgcctcga ccggaacgag ggccgacggc tcatcgacga acagctgagc   2220
cggacgatgg cccccccggtc ccacgcgttg acgctgcgga taaaagcggc gtacatgccg   2280
gagccgaagc gggtcgacct gctctacgaa gcggctgagc tgctgctctc ctgccgggac   2340
cagtatgagc gagcgcgggt gctcgccgat ctgggcgagg cgctcagcgc gctcgggaac   2400
taccggcagg cgcgaggtgt gctccggcag gctcggcatc tggccatgcg aaccggcgcg   2460
gacccgctgc tgcgccggct cggaatcagg cccggccggc aggacgaccc cgacccgcag   2520
ccgcggagca gatcgctgac caacgctgag cggcgtgcgg cgtcgctggc cgcgaccgga   2580
ctgaccaacc gggagatcgc cgaccggctc ttcgtcaccg ccagcaccgt ggagcagcac   2640
ctcaccaacg tcttccgcaa gctgggcgtc aagggccgca agcagctgcc ggccgagttg   2700
gacgacatgg aatag                                                    2715

<210> SEQ ID NO 26
<211> LENGTH: 894
<212> TYPE: PRT
<213> ORGANISM: Streptomyces hygroscopicus
```

<400> SEQUENCE: 26

```
Met Pro Ala Val Glu Cys Tyr Glu Leu Asp Ala Arg Asp Asp Glu Leu
1               5                   10                  15

Arg Lys Leu Glu Glu Val Val Thr Gly Arg Ala Asn Gly Arg Gly Val
            20                  25                  30

Val Val Thr Ile Thr Gly Pro Ile Ala Cys Gly Lys Thr Glu Leu Leu
        35                  40                  45

Asp Ala Ala Ala Lys Ala Asp Ala Ile Thr Leu Arg Ala Val Cys
    50                  55                  60

Ser Ala Glu Glu Gln Ala Leu Pro Tyr Ala Leu Ile Gly Gln Leu Ile
65                  70                  75                  80

Asp Asn Pro Ala Leu Ala Ser His Ala Leu Glu Pro Ala Cys Pro Thr
                85                  90                  95

Leu Pro Gly Glu His Leu Ser Pro Glu Ala Glu Asn Arg Leu Arg Ser
            100                 105                 110

Asp Leu Thr Arg Thr Leu Leu Ala Leu Ala Ala Glu Arg Pro Val Leu
        115                 120                 125

Ile Gly Ile Asp Glu Ser His Ala Asn Ala Leu Cys Leu Leu His Leu
    130                 135                 140

Ala Arg Arg Val Gly Ser Ala Arg Ile Ala Met Val Leu Thr Glu Leu
145                 150                 155                 160

Arg Arg Leu Thr Pro Ala His Ser Gln Phe Gln Ala Glu Leu Leu Ser
                165                 170                 175

Leu Gly His His Arg Glu Ile Ala Leu Arg Pro Leu Ser Pro Lys His
            180                 185                 190

Thr Ala Glu Leu Val Arg Ala Gly Leu Gly Pro Asp Val Asp Glu Asp
        195                 200                 205

Val Leu Thr Gly Leu Tyr Arg Ala Thr Gly Gly Asn Leu Asn Leu Thr
    210                 215                 220

Arg Gly Leu Ile Asn Asp Val Arg Glu Ala Trp Glu Thr Gly Gly Thr
225                 230                 235                 240

Gly Ile Ser Ala Gly Arg Ala Tyr Arg Leu Ala Tyr Leu Gly Ser Leu
                245                 250                 255

Tyr Arg Cys Gly Pro Val Pro Leu Arg Val Ala Arg Val Ala Ala Val
            260                 265                 270

Leu Gly Gln Ser Ala Asn Thr Thr Leu Val Arg Trp Ile Ser Gly Leu
        275                 280                 285

Asn Ala Asp Ala Val Gly Glu Ala Thr Glu Ile Leu Thr Glu Gly Gly
    290                 295                 300

Leu Leu His Asp Leu Arg Phe Pro His Pro Ala Ala Arg Ser Val Val
305                 310                 315                 320

Leu Asn Asp Met Ser Ala Gln Glu Arg Arg Leu His Arg Ser Ala
                325                 330                 335

Leu Glu Val Leu Asp Asp Val Pro Val Glu Val Val Ala His His Gln
            340                 345                 350

Val Gly Ala Gly Leu Leu His Gly Pro Lys Ala Ala Glu Ile Phe Ala
        355                 360                 365

Lys Ala Gly Gln Glu Leu His Val Arg Gly Glu Leu Asp Thr Ala Ser
    370                 375                 380

Asp Tyr Leu Gln Leu Ala His Gln Ala Ser Asp Ala Val Thr Gly
385                 390                 395                 400

Met Arg Ala Glu Ala Val Ala Ile Glu Arg Arg Arg Asn Pro Leu Ala
                405                 410                 415
```

```
Ser Ser Arg His Leu Asp Glu Leu Thr Val Ala Arg Ala Gly Leu
        420                 425                 430

Leu Phe Pro Glu His Thr Ala Leu Met Ile Arg Trp Leu Gly Val Gly
        435                 440                 445

Gly Arg Ser Gly Glu Ala Ala Gly Leu Leu Ala Ser Gln Arg Pro Arg
        450                 455                 460

Ala Val Thr Asp Gln Asp Arg Ala His Met Arg Ala Ala Glu Val Ser
465                 470                 475                 480

Leu Ala Leu Val Ser Pro Gly Thr Ser Gly Pro Asp Arg Arg Pro Arg
                485                 490                 495

Pro Leu Thr Pro Asp Glu Leu Ala Asn Leu Pro Lys Ala Ala Arg Leu
            500                 505                 510

Cys Ala Ile Ala Asp Asn Ala Val Met Ser Ala Leu Arg Gly Arg Pro
            515                 520                 525

Glu Leu Ala Ala Glu Ala Glu Asn Val Leu Gln His Ala Asp Ser
    530                 535                 540

Ala Ala Ala Gly Thr Thr Ala Leu Ala Ala Leu Thr Ala Leu Leu Tyr
545                 550                 555                 560

Ala Glu Asn Thr Asp Thr Ala Gln Leu Trp Ala Asp Lys Leu Val Ser
                565                 570                 575

Glu Thr Gly Ala Ser Asn Glu Glu Ala Gly Tyr Ala Gly Pro Arg
                580                 585                 590

Ala Glu Ala Ala Leu Arg Arg Gly Asp Leu Ala Ala Ala Val Glu Ala
                595                 600                 605

Gly Ser Thr Val Leu Asp His Arg Arg Leu Ser Thr Leu Gly Ile Thr
        610                 615                 620

Ala Ala Leu Pro Leu Ser Ser Ala Val Ala Ala Ile Arg Leu Gly
625                 630                 635                 640

Glu Thr Glu Arg Ala Glu Lys Trp Leu Ala Gln Pro Leu Pro Gln Ala
                645                 650                 655

Ile Gln Asp Gly Leu Phe Gly Leu His Leu Leu Ser Ala Arg Gly Gln
            660                 665                 670

Tyr Ser Leu Ala Thr Gly Gln His Glu Ser Ala Tyr Thr Ala Phe Arg
        675                 680                 685

Thr Cys Gly Glu Arg Met Arg Asn Trp Gly Val Asp Val Pro Gly Leu
        690                 695                 700

Ser Leu Trp Arg Val Asp Ala Ala Glu Ala Leu Leu His Gly Arg Asp
705                 710                 715                 720

Arg Asp Glu Gly Arg Arg Leu Val Asp Glu Gln Leu Thr Arg Ala Met
                725                 730                 735

Gly Pro Arg Ser Arg Ala Leu Thr Leu Arg Val Gln Ala Ala Tyr Ser
            740                 745                 750

Pro Pro Ala Lys Arg Val Asp Leu Leu Asp Glu Ala Ala Asp Leu Leu
            755                 760                 765

Leu Ser Cys Asn Asp Gln Tyr Glu Arg Ala Arg Val Leu Ala Asp Leu
        770                 775                 780

Ser Glu Thr Phe Ser Ala Leu Arg His His Ser Arg Ala Arg Gly Leu
785                 790                 795                 800

Leu Arg Gln Ala Arg His Leu Ala Ala Gln Arg Gly Ala Ile Pro Leu
                805                 810                 815

Leu Arg Arg Leu Gly Ala Lys Pro Gly Gly Pro Gly Trp Leu Glu Glu
                820                 825                 830
```

```
Ser Gly Leu Pro Gln Arg Ile Lys Ser Leu Thr Asp Ala Glu Arg Arg
            835                 840                 845

Val Ala Ser Leu Ala Ala Gly Gly Gln Thr Asn Arg Val Ile Ala Asp
850                 855                 860

Gln Leu Phe Val Thr Ala Ser Thr Val Glu Gln His Leu Thr Asp Val
865                 870                 875                 880

Ser Thr Gly Ser Arg Pro Ala Pro Ala Ala Glu Leu Val
                885                 890

<210> SEQ ID NO 27
<211> LENGTH: 923
<212> TYPE: PRT
<213> ORGANISM: Streptomyces kanamyceticus

<400> SEQUENCE: 27

Met Val Pro Glu Val Arg Ala Ala Pro Asp Glu Leu Ile Ala Arg Asp
1               5                   10                  15

Asp Glu Leu Ser Arg Leu Gln Arg Ala Leu Thr Arg Ala Gly Ser Gly
                20                  25                  30

Arg Gly Gly Val Val Ala Ile Thr Gly Pro Ile Ala Ser Gly Lys Thr
            35                  40                  45

Ala Leu Leu Asp Ala Gly Ala Ala Lys Ser Gly Phe Val Ala Leu Arg
        50                  55                  60

Ala Val Cys Ser Trp Glu Glu Arg Thr Leu Pro Tyr Gly Met Leu Gly
65                  70                  75                  80

Gln Leu Phe Asp His Pro Glu Leu Ala Ala Gln Ala Pro Asp Leu Ala
                85                  90                  95

His Phe Thr Ala Ser Cys Glu Ser Pro Gln Ala Gly Thr Asp Asn Arg
                100                 105                 110

Leu Arg Ala Glu Phe Thr Arg Thr Leu Leu Ala Leu Ala Ala Asp Trp
            115                 120                 125

Pro Val Leu Ile Gly Ile Asp Asp Val His His Ala Asp Ala Glu Ser
        130                 135                 140

Leu Arg Cys Leu Leu His Leu Ala Arg Arg Ile Gly Pro Ala Arg Ile
145                 150                 155                 160

Ala Val Val Leu Thr Glu Leu Arg Arg Pro Thr Pro Ala Asp Ser Arg
                165                 170                 175

Phe Gln Ala Glu Leu Leu Ser Leu Arg Ser Tyr Gln Glu Ile Ala Leu
            180                 185                 190

Arg Pro Leu Thr Glu Ala Gln Thr Gly Glu Leu Val Arg Arg His Leu
        195                 200                 205

Gly Ala Glu Thr His Glu Asp Val Ser Ala Asp Thr Phe Arg Ala Thr
    210                 215                 220

Gly Gly Asn Leu Leu Gly His Gly Leu Ile Asn Asp Ile Arg Glu
225                 230                 235                 240

Ala Arg Thr Ala Gly Arg Pro Gly Val Val Ala Gly Arg Ala Tyr Arg
                245                 250                 255

Leu Ala Tyr Leu Ser Ser Leu Tyr Arg Cys Gly Pro Ser Ala Leu Arg
            260                 265                 270

Val Ala Arg Ala Ser Ala Val Leu Gly Ala Ser Ala Glu Ala Val Leu
        275                 280                 285

Val Gln Arg Met Thr Gly Leu Asn Lys Asp Ala Val Glu Gln Val Tyr
    290                 295                 300

Glu Gln Leu Asn Glu Gly Arg Leu Leu Gln Gly Glu Arg Phe Pro His
305                 310                 315                 320
```

```
Pro Ala Ala Arg Ser Ile Val Leu Asp Asp Leu Ser Ala Leu Glu Arg
            325                 330                 335

Arg Asn Leu His Glu Ser Ala Leu Glu Leu Leu Arg Asp His Gly Val
            340                 345                 350

Ala Gly Asn Val Leu Ala Arg His Gln Ile Gly Ala Gly Arg Val His
            355                 360                 365

Gly Glu Glu Ala Val Glu Leu Phe Thr Gly Ala Ala Arg Glu His His
    370                 375                 380

Leu Arg Gly Glu Leu Asp Asp Ala Ala Gly Tyr Leu Glu Leu Ala His
385                 390                 395                 400

Arg Ala Ser Asp Asp Pro Val Thr Arg Ala Ala Leu Arg Val Gly Ala
                405                 410                 415

Ala Ala Ile Glu Arg Leu Cys Asn Pro Val Arg Ala Gly Arg His Leu
            420                 425                 430

Pro Glu Leu Leu Thr Ala Ser Arg Ala Gly Leu Leu Ser Ser Glu His
            435                 440                 445

Ala Val Ser Leu Ala Asp Trp Leu Ala Met Gly Gly Arg Pro Gly Glu
    450                 455                 460

Ala Ala Glu Val Leu Ala Thr Gln Arg Pro Ala Ala Asp Ser Glu Gln
465                 470                 475                 480

His Arg Ala Leu Leu Arg Ser Gly Leu Ser Leu Ala Leu Val His
                485                 490                 495

Pro Gly Ala Trp Asp Pro Leu Arg Arg Thr Asp Arg Phe Ala Ala Gly
            500                 505                 510

Gly Leu Gly Ser Leu Pro Gly Pro Ala Arg His Arg Ala Val Ala Asp
    515                 520                 525

Gln Ala Val Ile Ala Ala Leu Arg Gly Arg Leu Asp Arg Ala Asp Ala
    530                 535                 540

Asn Ala Glu Ser Val Leu Gln His Thr Asp Ala Thr Ala Asp Arg Thr
545                 550                 555                 560

Thr Ala Ile Met Ala Leu Leu Ala Leu Leu Tyr Ala Glu Asn Thr Asp
                565                 570                 575

Ala Val Gln Phe Trp Val Asp Lys Leu Ala Gly Asp Glu Gly Thr Arg
            580                 585                 590

Thr Pro Ala Asp Glu Ala Val His Ala Gly Phe Asn Ala Glu Ile Ala
            595                 600                 605

Leu Arg Arg Gly Asp Leu Met Arg Ala Val Glu Tyr Gly Glu Ala Ala
    610                 615                 620

Leu Gly His Arg His Leu Pro Thr Trp Gly Met Ala Ala Ala Leu Pro
625                 630                 635                 640

Leu Ser Ser Thr Val Val Ala Ala Ile Arg Leu Gly Asp Leu Asp Arg
                645                 650                 655

Ala Glu Arg Trp Leu Ala Glu Pro Leu Pro Gln Gln Thr Pro Glu Ser
            660                 665                 670

Leu Phe Gly Leu His Leu Leu Trp Ala Arg Gly Gln His His Leu Ala
            675                 680                 685

Thr Gly Arg His Gly Ala Ala Tyr Thr Ala Phe Arg Glu Cys Gly Glu
    690                 695                 700

Arg Met Arg Arg Trp Ala Val Asp Val Pro Gly Leu Ala Leu Trp Arg
705                 710                 715                 720

Val Asp Ala Ala Glu Ser Leu Leu Leu Leu Gly Arg Asp Arg Ala Glu
                725                 730                 735
```

```
Gly Leu Arg Leu Val Ser Glu Gln Leu Ser Arg Pro Met Arg Pro Arg
            740                 745                 750

Ala Arg Val Gln Thr Leu Arg Val Gln Ala Ala Tyr Ser Pro Pro Pro
            755                 760                 765

Gln Arg Ile Asp Leu Leu Glu Glu Ala Ala Asp Leu Leu Val Thr Cys
            770                 775                 780

Asn Asp Gln Tyr Glu Leu Ala Asn Val Leu Ser Asp Leu Ala Glu Ala
785                 790                 795                 800

Ser Ser Met Val Arg Gln His Ser Arg Ala Arg Gly Leu Leu Arg Arg
            805                 810                 815

Ala Arg His Leu Ala Thr Gln Cys Gly Ala Val Pro Leu Leu Arg Arg
            820                 825                 830

Leu Gly Ala Glu Pro Ser Asp Ile Gly Gly Ala Trp Asp Ala Thr Leu
            835                 840                 845

Gly Gln Arg Ile Ala Ser Leu Thr Glu Ser Glu Arg Arg Val Ala Ala
            850                 855                 860

Leu Ala Ala Val Gly Arg Thr Asn Arg Glu Ile Ala Glu Gln Leu Phe
865                 870                 875                 880

Val Thr Ala Ser Thr Val Glu Gln His Leu Thr Asn Val Phe Arg Lys
            885                 890                 895

Leu Ala Val Lys Gly Arg Gln Gln Leu Pro Lys Glu Leu Ala Asp Val
            900                 905                 910

Gly Glu Pro Ala Asp Arg Asp Arg Arg Cys Gly
            915                 920

<210> SEQ ID NO 28
<211> LENGTH: 913
<212> TYPE: PRT
<213> ORGANISM: Streptomyces ascomyceticus

<400> SEQUENCE: 28

Met Ile Ala Arg Leu Ser Pro Pro Asp Leu Ile Ala Arg Asp Asp Glu
1               5                   10                  15

Phe Gly Ser Leu His Arg Ala Leu Thr Arg Ala Gly Gly Arg Arg Gly
            20                  25                  30

Val Val Ala Ala Val Thr Gly Pro Ile Ala Cys Gly Lys Thr Glu Leu
            35                  40                  45

Leu Asp Ala Ala Ala Ala Lys Ala Gly Phe Val Thr Leu Arg Ala Val
            50                  55                  60

Cys Ser Met Glu Glu Arg Ala Leu Pro Tyr Gly Met Leu Gly Gln Leu
65                  70                  75                  80

Leu Asp Gln Pro Glu Leu Ala Ala Arg Thr Pro Glu Leu Val Arg Leu
            85                  90                  95

Thr Ala Ser Cys Glu Asn Leu Pro Ala Asp Val Asp Asn Arg Leu Gly
            100                 105                 110

Thr Glu Leu Thr Arg Thr Val Leu Thr Leu Ala Ala Glu Arg Pro Val
            115                 120                 125

Leu Ile Gly Ile Asp Asp Val His His Ala Asp Ala Pro Ser Leu Arg
            130                 135                 140

Cys Leu Leu His Leu Ala Arg Arg Ile Ser Arg Ala Arg Val Ala Ile
145                 150                 155                 160

Val Leu Thr Glu Leu Leu Arg Pro Thr Pro Ala His Ser Gln Phe Arg
            165                 170                 175

Ala Ala Leu Leu Ser Leu Arg His Tyr Gln Glu Ile Ala Leu Arg Pro
            180                 185                 190
```

```
Leu Thr Glu Ala Gln Thr Thr Glu Leu Val Arg Arg His Leu Gly Gln
            195                 200                 205

Asp Ala His Asp Asp Val Val Ala Gln Ala Phe Arg Ala Thr Gly Gly
        210                 215                 220

Asn Leu Leu Gly His Gly Leu Ile Asp Asp Ile Arg Glu Ala Arg
225                 230                 235                 240

Thr Arg Thr Ser Gly Cys Leu Glu Val Val Ala Gly Arg Ala Tyr Arg
                245                 250                 255

Leu Ala Tyr Leu Gly Ser Leu Tyr Arg Cys Gly Pro Ala Ala Leu Ser
            260                 265                 270

Val Ala Arg Ala Ser Ala Val Leu Gly Glu Ser Val Glu Leu Thr Leu
        275                 280                 285

Val Gln Arg Met Thr Gly Leu Asp Thr Glu Ala Val Glu Gln Ala His
        290                 295                 300

Glu Gln Leu Val Glu Gly Arg Leu Leu Arg Glu Gly Arg Phe Pro His
305                 310                 315                 320

Pro Ala Ala Arg Ser Val Val Leu Asp Asp Leu Ser Ala Ala Glu Arg
                325                 330                 335

Arg Gly Leu His Glu Leu Ala Leu Glu Leu Leu Arg Asp Arg Gly Val
            340                 345                 350

Ala Ser Lys Val Leu Ala Arg His Gln Met Gly Thr Gly Arg Val His
        355                 360                 365

Gly Ala Glu Val Ala Gly Leu Phe Thr Asp Ala Ala Arg Glu His His
        370                 375                 380

Leu Arg Gly Glu Leu Asp Glu Ala Val Thr Tyr Leu Glu Phe Ala Tyr
385                 390                 395                 400

Arg Ala Ser Asp Asp Pro Ala Val His Ala Ala Leu Arg Val Asp Thr
                405                 410                 415

Ala Ala Ile Glu Arg Leu Cys Asp Pro Ala Arg Ser Gly Arg His Val
            420                 425                 430

Pro Glu Leu Leu Thr Ala Ser Arg Glu Arg Leu Leu Ser Ser Glu His
        435                 440                 445

Ala Val Ser Leu Ala Cys Trp Leu Ala Met Asp Gly Arg Pro Gly Glu
        450                 455                 460

Ala Ala Glu Val Leu Ala Ala Gln Arg Ser Ala Pro Ser Glu Gln
465                 470                 475                 480

Gly Arg Ala His Leu Arg Val Ala Asp Leu Ser Leu Ala Leu Ile Tyr
                485                 490                 495

Pro Gly Ala Ala Asp Pro Pro Arg Pro Ala Asp Pro Ala Glu Asp
            500                 505                 510

Glu Val Ala Ser Phe Ser Gly Ala Val Arg His Arg Ala Val Ala Asp
        515                 520                 525

Lys Ala Leu Ser Asn Ala Leu Arg Gly Trp Ser Glu Gln Ala Glu Ala
        530                 535                 540

Lys Ala Glu Tyr Val Leu Gln His Ser Arg Val Thr Thr Asp Arg Thr
545                 550                 555                 560

Thr Thr Met Met Ala Leu Leu Ala Leu Leu Tyr Ala Glu Asp Thr Asp
                565                 570                 575

Ala Val Gln Ser Trp Val Asp Lys Leu Ala Gly Asp Asp Asn Met Arg
            580                 585                 590

Thr Pro Ala Asp Glu Ala Val His Ala Gly Phe Arg Ala Glu Ala Ala
        595                 600                 605
```

```
Leu Arg Arg Gly Asp Leu Thr Ala Ala Val Glu Cys Gly Glu Ala Ala
610                 615                 620

Leu Ala Pro Arg Val Val Pro Ser Trp Gly Met Ala Ala Ala Leu Pro
625                 630                 635                 640

Leu Ser Ser Thr Val Ala Ala Ala Ile Arg Leu Gly Asp Leu Asp Arg
                645                 650                 655

Ala Glu Arg Trp Leu Ala Glu Pro Leu Pro Glu Glu Thr Ser Asp Ser
                660                 665                 670

Leu Phe Gly Leu His Met Val Trp Ala Arg Gly Gln His Leu Ala
            675                 680                 685

Ala Gly Arg Tyr Arg Ala Ala Tyr Asn Ala Phe Arg Asp Cys Gly Glu
            690                 695                 700

Arg Met Arg Arg Trp Ser Val Asp Val Pro Gly Leu Ala Leu Trp Arg
705                 710                 715                 720

Val Asp Ala Ala Glu Ala Leu Leu Leu Gly Arg Gly Arg Asp Glu
                725                 730                 735

Gly Leu Arg Leu Ile Ser Glu Gln Leu Ser Arg Pro Met Gly Ser Arg
                740                 745                 750

Ala Arg Val Met Thr Leu Arg Val Gln Ala Ala Tyr Ser Pro Pro Ala
            755                 760                 765

Lys Arg Ile Glu Leu Leu Asp Glu Ala Ala Asp Leu Leu Ile Met Cys
770                 775                 780

Arg Asp Gln Tyr Glu Leu Ala Arg Val Leu Ala Asp Met Gly Glu Ala
785                 790                 795                 800

Cys Gly Met Leu Arg Arg His Ser Arg Ala Arg Gly Leu Phe Arg Arg
            805                 810                 815

Ala Arg His Leu Ala Thr Gln Cys Gly Ala Val Pro Leu Leu Arg Arg
            820                 825                 830

Leu Gly Gly Glu Ser Ser Asp Ala Asp Gly Thr Gln Asp Val Thr Pro
            835                 840                 845

Ala Gln Arg Ile Thr Ser Leu Thr Glu Ala Glu Arg Arg Val Ala Ser
850                 855                 860

His Ala Ala Val Gly Arg Thr Asn Lys Glu Ile Ala Ser Gln Leu Phe
865                 870                 875                 880

Val Thr Ser Ser Thr Val Glu Gln His Leu Thr Asn Val Phe Arg Lys
                885                 890                 895

Leu Gly Val Lys Gly Arg Gln Gln Leu Pro Lys Glu Leu Ser Asp Ala
            900                 905                 910

Gly

<210> SEQ ID NO 29
<211> LENGTH: 901
<212> TYPE: PRT
<213> ORGANISM: Micromonospora sp. S92-306401

<400> SEQUENCE: 29

Met Glu Phe Tyr Asp Leu Val Ala Arg Asp Asp Glu Leu Arg Arg Leu
1               5                   10                  15

Asp Gln Ala Leu Gly Arg Ala Gly Gly Arg Gly Val Val Thr
                20                  25                  30

Val Thr Gly Pro Val Gly Cys Gly Lys Thr Glu Leu Leu Asp Ala Ala
                35                  40                  45

Ala Ala Glu Glu Glu Phe Ile Thr Leu Arg Ala Val Cys Ser Ala Glu
            50                  55                  60
```

```
Glu Arg Ala Leu Pro Tyr Ala Val Ile Gly Gln Leu Leu Asp His Pro
 65                  70                  75                  80

Val Leu Ser Ala Arg Ala Pro Asp Leu Ala Cys Val Thr Ala Pro Gly
                 85                  90                  95

Arg Thr Leu Pro Ala Asp Thr Glu Asn Arg Leu Arg Arg Asp Leu Thr
                100                 105                 110

Arg Ala Leu Leu Ala Leu Ala Ser Glu Arg Pro Val Leu Ile Cys Ile
            115                 120                 125

Asp Asp Val His Gln Ala Asp Thr Ala Ser Leu Asn Cys Leu Leu His
130                 135                 140

Leu Ala Arg Arg Val Ala Ser Ala Arg Ile Ala Met Ile Leu Thr Glu
145                 150                 155                 160

Leu Arg Arg Leu Thr Pro Ala His Ser Arg Phe Glu Ala Glu Leu Leu
                165                 170                 175

Ser Leu Arg His Arg His Glu Ile Ala Leu Arg Pro Leu Gly Pro Ala
            180                 185                 190

Asp Thr Ala Glu Leu Ala Arg Ala Arg Leu Gly Ala Gly Val Thr Ala
            195                 200                 205

Asp Glu Leu Ala Gln Val His Glu Ala Thr Ser Gly Asn Pro Asn Leu
210                 215                 220

Val Gly Gly Leu Val Asn Asp Val Arg Glu Ala Trp Ala Ala Gly Gly
225                 230                 235                 240

Thr Gly Ile Ala Ala Gly Arg Ala Tyr Arg Leu Ala Tyr Leu Ser Ser
                245                 250                 255

Val Tyr Arg Cys Gly Pro Val Pro Leu Arg Ile Ala Gln Ala Ala Ala
            260                 265                 270

Val Leu Gly Pro Ser Ala Thr Val Thr Leu Val Arg Arg Ile Ser Gly
            275                 280                 285

Leu Asp Ala Glu Thr Val Asp Glu Ala Thr Ala Ile Leu Thr Glu Gly
290                 295                 300

Gly Leu Leu Arg Asp His Arg Phe Pro His Pro Ala Ala Arg Ser Val
305                 310                 315                 320

Val Leu Asp Asp Met Ser Ala Gln Glu Arg Arg Arg Leu His Arg Ser
                325                 330                 335

Thr Leu Asp Val Leu Asp Gly Val Pro Val Asp Val Leu Ala His His
            340                 345                 350

Gln Ala Gly Ala Gly Leu Leu His Gly Pro Gln Ala Ala Glu Met Phe
            355                 360                 365

Ala Arg Ala Ser Gln Glu Leu Arg Val Arg Gly Glu Leu Asp Ala Ala
            370                 375                 380

Thr Glu Tyr Leu Gln Leu Ala Tyr Arg Ala Ser Asp Asp Ala Gly Ala
385                 390                 395                 400

Arg Ala Ala Leu Gln Val Glu Thr Val Ala Gly Glu Arg Arg Asn
                405                 410                 415

Pro Leu Ala Ala Ser Arg His Leu Asp Glu Leu Ala Ala Ala Ala Arg
                420                 425                 430

Ala Gly Leu Leu Ser Ala Glu His Ala Ala Leu Val Val His Trp Leu
            435                 440                 445

Ala Asp Ala Gly Arg Pro Gly Glu Ala Ala Glu Val Leu Ala Leu Gln
            450                 455                 460

Arg Ala Leu Ala Val Thr Asp His Asp Arg Ala Arg Leu Arg Ala Ala
465                 470                 475                 480

Glu Val Ser Leu Ala Leu Phe His Pro Gly Val Pro Gly Ser Asp Pro
```

```
                485                 490                 495
Arg Pro Leu Ala Pro Glu Glu Leu Ala Ser Leu Ser Leu Ser Ala Arg
            500                 505                 510
His Gly Val Thr Ala Asp Asn Ala Val Leu Ala Leu Arg Gly Arg
            515                 520                 525
Pro Glu Ser Ala Ala Ala Glu Ala Glu Asn Val Leu Arg Asn Ala Asp
            530                 535                 540
Ala Ala Ala Ser Gly Pro Thr Ala Leu Ala Ala Leu Thr Ala Leu Leu
545                 550                 555                 560
Tyr Ala Glu Asn Thr Asp Ala Ala Gln Leu Trp Ala Asp Lys Leu Ala
                565                 570                 575
Ala Gly Ile Gly Ala Gly Gly Glu Ala Gly Tyr Ala Gly Pro Arg
            580                 585                 590
Thr Val Ala Ala Leu Arg Arg Gly Asp Leu Thr Thr Ala Val Gln Ala
            595                 600                 605
Ala Gly Ala Val Leu Asp Arg Gly Arg Pro Ser Ser Leu Gly Ile Thr
            610                 615                 620
Ala Val Leu Pro Leu Ser Gly Ala Val Ala Ala Ile Arg Leu Gly
625                 630                 635                 640
Glu Leu Glu Arg Ala Glu Lys Trp Leu Ala Glu Pro Leu Pro Glu Ala
                645                 650                 655
Val His Asp Ser Leu Phe Gly Leu His Leu Leu Met Ala Arg Gly Arg
            660                 665                 670
Tyr Ser Leu Ala Val Gly Arg His Glu Ala Ala Tyr Ala Ala Phe Arg
            675                 680                 685
Asp Cys Gly Glu Arg Met Arg Arg Trp Asp Val Asp Val Pro Gly Leu
            690                 695                 700
Ala Leu Trp Arg Val Asp Ala Ala Glu Ala Leu Pro Gly Asp Asp
705                 710                 715                 720
Arg Ala Glu Gly Arg Leu Ile Asp Glu Gln Leu Thr Arg Pro Met
                725                 730                 735
Gly Pro Arg Ser Arg Ala Leu Thr Leu Arg Val Arg Ala Ala Tyr Ala
            740                 745                 750
Pro Pro Ala Lys Arg Ile Asp Leu Leu Asp Glu Ala Ala Asp Leu Leu
            755                 760                 765
Leu Ser Ser Asn Asp Gln Tyr Glu Arg Ala Arg Val Leu Ala Asp Leu
            770                 775                 780
Ser Glu Ala Phe Ser Ala Leu Arg Gln Asn Gly Arg Ala Arg Gly Ile
785                 790                 795                 800
Leu Arg Gln Ala Arg His Leu Ala Ala Gln Cys Gly Ala Val Pro Leu
                805                 810                 815
Leu Arg Arg Leu Gly Val Lys Ala Gly Arg Ser Gly Arg Leu Gly Arg
            820                 825                 830
Pro Pro Gln Gly Ile Arg Ser Leu Thr Glu Ala Glu Arg Arg Val Ala
            835                 840                 845
Thr Leu Ala Ala Ala Gly Gln Thr Asn Arg Glu Ile Ala Asp Gln Leu
850                 855                 860
Phe Val Thr Ala Ser Thr Val Glu Gln His Leu Thr Asn Val Phe Arg
865                 870                 875                 880
Lys Leu Gly Val Lys Gly Arg Gln Gln Leu Pro Ala Glu Leu Ala Asp
                885                 890                 895
Leu Arg Pro Pro Gly
                900
```

<210> SEQ ID NO 30
<211> LENGTH: 906
<212> TYPE: PRT
<213> ORGANISM: Streptomyces violaceusniger

<400> SEQUENCE: 30

Met Tyr Ser Gly Thr Cys Arg Glu Gly Tyr Glu Leu Val Ala Arg Glu
1               5                   10                  15

Asp Glu Leu Gly Ile Leu Gln Arg Ser Leu Glu Gln Ala Ser Ser Gly
            20                  25                  30

Gln Gly Val Val Val Thr Val Thr Gly Pro Ile Ala Cys Gly Lys Thr
        35                  40                  45

Glu Leu Leu Asp Ala Ala Ala Lys Ala Glu Ala Ile Ile Leu Arg
50                  55                  60

Ala Val Cys Ala Pro Glu Glu Arg Ala Met Pro Tyr Ala Met Ile Gly
65                  70                  75                  80

Gln Leu Ile Asp Asp Pro Ala Leu Ala His Arg Ala Pro Gly Leu Ala
                85                  90                  95

Asp Arg Ile Ala Gln Gly Gly Gln Leu Ser Leu Arg Ala Glu Asn Arg
            100                 105                 110

Leu Arg Arg Asp Leu Thr Arg Ala Leu Leu Ala Leu Ala Val Asp Arg
        115                 120                 125

Pro Val Leu Ile Gly Val Asp Val His His Ala Asp Thr Ala Ser
130                 135                 140

Leu Asn Cys Leu Leu His Leu Ala Arg Arg Val Arg Pro Ala Arg Ile
145                 150                 155                 160

Ser Met Ile Phe Thr Glu Leu Arg Ser Leu Thr Pro Thr Gln Ser Arg
                165                 170                 175

Phe Lys Ala Glu Leu Leu Ser Leu Pro Tyr His His Glu Ile Ala Leu
            180                 185                 190

Arg Pro Phe Gly Pro Glu Gln Ser Ala Glu Leu Ala Arg Ala Ala Phe
        195                 200                 205

Gly Pro Gly Leu Ala Glu Asp Val Leu Val Gly Leu Tyr Lys Thr Thr
    210                 215                 220

Arg Gly Asn Leu Ser Leu Ser Arg Gly Leu Ile Ser Asp Val Arg Glu
225                 230                 235                 240

Ala Leu Ala Asn Gly Glu Ser Ala Phe Glu Ala Gly Arg Ala Phe Arg
                245                 250                 255

Leu Ala Tyr Leu Gly Ser Leu Tyr Arg Cys Gly Pro Val Ala Leu Arg
            260                 265                 270

Val Ala Arg Val Ala Ala Val Leu Gly Pro Ser Ala Thr Thr Thr Leu
        275                 280                 285

Val Arg Arg Leu Ser Gly Leu Ser Ala Glu Thr Ile Asp Arg Ala Thr
    290                 295                 300

Lys Ile Leu Thr Glu Gly Gly Leu Leu Leu Asp Gln Gln Phe Pro His
305                 310                 315                 320

Pro Ala Ala Arg Ser Val Val Leu Asp Asp Met Ser Ala Gln Glu Arg
                325                 330                 335

Arg Gly Leu His Thr Leu Ala Leu Leu Glu Leu Asp Glu Ala Pro Val
            340                 345                 350

Glu Val Leu Ala His His Gln Val Gly Ala Gly Leu Ile His Gly Pro
        355                 360                 365

Lys Ala Ala Glu Met Phe Ala Lys Ala Gly Lys Ala Leu Val Val Arg

```
            370                 375                 380
Asn Glu Leu Gly Asp Ala Ala Glu Tyr Leu Gln Leu Ala His Arg Ala
385                 390                 395                 400

Ser Asp Asp Val Ser Thr Arg Ala Ala Leu Arg Val Glu Ala Val Ala
                405                 410                 415

Ile Glu Arg Arg Arg Asn Pro Leu Ala Ser Ser Arg His Met Asp Glu
            420                 425                 430

Leu Ser Ala Ala Gly Arg Ala Gly Leu Leu Ser Pro Lys His Ala Ala
            435                 440                 445

Leu Ala Val Phe Trp Leu Ala Asp Gly Gly Arg Ser Gly Glu Ala Ala
            450                 455                 460

Glu Val Leu Ala Ser Glu Arg Pro Leu Ala Thr Thr Asp Gln Asn Arg
465                 470                 475                 480

Ala His Leu Arg Phe Val Glu Val Thr Leu Ala Leu Phe Ser Pro Gly
                485                 490                 495

Ala Phe Gly Ser Asp Arg Arg Pro Pro Pro Leu Thr Pro Asp Glu Leu
                500                 505                 510

Ala Ser Leu Pro Lys Ala Ala Trp Gln Cys Ala Val Ala Asp Asn Ala
                515                 520                 525

Ala Met Thr Ala Leu His Gly His Pro Glu Leu Ala Thr Ala Gln Ala
            530                 535                 540

Glu Thr Val Leu Arg Gln Ala Asp Ser Ala Ala Asp Ala Ile Pro Ala
545                 550                 555                 560

Ala Leu Ile Ala Leu Leu Tyr Ala Glu Asn Thr Glu Ser Ala His Ile
                565                 570                 575

Trp Ala Asp Lys Leu Gly Ser Thr Asn Gly Gly Val Ser Asn Glu Ala
                580                 585                 590

Glu Ala Gly Tyr Ala Gly Pro Cys Ala Glu Ile Ala Leu Arg Arg Gly
                595                 600                 605

Asp Leu Ala Thr Ala Phe Glu Ala Gly Ser Thr Val Leu Asp Asp Arg
            610                 615                 620

Ser Leu Pro Ser Leu Gly Ile Thr Ala Ala Leu Leu Leu Ser Ser Lys
625                 630                 635                 640

Thr Ala Ala Ala Val Arg Leu Gly Glu Leu Glu Arg Ala Glu Lys Leu
                645                 650                 655

Leu Ala Glu Pro Leu Pro Asn Gly Val Gln Asp Ser Leu Phe Gly Leu
                660                 665                 670

His Leu Leu Ser Ala Tyr Gly Gln Tyr Ser Leu Ala Met Gly Arg Tyr
            675                 680                 685

Glu Ser Ala Leu Arg Ala Phe His Thr Cys Gly Glu Arg Met Arg Ser
690                 695                 700

Trp Asp Val Asp Val Pro Gly Leu Ala Leu Trp Arg Val Asp Ala Ala
705                 710                 715                 720

Glu Ala Leu Leu Ser Leu Asp Arg Asn Glu Gly Gln Arg Leu Ile Asp
                725                 730                 735

Glu Gln Leu Thr Arg Pro Met Gly Pro Arg Ser Arg Ala Leu Thr Leu
            740                 745                 750

Arg Ile Lys Ala Ala Tyr Leu Pro Arg Thr Lys Arg Ile Pro Leu Leu
            755                 760                 765

His Glu Ala Ala Glu Leu Leu Leu Pro Cys Pro Asp Pro Tyr Glu Gln
            770                 775                 780

Ala Arg Val Leu Ala Asp Leu Gly Asp Thr Leu Ser Ala Leu Arg Arg
785                 790                 795                 800
```

```
Tyr Ser Arg Ala Arg Gly Val Leu Arg Gln Ala Arg His Leu Ala Ala
                805                 810                 815

Gln Cys Gly Ala Val Pro Leu Leu Arg Arg Leu Gly Gly Glu Pro Gly
            820                 825                 830

Arg Ile Asp Asp Ala Gly Leu Pro Gln Arg Ser Thr Ser Leu Thr Asp
        835                 840                 845

Ala Glu Arg Arg Val Ala Ala Leu Ala Ala Ala Gly Gln Thr Asn Arg
    850                 855                 860

Glu Ile Ala Lys Gln Leu Phe Val Thr Ala Ser Thr Val Glu Gln His
865                 870                 875                 880

Leu Thr Ser Val Phe Arg Lys Leu Gly Val Lys Gly Arg Lys Gln Leu
                885                 890                 895

Pro Thr Ala Leu Ala Asp Val Glu Gln Thr
            900                 905

<210> SEQ ID NO 31
<211> LENGTH: 914
<212> TYPE: PRT
<213> ORGANISM: Streptomyces hygroscopicus

<400> SEQUENCE: 31

Met Pro Ala Val Glu Ser Tyr Glu Leu Asp Ala Arg Asp Asp Glu Leu
1               5                   10                  15

Arg Arg Leu Glu Glu Ala Val Gly Gln Ala Gly Asn Gly Arg Gly Val
            20                  25                  30

Val Val Thr Ile Thr Gly Pro Ile Ala Cys Gly Lys Thr Glu Leu Leu
        35                  40                  45

Asp Ala Ala Ala Lys Ser Asp Ala Ile Thr Leu Arg Ala Val Cys
    50                  55                  60

Ser Glu Glu Glu Arg Ala Leu Pro Tyr Ala Leu Ile Gly Gln Leu Ile
65                  70                  75                  80

Asp Asn Pro Ala Val Ala Ser Gln Leu Pro Asp Pro Val Ser Met Ala
                85                  90                  95

Leu Pro Gly Glu His Leu Ser Pro Glu Ala Glu Asn Arg Leu Arg Gly
            100                 105                 110

Asp Leu Thr Arg Thr Leu Leu Ala Leu Ala Ala Glu Arg Pro Val Leu
        115                 120                 125

Ile Gly Ile Asp Asp Met His His Ala Asp Thr Ala Ser Leu Asn Cys
    130                 135                 140

Leu Leu His Leu Ala Arg Arg Val Gly Pro Ala Arg Ile Ala Met Val
145                 150                 155                 160

Leu Thr Glu Leu Arg Arg Leu Thr Pro Ala His Ser Gln Phe His Ala
                165                 170                 175

Glu Leu Leu Ser Leu Gly His His Arg Glu Ile Ala Leu Arg Pro Leu
            180                 185                 190

Gly Pro Lys His Ile Ala Glu Leu Ala Arg Ala Gly Leu Gly Pro Asp
        195                 200                 205

Val Asp Glu Asp Val Leu Thr Gly Leu Tyr Arg Ala Thr Gly Gly Asn
    210                 215                 220

Leu Asn Leu Gly His Gly Leu Ile Lys Asp Val Arg Glu Ala Trp Ala
225                 230                 235                 240

Thr Gly Gly Thr Gly Ile Asn Ala Gly Arg Ala Tyr Arg Leu Ala Tyr
                245                 250                 255

Leu Gly Ser Leu Tyr Arg Cys Gly Pro Val Pro Leu Arg Val Ala Arg
```

```
              260                 265                 270
Val Ala Ala Val Leu Gly Gln Ser Ala Asn Thr Thr Leu Val Arg Trp
            275                 280                 285

Ile Ser Gly Leu Asn Ala Asp Ala Val Gly Glu Ala Thr Glu Ile Leu
290                 295                 300

Thr Glu Gly Gly Leu Leu His Asp Leu Arg Phe Pro His Pro Ala Ala
305                 310                 315                 320

Arg Ser Val Val Leu Asn Asp Leu Ser Ala Arg Glu Arg Arg Arg Leu
            325                 330                 335

His Arg Ser Ala Leu Glu Val Leu Asp Asp Val Pro Val Glu Val Val
        340                 345                 350

Ala His His Gln Ala Gly Ala Gly Phe Ile His Gly Pro Lys Ala Ala
    355                 360                 365

Glu Ile Phe Ala Lys Ala Gly Gln Glu Leu His Val Arg Gly Glu Leu
370                 375                 380

Asp Ala Ala Ser Asp Tyr Leu Gln Leu Ala His His Ala Ser Asp Asp
385                 390                 395                 400

Ala Val Thr Arg Ala Ala Leu Arg Val Glu Ala Val Ala Ile Glu Arg
            405                 410                 415

Arg Arg Asn Pro Leu Ala Ser Ser Arg His Leu Asp Glu Leu Thr Val
        420                 425                 430

Ala Ala Arg Ala Gly Leu Leu Ser Leu Glu His Ala Ala Leu Met Ile
    435                 440                 445

Arg Trp Leu Ala Leu Gly Gly Arg Ser Gly Glu Ala Ala Glu Val Leu
450                 455                 460

Ala Ala Gln Arg Pro Arg Ala Val Thr Asp Gln Asp Arg Ala His Leu
465                 470                 475                 480

Arg Ala Ala Glu Val Ser Leu Ala Leu Val Ser Pro Gly Ala Ser Gly
            485                 490                 495

Val Ser Pro Gly Ala Ser Gly Pro Asp Arg Arg Pro Arg Pro Leu Pro
        500                 505                 510

Pro Asp Glu Leu Ala Asn Leu Pro Lys Ala Ala Arg Leu Cys Ala Ile
    515                 520                 525

Ala Asp Asn Ala Val Ile Ser Ala Leu His Gly Arg Pro Glu Leu Ala
530                 535                 540

Ser Ala Glu Ala Glu Asn Val Leu Lys Gln Ala Asp Ser Ala Ala Asp
545                 550                 555                 560

Gly Ala Thr Ala Leu Ser Ala Leu Thr Ala Leu Leu Tyr Ala Glu Asn
            565                 570                 575

Thr Asp Thr Ala Gln Leu Trp Ala Asp Lys Leu Val Ser Glu Thr Gly
        580                 585                 590

Ala Ser Asn Glu Glu Gly Ala Gly Tyr Ala Gly Pro Arg Ala Glu
    595                 600                 605

Thr Ala Leu Arg Arg Gly Asp Leu Ala Ala Val Glu Ala Gly Ser
610                 615                 620

Ala Ile Leu Asp His Arg Arg Gly Ser Leu Leu Gly Ile Thr Ala Ala
625                 630                 635                 640

Leu Pro Leu Ser Ser Ala Val Ala Ala Ile Arg Leu Gly Glu Thr
            645                 650                 655

Glu Arg Ala Glu Lys Trp Leu Ala Glu Pro Leu Pro Glu Ala Ile Arg
        660                 665                 670

Asp Ser Leu Phe Gly Leu His Leu Leu Ser Ala Arg Gly Gln Tyr Cys
    675                 680                 685
```

```
Leu Ala Thr Gly Arg His Glu Ser Ala Tyr Thr Ala Phe Arg Thr Cys
    690                 695                 700

Gly Glu Arg Met Arg Asn Trp Gly Val Asp Val Pro Gly Leu Ser Leu
705                 710                 715                 720

Trp Arg Val Asp Ala Ala Glu Ala Leu Leu His Gly Arg Asp Arg Asp
                725                 730                 735

Glu Gly Arg Arg Leu Ile Asp Glu Gln Leu Thr His Ala Met Gly Pro
            740                 745                 750

Arg Ser Arg Ala Leu Thr Leu Arg Val Gln Ala Ala Tyr Ser Pro Gln
        755                 760                 765

Ala Gln Arg Val Asp Leu Leu Glu Glu Ala Ala Asp Leu Leu Leu Ser
770                 775                 780

Cys Asn Asp Gln Tyr Glu Arg Ala Arg Val Leu Ala Asp Leu Ser Glu
785                 790                 795                 800

Ala Phe Ser Ala Leu Arg His His Ser Arg Ala Arg Gly Leu Leu Arg
                805                 810                 815

Gln Ala Arg His Leu Ala Ala Gln Cys Gly Ala Thr Pro Leu Leu Arg
            820                 825                 830

Arg Leu Gly Ala Lys Pro Gly Gly Pro Gly Trp Leu Glu Glu Ser Gly
        835                 840                 845

Leu Pro Gln Arg Ile Lys Ser Leu Thr Asp Ala Glu Arg Arg Val Ala
850                 855                 860

Ser Leu Ala Ala Gly Gly Gln Thr Asn Arg Val Ile Ala Asp Gln Leu
865                 870                 875                 880

Phe Val Thr Ala Ser Thr Val Glu Gln His Leu Thr Asn Val Phe Arg
                885                 890                 895

Lys Leu Gly Val Lys Gly Arg Gln His Leu Pro Ala Glu Leu Ala Asn
            900                 905                 910

Ala Glu

<210> SEQ ID NO 32
<211> LENGTH: 875
<212> TYPE: PRT
<213> ORGANISM: Actinoplanes sp. N01-109

<400> SEQUENCE: 32

Met Pro Ala Val Lys Arg Asn Asp Leu Val Ala Arg Asp Gly Glu Leu
1               5                   10                  15

Arg Trp Met Gln Glu Ile Leu Ser Gln Ala Ser Glu Gly Arg Gly Ala
            20                  25                  30

Val Val Thr Ile Thr Gly Ala Ile Ala Cys Gly Lys Thr Val Leu Leu
        35                  40                  45

Asp Ala Ala Ala Ser Gln Asp Val Ile Gln Leu Arg Ala Val Cys
    50                  55                  60

Ser Ala Glu Glu Gln Glu Leu Pro Tyr Ala Met Val Gly Gln Leu Leu
65                  70                  75                  80

Asp Asn Pro Val Leu Ala Ala Arg Val Pro Ala Leu Gly Asn Leu Ala
                85                  90                  95

Ala Ala Gly Glu Arg Leu Leu Pro Gly Thr Glu Asn Arg Ile Arg Arg
            100                 105                 110

Glu Leu Thr Arg Thr Leu Leu Ala Leu Ala Asp Glu Arg Pro Val Leu
        115                 120                 125

Ile Gly Val Asp Asp Met His His Ala Asp Pro Ala Ser Leu Asp Cys
130                 135                 140
```

```
Leu Leu His Leu Ala Arg Arg Val Gly Pro Ala Arg Ile Ala Ile Val
145                 150                 155                 160

Leu Thr Glu Leu Arg Arg Leu Thr Pro Ala His Ser Arg Phe Gln Ser
            165                 170                 175

Glu Leu Leu Ser Leu Arg Tyr His His Glu Ile Gly Leu Gln Pro Leu
        180                 185                 190

Thr Ala Glu His Thr Ala Asp Leu Ala Arg Val Gly Leu Gly Ala Glu
            195                 200                 205

Val Asp Asp Asp Val Leu Thr Glu Leu Tyr Glu Ala Thr Gly Gly Asn
210                 215                 220

Pro Ser Leu Cys Cys Gly Leu Ile Arg Asp Val Arg Gln Asp Trp Glu
225                 230                 235                 240

Ala Gly Val Thr Gly Ile His Val Gly Arg Ala Tyr Arg Leu Ala Tyr
                245                 250                 255

Leu Ser Ser Leu Tyr Arg Cys Gly Pro Ala Ala Leu Arg Thr Ala Arg
            260                 265                 270

Ala Ala Ala Val Leu Gly Asp Ser Ala Asp Ala Cys Leu Ile Arg Arg
            275                 280                 285

Val Ser Gly Leu Gly Thr Glu Ala Val Gly Gln Ala Ile Gln Gln Leu
290                 295                 300

Thr Glu Gly Gly Leu Leu Arg Asp Gln Gln Phe Pro His Pro Ala Ala
305                 310                 315                 320

Arg Ser Val Val Leu Asp Asp Met Ser Ala Gln Glu Arg His Ala Met
                325                 330                 335

Tyr Arg Ser Ala Arg Glu Ala Ala Glu Gly Gln Ala Asp Pro Gly
            340                 345                 350

Thr Pro Gly Glu Pro Arg Ala Ala Thr Ala Tyr Ala Gly Cys Gly Glu
            355                 360                 365

Gln Ala Gly Asp Tyr Pro Glu Pro Ala Gly Arg Ala Cys Val Asp Gly
370                 375                 380

Ala Gly Pro Ala Glu Tyr Cys Gly Asp Pro His Gly Ala Asp Asp Asp
385                 390                 395                 400

Pro Asp Glu Leu Val Ala Ala Leu Gly Gly Leu Leu Pro Ser Arg Leu
                405                 410                 415

Val Ala Met Lys Ile Arg Arg Leu Ala Val Ala Gly Arg Pro Gly Ala
            420                 425                 430

Ala Ala Glu Leu Leu Thr Ser Gln Arg Leu His Ala Val Thr Ser Glu
            435                 440                 445

Asp Arg Ala Ser Leu Arg Ala Ala Glu Val Ala Leu Ala Thr Leu Trp
450                 455                 460

Pro Gly Ala Thr Gly Pro Asp Arg His Pro Leu Thr Glu Gln Glu Ala
465                 470                 475                 480

Ala Ser Leu Pro Glu Gly Pro Arg Leu Leu Ala Ala Ala Asp Asp Ala
            485                 490                 495

Val Gly Ala Ala Leu Arg Gly Arg Ala Glu Tyr Ala Ala Ala Glu Ala
            500                 505                 510

Glu Asn Val Leu Arg His Ala Asp Pro Ala Ala Gly Gly Asp Ala Tyr
            515                 520                 525

Ala Ala Met Ile Ala Leu Leu Tyr Thr Glu His Pro Glu Asn Val Leu
            530                 535                 540

Phe Trp Ala Asp Lys Leu Asp Ala Gly Arg Pro Asp Glu Glu Thr Ser
545                 550                 555                 560
```

```
Tyr Pro Gly Leu Arg Ala Glu Thr Ala Val Arg Leu Gly Asp Leu Glu
            565                 570                 575

Thr Ala Met Glu Leu Gly Arg Thr Val Leu Asp Gln Arg Arg Leu Pro
        580                 585                 590

Ser Leu Gly Val Ala Ala Gly Leu Leu Gly Gly Ala Val Thr Ala
        595                 600                 605

Ala Ile Arg Leu Gly Asp Leu Asp Arg Ala Glu Lys Trp Leu Ala Glu
    610                 615                 620

Pro Ile Pro Asp Ala Ile Arg Thr Ser Leu Tyr Gly Leu His Val Leu
625                 630                 635                 640

Ala Ala Arg Gly Arg Leu Asp Leu Ala Ala Gly Arg Tyr Glu Ala Ala
                645                 650                 655

Tyr Thr Ala Phe Arg Leu Cys Gly Glu Arg Met Ala Gly Trp Asp Ala
            660                 665                 670

Asp Val Ser Gly Leu Ala Leu Trp Arg Val Asp Ala Ala Glu Ala Leu
        675                 680                 685

Leu Ser Ala Gly Ile Arg Pro Asp Glu Gly Arg Lys Leu Ile Asp Asp
    690                 695                 700

Gln Leu Thr Arg Glu Met Gly Ala Arg Ser Arg Ala Leu Thr Leu Arg
705                 710                 715                 720

Ala Gln Ala Ala Tyr Ser Leu Pro Val His Arg Val Gly Leu Leu Asp
                725                 730                 735

Glu Ala Ala Gly Leu Leu Ala Cys His Asp Gly Tyr Glu Arg Ala
            740                 745                 750

Arg Val Leu Ala Asp Leu Gly Glu Thr Leu Arg Thr Leu Arg His Thr
        755                 760                 765

Asp Ala Ala Gln Arg Val Leu Arg Gln Ala Glu Gln Ala Ala Ala Arg
    770                 775                 780

Cys Gly Ser Val Pro Leu Leu Arg Arg Leu Gly Ala Glu Pro Val Arg
785                 790                 795                 800

Ile Gly Thr Arg Arg Gly Glu Pro Gly Leu Pro Gln Arg Ile Arg Leu
                805                 810                 815

Leu Thr Asp Ala Glu Arg Arg Val Ala Ala Met Ala Ala Ala Gly Gln
            820                 825                 830

Thr Asn Arg Glu Ile Ala Gly Arg Leu Phe Val Thr Ala Ser Thr Val
        835                 840                 845

Glu Gln His Leu Thr Ser Val Phe Arg Lys Leu Gly Val Lys Gly Arg
    850                 855                 860

Arg Phe Leu Pro Thr Glu Leu Ala Gln Ala Val
865                 870                 875

<210> SEQ ID NO 33
<211> LENGTH: 906
<212> TYPE: PRT
<213> ORGANISM: Streptomyces malaysiensis

<400> SEQUENCE: 33

Met Tyr Ser Gly Thr Cys Arg Glu Gly Tyr Glu Leu Val Ala Arg Glu
1               5                   10                  15

Asp Glu Leu Gly Ile Leu Gln Arg Ser Leu Glu Gln Ala Ser Ser Gly
            20                  25                  30

Gln Gly Val Val Val Thr Val Thr Gly Pro Ile Ala Cys Gly Lys Thr
        35                  40                  45

Glu Leu Leu Asp Ala Ala Ala Ala Lys Ala Glu Ala Ile Ile Leu Arg
    50                  55                  60
```

-continued

```
Ala Val Cys Ala Pro Glu Glu Arg Ala Met Pro Tyr Ala Met Ile Gly
 65                  70                  75                  80

Gln Leu Ile Asp Asp Pro Ala Leu Ala His Arg Ala Pro Gly Leu Ala
                 85                  90                  95

Asp Arg Ile Ala Gln Gly Gly Gln Leu Ser Leu Arg Ala Glu Asn Arg
                100                 105                 110

Leu Arg Arg Asp Leu Thr Arg Ala Leu Leu Ala Leu Ala Val Asp Arg
            115                 120                 125

Pro Val Leu Ile Gly Val Asp Asp Val His His Ala Asp Thr Ala Ser
130                 135                 140

Leu Asn Cys Leu Leu His Leu Ala Arg Arg Val Arg Pro Ala Arg Ile
145                 150                 155                 160

Ser Met Ile Phe Thr Glu Leu Arg Ser Leu Thr Pro Thr Gln Ser Arg
                165                 170                 175

Phe Lys Ala Glu Leu Leu Ser Leu Pro Tyr His His Glu Ile Ala Leu
                180                 185                 190

Arg Pro Phe Gly Pro Glu Gln Ser Ala Glu Leu Ala Arg Ala Ala Phe
            195                 200                 205

Gly Pro Gly Leu Ala Glu Asp Val Leu Ala Gly Leu Tyr Lys Thr Thr
210                 215                 220

Arg Gly Asn Leu Ser Leu Ser Arg Gly Leu Ile Ser Asp Val Arg Glu
225                 230                 235                 240

Ala Leu Ala Asn Gly Glu Ser Ala Phe Glu Ala Gly Arg Ala Phe Arg
                245                 250                 255

Leu Ala Tyr Leu Ser Ser Leu Tyr Arg Cys Gly Pro Val Ala Leu Arg
                260                 265                 270

Val Ala Arg Val Ala Ala Val Leu Gly Pro Ser Ala Thr Thr Thr Leu
            275                 280                 285

Val Arg Arg Leu Ser Gly Leu Ser Ala Glu Thr Ile Asp Arg Ala Thr
290                 295                 300

Lys Ile Leu Thr Glu Gly Gly Leu Leu Leu Asp Gln Gln Phe Pro His
305                 310                 315                 320

Pro Ala Ala Arg Ser Val Val Leu Asp Asp Met Ser Ala Gln Glu Arg
                325                 330                 335

Arg Ser Leu His Thr Leu Ala Leu Glu Leu Leu Asp Glu Ala Pro Val
                340                 345                 350

Glu Val Leu Ala His His Gln Val Gly Ala Gly Leu Ile His Gly Pro
            355                 360                 365

Lys Ala Ala Glu Met Phe Ala Lys Ala Gly Lys Ala Leu Val Val Arg
370                 375                 380

Asn Glu Leu Gly Asp Ala Ala Glu Tyr Leu Gln Leu Ala His Arg Ala
385                 390                 395                 400

Ser Asp Asp Val Ser Thr Arg Ala Ala Leu Arg Val Glu Ala Val Ala
                405                 410                 415

Ile Glu Arg Arg Arg Asn Pro Leu Ala Ser Ser Arg His Met Asp Glu
                420                 425                 430

Leu Ser Ala Ala Gly Arg Ala Gly Leu Leu Ser Pro Lys His Ala Ala
            435                 440                 445

Leu Ala Val Phe Trp Leu Ala Asp Gly Gly Arg Ser Gly Glu Ala Ala
450                 455                 460

Glu Val Leu Ala Ser Glu Arg Pro Leu Ala Thr Thr Asp Gln Asn Arg
465                 470                 475                 480
```

```
Ala His Leu Arg Phe Val Glu Val Thr Leu Ala Leu Phe Ser Pro Gly
            485                 490                 495
Ala Phe Gly Ser Asp Arg Arg Pro Pro Leu Thr Pro Asp Glu Leu
        500                 505                 510
Ala Ser Leu Pro Lys Ala Ala Trp Gln Cys Ala Val Ala Asp Asn Ala
            515                 520                 525
Ala Met Thr Ala Leu His Gly His Pro Glu Leu Ala Thr Ala Gln Ala
        530                 535                 540
Glu Thr Val Leu Arg Gln Ala Asp Ser Ala Ala Asp Ala Ile Pro Ala
545                 550                 555                 560
Ala Leu Ile Ala Leu Leu Tyr Ala Glu Asn Thr Glu Ser Ala His Ile
            565                 570                 575
Trp Ala Asp Lys Leu Gly Ser Thr Asn Ala Gly Val Ser Asn Glu Ala
            580                 585                 590
Glu Ala Gly Tyr Ala Gly Pro Cys Ala Glu Ile Ala Leu Arg Arg Gly
            595                 600                 605
Asp Leu Ala Thr Ala Phe Glu Ala Gly Ser Ala Val Leu Asp Asp Arg
        610                 615                 620
Ser Leu Pro Ser Leu Gly Ile Thr Ala Ala Leu Leu Leu Ser Ser Lys
625                 630                 635                 640
Thr Ala Ala Ala Val Arg Leu Gly Glu Leu Glu Arg Ala Glu Lys Leu
            645                 650                 655
Leu Ala Glu Pro Leu Pro Asn Gly Val Gln Asp Ser Leu Phe Gly Leu
            660                 665                 670
His Leu Leu Ser Ala Tyr Gly Gln Tyr Ser Leu Ala Met Gly Arg Tyr
        675                 680                 685
Glu Ser Ala His Arg Ala Phe Arg Thr Cys Gly Glu Arg Met Arg Ser
        690                 695                 700
Trp Asp Val Asp Val Pro Gly Leu Ala Leu Trp Arg Val Asp Ala Ala
705                 710                 715                 720
Glu Ala Leu Leu Ser Leu Asp Arg Asn Glu Gly Gln Arg Leu Ile Asp
            725                 730                 735
Glu Gln Leu Thr Arg Pro Met Gly Pro Arg Ser His Ala Leu Thr Leu
        740                 745                 750
Arg Ile Lys Ala Ala Tyr Leu Pro Arg Thr Lys Arg Ile Pro Leu Leu
        755                 760                 765
His Glu Ala Ala Glu Leu Leu Leu Pro Cys Pro Asp Pro Tyr Glu Gln
        770                 775                 780
Ala Arg Val Leu Ala Asp Leu Gly Asp Thr Leu Ser Ala Leu Arg Arg
785                 790                 795                 800
Tyr Ser Arg Ala Arg Gly Val Leu Arg Gln Ala Arg His Leu Ala Thr
            805                 810                 815
Gln Cys Gly Ala Val Pro Leu Leu Arg Arg Leu Gly Gly Glu Pro Gly
            820                 825                 830
Arg Ile Asp Asp Ala Gly Leu Pro Gln Arg Ser Thr Ser Leu Thr Asp
        835                 840                 845
Ala Glu Arg Arg Val Ala Ala Leu Ala Ala Gly Gln Thr Asn Arg
850                 855                 860
Glu Ile Ala Glu Gln Leu Phe Val Thr Ala Ser Thr Val Glu Gln His
865                 870                 875                 880
Leu Thr Ser Val Phe Arg Lys Leu Gly Val Lys Gly Arg Lys Gln Leu
            885                 890                 895
Pro Thr Ala Leu Ala Asp Val Glu Gln Thr
```

-continued

```
            900             905
```

<210> SEQ ID NO 34
<211> LENGTH: 904
<212> TYPE: PRT
<213> ORGANISM: Streptomyces violaceusniger

<400> SEQUENCE: 34

Met Tyr Ser Gly Thr Cys Arg Glu Gly Tyr Glu Leu Val Ala Arg Glu
1               5                   10                  15

Asp Glu Leu Gly Ile Leu Gln Arg Ser Leu Glu Glu Ala Gly Ser Gly
            20                  25                  30

Gln Gly Ala Val Val Thr Val Gly Pro Ile Ala Cys Gly Lys Thr
        35                  40                  45

Glu Leu Leu Asp Ala Ala Ala Lys Ala Asp Ala Ile Ile Leu Arg
    50                  55                  60

Ala Val Cys Ala Pro Glu Glu Arg Ala Met Pro Tyr Ala Met Ile Gly
65                  70                  75                  80

Gln Leu Ile Asp Asp Pro Ala Leu Ala His Arg Ala Pro Glu Leu Ala
                85                  90                  95

Asp Arg Ile Ala Gln Gly Gly His Leu Ser Leu Arg Ala Glu Asn Arg
            100                 105                 110

Leu Arg Arg Asp Leu Thr Arg Ala Leu Leu Ala Leu Val Asp Arg
        115                 120                 125

Pro Val Leu Ile Gly Val Asp Asp Val His His Ala Asp Thr Ala Ser
130                 135                 140

Leu Asn Cys Leu Leu His Leu Ala Arg Arg Val Arg Pro Ala Arg Ile
145                 150                 155                 160

Ser Met Ile Phe Thr Glu Leu Arg Ser Leu Thr Pro Thr Gln Ser Arg
                165                 170                 175

Phe Lys Ala Glu Leu Leu Ser Leu Pro Tyr His His Glu Ile Ala Leu
            180                 185                 190

Arg Pro Leu Gly Pro Glu Gln Ser Ala Glu Leu Ala His Ala Ala Phe
        195                 200                 205

Gly Pro Gly Leu Ala Glu Asp Val Leu Ala Gly Leu Tyr Gly Met Thr
    210                 215                 220

Arg Gly Asn Leu Ser Leu Ser Arg Gly Leu Ile Ser Asp Val Arg Glu
225                 230                 235                 240

Ala Gln Ala Asn Gly Glu Ser Ala Phe Glu Val Gly Arg Ala Phe Arg
                245                 250                 255

Leu Ala Tyr Leu Ser Ser Leu Tyr Arg Cys Gly Pro Ile Ala Leu Arg
            260                 265                 270

Val Ala Arg Val Ala Ala Val Leu Gly Pro Ser Ala Thr Thr Thr Leu
        275                 280                 285

Val Arg Arg Leu Ser Gly Leu Ser Ala Glu Thr Ile Asp Arg Ala Thr
    290                 295                 300

Lys Ile Leu Thr Glu Gly Gly Leu Leu Leu Asp His Gln Phe Pro His
305                 310                 315                 320

Pro Ala Ala Arg Ser Val Val Leu Asp Asp Met Ser Ala Gln Glu Arg
                325                 330                 335

Arg Ser Leu His Thr Leu Ala Leu Glu Leu Leu Asp Glu Ala Pro Val
            340                 345                 350

Glu Val Leu Ala His His Gln Val Gly Ala Gly Leu Ile His Gly Pro
        355                 360                 365

```
Lys Ala Ala Glu Ile Phe Ala Arg Ala Gly Gln Ala Leu Val Val Arg
370                 375                 380

Asn Glu Leu Gly Asp Ala Ala Glu Tyr Leu Gln Leu Ala His Arg Ala
385                 390                 395                 400

Ser Asp Asp Val Ser Thr Arg Ala Ala Leu Arg Val Glu Ala Val Ala
            405                 410                 415

Ile Glu Arg Arg Arg Asn Pro Leu Ala Ser Arg His Met Asp Glu
                420                 425                 430

Leu Ser Ala Ala Gly Arg Ala Gly Leu Leu Ser Pro Lys His Ala Ala
        435                 440                 445

Leu Ala Val Phe Trp Leu Ala Asp Gly Gly Arg Ser Gly Glu Ala Ala
        450                 455                 460

Glu Val Leu Ala Ser Glu His Pro Leu Ala Thr Thr Asp Gln Asn Arg
465                 470                 475                 480

Ala His Leu Arg Phe Ala Glu Val Thr Leu Ala Leu Phe Cys Pro Gly
                485                 490                 495

Ala Phe Gly Ser Asp Arg Arg Pro Pro Pro Leu Ala Pro Asp Glu Leu
            500                 505                 510

Ala Ser Leu Pro Lys Ala Ala Trp Gln Cys Ala Val Ala Asp Asn Ala
        515                 520                 525

Val Met Thr Ala Leu His Ala His Pro Glu Leu Ala Thr Ala Gln Ala
530                 535                 540

Glu Thr Val Leu Arg Gln Ala Asp Ser Ala Ala Asp Ala Ile Pro Ala
545                 550                 555                 560

Ala Leu Ile Ala Leu Leu Tyr Ala Glu Asn Thr Glu Ser Ala Gln Ile
                565                 570                 575

Trp Ala Asp Lys Leu Gly Ser Thr Asn Ala Gly Val Ser Asn Glu Ala
            580                 585                 590

Glu Ala Gly Tyr Ala Gly Pro Cys Ala Glu Ile Ala Leu Arg Arg Gly
        595                 600                 605

Asp Leu Ala Thr Ala Phe Glu Ala Gly Gly Thr Val Leu Asp Asp Arg
        610                 615                 620

Pro Leu Pro Ser Leu Gly Ile Thr Ala Ala Leu Leu Leu Ser Ser Lys
625                 630                 635                 640

Thr Ala Ala Ala Val Arg Leu Gly Glu Leu Glu Arg Ala Glu Lys Leu
                645                 650                 655

Leu Ala Glu Pro Leu Pro Asn Gly Val Gln Asp Ser Leu Phe Gly Leu
            660                 665                 670

His Leu Leu Ser Ala His Gly Gln Tyr Ser Leu Ala Met Gly Arg Tyr
        675                 680                 685

Glu Ser Ala His Arg Ala Phe His Thr Cys Gly Glu Arg Met Arg Ser
690                 695                 700

Trp Gly Val Asp Val Pro Gly Leu Ala Leu Trp Arg Val Asp Ala Ala
705                 710                 715                 720

Glu Ala Leu Leu Ser Leu Asp Arg Asn Glu Gly Gln Arg Leu Ile Asp
                725                 730                 735

Glu Gln Leu Ala Arg Pro Met Gly Pro Arg Ser Arg Ala Leu Thr Leu
            740                 745                 750

Arg Ile Lys Ala Ala Tyr Leu Pro Arg Thr Lys Arg Ile Pro Leu Leu
        755                 760                 765

His Glu Ala Ala Glu Leu Leu Leu Ser Cys Pro Asp Pro Tyr Glu Gln
770                 775                 780

Ala Arg Val Leu Ala Asp Leu Gly Asp Thr Leu Ser Ala Leu Arg Arg
```

```
            785                 790                 795                 800
        Tyr Ser Arg Ala Arg Gly Val Leu Arg Gln Ala Arg His Leu Ala Thr
                        805                 810                 815
        Gln Cys Gly Ala Val Pro Leu Leu Arg Arg Leu Gly Gly Glu Pro Gly
                        820                 825                 830
        Arg Ile Asp Asp Ala Gly Leu Pro Gln Arg Ser Thr Ser Leu Thr Asp
                        835                 840                 845
        Ala Glu Arg Arg Val Ser Ala Leu Ala Ala Ala Gly Gln Thr Asn Arg
                        850                 855                 860
        Glu Ile Ala Lys Gln Leu Phe Val Thr Ala Ser Thr Val Glu Gln His
        865                 870                 875                 880
        Leu Thr Ser Val Phe Arg Lys Leu Gly Val Lys Gly Arg Arg Gln Leu
                        885                 890                 895
        Pro Thr Ala Leu Ala Asp Val Glu
                        900

<210> SEQ ID NO 35
<211> LENGTH: 906
<212> TYPE: PRT
<213> ORGANISM: Streptomyces Sp. NRRL F-4729

<400> SEQUENCE: 35

Met Tyr Ser Gly Thr Cys Arg Glu Gly Tyr Glu Leu Val Ala Arg Glu
        1               5                   10                  15
        Asp Glu Leu Gly Ile Leu Gln Arg Ser Leu Glu Gln Ala Ser Ser Gly
                        20                  25                  30
        Gln Gly Val Val Val Thr Val Thr Gly Pro Ile Ala Cys Gly Lys Thr
                        35                  40                  45
        Glu Leu Leu Asp Ala Ala Ala Lys Ala Glu Ala Ile Ile Leu Arg
        50                  55                  60
        Ala Val Cys Ala Pro Glu Glu Arg Ala Met Pro Tyr Ala Met Ile Gly
        65                  70                  75                  80
        Gln Leu Ile Asp Asp Pro Ala Leu Ala His Arg Ala Pro Gly Leu Ala
                        85                  90                  95
        Asp Arg Ile Ala Gln Gly Gly Gln Leu Ser Leu Arg Ala Glu Asn Arg
                        100                 105                 110
        Leu Arg Arg Asp Leu Thr Arg Ala Leu Leu Ala Leu Ala Val His Arg
                        115                 120                 125
        Pro Val Leu Ile Gly Val Asp Asp Val His His Ala Asp Thr Ala Ser
                        130                 135                 140
        Leu Asn Cys Leu Leu His Leu Ala Arg Arg Val Arg Pro Ala Arg Ile
        145                 150                 155                 160
        Ser Met Ile Phe Thr Glu Leu Arg Ser Leu Thr Pro Thr Gln Ser Arg
                        165                 170                 175
        Phe Lys Ala Glu Leu Leu Ser Leu Pro Tyr His His Glu Ile Ala Leu
                        180                 185                 190
        Arg Pro Phe Gly Pro Glu Gln Ser Ala Glu Leu Ala Arg Ala Ala Phe
                        195                 200                 205
        Gly Pro Gly Leu Ala Glu Asp Val Leu Ala Gly Leu Tyr Lys Thr Thr
                        210                 215                 220
        Arg Gly Asn Leu Ser Leu Ser Arg Gly Leu Ile Ser Asp Val Arg Glu
        225                 230                 235                 240
        Ala Leu Ala Asn Gly Glu Ser Ala Phe Glu Ala Gly Arg Ala Phe Arg
                        245                 250                 255
```

-continued

```
Leu Ala Tyr Leu Ser Ser Leu Tyr Arg Cys Gly Pro Val Ala Leu Arg
            260                 265                 270

Val Ala Arg Val Ala Ala Val Leu Gly Pro Ser Ala Thr Thr Thr Leu
        275                 280                 285

Val Arg Arg Leu Ser Gly Leu Ser Ala Glu Thr Ile Asp Arg Ala Thr
290                 295                 300

Lys Ile Leu Thr Glu Gly Gly Leu Leu Leu Asp Gln Gln Phe Pro His
305                 310                 315                 320

Pro Ala Ala Arg Ser Val Val Leu Asp Asp Met Ser Ala Gln Glu Arg
                325                 330                 335

Arg Gly Leu His Thr Leu Ala Leu Glu Leu Leu Asp Glu Ala Pro Val
            340                 345                 350

Glu Val Leu Ala His His Gln Val Gly Ala Gly Leu Ile His Gly Pro
        355                 360                 365

Lys Ala Ala Glu Met Phe Ala Lys Ala Gly Lys Ala Leu Val Val Arg
    370                 375                 380

Asn Glu Leu Gly Asp Ala Ala Glu Tyr Leu Gln Leu Ala His Arg Ala
385                 390                 395                 400

Ser Asp Asp Val Ser Thr Arg Ala Ala Leu Arg Val Glu Ala Val Ala
                405                 410                 415

Ile Glu Arg Arg Arg Asn Pro Leu Ala Ser Ser Arg His Met Asp Glu
            420                 425                 430

Leu Ser Ala Ala Gly Arg Ala Gly Leu Leu Ser Pro Lys His Ala Ala
        435                 440                 445

Leu Ala Val Phe Trp Leu Ala Asp Gly Gly Arg Ser Gly Glu Ala Ala
    450                 455                 460

Gln Val Leu Ala Ser Glu Arg Pro Leu Ala Thr Thr Asp Gln Asn Arg
465                 470                 475                 480

Ala His Leu Arg Phe Val Glu Val Thr Leu Ala Leu Phe Ser Pro Gly
                485                 490                 495

Ala Phe Gly Ser Asp Arg Arg Pro Pro Leu Thr Pro Asp Glu Leu
            500                 505                 510

Ala Ser Leu Pro Lys Ala Ala Trp Gln Cys Ala Val Ala Asp Asn Ala
    515                 520                 525

Ala Met Thr Ala Leu His Gly His Pro Glu Leu Ala Thr Ala Gln Ala
530                 535                 540

Glu Thr Val Leu Arg Gln Ala Asp Ser Ala Ala Asp Ala Ile Pro Ala
545                 550                 555                 560

Ala Leu Ile Ala Leu Leu Tyr Ala Glu Asn Thr Glu Ser Ala His Ile
                565                 570                 575

Trp Ala Asp Lys Leu Gly Ser Met Asn Ala Gly Val Ser Asn Glu Ala
            580                 585                 590

Glu Ala Gly Tyr Ala Gly Pro Cys Ala Glu Ile Ala Leu Arg Arg Gly
        595                 600                 605

Asp Leu Ala Thr Ala Phe Glu Ala Gly Ser Thr Val Leu Asp Asp Arg
    610                 615                 620

Ser Leu Pro Ser Leu Gly Ile Thr Ala Leu Leu Leu Ser Ser Lys
625                 630                 635                 640

Thr Ala Ala Ala Val Arg Leu Gly Glu Leu Glu Arg Ala Glu Lys Leu
                645                 650                 655

Leu Ala Glu Pro Leu Pro Asn Gly Val Gln Asp Ser Leu Phe Gly Leu
            660                 665                 670

His Leu Leu Ser Ala Tyr Gly Gln Tyr Ser Leu Ala Met Gly Arg Tyr
```

```
                675                 680                 685
Glu Ser Ala His Arg Ala Phe Arg Thr Cys Gly Glu Arg Met Arg Ser
690                 695                 700

Trp Asp Val Asp Val Pro Gly Leu Ala Leu Trp Arg Val Asp Ala Ala
705                 710                 715                 720

Glu Ala Leu Leu Ser Leu Asp Arg Asn Glu Gly Gln Arg Leu Ile Asp
                725                 730                 735

Glu Gln Leu Thr Arg Pro Met Gly Pro Arg Ser Arg Ala Leu Thr Leu
            740                 745                 750

Arg Ile Lys Ala Ala Tyr Leu Pro Arg Thr Lys Arg Ile Pro Leu Leu
        755                 760                 765

His Glu Ala Ala Glu Leu Leu Leu Pro Cys Pro Asp Pro Tyr Glu Gln
    770                 775                 780

Ala Arg Val Leu Ala Asp Leu Gly Asp Thr Leu Ser Ala Leu Arg Arg
785                 790                 795                 800

Tyr Ser Arg Ala Arg Gly Val Leu Arg Gln Ala Arg His Leu Ala Thr
                805                 810                 815

Gln Cys Gly Ala Val Pro Leu Leu Arg Arg Leu Gly Gly Glu Pro Gly
            820                 825                 830

Arg Ile Asp Asp Ala Gly Leu Pro Gln Arg Ser Thr Ser Leu Thr Asp
        835                 840                 845

Ala Glu Arg Arg Val Ala Ala Leu Ala Ala Ala Gly Gln Thr Asn Arg
    850                 855                 860

Glu Ile Ala Glu Gln Leu Phe Val Thr Ala Ser Thr Val Glu Gln His
865                 870                 875                 880

Leu Thr Ser Val Phe Arg Lys Leu Gly Val Lys Gly Arg Lys Gln Leu
                885                 890                 895

Pro Thr Ala Leu Ala Asp Val Glu Gln Thr
            900                 905

<210> SEQ ID NO 36
<211> LENGTH: 904
<212> TYPE: PRT
<213> ORGANISM: Streptomyces filamentosus

<400> SEQUENCE: 36

Met Arg Ala Ile Asn Ala Ser Asp Thr Gly Pro Glu Leu Val Ala Arg
1               5                   10                  15

Glu Asp Glu Leu Gly Arg Val Arg Ser Ala Leu Asn Arg Ala Asn Gly
            20                  25                  30

Gly Gln Gly Val Leu Ile Ser Ile Thr Gly Pro Ile Ala Cys Gly Lys
        35                  40                  45

Thr Glu Leu Leu Glu Ala Ala Ser Glu Val Asp Ala Ile Thr Leu
    50                  55                  60

Arg Ala Val Cys Ala Ala Glu Glu Arg Ala Ile Pro Tyr Ala Leu Ile
65                  70                  75                  80

Gly Gln Leu Ile Asp Asn Pro Ala Leu Gly Ile Pro Val Pro Asp Pro
                85                  90                  95

Ala Gly Leu Thr Ala Gln Gly Gly Arg Leu Ser Ser Ser Ala Glu Asn
            100                 105                 110

Arg Leu Arg Arg Asp Leu Thr Arg Ala Leu Leu Thr Leu Ala Thr Asp
        115                 120                 125

Arg Leu Val Leu Ile Cys Val Asp Asp Val Gln His Ala Asp Asn Ala
    130                 135                 140
```

-continued

```
Ser Leu Ser Cys Leu Leu Tyr Leu Ala Arg Arg Leu Val Pro Ala Arg
145                 150                 155                 160

Ile Ala Leu Val Phe Thr Glu Leu Arg Val Leu Thr Ser Ser Gln Leu
                165                 170                 175

Arg Phe Asn Ala Glu Leu Leu Ser Leu Arg Asn His Cys Glu Ile Ala
            180                 185                 190

Leu Arg Pro Leu Gly Pro Gly His Ala Ala Glu Leu Ala Arg Ala Thr
        195                 200                 205

Leu Gly Pro Gly Leu Ser Asp Glu Thr Leu Thr Glu Leu Tyr Arg Val
    210                 215                 220

Thr Gly Asn Leu Ser Leu Ser Arg Gly Leu Ile Asp Asp Val Arg
225                 230                 235                 240

Asp Ala Trp Ala Arg Gly Glu Thr Gly Val Gln Val Gly Arg Ala Phe
                245                 250                 255

Arg Leu Ala Tyr Leu Gly Ser Leu His Arg Cys Gly Pro Leu Ala Leu
                260                 265                 270

Arg Val Ala Arg Val Ala Ala Val Leu Gly Pro Ser Ala Thr Ser Val
            275                 280                 285

Leu Val Arg Arg Ile Ser Gly Leu Ser Ala Glu Ala Met Ala Gln Ala
        290                 295                 300

Thr Asp Ile Leu Ala Asp Gly Gly Leu Leu Arg Asp Gln Arg Phe Thr
305                 310                 315                 320

His Pro Ala Ala Arg Ser Val Val Leu Asp Asp Met Ser Ala Glu Glu
                325                 330                 335

Arg Arg Ser Val His Ser Leu Ala Leu Glu Leu Leu Asp Glu Ala Pro
            340                 345                 350

Ala Glu Met Leu Ala His His Arg Val Gly Ala Gly Leu Val His Gly
        355                 360                 365

Pro Lys Ala Ala Glu Thr Phe Thr Gly Ala Gly Arg Ala Leu Ala Val
    370                 375                 380

Arg Gly Met Leu Gly Glu Ala Ala Asp Tyr Leu Gln Leu Ala Tyr Arg
385                 390                 395                 400

Ala Ser Gly Asp Ala Ala Thr Lys Ala Ala Ile Arg Val Glu Ser Val
                405                 410                 415

Ala Val Glu Arg Arg Asn Pro Leu Val Val Ser Arg His Trp Asp
            420                 425                 430

Glu Leu Ser Val Ala Ala Arg Ala Gly Leu Leu Ser Cys Glu His Val
        435                 440                 445

Ser Arg Thr Ala Arg Trp Leu Thr Val Gly Arg Pro Gly Glu Ala
    450                 455                 460

Ala Arg Val Leu Ala Ser Gln His Arg Val Val Thr Asp Gln Asp
465                 470                 475                 480

Arg Ala His Leu Arg Val Ala Glu Phe Ser Leu Ala Leu Tyr Pro
                485                 490                 495

Gly Thr Ser Gly Ser Asp Arg Arg Pro His Pro Leu Thr Ser Asp Glu
            500                 505                 510

Leu Ala Ala Leu Pro Thr Ala Thr Arg His Cys Ala Ile Ala Asp Asn
        515                 520                 525

Ala Val Met Ala Ala Leu Arg Gly His Pro Glu Leu Ala Thr Ala Glu
    530                 535                 540

Ala Glu Ala Val Leu Gln Gln Ala Asp Ala Ala Asp Gly Ala Ala Leu
545                 550                 555                 560

Thr Ala Leu Met Ala Leu Leu Tyr Ala Glu Ser Ile Glu Val Ala Glu
```

Val Trp Ala Asp Lys Leu Ala Ala Glu Ala Gly Ala Ser Asn Gly Gln
              565                 570                 575
            580                 585                 590

Asp Ala Glu Tyr Ala Gly Ile Arg Ala Glu Ile Ala Leu Arg Arg Gly
            595                 600                 605

Asp Leu Thr Ala Ala Val Glu Thr Ala Gly Met Val Leu Asp Gly Arg
            610                 615                 620

Pro Leu Pro Ser Leu Asp Ile Thr Ala Thr Leu Leu Ala Gly Arg
625                 630                 635                 640

Ala Ser Val Ala Val Arg Leu Gly Glu Leu Asp His Ala Glu Glu Leu
                645                 650                 655

Phe Ala Ala Pro Pro Glu Asp Ala Phe Gln Asp Ser Leu Phe Gly Leu
                660                 665                 670

His Leu Leu Ser Ala His Gly Gln Tyr Ser Leu Ala Thr Gly Arg Pro
                675                 680                 685

Glu Ser Ala Tyr Arg Ala Phe Arg Ala Cys Gly Glu Arg Met Arg Asp
            690                 695                 700

Trp Gly Phe Asp Ala Pro Gly Val Ala Leu Trp Arg Val Gly Ala Ala
705                 710                 715                 720

Glu Ala Leu Leu Gly Leu Asp Arg Asn Glu Gly Arg Leu Ile Asp
                    725                 730                 735

Glu Gln Leu Ser Arg Thr Met Ala Pro Arg Ser His Ala Leu Thr Leu
                740                 745                 750

Arg Ile Lys Ala Ala Tyr Met Pro Glu Pro Lys Arg Val Asp Leu Leu
                755                 760                 765

Tyr Glu Ala Ala Glu Leu Leu Leu Ser Cys Arg Asp Gln Tyr Glu Arg
                770                 775                 780

Ala Arg Val Leu Ala Asp Leu Gly Glu Ala Leu Ser Ala Leu Gly Asn
785                 790                 795                 800

Tyr Arg Gln Ala Arg Gly Val Leu Arg Gln Ala Arg His Leu Ala Met
                    805                 810                 815

Arg Thr Gly Ala Asp Pro Leu Leu Arg Arg Leu Gly Ile Arg Pro Gly
                820                 825                 830

Arg Gln Asp Asp Pro Asp Pro Gln Pro Arg Ser Arg Ser Leu Thr Asn
                835                 840                 845

Ala Glu Arg Arg Ala Ala Ser Leu Ala Ala Thr Gly Leu Thr Asn Arg
            850                 855                 860

Glu Ile Ala Asp Arg Leu Phe Val Thr Ala Ser Thr Val Glu Gln His
865                 870                 875                 880

Leu Thr Asn Val Phe Arg Lys Leu Gly Val Lys Gly Arg Lys Gln Leu
                    885                 890                 895

Pro Ala Glu Leu Asp Asp Met Glu
            900

<210> SEQ ID NO 37
<211> LENGTH: 75
<212> TYPE: DNA
<213> ORGANISM: Artificial Sequence
<220> FEATURE:
<223> OTHER INFORMATION: synthetic construct

<400> SEQUENCE: 37
caaagcgatt cggagagcgg ccggatcaga tccaggcgtg acattcatac ccttccggcg      60
aagtgcagtt caccc                                                      75

<210> SEQ ID NO 38
<211> LENGTH: 73
<212> TYPE: DNA
<213> ORGANISM: Artificial Sequence
<220> FEATURE:
<223> OTHER INFORMATION: synthetic construct

<400> SEQUENCE: 38
cgatcttctc gaaactgcac tgaggaggtt cgtcggagac tgccattcac ctctcccgga    60
aaggtattgc tcg    73

<210> SEQ ID NO 39
<211> LENGTH: 429
<212> TYPE: DNA
<213> ORGANISM: Streptomyces filamentosus

<400> SEQUENCE: 39
gcgttcggca ttgacgcgaa gcaagtcatg aatcggctga atcaattccg cgcgcgacat    60
tcgcacccct tccggtgaagt gcggtattgc tcagacataa cccggatcgc aatccaacga   120
ccagccatgc actaccgata atcgaatcgg aacaatagca agctcgttga gcatattttc   180
catgcggcac cacctcggcg ccacccccta gttttgccga cccccatgt gtatttcggc    240 aggcagacta gggggttgcg tgggccgcac cgaggcatt cgattggcgc acggcgcact    300
cgggccatgt caccgaccgt gaatgtttca tcgctacggg tagcaatagt cctttctcgg   360
gagaagtgaa tggcttccaa aagtccccgc ccagggtccg agagagcggg ttctgcgatt   420
tcccgggca    429

<210> SEQ ID NO 40
<211> LENGTH: 433
<212> TYPE: DNA
<213> ORGANISM: Streptomyces filamentosus

<400> SEQUENCE: 40
gcgttcggca ttgacgcgaa gcaagtcatg aatcggctga atcaattccg cgcgcgacat    60
tcgcacccct tccggtgaagt gcggtattgc tcagacataa cccggatcgc aatccaacga   120
ccagccatgc actaccgata atcgaatcgg aacaatagca agctcgttga gcatattttc   180
catgcggcac cacctcggcg ccacccccta gttttgccga cccccatgt gtatttcggc    240 aggcagaaca cctagggggt tgcgtgggcc gcacccgagg cattcgattg cgcacggcg    300 cactcgggcc atgtcaccga ccgtgaatgt ttcatcgcta cgggtagcaa tagtcctttc   360
tcgggagaag tgaatggctt ccaaaagtcc ccgcccaggg tccgagagag cgggttctgc   420
gatttcccgg gca    433

<210> SEQ ID NO 41
<211> LENGTH: 432
<212> TYPE: DNA
<213> ORGANISM: Streptomyces violaceusniger

<400> SEQUENCE: 41
gcgttcggca ttgacgcgaa gcaagtcatg aatcggctga atcaattccg cgcgcgacat    60
tcgcatcctt ctggtgaggt gcagtattgc tgagacataa tccggccgt aatccaacga    120 ccagccatgc gccgccgata gtcgaatccg atagtcgaat ctgaacgcta gcagctcgtc   180
gcaggggctc cggggagccc aaccccctaa ttttccgcc cccctataca tatccactgc    240
aggcagaaca cctagggggt tgcgcgaacc gggcgcgcgg tatcggattt accgcacggc   300

```
acactcgggc gacgtcaccg accgtgaatc cttcatcgct acgggtagca cagtcctttc    360
cgggagaagt gaatggcttc caaaagtccc cgcccagggt ccgagagagc gggttctgcg    420
atttcccggg ca                                                        432
```

<210> SEQ ID NO 42
<211> LENGTH: 350
<212> TYPE: DNA
<213> ORGANISM: Streptomyces violaceusniger

<400> SEQUENCE: 42

```
gcgttcggca ttgacgcgaa gcaagtcatg aatcggctga atcaattccg cgcgcgacat     60 tcatacccctt ccggcgaagt gcagttcacc cggtaatgca ttccggaccg tagcagtccg   120
atacagacgt ccgccatgcc gtgccaccct tgtttttcac cccctacgc ccgtttcgcc    180 tggccggaaa cctagggggt tgcgtggaaa gcaccggcgg gtgttcgctt gcacagcgcc    240
acctcgggca ttttctggat gcgcgagcaa tacctttccg ggagaggtga atggcttcca    300
aaagtccccg cccagggtcc gagagagcgg gttctgcgat ttcccgggca                350
```

<210> SEQ ID NO 43
<211> LENGTH: 52
<212> TYPE: DNA
<213> ORGANISM: Artificial Sequence
<220> FEATURE:
<223> OTHER INFORMATION: synthetic construct

<400> SEQUENCE: 43

```
gcgcccacct taatcgcagg tgtccacgca accccctagg tttccggcca gg             52
```

<210> SEQ ID NO 44
<211> LENGTH: 59
<212> TYPE: DNA
<213> ORGANISM: Artificial Sequence
<220> FEATURE:
<223> OTHER INFORMATION: synthetic construct

<400> SEQUENCE: 44

```
gttcatagct ctccacggca ggcattcata cccttccggc gaagtgcagt tcacccggt      59
```

<210> SEQ ID NO 45
<211> LENGTH: 53
<212> TYPE: DNA
<213> ORGANISM: Artificial Sequence
<220> FEATURE:
<223> OTHER INFORMATION: synthetic construct

<400> SEQUENCE: 45

```
gcgcccacct taatcgcagg tgccaccctt gttttcacc ccctacgcc cgt              53
```

<210> SEQ ID NO 46
<211> LENGTH: 60
<212> TYPE: DNA
<213> ORGANISM: Artificial Sequence
<220> FEATURE:
<223> OTHER INFORMATION: synthetic construct

<400> SEQUENCE: 46

```
gttcatagct ctccacggca ggcattcacc tctcccggaa aggtattgct cgtgcatcca     60
```

<210> SEQ ID NO 47
<211> LENGTH: 57
<212> TYPE: DNA

```
<213> ORGANISM: Artificial Sequence
<220> FEATURE:
<223> OTHER INFORMATION: synthetic construct

<400> SEQUENCE: 47
actgcacttc gccggaaggg tatgaatgcc tgccgtggag agctatgaac tggacgc         57

<210> SEQ ID NO 48
<211> LENGTH: 23
<212> TYPE: DNA
<213> ORGANISM: Artificial Sequence
<220> FEATURE:
<223> OTHER INFORMATION: synthetic construct

<400> SEQUENCE: 48
ccgggagggc catggagacc gga                                              23

<210> SEQ ID NO 49
<211> LENGTH: 57
<212> TYPE: DNA
<213> ORGANISM: Artificial Sequence
<220> FEATURE:
<223> OTHER INFORMATION: synthetic construct

<400> SEQUENCE: 49
agcaatacct ttccgggaga ggtgaatgcc tgccgtggag agctatgaac tggacgc         57

<210> SEQ ID NO 50
<211> LENGTH: 23
<212> TYPE: DNA
<213> ORGANISM: Artificial Sequence
<220> FEATURE:
<223> OTHER INFORMATION: synthetic construct

<400> SEQUENCE: 50
ccgggagggc catggagacc gga                                              23

<210> SEQ ID NO 51
<211> LENGTH: 82
<212> TYPE: DNA
<213> ORGANISM: Artificial Sequence
<220> FEATURE:
<223> OTHER INFORMATION: synthetic construct

<400> SEQUENCE: 51
ctacccgaat acatcgcctt ctggggccca gcccaaacca gcgccctcat ccacactcca      60
cgcaaccccc taggtttccg gc                                               82

<210> SEQ ID NO 52
<211> LENGTH: 91
<212> TYPE: DNA
<213> ORGANISM: Artificial Sequence
<220> FEATURE:
<223> OTHER INFORMATION: synthetic construct

<400> SEQUENCE: 52
gcggcccaca acgtgcacga gcgtggcgat atcggacgcg gaaagaacca gcgtgctcat      60
tcataccctt ccggcgaagt gcagttcacc c                                     91

<210> SEQ ID NO 53
<211> LENGTH: 26
<212> TYPE: DNA
<213> ORGANISM: Artificial Sequence
<220> FEATURE:
<223> OTHER INFORMATION: synthetic construct
```

<400> SEQUENCE: 53
cgccgtctac ccagcccaaa gccagc                                              26

<210> SEQ ID NO 54
<211> LENGTH: 26
<212> TYPE: DNA
<213> ORGANISM: Artificial Sequence
<220> FEATURE:
<223> OTHER INFORMATION: synthetic construct

<400> SEQUENCE: 54
cgggttcgtg gtgcggcatc cattcg                                              26

<210> SEQ ID NO 55
<211> LENGTH: 69
<212> TYPE: DNA
<213> ORGANISM: Artificial Sequence
<220> FEATURE:
<223> OTHER INFORMATION: synthetic construct

<400> SEQUENCE: 55
caaagcgatt cggagagcgg ccggatcaga tccaggcgtg acatggcctg gtgatgatgg         60
cgggatcgt                                                                 69

<210> SEQ ID NO 56
<211> LENGTH: 74
<212> TYPE: DNA
<213> ORGANISM: Artificial Sequence
<220> FEATURE:
<223> OTHER INFORMATION: synthetic construct

<400> SEQUENCE: 56
cgatcttctc gaaactgcac tgaggaggtt cgtcggagac tgccattcat cgcagtactg         60
ttgtattcat taag                                                           74

<210> SEQ ID NO 57
<211> LENGTH: 75
<212> TYPE: DNA
<213> ORGANISM: Artificial Sequence
<220> FEATURE:
<223> OTHER INFORMATION: synthetic construct

<400> SEQUENCE: 57
caaagcgatt cggagagcgg ccggatcaga tccaggcgtg acattcatac ccttccggcg         60
aagtgcagtt caccc                                                          75

<210> SEQ ID NO 58
<211> LENGTH: 73
<212> TYPE: DNA
<213> ORGANISM: Artificial Sequence
<220> FEATURE:
<223> OTHER INFORMATION: synthetic construct

<400> SEQUENCE: 58
cgatcttctc gaaactgcac tgaggaggtt cgtcggagac tgccattcac ctctcccgga         60
aaggtattgc tcg                                                            73

<210> SEQ ID NO 59
<211> LENGTH: 98
<212> TYPE: DNA
<213> ORGANISM: Artificial Sequence
<220> FEATURE:

<223> OTHER INFORMATION: synthetic construct

<400> SEQUENCE: 59
gcaaagcgat tcggagagcg gccggatcag atccaggcgt gacatgttta aacacaacgt    60
acctttcgga caagagtgcc gcggtgcaca gcctgacc    98

<210> SEQ ID NO 60
<211> LENGTH: 98
<212> TYPE: DNA
<213> ORGANISM: Artificial Sequence
<220> FEATURE:
<223> OTHER INFORMATION: synthetic construct

<400> SEQUENCE: 60
ggtcaggctg tgcaccgcgg cactcttgtc cgaaaggtac gttgtgttta aacatgtcac    60
gcctggatct gatccggccg ctctccgaat cgctttgc    98

<210> SEQ ID NO 61
<211> LENGTH: 98
<212> TYPE: DNA
<213> ORGANISM: Artificial Sequence
<220> FEATURE:
<223> OTHER INFORMATION: synthetic construct

<400> SEQUENCE: 61
tccacacctc tcggttcaca aacgtccgag cataagggag gtaaagttta aacatggcag    60
tctccgacga acctcctcag tgcagtttcg agaagatc    98

<210> SEQ ID NO 62
<211> LENGTH: 98
<212> TYPE: DNA
<213> ORGANISM: Artificial Sequence
<220> FEATURE:
<223> OTHER INFORMATION: synthetic construct

<400> SEQUENCE: 62
gatcttctcg aaactgcact gaggaggttc gtcggagact gccatgttta aactttacct    60
cccttatgct cggacgtttg tgaaccgaga ggtgtgga    98

<210> SEQ ID NO 63
<211> LENGTH: 75
<212> TYPE: DNA
<213> ORGANISM: Artificial Sequence
<220> FEATURE:
<223> OTHER INFORMATION: synthetic construct

<400> SEQUENCE: 63
caaagcgatt cggagagcgg ccggatcaga tccaggcgtg acattcatac ccttccggcg    60
aagtgcagtt caccc    75

<210> SEQ ID NO 64
<211> LENGTH: 73
<212> TYPE: DNA
<213> ORGANISM: Artificial Sequence
<220> FEATURE:
<223> OTHER INFORMATION: synthetic construct

<400> SEQUENCE: 64
cgatcttctc gaaactgcac tgaggaggtt cgtcggagac tgccattcac ctctcccgga    60
aaggtattgc tcg    73

<210> SEQ ID NO 65
<211> LENGTH: 87
<212> TYPE: DNA
<213> ORGANISM: Artificial Sequence
<220> FEATURE:
<223> OTHER INFORMATION: synthetic construct

<400> SEQUENCE: 65
cccgaaccac gatgagcact tgcctatgcg gtgtagggat aacagggtaa ttaattaatg    60
acctgcgccc accttaatcg caggtgc                                       87

<210> SEQ ID NO 66
<211> LENGTH: 98
<212> TYPE: DNA
<213> ORGANISM: Artificial Sequence
<220> FEATURE:
<223> OTHER INFORMATION: synthetic construct

<400> SEQUENCE: 66
tactttctat ttttaattta tatatttata ttaaaaaatt taaaatataa ttatttttat    60
agcacgtgat ggagcctatg gaaaaacgcc agcaacgc                           98

<210> SEQ ID NO 67
<211> LENGTH: 45
<212> TYPE: DNA
<213> ORGANISM: Artificial Sequence
<220> FEATURE:
<223> OTHER INFORMATION: synthetic construct

<400> SEQUENCE: 67
ggtagtattt gttggcgatc cccctagagt cttttacatc ttcgg                   45

<210> SEQ ID NO 68
<211> LENGTH: 22
<212> TYPE: DNA
<213> ORGANISM: Artificial Sequence
<220> FEATURE:
<223> OTHER INFORMATION: synthetic construct

<400> SEQUENCE: 68
agcctgcccc tcatctgtca ac                                            22

<210> SEQ ID NO 69
<211> LENGTH: 99
<212> TYPE: DNA
<213> ORGANISM: Artificial Sequence
<220> FEATURE:
<223> OTHER INFORMATION: synthetic construct

<400> SEQUENCE: 69
gttgatcgtg tggggcggcc tgccgagcag ctggtggacc cctggggcga gctggcgcat    60
tcacctgtat actgagagtg caccataaac gacattact                          99

<210> SEQ ID NO 70
<211> LENGTH: 94
<212> TYPE: DNA
<213> ORGANISM: Artificial Sequence
<220> FEATURE:
<223> OTHER INFORMATION: synthetic construct

<400> SEQUENCE: 70
gacgaccgcg gtccccacga ggacagcggc cgacgcaaca gctttgcgaa gacgagtcat    60
tcatacgtat acaggcaagt gcacaaacaa tact                               94

<210> SEQ ID NO 71
<211> LENGTH: 100
<212> TYPE: DNA
<213> ORGANISM: Artificial Sequence
<220> FEATURE:
<223> OTHER INFORMATION: synthetic construct

<400> SEQUENCE: 71
cgccggtgag gccagaccca tgagggtcag tgctgcgacc accgcgtacc tgatccgcat    60
tcacctgtta actcctgatg cggtattttc tccttacgca                         100

<210> SEQ ID NO 72
<211> LENGTH: 90
<212> TYPE: DNA
<213> ORGANISM: Artificial Sequence
<220> FEATURE:
<223> OTHER INFORMATION: synthetic construct

<400> SEQUENCE: 72
ctcggccggc agcaaggtct gctcgatcgc gatgatccgg ccgttccccc agtcgatcgt    60
gttaaccgac tacgtcgtaa ggccgtttct                                     90

<210> SEQ ID NO 73
<211> LENGTH: 102
<212> TYPE: DNA
<213> ORGANISM: Artificial Sequence
<220> FEATURE:
<223> OTHER INFORMATION: synthetic construct

<400> SEQUENCE: 73
gacgaacgcg aagtcgtcgc cgccctcctt catgcccagt ccggtggtcc agccgcggaa    60
gccgtgcgga tgcattcacc tctcccggaa aggtattgct cg                      102

<210> SEQ ID NO 74
<211> LENGTH: 102
<212> TYPE: DNA
<213> ORGANISM: Artificial Sequence
<220> FEATURE:
<223> OTHER INFORMATION: synthetic construct

<400> SEQUENCE: 74
tcgccacggg cggtcgagga actcgtcgcg gaccgccgcg acccgtgttc gcgcgccgtc    60
accgccgacg cgcattcata cccttccggc gaagtgcagt tc                      102

<210> SEQ ID NO 75
<211> LENGTH: 24
<212> TYPE: DNA
<213> ORGANISM: Artificial Sequence
<220> FEATURE:
<223> OTHER INFORMATION: synthetic construct

<400> SEQUENCE: 75
ggcgtggctg gagccgaagt ggtc                                           24

<210> SEQ ID NO 76
<211> LENGTH: 33
<212> TYPE: DNA
<213> ORGANISM: Artificial Sequence
<220> FEATURE:
<223> OTHER INFORMATION: synthetic construct

<400> SEQUENCE: 76
tcttccacta ctgccatctg gcgtcataac tgc                                 33

<210> SEQ ID NO 77
<211> LENGTH: 49
<212> TYPE: DNA
<213> ORGANISM: Artificial Sequence
<220> FEATURE:
<223> OTHER INFORMATION: synthetic construct

<400> SEQUENCE: 77
aggttattac tgagtagtat ttatttaagt attgtttgtg cacttgcct          49

<210> SEQ ID NO 78
<211> LENGTH: 21
<212> TYPE: DNA
<213> ORGANISM: Artificial Sequence
<220> FEATURE:
<223> OTHER INFORMATION: synthetic construct

<400> SEQUENCE: 78
actcggcggc gttggcgtgg c                                        21

<210> SEQ ID NO 79
<211> LENGTH: 19
<212> TYPE: DNA
<213> ORGANISM: Artificial Sequence
<220> FEATURE:
<223> OTHER INFORMATION: synthetic construct

<400> SEQUENCE: 79
accgtcgccc cgccgcagc                                           19

<210> SEQ ID NO 80
<211> LENGTH: 36
<212> TYPE: DNA
<213> ORGANISM: Artificial Sequence
<220> FEATURE:
<223> OTHER INFORMATION: synthetic construct

<400> SEQUENCE: 80
cgcacagatt cgtaaggaga aaataccgca tcagga                        36

<210> SEQ ID NO 81
<211> LENGTH: 32
<212> TYPE: DNA
<213> ORGANISM: Artificial Sequence
<220> FEATURE:
<223> OTHER INFORMATION: synthetic construct

<400> SEQUENCE: 81
actctgtcag aaacggcctt acgacgtagt cg                            32

<210> SEQ ID NO 82
<211> LENGTH: 22
<212> TYPE: DNA
<213> ORGANISM: Artificial Sequence
<220> FEATURE:
<223> OTHER INFORMATION: synthetic construct

<400> SEQUENCE: 82
cgggcggcac gcaaccgaag tg                                       22

<210> SEQ ID NO 83
<211> LENGTH: 23
<212> TYPE: DNA
<213> ORGANISM: Artificial Sequence
<220> FEATURE:

<223> OTHER INFORMATION: synthetic construct

<400> SEQUENCE: 83
gtgaagaccg ccgataccgc cgc                                    23

<210> SEQ ID NO 84
<211> LENGTH: 26
<212> TYPE: DNA
<213> ORGANISM: Artificial Sequence
<220> FEATURE:
<223> OTHER INFORMATION: synthetic construct

<400> SEQUENCE: 84
gggtgaaaaa caagggtggc acggca                                 26

<210> SEQ ID NO 85
<211> LENGTH: 26
<212> TYPE: DNA
<213> ORGANISM: Artificial Sequence
<220> FEATURE:
<223> OTHER INFORMATION: synthetic construct

<400> SEQUENCE: 85
tgccgtgcca cccttgtttt tcaccc                                 26

<210> SEQ ID NO 86
<211> LENGTH: 26
<212> TYPE: DNA
<213> ORGANISM: Artificial Sequence
<220> FEATURE:
<223> OTHER INFORMATION: synthetic construct

<400> SEQUENCE: 86
acgccaggcc cgttcacgac gaccgc                                 26

<210> SEQ ID NO 87
<211> LENGTH: 59
<212> TYPE: DNA
<213> ORGANISM: Artificial Sequence
<220> FEATURE:
<223> OTHER INFORMATION: synthetic construct

<400> SEQUENCE: 87
gctggtggac ccctggggcg agctggcgca ttcacctctc ccggaaaggt attgctcgc    59

<210> SEQ ID NO 88
<211> LENGTH: 65
<212> TYPE: DNA
<213> ORGANISM: Artificial Sequence
<220> FEATURE:
<223> OTHER INFORMATION: synthetic construct

<400> SEQUENCE: 88
aacagctttg cgaagacgag tcattcatac cattcatacc cttccggcga agtgcagttc    60
acccg                                                              65

<210> SEQ ID NO 89
<211> LENGTH: 62
<212> TYPE: DNA
<213> ORGANISM: Artificial Sequence
<220> FEATURE:
<223> OTHER INFORMATION: synthetic construct

<400> SEQUENCE: 89
tcagtgctgc gaccaccgcg tacctgatcc gcattcacct ctcccggaaa ggtattgctc    60

```
gc                                                              62

<210> SEQ ID NO 90
<211> LENGTH: 73
<212> TYPE: DNA
<213> ORGANISM: Artificial Sequence
<220> FEATURE:
<223> OTHER INFORMATION: synthetic construct

<400> SEQUENCE: 90
atcgcgatga tccggccgtt cccccagtcg atcgtccgca ttcataccct tccggcgaag    60
tgcagttcac ccg                                                      73

<210> SEQ ID NO 91
<211> LENGTH: 49
<212> TYPE: DNA
<213> ORGANISM: Streptomyces violaceusniger

<400> SEQUENCE: 91
tggccggaaa cctaggggt tgcgtggaaa gcaccggcgg gtgttcgct               49

<210> SEQ ID NO 92
<211> LENGTH: 49
<212> TYPE: DNA
<213> ORGANISM: Streptomyces rapamycinicus

<400> SEQUENCE: 92
aggcaggacg tctaggggt tgcgtggact gcggcctgag gtgtcttct               49

<210> SEQ ID NO 93
<211> LENGTH: 49
<212> TYPE: DNA
<213> ORGANISM: Streptomyces hygroscopicus

<400> SEQUENCE: 93
aggcaggaag cctaggggt tgcgtggact gcgacctggg gtgtcttct               49

<210> SEQ ID NO 94
<211> LENGTH: 47
<212> TYPE: DNA
<213> ORGANISM: Micromonospora sp. S92-306401

<400> SEQUENCE: 94
aggtacgaca cctaggggt tgcgtcggct gcgaccccgg tgtctcc                 47

<210> SEQ ID NO 95
<211> LENGTH: 48
<212> TYPE: DNA
<213> ORGANISM: Actinoplanes sp. N01-109

<400> SEQUENCE: 95
agctcggccc cctaggggt tgcgcccgct gaggcggagg tgtttggc                48

<210> SEQ ID NO 96
<211> LENGTH: 43
<212> TYPE: DNA
<213> ORGANISM: Streptomyces kanamyceticus

<400> SEQUENCE: 96
tgttgcccat ctaggggtt gcacgaataa cgtcacacgt act                     43

<210> SEQ ID NO 97
```

<211> LENGTH: 43
<212> TYPE: DNA
<213> ORGANISM: Streptomyces tacrolimicus

<400> SEQUENCE: 97
tgtcatatgt ctaggggggtt gcacgaatac cgtcgcgcgt act        43

<210> SEQ ID NO 98
<211> LENGTH: 43
<212> TYPE: DNA
<213> ORGANISM: Streptomyces ascomyceticus

<400> SEQUENCE: 98
ggacgctcat ctaggggggtt gcacgcatac cgccgtgcgt aat        43

<210> SEQ ID NO 99
<211> LENGTH: 39
<212> TYPE: DNA
<213> ORGANISM: Streptomyces violaceusniger

<400> SEQUENCE: 99
ggcgcctgtt ctaggggggtt gcggggagtg gcgcgcaca        39

<210> SEQ ID NO 100
<211> LENGTH: 66
<212> TYPE: PRT
<213> ORGANISM: Micromonospora sp. S92-306401

<400> SEQUENCE: 100

Gln Gly Ile Arg Ser Leu Thr Glu Ala Glu Arg Arg Val Ala Thr Leu
1               5                   10                  15

Ala Ala Ala Gly Gln Thr Asn Arg Glu Ile Ala Asp Gln Leu Phe Val
            20                  25                  30

Thr Ala Ser Thr Val Glu Gln His Leu Thr Asn Val Phe Arg Lys Leu
        35                  40                  45

Gly Val Lys Gly Arg Gln Gln Leu Pro Ala Glu Leu Ala Asp Leu Arg
    50                  55                  60

Pro Pro
65

<210> SEQ ID NO 101
<211> LENGTH: 66
<212> TYPE: PRT
<213> ORGANISM: Streptomyces violaceusniger

<400> SEQUENCE: 101

Gln Arg Ser Thr Ser Leu Thr Asp Ala Glu Arg Arg Val Ala Ala Leu
1               5                   10                  15

Ala Ala Ala Gly Gln Thr Asn Arg Glu Ile Ala Lys Gln Leu Phe Val
            20                  25                  30

Thr Ala Ser Thr Val Glu Gln His Leu Thr Ser Val Phe Arg Lys Leu
        35                  40                  45

Gly Val Lys Gly Arg Lys Gln Leu Pro Thr Ala Leu Ala Asp Val Glu
    50                  55                  60

Gln Thr
65

<210> SEQ ID NO 102
<211> LENGTH: 58
<212> TYPE: PRT
<213> ORGANISM: Streptomyces hygroscopicus

<400> SEQUENCE: 102

Gln Arg Ile Lys Ser Leu Thr Asp Ala Glu Arg Val Ala Ser Leu
1               5                   10                  15

Ala Ala Gly Gly Gln Thr Asn Arg Val Ile Ala Asp Gln Leu Phe Val
            20                  25                  30

Thr Ala Ser Thr Val Glu Gln His Leu Thr Asp Val Ser Thr Gly Ser
        35                  40                  45

Arg Pro Pro Ala Pro Ala Ala Glu Leu Val
    50                  55

<210> SEQ ID NO 103
<211> LENGTH: 64
<212> TYPE: PRT
<213> ORGANISM: Streptomyces ascomyceticus

<400> SEQUENCE: 103

Gln Arg Ile Thr Ser Leu Thr Glu Ala Glu Arg Val Ala Ser His
1               5                   10                  15

Ala Ala Val Gly Arg Thr Asn Lys Glu Ile Ala Ser Gln Leu Phe Val
            20                  25                  30

Thr Ser Ser Thr Val Glu Gln His Leu Thr Asn Val Phe Arg Lys Leu
        35                  40                  45

Gly Val Lys Gly Arg Gln Gln Leu Pro Lys Glu Leu Ser Asp Ala Gly
    50                  55                  60

<210> SEQ ID NO 104
<211> LENGTH: 74
<212> TYPE: PRT
<213> ORGANISM: Streptomyces kanamyceticus

<400> SEQUENCE: 104

Gln Arg Ile Ala Ser Leu Thr Glu Ser Glu Arg Val Ala Ala Leu
1               5                   10                  15

Ala Ala Val Gly Arg Thr Asn Arg Glu Ile Ala Glu Gln Leu Phe Val
            20                  25                  30

Thr Ala Ser Thr Val Glu Gln His Leu Thr Asn Val Phe Arg Lys Leu
        35                  40                  45

Ala Val Lys Gly Arg Gln Gln Leu Pro Lys Glu Leu Ala Asp Val Gly
    50                  55                  60

Glu Pro Ala Asp Arg Asp Arg Arg Cys Gly
65                  70

<210> SEQ ID NO 105
<211> LENGTH: 71
<212> TYPE: PRT
<213> ORGANISM: Artificial Sequence
<220> FEATURE:
<223> OTHER INFORMATION: synthetic construct

<400> SEQUENCE: 105

Ile Arg Thr Ser Pro Leu Thr Gln Arg Glu Trp Gln Val Leu Gly Leu
1               5                   10                  15

Ile Tyr Ser Gly Tyr Ser Asn Glu Gln Ile Ala Gly Glu Leu Glu Val
            20                  25                  30

Ala Ala Thr Thr Ile Lys Thr His Ile Arg Asn Leu Tyr Gln Lys Leu
        35                  40                  45

Gly Val Ala His Arg Gln Asp Ala Val Gln His Ala Gln Gln Leu Leu
    50                  55                  60

Lys Met Met Gly Tyr Gly Val
65                    70

<210> SEQ ID NO 106
<211> LENGTH: 45
<212> TYPE: PRT
<213> ORGANISM: Streptomyces rapamycinicus

<400> SEQUENCE: 106

Leu Thr Asp Ala Glu Arg Arg Val Ala Ser Leu Ala Ala Gly Gly Gln
1               5                   10                  15

Thr Asn Arg Val Ile Ala Asp Gln Leu Phe Val Thr Ala Ser Thr Val
            20                  25                  30

Glu Gln His Leu Thr Asn Val Phe Arg Lys Leu Gly Val
        35                  40                  45

<210> SEQ ID NO 107
<211> LENGTH: 54
<212> TYPE: DNA
<213> ORGANISM: Streptomyces violaceusniger

<400> SEQUENCE: 107
cgcctggccg aaacctagg gggttgcgtg gaaagcaccg gcgggtgttc gctt        54

<210> SEQ ID NO 108
<211> LENGTH: 48
<212> TYPE: DNA
<213> ORGANISM: Streptomyces filamentosus

<400> SEQUENCE: 108
cggcaggcag actaggggtt gcgtgggccg cacccgaggc attcgatt        48

<210> SEQ ID NO 109
<211> LENGTH: 49
<212> TYPE: DNA
<213> ORGANISM: Streptomyces filamentosus

<400> SEQUENCE: 109
cggcaggcag actaggggt tgcgtgggcc gcacccgagg cattcgatt        49

<210> SEQ ID NO 110
<211> LENGTH: 53
<212> TYPE: DNA
<213> ORGANISM: Streptomyces filamentosus

<400> SEQUENCE: 110
cggcaggcag aacacctagg gggttgcgtg ggccgcaccc gaggcattcg att        53

<210> SEQ ID NO 111
<211> LENGTH: 52
<212> TYPE: DNA
<213> ORGANISM: Streptomyces violaceusniger

<400> SEQUENCE: 111
ctgcaggcag aacacctggg ggttgcgcga accgggcgcg cggtatcgga tt        52

<210> SEQ ID NO 112
<211> LENGTH: 53

```
<212> TYPE: DNA
<213> ORGANISM: Streptomyces violaceusniger

<400> SEQUENCE: 112
ctgcaggcag aacacctagg gggttgcgcg aaccgggcgc gcggtatcgg att          53
```

COMPOSITIONS AND METHODS FOR THE PRODUCTION OF COMPOUNDS

BACKGROUND

The Large ATP-binding regulators of the LuxR family of transcriptional activators (LALs) are known transcriptional regulators of polyketides such as FK506 or rapamycin. The LAL family has been found to have an active role in the induction of expression of some types of natural product gene clusters, for example PikD for pikromycin production and RapH for rapamycin production. The LAL proteins contain three domains; a nucleotide-binding domain, an inducer-binding domain, and a helix-turn-helix (DNA binding) domain. The structure of the DNA-binding domain is a four helix bundle. The specific protein residue sequence of Helix 3 in this motif directs the LAL to specific DNA sequences contained in prokaryal transcriptional promoter regions (i.e., the LAL binding site). Binding of the LAL or multiple LALs in a complex to specific sites in the promoters of genes within a gene cluster that produces a small molecule (e.g., a polyketide synthase gene cluster or a β-lactam compound producing protein gene cluster) potentiates expression of the gene cluster and hence promotes production of the compound (e.g., a polyketide or a β-lactam compound). Thus, there is an opportunity for compositions and methods to be developed that lead to more efficient and/or increased production of compounds (e.g., polyketides or β-lactam compounds) by optimizing regulation of the corresponding gene cluster that produces a small molecule (e.g., a PKS gene cluster or a β-lactam compound gene cluster).

SUMMARY OF THE INVENTION

The present disclosure provides nucleic acids encoding a recombinant LAL, vectors and host cells including recombinant LALs, and methods of using these nucleic acids, vectors, and host cells in methods for the production of compounds (e.g., polyketides, fatty acids, terpenoids, non-ribosomal polypeptides, β-lactam compounds, and alkaloids). Accordingly, in a first aspect, the present disclosure provides a host cell (e.g., a host cell naturally lacking an LAL and/or an LAL binding site) engineered to express a recombinant LAL (e.g., a heterologous LAL). In some embodiments, the LAL is constitutively active. In some embodiments, the host cell is engineered by insertion of a LAL binding site in a nucleic acid. In some embodiments, the binding of the recombinant LAL to the LAL binding site promotes transcription of the nucleic acid (e.g., a nucleic acid encoding a compound-producing protein such as a polyketide synthase or a β-lactam compound producing protein). In some embodiments, the LAL binding site is heterologous to the LAL. In some embodiments, the LAL binding site is endogenous to the LAL. In some embodiments, the LAL binding site includes the sequence GGGGGT.

In some embodiments, the host cell includes a nucleic acid including a heterologous LAL binding site operably linked to an open reading frame such that binding of an LAL to the heterologous LAL binding site promotes expression of the open reading frame. In some embodiments, the heterologous LAL binding site is a synthetic LAL binding site. In some embodiments, the heterologous LAL binding site promotes greater expression than the endogenous LAL binding site operably linked to the open reading frame. In some embodiments, the heterologous LAL binding site includes at least 8 contiguous nucleotides of $C_1$-$T_2$-$A_3$-$G_4$-$G_5$-$G_6$-$G_7$-$G_8$-$T_9$-$T_{10}$-$G_{11}$-$C_{12}$ (SEQ ID NO: 2), wherein none or up to six nucleotides other than any three nucleotides of $G_4$, $G_5$, $G_6$, $G_7$, $G_8$, $T_9$, and $T_{10}$ (e.g., $G_4$, $G_7$, and $T_9$; $G_5$, $G_8$, and $T_{10}$; or $G_6$, $G_7$, and $G_8$) are replaced by any other nucleotide.

In some embodiments, the recombinant LAL includes a portion having at least 70% (e.g., at least 75%, at least 80%, at least 85%, at least 90%, at least 95%, at least 99%) sequence identity to the sequence of SEQ ID NO: 1. In some embodiments, the recombinant LAL includes a portion having the sequence of SEQ ID NO: 1. In some embodiments, the recombinant LAL has the amino acid sequence of SEQ ID NO: 1.

```
                                              (SEQ ID NO: 1)
MPAVESYELDARDDELRRLEEAVGQAGNGRGVVVTITGPIACGKTELLDA

AAAKSDAITLRAVCSEEERALPYALIGQLIDNPAVASQLPDPVSMALPGE

HLSPEAENRLRGDLTRTLLALAAERPVLIGIDDMHHADTASLNCLLHLAR

RVGPARIAMVLTELRRLTPAHSQFHAELLSLGHHREIALRPLGPKHIAEL

ARAGLGPDVDEDVLTGLYRATGGNLNLGHGLIKDVREAWATGGTGINAGR

AYRLAYLGSLYRCGPVPLRVARVAAVLGQSANTTLVRWISGLNADAVGEA

TEILTEGGLLHDLRFPHPAARSVVLNDLSARERRRLHRSALEVLDDVPVE

VVAHHQAGAGFIHGPKAAEIFAKAGQELHVRGELDAASDYLQLAHHASDD

AVTRAALRVEAVAIERRRNPLASSRHLDELTVAARAGLLSLEHAALMIRW

LALGGRSGEAAEVLAAQRPRAVTDQDRAHLRAAEVSLALVSPGASGVSPG

ASGPDRRPRPLPPDELANLPKAARLCAIADNAVISALHGRPELASAEAEN

VLKQADSAADGATALSALTALLYAENTDTAQLWADKLVSETGASNEEEGA

GYAGPRAETALRRGDLAAAVEAGSAILDHRRGSLLGITAALPLSSAVAAA

IRLGETERAEKWLAEPLPEAIRDSLFGLHLLSARGQYCLATGRHESAYTA

FRTCGERMRNWGVDVPGLSLWRVDAAEALLHGRDRDEGRRLIDEQLTHAM

GPRSRALTLRVQAAYSPQAQRVDLLEEAADLLLSCNDQYERARVLADLSE

AFSALRHHSRARGLLRQARHLAAQCGATPLLRRLGAKPGGPGWLEESGLP

QRIKSLTDAERRVASLAAGGQTNRVIADQLFVTASTVEQHLTNVFRKLGV

KGRQHLPAELANAE.
```

In some embodiments, the host cell is a bacterium (e.g., an actinobacterium such as *Streptomyces ambofaciens*, *Streptomyces hygroscopicus*, or *Streptomyces malayensis*). In some embodiments, the actinobaceterium is S1391, S1496, or S2441.

In some embodiments, the host cell has been modified to enhance expression of a compound-producing protein (e.g., a polyketide synthase or a β-lactam compound producing protein). For example, in some embodiments, the host cell has been modified to enhance expression of a compound-producing protein (e.g., a polyketide synthase or a β-lactam compound producing protein) by (i) deletion of an endogenous gene cluster which expresses a compound-producing protein (e.g., a polyketide synthase or a β-lactam compound producing protein); (ii) insertion of a heterologous gene cluster which expresses a compound-producing protein (e.g., a polyketide synthase or a β-lactam compound producing protein); (iii) exposure of said host cell to an antibiotic challenge; and/or (iv) introduction of a heterologous promoter that results in at least a two-fold increase in expression of a compound compared to the homologous promoter. An additional method to enhance the expression of a compound (e.g., a polyketide or a β-lactam compound) is to optimize media conditions for growth. This includes the specific chemical and nutrient composition of the media, whether the fermentation is conducted in liquid or solid media, the time course of the fermentation, and the volume/scale of the fermentation run.

In another aspect, the disclosure provides a nucleic acid encoding an LAL, wherein the LAL includes a portion having at least 70% (e.g., at least 75%, at least 80%, at least 85%, at least 90%, at least 95%, at least 99%) sequence identity to the amino acid sequence of SEQ ID NO: 1. In some embodiments, the LAL includes a portion having the sequence of SEQ ID NO: 1. In some embodiments, the LAL has the sequence of SEQ ID NO: 1. In some embodiments, the nucleic acid lacks a TTA regulatory codon in at least one open reading frame.

In some embodiments, the nucleic acid further comprises an LAL binding site, e.g., an LAL binding site having at least 80% (e.g., at least 85%, at least 90%, at least 95%, at least 99%) identity to the sequence of SEQ ID NO: 2 (CTAGGGGGTTGC). In some embodiments, the LAL binding site includes the sequence of SEQ ID NO: 2. In some embodiments, the LAL binding site has the sequence of SEQ ID NO: 2. In some embodiments, the LAL binding site includes the sequence SEQ ID NO: 3 (GGGGGT).

In some embodiments, the nucleic acid further includes an open reading frame positioned such that binding of the LAL to the LAL binding site promotes expression of the open reading frame. In some embodiments, the open reading frame encodes a compound-producing protein (e.g., a polyketide synthase or a β-lactam compound producing protein).

In some embodiments, the open reading frame encodes a polyketide synthase. In some embodiments, the nucleic acid further encodes a nonribosomal peptide synthase. In some embodiments, the nucleic acid further encodes a first P450 enzyme. In some embodiments, the nucleic acid further encodes a second P450 enzyme.

In some embodiments, the open reading frame encodes a β-lactam compound producing protein. In some embodiments, the open reading frame encodes two more (e.g., three or more, four or more, five or more, six or more, seven or more, or eight or more) β-lactam compound producing proteins. In some embodiments, the nucleic acid further encodes one or more tailoring proteins.

In another aspect, the disclosure provides an expression vector including any of the foregoing nucleic acids. In some embodiments, the expression vector is an artificial chromosome (e.g., a bacterial artificial chromosome).

In another aspect, the disclosure provides a host cell including any of the foregoing vectors.

In another aspect, the disclosure provides a method of producing a compound (e.g., a polyketide, a fatty acid, a terpenoid, a β-lactam compound, a non-ribosomal polypeptide, or an alkaloid). This method includes: (a) providing a host cell engineered to express a recombinant LAL and including an LAL binding site operably linked to an open reading frame such that binding of the recombinant LAL to the LAL binding site promotes expression of the open reading frame, wherein the host cell includes a nucleic acid encoding a compound-producing protein (e.g., polyketide synthase or a β-lactam compound producing protein); and (b) culturing the host cell under conditions suitable to allow expression of a compound by the compound-producing protein (e.g., polyketide synthase or a β-lactam compound producing protein); thereby producing a compound.

In another aspect, the disclosure provides a method of identifying a synthetic LAL binding site, the method including: (a) providing a plurality of synthetic nucleic acids including at least eight nucleotides; (b) contacting one or more of the plurality of nucleotides including at least eight nucleotides with one or more LALs; (c) determining the binding affinity between a nucleic acid of step (a) and an LAL of step (b), wherein a synthetic nucleic acid is identified as a synthetic LAL binding site if the synthetic binding site, when linked to a downstream gene, is capable of inducing transcription of the linked gene, as measured by at least a 2-fold increase in RNA transcription. In some embodiments, wherein a synthetic nucleic acid is identified as a synthetic LAL binding site if the affinity between the synthetic nucleic acid and an LAL is less than 500 nM (e.g., less than 250 nm, less than 100 nM, less than 50 nM, less than 20 nM or between 1-50 nM, between 5-75 nM, between 50 and 100 nM, between 75 and 250 nM).

Definitions

The term "compound-producing protein," as used herein refers to a protein such as a polyketide synthase that when expressed in a cell under suitable conditions produces a small molecule (e.g., a polyketide, a fatty acid, a terpenoid, a β-lactam compound, a non-ribosomal polypeptide, or an alkaloid)

A cell that is "engineered to contain" and/or "engineered to express" refers to a cell that has been modified to contain and/or express a protein that does not naturally occur in the cell. A cell may be engineered to contain a protein, e.g., by introducing a nucleic acid encoding the protein by introduction of a vector including the nucleic acid.

The term "gene cluster that produces a small molecule," as used herein refers to a cluster of genes which encodes one or more compound-producing proteins.

The term "heterologous," as used herein, refers to a relationship between two or more proteins, nucleic acids, compounds, and/or cell that is not present in nature. For example, the LAL having the sequence of SEQ ID NO: 1 is naturally occurring in the S18 *Streptomyces* strain and is thus homologous to that strain and would thus be heterologous to the S12 *Streptomyces* strain.

The term "homologous," as used herein, refers to a relationship between two or more proteins, nucleic acids, compounds, and/or cells that is present naturally. For example, the LAL having the sequence of SEQ ID NO: 1 is naturally occurring in the S18 *Streptomyces* strain and is thus homologous to that strain.

A "polyketide synthase" refers to an enzyme belonging to the family of multi-domain enzymes capable of producing a polyketide. A polyketide synthase may be expressed naturally in bacteria, fungi, plants, or animals.

A "β-lactam compound" refers to any compound having a structure that includes a β-lactam ring, including β-lactam antibiotics and β-lactam inhibitors. The structure of a β-lactam ring is provided in Formula I.

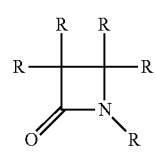

Formula I

β-lactam compounds of the invention are considered to include, at least, 5-membered unsaturated β-lactam compounds (e.g., carbapanems), 5-membered saturated β-lactam compounds (e.g., penams, such as penicillin, and clavams, such as clavulanic acid), monocyclic β-lactam compounds (e.g., nocardicins and monobactams) and 6-membered unsaturated β-lactam compounds (e.g., cephems, such as cephalosporin). Exemplary β-lactam compounds are described in Hamed, R. B., et al., The enzymes of β-lactam biosynthesis. Nat Prod Rep. 31(9):1127 (2014), the compounds of which are incorporated herein by reference.

A "β-lactam compound producing protein" refers to any protein (e.g., enzyme) in a biosynthetic pathway that produces a β-lactam compound. β-lactam compound producing enzymes may be considered to include a protein that produces the biosynthetic precursor to a β-lactam ring (e.g., ACV synthetase, carboxyethylarginine synthase), a protein that catalyzes the formation of a beta lactam ring (e.g. isopenicillin N synthetase, β-lactam synthetase, CarA, CarB, CarC, or ThnM), or any protein that modifies the β-lactam ring (e.g., a tailoring enzyme). Exemplary β-lactam producing enzymes are described in Hamed, R. B., et al., The enzymes of β-lactam biosynthesis. Nat Prod Rep. 31(9):1127 (2014), the enzymes of which are incorporated herein by reference.

A "β-lactam compound producing protein gene cluster" refers to any gene cluster that encodes the production of a β-lactam compound producing protein. In some embodiments, β-lactam compound producing protein gene clusters of the invention may encode a naturally-occurring β-lactam compound. In other embodiments, β-lactam compound producing protein gene clusters of the invention may encode an engineered variant of a naturally-occurring β-lactam compound.

The term "recombinant," as used herein, refers to a protein that is produced using synthetic methods.

BRIEF DESCRIPTION OF THE DRAWINGS

FIGS. 1A-1C are diagrams showing a strategy for use of LAL transcriptional regulators for general induction and overexpression of biosynthetic loci. FIG. 1A shows the design for the X1 biosynthetic locus, including two bidirectional promoter regions and an LAL-encoding gene. FIG. 1B shows a series of conserved putative LAL binding domains extracted from FK cluster promoter regions. FIG. 1C shows a scheme for phage-integrating constitutive LAL construction.

FIG. 2 is a diagram showing LAL sequence analysis based on a genomic database. The amino acid sequences of a series of FK LALs were aligned and used to design a query for clading of the LALs. Conserved residues in the designed query are indicated (*=100% conserved in FK LALs; :=strongly similar residues; .=weakly similar residues).

FIG. 17A shows the design for the biosynthetic locus, including three bidirectional X1 promoter regions (P2, P3, and P5) inserted into the WAC292 β-lactam gene cluster. FIG. 17B is a table showing the normalized mRNA levels measured by NanoString displayed as log 2 values. The NanoString analysis shows that transcripts linked to the P2, P3, and P5 promoters were significantly upregulated in WAC292-p2p3p5 as compared to WAC292-WT.

DETAILED DESCRIPTION

Figure 3:
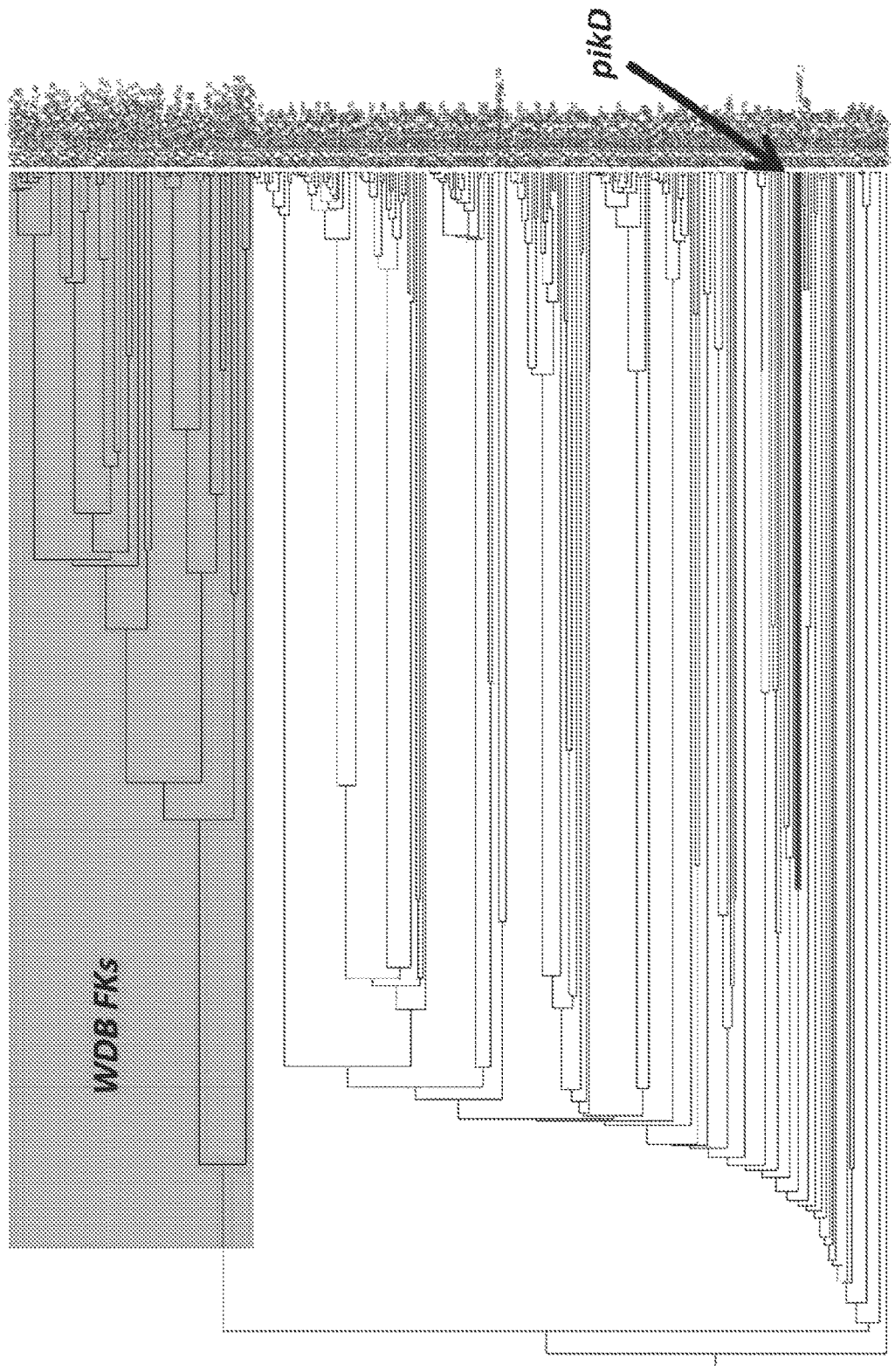
FIG. 3 is a cladogram showing that FkPhDs cluster together and are distinct from other PKS-associated LALs, such as pikD.

The present inventors discovered the amino acid sequence within helix 3 of the Helix-Turn-Helix DNA-binding motif of LALs associated with known polyketide synthases is 100% conserved. As a result of the conservation of helix 3 of the LALs, there are predictable DNA sequence motifs including likely LAL binding sites in the promoter-operator regions of genes that encode polyketide synthases. The conservation of the LAL-DNA interaction motifs at both the protein and DNA levels enables interchangeable use of the LALs for the activation of transcription of natural product gene clusters.

Compounds

Compounds that may be produced with the methods of the invention include, but are not limited to, polyketides and polyketide macrolide antibiotics such as erythromycin; hybrid polyketides/non-ribosomal peptides such as rapamycin and FK506; carbohydrates including aminoglycoside antibiotics such as gentamicin, kanamycin, neomycin, tobramycin; benzofuranoids; benzopyranoids; flavonoids; glycopeptides including vancomycin; lipopeptides including daptomycin; tannins; lignans; polycyclic aromatic natural products, terpenoids, steroids, sterols, oxazolidinones including linezolid; amino acids, peptides and peptide antibiotics including polymyxins, non-ribosomal peptides, β-lactam compounds including β-lactam antibiotics and β-lactamase inhibitors (e.g., carbapenems, cephalosporins, penicillins, clavulanic acid, monobactams, nocardicins, tabtoxins, and conjugate β-lactams); purines, pteridines, polypyrroles, tetracyclines, quinolones and fluoroquinolones; and sulfonamides.

Proteins

LALs

LALs include three domains, a nucleotide-binding domain, an inducer-binding domain, and a DNA-binding domain. A defining characteristic of the structural class of regulatory proteins that include the LALs is the presence of the AAA+ ATPase domain. Nucleotide hydrolysis is coupled to large conformational changes in the proteins and/or multimerization, and nucleotide binding and hydrolysis represents a "molecular timer" that controls the activity of the LAL (e.g., the duration of the activity of the LAL). The LAL is activated by binding of a small-molecule ligand to the inducer binding site. In most cases the allosteric inducer of the LAL is unknown. In the case of the related protein MalT, the allosteric inducer is maltotriose. Possible inducers for LAL proteins include small molecules found in the environment that trigger compound (e.g., polyketide or a β-lactam compound) biosynthesis. The regulation of the LAL controls production of compound-producing proteins (e.g., polyketide synthases or β-lactam compound producing proteins) resulting in activation of compound (e.g., polyketide or a β-lactam compound) production in the presence of external environmental stimuli. Therefore, there are gene clusters that produce small molecules (e.g., PKS gene clusters or β-lactam compound producing protein gene clusters) which, while present in a strain, do not produce compound either because (i) the LAL has not been activated, (ii) the strain has LAL binding sites that differ from consensus, (iii) the strain lacks an LAL regulator, or (iv) the LAL regulator may be poorly expressed or not expressed under laboratory conditions. Since the DNA binding region of the LALs of the known PKS LALs are highly conserved, the known LALs may be used interchangeably to activate PKS gene clusters and other compound producing gene clusters, such as β-lactam compound producing protein gene clusters, other than those which they naturally regulate. In some embodiments, the LAL is a fusion protein.

In some embodiments, an LAL may be modified to include a non-LAL DNA-binding domain, thereby forming a fusion protein including an LAL nucleotide-binding domain and a non-LAL DNA-binding domain. In certain embodiments, the non-LAL DNA-binding domain is capable of binding to a promoter including a protein-binding site positioned such that binding of the DNA-binding domain to the protein-binding site of the promoter promotes expression of a gene of interest (e.g., a gene encoding a compound-producing protein, as described herein). The non-LAL DNA binding domain may include any DNA binding domain known in the art. In some instances, the non-LAL DNA binding domain is a transcription factor DNA binding domain. Examples of non-LAL DNA binding domains include, without limitation, a basic helix-loop-helix (bHLH) domain, leucine zipper domain (e.g., a basic leucine zipper domain), GCC box domain, helix-turn-helix domain, homeodomain, srf-like domain, paired box domain, winged helix domain, zinc finger domain, HMG-box domain, Wor3 domain, OB-fold domain, immunoglobulin domain, B3 domain, TAL effector domain, Cas9 DNA binding domain, GAL4 DNA binding domain, and any other DNA binding domain known in the art. In some instances, the promoter is positioned upstream to the gene of interest, such that the fusion protein may bind to the promoter and induce or inhibit expression of the gene of interest. In certain instances, the promoter is a heterologous promoter introduced to the nucleic acid (e.g., a chromosome, plasmid, fosmid, or any other nucleic acid construct known in the art) containing the gene of interest. In other instances, the promoter is a pre-existing promoter positioned upstream to the gene of interest. The protein-binding site within the promoter may, for example, be a non-LAL protein-binding site. In certain embodiments, the protein-binding site binds to the non-LAL DNA binding domain, thereby forming a cognate DNA binding domain/protein-binding site pair.

In some embodiments, the LAL is encoded by a nucleic acid having at least 70% (e.g., at least 75%, at least 80%, at least 85%, at least 90%, at least 95%, at least 99%) sequence identity to any one of SEQ ID Nos: 4-25 or has a sequences with at least 70% (e.g., at least 75%, at least 80%, at least 85%, at least 90%, at least 95%, at least 99%) sequence identity to any one of SEQ ID Nos: 26-36.

```
SEQ ID NO: 4:
ATGCCTGCCGTGGAGTGCTATGAACTGGACGCCCGCGATGACGAGCTCAGAAAACTGGAGGAGGTTGTGAC

CGGGCGGGCCAACGGCCGGGGTGTGGTGGTCACCATCACCGGACCGATCGCCTGCGGCAAGACCGAACTGC

TCGACGCAGCCGCCGCGAAGGCCGACGCCATCACGTTACGAGCGGTCTGCTCCGCGGAGGAACAGGCACTC

CCGTACGCCCTGATCGGGCAGCTCATCGACAACCCGGCGCTCGCCTCCCACGCGCTGGAGCCGGCCTGCCC

GACCCTCCCGGGCGAGCACCTGTCGCCGGAGGCCGAGAACCGGCTGCGCAGCGACCTCACCCGTACCCTGC

TGGCGCTCGCCGCCGAACGGCCGGTGCTGATCGGCATCGACGAGTCACACGCGAACGCTTTGTGTCTGCTC

CACCTGGCCCGAAGGGTCGGCTCGGCCCGGATCGCCATGGTCCTCACCGAGTTGCGCCGGCTCACCCCGGC

CCACTCACAGTTCCAGGCCGAGCTGCTCAGCCTGGGGCACCACCGCGAGATCGCGCTGCGCCCGCTCAGCC

CGAAGCACACCGCCGAGCTGGTCCGCGCCGGTCTCGGTCCCGACGTCGACGAGGACGTGCTCACGGGGTTG
```

-continued

```
TACCGGGCGACCGGCGGCAACCTGAACCTCACCCGCGGACTGATCAACGATGTGCGGGAGGCCTGGGAGAC
GGGAGGGACGGGCATCAGCGCGGGCCGCGCGTACCGGCTGGCATACCTCGGTTCCCTCTACCGCTGCGGCC
CGGTCCCGTTGCGGGTCGCACGGGTGGCCGCCGTGCTGGGCCAGAGCGCCAACACCACCCTGGTGCGCTGG
ATCAGCGGGCTCAACGCGGACGCGGTGGGCGAGGCAACCGAGATCCTCACCGAAGGCGGCCTGCTGCACGA
CCTGCGGTTCCCGCACCCGGCGGCCCGTTCGGTGGTACTCAACGACATGTCCGCCCAGGAACGACGCCGCC
TGCACCGGTCCGCTCTGGAAGTGCTGGACGACGTGCCCGTGGAAGTGGTCGCGCACCACCAGGTCGGCGCC
GGTCTCCTGCACGGCCCGAAGGCCGCCGAGATATTCGCCAAGGCCGGCCAGGAGCTGCATGTGCGCGGCGA
GTTGGACACCGCGTCCGACTATCTGCAACTGGCCCACCAGGCCTCCGACGACGCCGTCACCGGGATGCGGG
CCGAGGCCGTGGCGATCGAGCGCCGCCGCAACCCGCTGGCCTCGAGCCGGCACCTCGACGAGCTGACCGTC
GTCGCCCGTGCCGGGCTGCTCTTCCCCGAGCACACGGCGCTGATGATCCGCTGGCTGGGCGTCGGCGGGCG
GTCCGGCGAGGCAGCCGGGCTGCTGGCCTCGCAGCGCCCCCGTGCGGTCACCGACCAGGACAGGGCCCATA
TGCGGGCCGCCGAGGTATCGCTCGCGCTGGTCAGCCCCGGCACGTCCGGCCCGGACCGGCGGCCGCGTCCG
CTCACGCCGGATGAGCTCGCGAACCTGCCGAAGGCGGCCCGGCTCTGCGCGATCGCCGACAATGCCGTCAT
GTCGGCCCTGCGCGGTCGTCCCGAGCTCGCCGCGGCCGAGGCGGAGAACGTCCTGCAGCACGCCGACTCGG
CGGCGGCCGGCACCACCGCCCTCGCCGCGCTGACCGCCTTGCTGTACGCGGAGAACACCGACACCGCTCAG
CTCTGGGCCGACAAGCTGGTCTCCGAGACCGGGGCGTCGAACGAGGAGGAGGCGGGCTACGCGGGGCCGCG
CGCCGAAGCCGCGTTGCGTCGCGGCGACCTGGCCGCGGCGGTCGAGGCAGGCAGCACCGTTCTGGACCACC
GGCGGCTCTCGACGCTCGGCATCACCGCCGCGCTACCGCTGAGCAGCGCGGTGGCCGCCGCCATCCGGCTG
GGCGAGACCGAGCGGGCGGAGAAGTGGCTCGCCCAGCCGCTGCCGCAGGCCATCCAGGACGGCCTGTTCGG
CCTGCACCTGCTCTCGGCGCGCGGCCAGTACAGCCTCGCCACGGGCCAGCACGAGTCGGCGTACACGGCGT
TTCGCACCTGCGGGGAACGTATGCGGAACTGGGGCGTTGACGTGCCGGGTCTGTCCCTGTGGCGCGTCGAC
GCCGCCGAGGCGCTGCTGCACGGCCGCGACCGGGACGAGGGCCGACGGCTCGTCGACGAGCAACTCACCCG
TGCGATGGGACCCCGTTCCCGCGCCTTGACGCTGCGGGTGCAGGCGGCGTACAGCCCGCCGGCGAAGCGGG
TCGACCTGCTCGATGAAGCGGCCGACCTGCTGCTCTCCTGCAACGACCAGTACGAGCGGGCACGGGTGCTC
GCCGACCTGAGCGAGACGTTCAGCGCGCTCCGGCACCACAGCCGGGCGCGGGGACTGCTTCGGCAGGCCCG
GCACCTGGCCGCCCAGCGCGGCGCGATACCGCTGCTGCGCCGACTCGGGGCCAAGCCCGGAGGCCCCGGCT
GGCTGGAGGAATCCGGCCTGCCGCAGCGGATCAAGTCGCTGACCGACGCGGAGCGGCGGGTGGCGTCGCTG
GCCGCCGGCGGACAGACCAACCGCGTGATCGCCGACCAGCTCTTCGTCACGGCCAGCACGGTGGAGCAGCA
CCTCACGGACGTCTCCACTGGGTCAAGGCCGCCAGCACCTGCCGCCGAACTCGTCTAG
```

SEQ ID NO: 5
```
ATGCCTGCCGTGGAGTGCTATGAACTGGACGCCCGCGATGACGAGCTCAGAAAACTGGAGGAGGTTGTGAC
CGGGCGGGCCAACGGCCGGGGTGTGGTGGTCACCATCACCGGACCGATCGCCTGCGGCAAGACCGAACTGC
TCGACGCAGCCGCCGCGAAGGCCGACGCCATCACGCTGCGAGCGGTCTGCTCCGCGGAGGAACAGGCACTC
CCGTACGCCCTGATCGGGCAGCTCATCGACAACCCGGCGCTCGCCTCCCACGCGCTGGAGCCGGCCTGCCC
GACCCTCCCGGGCGAGCACCTGTCGCCGGAGGCCGAGAACCGGCTGCGCAGCGACCTCACCCGTACCCTGC
TGGCGCTCGCCGCCGAACGGCCGGTGCTGATCGGCATCGACGAGTCACACGCGAACGCTTTGTGTCTGCTC
CACCTGGCCCGAAGGGTCGGCTCGGCCCGGATCGCCATGGTCCTCACCGAGTTGCGCCGGCTCACCCCGGC
CCACTCACAGTTCCAGGCCGAGCTGCTCAGCCTGGGGCACCACCGCGAGATCGCGCTGCGCCCGCTCAGCC
CGAAGCACACCGCCGAGCTGGTCCGCGCCGGTCTCGGTCCCGACGTCGACGAGGACGTGCTCACGGGGTTG
TACCGGGCGACCGGCGGCAACCTGAACCTCACCCGCGGACTGATCAACGATGTGCGGGAGGCCTGGGAGAC
GGGAGGGACGGGCATCAGCGCGGGCCGCGCGTACCGGCTGGCATACCTCGGTTCCCTCTACCGCTGCGGCC
```

-continued

CGGTCCCGTTGCGGGTCGCACGGGTGGCCGCCGTGCTGGGCCAGAGCGCCAACACCACCCTGGTGCGCTGG
ATCAGCGGGCTCAACGCGGACGCGGTGGGCGAGGCAACCGAGATCCTCACCGAAGGCGGCCTGCTGCACGA
CCTGCGGTTCCCGCACCCGGCGGCCCGTTCGGTGGTACTCAACGACATGTCCGCCCAGGAACGACGCCGCC
TGCACCGGTCCGCTCTGGAAGTGCTGGACGACGTGCCCGTGGAAGTGGTCGCGCACCACCAGGTCGGCGCC
GGTCTCCTGCACGGCCCGAAGGCCGCCGAGATATTCGCCAAGGCCGGCCAGGAGCTGCATGTGCGCGGCGA
GTTGGACACCGCGTCCGACTATCTGCAACTGGCCCACCAGGCCTCCGACGACGCCGTCACCGGGATGCGGG
CCGAGGCCGTGGCGATCGAGCGCCGCCGCAACCCGCTGGCCTCGAGCCGGCACCTCGACGAGCTGACCGTC
GTCGCCCGTGCCGGGCTGCTCTTCCCCGAGCACACGGCGCTGATGATCCGCTGGCTGGGCGTCGGCGGGCG
GTCCGGCGAGGCAGCCGGGCTGCTGGCCTCGCAGCGCCCCGTGCGGTCACCGACCAGGACAGGGCCCATA
TGCGGGCCGCCGAGGTATCGCTCGCGCTGGTCAGCCCCGGCACGTCCGGCCCGGACCGGCGGCCGCGTCCG
CTCACGCCGGATGAGCTCGCGAACCTGCCGAAGGCGGCCCGGCTCTGCGCGATCGCCGACAATGCCGTCAT
GTCGGCCCTGCGCGGTCGTCCCGAGCTCGCCGCGGCCGAGGCGGAGAACGTCCTGCAGCACGCCGACTCGG
CGGCGGCCGGCACCACCGCCCTCGCCGCGCTGACCGCCTTGCTGTACGCGGAGAACACCGACACCGCTCAG
CTCTGGGCCGACAAGCTGGTCTCCGAGACCGGGGCGTCGAACGAGGAGGAGGCGGGCTACGCGGGGCCGCG
CGCCGAAGCCGCGTTGCGTCGCGGCGACCTGGCCGCGGCGGTCGAGGCAGGCAGCACCGTTCTGGACCACC
GGCGGCTCTCGACGCTCGGCATCACCGCCGCGCTACCGCTGAGCAGCGCGGTGGCCGCCGCCATCCGGCTG
GGCGAGACCGAGCGGGCGGAGAAGTGGCTCGCCCAGCCGCTGCCGCAGGCCATCCAGGACGGCCTGTTCGG
CCTGCACCTGCTCTCGGCGCGCGGCCAGTACAGCCTCGCCACGGGCCAGCACGAGTCGGCGTACACGGCGT
TTCGCACCTGCGGGGAACGTATGCGGAACTGGGGCGTTGACGTGCCGGGTCTGTCCCTGTGGCGCGTCGAC
GCCGCCGAGGCGCTGCTGCACGGCCGCGACCGGGACGAGGGCCGACGGCTCGTCGACGAGCAACTCACCCG
TGCGATGGGACCCCGTTCCCGCGCCTTGACGCTGCGGGTGCAGGCGGCGTACAGCCCGCCGGCGAAGCGGG
TCGACCTGCTCGATGAAGCGGCCGACCTGCTGCTCTCCTGCAACGACCAGTACGAGCGGGCACGGGTGCTC
GCCGACCTGAGCGAGACGTTCAGCGCGCTCCGGCACCACAGCCGGGCGCGGGGACTGCTTCGGCAGGCCCG
GCACCTGGCCGCCCAGCGCGGCGCGATACCGCTGCTGCGCCGACTCGGGGCCAAGCCCGGAGGCCCCGGCT
GGCTGGAGGAATCCGGCCTGCCGCAGCGGATCAAGTCGCTGACCGACGCGGAGCGGCGGGTGGCGTCGCTG
GCCGCCGGCGGACAGACCAACCGCGTGATCGCCGACCAGCTCTTCGTCACGGCCAGCACGGTGGAGCAGCA
CCTCACGGACGTCTCCACTGGGTCAAGGCCGCCAGCACCTGCCGCCGAACTCGTCTAG

SEQ ID NO: 6
GTGGTTCCTGAAGTGCGAGCAGCCCCGACGAACTGATCGCCCGCGATGACGAGCTGAGCCGCCTCCAACG
GGCACTCACCAGGGCGGGGAGCGGAAGGGGCGGCGTCGTCGCCATCACCGGGCCCATCGCCAGCGGAAAGA
CGGCGCTGCTCGACGCCGGAGCGGCCAAGTCCGGCTTCGTCGCACTCCGTGCGGTGTGCTCCTGGGAAGAG
CGCACTCTGCCGTACGGGATGCTGGGCCAGCTCTTCGACCATCCCGAACTGGCCGCCCAGGCGCCGGACCT
TGCCCACTTCACGCGCTTCGTGCGAGAGCCCTCAGGCCGGTACCGACAACCGCCTGCGGGCCGAGTTCACCC
GCACCCTGCTGGCGCTCGCCGCGGACTGGCCCGTCCTGATCGGCATCGACGACGTGCACCACGCCGACGCG
GAATCACTGCGCTGTCTGCTCCACCTCGCCCGCCGCATCGGCCCGGCCCGCATCGCGGTCGTACTGACCGA
GCTGCGCAGACCGACGCCCGCCGACTCCCGCTTCCAGGCGGAACTGCTGAGCCTGCGCTCCTACCAGGAGA
TCGCGCTCAGACCGCTCACCGAGGCGCAGACCGGCGAACTCGTACGTCGGCACCTCGGCGCGGAGACCCAC
GAGGACGTCTCCGCCGATACGTTCCGGGCGACCGGCGGGAACCTGCTCCTCGGGCACGGTTTGATCAATGA
CATCCGGGAGGCGCGGACAGCGGGACGGCCGGGGGTCGTCGCGGGCGGGCGTACCGGCTCGCGTACCTCA
GCTCGCTCTACCGCTGCGGCCCGAGCGCGCTGCGTGTCGCCCGGGCGTCCGCCGTGCTCGGCGCGAGCGCC
GAAGCCGTGCTCGTCCAGCGGATGACCGGACTGAACAAGGACGCGGTCGAACAGGTCTATGAGCAGCTGAA

-continued

CGAGGGACGGCTGCTGCAGGGCGAGCGGTTTCCGCACCCGGCGGCCCGCTCCATCGTCCTTGACGACCTGT

CGGCCCTGGAACGCAGAAACCTGCACGAGTCGGCGCTGGAGCTGCTGCGGGACCACGGCGTGGCCGGCAAC

GTGCTCGCCCGCCACCAGATCGGCGCCGGCCGGGTGCACGGCGAGGAGGCCGTCGAGCTGTTCACCGGGGC

CGCACGGGAGCACCACCTGCGCGGTGAACTGGACGACGCGGCCGGATACCTGGAACTCGCCCACCGTGCCT

CCGACGACCCCGTCACGCGCGCCGCACTACGCGTCGGCGCCGCCGCGATCGAGCGCCTCTGCAATCCGGTA

CGGGCAGGCCGGCATCTGCCCGAGCTGCTCACCGCGTCGCGCGCGGGACTGCTCTCCAGCGAGCACGCCGT

GTCGCTCGCCGACTGGCTGGCGATGGGCGGGCGCCCGGGCGAGGCGGCCGAGGTCCTCGCGACGCAGCGTC

CCGCGGCCGACAGCGAGCAGCACCGCGCACTCCTGCGCAGCGGCGAGTTGTCCCTCGCGCTGGTCCACCCC

GGCGCGTGGGATCCGTTGCGCCGGACCGATCGGTTCGCCGCGGGCGGGCTCGGCTCGCTTCCCGGACCCGC

CCGGCACCGCGCGGTCGCCGACCAAGCCGTCATCGCGGCGCTGCGTGGACGTCTCGACCGGGCGGACGCCA

ACGCGGAGAGCGTTCTCCAGCACACCGACGCCACGGCGGACCGGACCACGGCCATCATGGCGTTGCTGGCC

CTGCTCTACGCGGAGAACACCGATGCTGTCCAGTTCTGGGTCGACAAACTGGCCGGTGACGAGGGCACCAG

GACACCGGCCGACGAGGCGGTCCACGCGGGGTTCAACGCCGAGATCGCGCTGCGCCGCGGCGACTTGATGA

GAGCCGTCGAGTACGGCGAGGCAGCGCTCGGCCACCGGCACCTGCCCACCTGGGGAATGGCCGCCGCTCTG

CCGCTGAGCAGCACCGTGGTTGCCGCGATCCGGCTCGGCGACCTCGACAGGGCCGAGCGGTGGCTCGCCGA

GCCGCTGCCGCAGCAGACGCCGGAGAGCCTCTTCGGGCTGCACCTGCTCTGGGCCCGCGGGCAGCACCACC

TCGCGACCGGGCGGCACGGGCGGCGTACACGGCGTTCAGGGAATGCGGCGAGCGGATGCGGCGGTGGGCC

GTCGACGTGCCGGGCCTGGCCCTGTGGCGGGTCGACGCCGCCGAATCGCTGCTGCTGCTCGGCCGTGACCG

TGCCGAAGGACTGCGGCTCGTCTCCGAGCAGCTGTCCCGGCCGATGCGCCCTCGCGCGCGCGTGCAGACGT

TACGGGTACAGGCGGCCTACAGTCCGCCGCCCCAACGGATCGACCTGCTCGAAGAGGCCGCCGACCTGCTG

GTCACCTGCAACGACCAGTACGAACTGGCAAACGTACTCAGCGACTTGGCAGAGGCCTCCAGCATGGTCCG

GCAGCACAGCAGGGCGCGGGTCTGCTCCGCCGGGCACGGCACCTCGCCACCCAGTGCGGCGCCGTGCCGC

TCCTGCGGCGGCTCGGCGCGGAACCCTCGGACATCGGCGGAGCCTGGGACGCGACGCTGGGACAGCGGATC

GCGTCACTGACGGAGTCGGAGCGGCGGGTGGCCGCGCTCGCCGCGGTCGGGCGTACGAACAGGGAGATCGC

CGAGCAGCTGTTCGTCACGGCCAGCACGGTGGAACAGCACCTCACGAACGTGTTCCGCAAACTGGCGGTGA

AGGGCCGCCAGCAGCTTCCGAAGGAACTGGCCGACGTCGGCGAGCCGGCGGACCGCGACCGCCGGTGCGGG

TAG

SEQ ID NO: 7
ATGGTTCCTGAAGTGCGAGCAGCCCCCGACGAACTGATCGCCCGCGATGACGAGCTGAGCCGCCTCCAACG

GGCACTCACCAGGGCGGGGAGCGGAAGGGGCGGCGTCGTCGCCATCACCGGGCCCATCGCCAGCGGAAAGA

CGGCGCTGCTCGACGCCGGAGCGGCCAAGTCCGGCTTCGTCGCACTCCGTGCGGTGTGCTCCTGGGAAGAG

CGCACTCTGCCGTACGGGATGCTGGGCCAGCTCTTCGACCATCCCGAACTGGCCGCCCAGGCGCCGGACCT

TGCCCACTTCACGGCGTTCGTGCGAGAGCCCTCAGGCCGGTACCGACAACCGCCTGCGGGCCGAGTTCACCC

GCACCCTGCTGGCGCTCGCCGCGGACTGGCCCGTCCTGATCGGCATCGACGACGTGCACCACGCCGACGCG

GAATCACTGCGCTGTCTGCTCCACCTCGCCCGCCGCATCGGCCCGGCCCGCATCGCGGTCGTACTGACCGA

GCTGCGCAGACCGACGCCCGCCGACTCCCGCTTCCAGGCGGAACTGCTGAGCCTGCGCTCCTACCAGGAGA

TCGCGCTCAGACCGCTCACCGAGGCGCAGACCGGCGAACTCGTACGTCGGCACCTCGGCGCGGAGACCCAC

GAGGACGTCTCCGCCGATACGTTCCGGGCGACCGGCGGGAACCTGCTCCTCGGGCACGGTTTGATCAATGA

CATCCGGGAGGCGCGGACAGCGGGACGGCCGGGGGTCGTCGCGGGCGGGCGTACCGGCTCGCGTACCTCA

GCTCGCTCTACCGCTGCGGCCCGAGCGCGCTGCGTGTCGCCCGGGCGTCCGCCGTGCTCGGCGCGAGCGCC

GAAGCCGTGCTCGTCCAGCGGATGACCGGACTGAACAAGGACGCGGTCGAACAGGTCTATGAGCAGCTGAA

-continued

CGAGGGACGGCTGCTGCAGGGCGAGCGGTTTCCGCACCCGGCGGCCCGCTCCATCGTCCTTGACGACCTGT
CGGCCCTGGAACGCAGAAACCTGCACGAGTCGGCGCTGGAGCTGCTGCGGGACCACGGCGTGGCCGGCAAC
GTGCTCGCCCGCCACCAGATCGGCGCCGGCCGGGTGCACGGCGAGGAGGCCGTCGAGCTGTTCACCGGGGC
CGCACGGGAGCACCACCTGCGCGGTGAACTGGACGACGCGGCCGGATACCTGGAACTCGCCCACCGTGCCT
CCGACGACCCCGTCACGCGCGCCGCACTACGCGTCGGCGCCGCCGCGATCGAGCGCCTCTGCAATCCGGTA
CGGGCAGGCCGGCATCTGCCCGAGCTGCTCACCGCGTCGCGCGCGGGACTGCTCTCCAGCGAGCACGCCGT
GTCGCTCGCCGACTGGCTGGCGATGGGCGGGCGCCCGGGCGAGGCGGCCGAGGTCCTCGCGACGCAGCGTC
CCGCGGCCGACAGCGAGCAGCACCGCGCACTCCTGCGCAGCGGCGAGTTGTCCCTCGCGCTGGTCCACCCC
GGCGCGTGGGATCCGTTGCGCCGGACCGATCGGTTCGCCGCGGGCGGGCTCGGCTCGCTTCCCGGACCCGC
CCGGCACCGCGCGGTCGCCGACCAAGCCGTCATCGCGGCGCTGCGTGGACGTCTCGACCGGGCGGACGCCA
ACGCGGAGAGCGTTCTCCAGCACACCGACGCCACGGCGGACCGGACCACGGCCATCATGGCGTTGCTGGCC
CTGCTCTACGCGGAGAACACCGATGCTGTCCAGTTCTGGGTCGACAAACTGGCCGGTGACGAGGGCACCAG
GACACCGGCCGACGAGGCGGTCCACGCGGGGTTCAACGCCGAGATCGCGCTGCGCCGCGGCGACTTGATGA
GAGCCGTCGAGTACGGCGAGGCAGCGCTCGGCCACCGGCACCTGCCCACCTGGGGAATGGCCGCCGCTCTG
CCGCTGAGCAGCACCGTGGTTGCCGCGATCCGGCTCGGCGACCTCGACAGGGCCGAGCGGTGGCTCGCCGA
GCCGCTGCCGCAGCAGACGCCGGAGAGCCTCTTCGGGCTGCACCTGCTCTGGGCCCGCGGGCAGCACCACC
TCGCGACCGGGCGGCACGGGCGGCGTACACGGCGTTCAGGGAATGCGGCGAGCGGATGCGGCGGTGGGCC
GTCGACGTGCCGGGCCTGGCCCTGTGGCGGGTCGACGCCGCCGAATCGCTGCTGCTGCTCGGCCGTGACCG
TGCCGAAGGACTGCGGCTCGTCTCCGAGCAGCTGTCCCGGCCGATGCGCCCTCGCGCGCGCGTGCAGACGC
TGCGGGTACAGGCGGCCTACAGTCCGCCGCCCCAACGGATCGACCTGCTCGAAGAGGCCGCCGACCTGCTG
GTCACCTGCAACGACCAGTACGAACTGGCAAACGTACTCAGCGACTTGGCAGAGGCCTCCAGCATGGTCCG
GCAGCACAGCAGGGCGCGGGTCTGCTCCGCCGGGCACGGCACCTCGCCCACCCAGTGCGGCGCCGTGCCGC
TCCTGCGGCGGCTCGGCGCGGAACCCTCGGACATCGGCGGAGCCTGGGACGCGACGCTGGGACAGCGGATC
GCGTCACTGACGGAGTCGGAGCGGCGGGTGGCCGCGCTCGCCGCGGTCGGGCGTACGAACAGGGAGATCGC
CGAGCAGCTGTTCGTCACGGCCAGCACGGTGGAACAGCACCTCACGAACGTGTTCCGCAAACTGGCGGTGA
AGGGCCGCCAGCAGCTTCCGAAGGAACTGGCCGACGTCGGCGAGCCGGCGGACCGCGACCGCCGGTGCGGG
TAG

SEQ ID NO: 8

GTGATAGCGCGCTTATCTCCCCCAGACCTGATCGCCCGCGATGACGAGTTCGGTTCCCTCCACCGGGCGCT
CACCCGAGCGGGGGCGGGCGGGCGTCGTCGCCGCCGTCACCGGGCCGATCGCCTGCGGCAAGACCGAAC
TCCTCGACGCCGCCGCGGCCAAGGCCGGCTTCGTCACCCTTCGCGCGGTGTGCTCCATGGAGGAGCGGGCC
CTGCCGTACGGCATGCTCGGCCAGCTCCTCGACCAGCCCGAGCTGGCCGCCCGGACACCGGAGCTGGTCCG
GCTGACGGCATCGTGCGAAAACCTGCCGGCCGACGTCGACAACCGCCTGGGGACCGAACTCACCCGCACGG
TGCTGACGCTCGCCGCGGAGCGGCCCGTACTGATCGGCATCGACGACGTGCACCACGCCGACGCGCCGTCG
CTGCGCTGCCTGCTCCACCTCGCGCGCCGCATCAGCCGGGCCCGTGTCGCCATCGTGCTGACCGAGCTGCT
CCGGCCGACGCCCGCCCACTCCCAATTCCGGGCGGCACTGCTGAGTCTGCGCCACTACCAGGAGATCGCGC
TGCGCCCGCTCACCGAGGCGCAGACCACCGAACTCGTGCGCCGGCACCTCGGCCAGGACGCGCACGACGAC
GTGGTGGCCCAGGCGTTCCGGGCGACCGGCGGCAACCTGCTCCTCGGCCACGGCCTGATCGACGACATCCG
GGAGGCACGGACACGGACCTCAGGGTGCCTGGAAGTGGTCGCGGGGCGGGCGTACCGGCTCGCCTACCTCG
GGTCGCTCTATCGTTGCGGCCCGGCCGCGCTGAGCGTCGCCCGAGCTTCCGCCGTGCTCGGCGAGAGTGTC
GAACTCACCCTCGTCCAGCGGATGACCGGCCTCGACACCGAGGCGGTCGAGCAGGCCCACGAACAGCTGGT

-continued

```
CGAGGGGCGGCTGCTGCGGGAAGGGCGGTTCCCGCACCCCGCGGCCCGCTCCGTCGTACTCGACGACCTCT

CCGCCGCCGAGCGGCGTGGCCTGCACGAGCTGGCGCTGGAACTGCTGCGGGACCGCGGCGTGGCCAGCAAG

GTGCTCGCCCGCCACCAGATGGGTACCGGCCGGGTGCACGGCGCCGAGGTCGCCGGGCTGTTCACCGACGC

CGCGCGCGAGCACCACCTGCGCGGCGAGCTCGACGAGGCCGTCACCTACCTGGAGTTCGCCTACCGGGCCT

CCGACGACCCCGCCGTCCACGCCGCACTGCGCGTCGACACCGCCGCCATCGAGCGGCTCTGCGATCCCGCC

AGATCCGGCCGGCATGTGCCCGAGCTGCTCACCGCGTCGCGGGAACGGCTCCTCTCCAGCGAGCACGCCGT

GTCGCTCGCCTGCTGGCTGGCGATGGACGGGCGGCCGGGCGAGGCCGCCGAGGTCCTGGCGGCCCAGCGCT

CCGCCGCCCCGAGCGAGCAGGGCCGGGCGCACCTGCGCGTCGCGGACCTGTCCCTCGCGCTGATCTATCCC

GGCGCGGCCGATCCGCCGCGTCCGGCCGATCCGCCGGCCGAGGACGAGGTCGCCTCGTTTTCCGGAGCCGT

CCGGCACCGCGCCGTCGCCGACAAGGCCCTGAGCAACGCGCTGCGCGGCTGGTCCGAACAGGCCGAGGCCA

AAGCCGAGTACGTGCTCCAGCACTCCCGGGTCACGACGGACCGGACCACGACCATGATGGCGTTGCTGGCC

CTGCTCTACGCCGAGGACACCGATGCCGTCCAGTCCTGGGTCGACAAGCTGGCCGGTGACGACAACATGCG

GACCCCGGCCGACGAGGCGGTCCACGCGGGGTTCCGCGCCGAGGCCGCGCTGCGCCGCGGCGACCTGACCG

CCGCCGTCGAATGCGGCGAGGCCGCGCTCGCCCCCCGGGTCGTGCCCTCCTGGGGGATGGCCGCCGCATTG

CCGCTGAGCAGCACCGTGGCCGCCGCGATCCGACTGGGCGACCTGGACCGGGCGGAGCGGTGGCTCGCCGA

GCCGTTGCCGGAGGAGACCTCCGACAGCCTCTTCGGACTGCACATGGTCTGGGCCCGTGGGCAACACCATC

TCGCGGCCGGGCGGTACCGGGCGGCGTACAACGCGTTCCGGGACTGCGGGGAGCGGATGCGACGCTGGTCC

GTCGACGTGCCGGGCCTGGCCCTGTGGCGGGTCGACGCCGCCGAAGCGCTTCTGCTGCTCGGCCGCGGCCG

TGACGAGGGGCTGAGGCTCATCTCCGAGCAGCTGTCCCGGCCGATGGGGTCCCGGGCGCGGGTGATGACGC

TGCGGGTGCAGGCGGCCTACAGTCCGCCGGCCAAGCGGATCGAACTGCTCGACGAGGCCGCCGATCTGCTC

ATCATGTGCCGCGACCAGTACGAGCTGGCCCGCGTCCTCGCCGACATGGGCGAAGCGTGCGGCATGCTCCG

GCGGCACAGCCGTGCGCGGGGACTGTTCCGCCGCGCACGGCACCTCGCGACCCAGTGCGGAGCCGTGCCGC

TCCTCCGGCGGCTCGGTGGGGAGTCCTCGGACGCGGACGGCACCCAGGACGTGACGCCGGCGCAGCGGATC

ACATCGCTGACCGAGGCGGAGCGGCGGGTGGCGTCGCACGCCGCGGTCGGGCGCACCAACAAGGAGATCGC

CAGCCAGCTGTTCGTCACCTCCAGCACGGTGGAACAGCACCTCACCAACGTGTTCCGCAAGCTGGGGGTGA

AGGGCCGTCAGCAACTGCCCAAGGAACTGTCCGACGCCGGCTGA
                                                             SEQ ID NO: 9
ATGATAGCGCGCCTGTCTCCCCCAGACCTGATCGCCCGCGATGACGAGTTCGGTTCCCTCCACCGGGCGCT

CACCCGAGCGGGGGCGGGCGGGGCGTCGTCGCCGCCGTCACCGGGCCGATCGCCTGCGGCAAGACCGAAC

TCCTCGACGCCGCCGCGGCCAAGGCCGGCTTCGTCACCCTTCGCGCGGTGTGCTCCATGGAGGAGCGGGCC

CTGCCGTACGGCATGCTCGGCCAGCTCCTCGACCAGCCCGAGCTGGCCGCCCGGACACCGGAGCTGGTCCG

GCTGACGGCATCGTGCGAAAACCTGCCGGCCGACGTCGACAACCGCCTGGGGACCGAACTCACCCGCACGG

TGCTGACGCTCGCCGCGGGAGCGGCCCGTACTGATCGGCATCGACGACGTGCACCACGCCGACGCGCCGTCG

CTGCGCTGCCTGCTCCACCTCGCGCGCCGCATCAGCCGGGCCCGTGTCGCCATCGTGCTGACCGAGCTGCT

CCGGCCGACGCCCGCCCACTCCCAATTCCGGGCGGCACTGCTGAGTCTGCGCCACTACCAGGAGATCGCGC

TGCGCCCGCTCACCGAGGCGCAGACCACCGAACTCGTGCGCCGGCACCTCGGCCAGGACGCGCACGACGAC

GTGGTGGCCCAGGCGTTCCGGGCGACCGGCGGCAACCTGCTCCTCGGCCACGGCCTGATCGACGACATCCG

GGAGGCACGGACACGGACCTCAGGGTGCCTGGAAGTGGTCGCGGGCGGGCGTACCGGCTCGCCTACCTCG

GGTCGCTCTATCGTTGCGGCCCGGCCGCGCTGAGCGTCGCCCGAGCTTCCGCCGTGCTCGGCGAGAGTGTC

GAACTCACCCTCGTCCAGCGGATGACCGGCCTCGACACCGAGGCGGTCGAGCAGGCCCACGAACAGCTGGT

CGAGGGGCGGCTGCTGCGGGAAGGGCGGTTCCCGCACCCCGCGGCCCGCTCCGTCGTACTCGACGACCTCT
```

-continued

CCGCCGCCGAGCGGCGTGGCCTGCACGAGCTGGCGCTGGAACTGCTGCGGGACCGCGGCGTGGCCAGCAAG
GTGCTCGCCCGCCACCAGATGGGTACCGGCCGGGTGCACGGCGCCGAGGTCGCCGGGCTGTTCACCGACGC
CGCGCGCGAGCACCACCTGCGCGGCGAGCTCGACGAGGCCGTCACCTACCTGGAGTTCGCCTACCGGGCCT
CCGACGACCCCGCCGTCCACGCCGCACTGCGCGTCGACACCGCCGCCATCGAGCGGCTCTGCGATCCCGCC
AGATCCGGCCGGCATGTGCCCGAGCTGCTCACCGCGTCGCGGGAACGGCTCCTCTCCAGCGAGCACGCCGT
GTCGCTCGCCTGCTGGCTGGCGATGGACGGGCGGCCGGGCGAGGCCGCCGAGGTCCTGGCGGCCCAGCGCT
CCGCCGCCCCGAGCGAGCAGGGCCGGGCGCACCTGCGCGTCGCGGACCTGTCCCTCGCGCTGATCTATCCC
GGCGCGGCCGATCCGCCGCGTCCGGCCGATCCGCCGGCCGAGGACGAGGTCGCCTCGTTTTCCGGAGCCGT
CCGGCACCGCGCCGTCGCCGACAAGGCCCTGAGCAACGCGCTGCGCGGCTGGTCCGAACAGGCCGAGGCCA
AAGCCGAGTACGTGCTCCAGCACTCCCGGGTCACGACGGACCGGACCACGACCATGATGGCGTTGCTGGCC
CTGCTCTACGCCGAGGACACCGATGCCGTCCAGTCCTGGGTCGACAAGCTGGCCGGTGACGACAACATGCG
GACCCCGGCCGACGAGGCGGTCCACGCGGGGTTCCGCGCCGAGGCCGCGCTGCGCCGCGGCGACCTGACCG
CCGCCGTCGAATGCGGCGAGGCCGCGCTCGCCCCCCGGGTCGTGCCCTCCTGGGGGATGGCCGCCGCATTG
CCGCTGAGCAGCACCGTGGCCGCCGCGATCCGACTGGGCGACCTGGACCGGGCGGAGCGGTGGCTCGCCGA
GCCGTTGCCGGAGGAGACCTCCGACAGCCTCTTCGGACTGCACATGGTCTGGGCCCGTGGGCAACACCATC
TCGCGGCCGGGCGGTACCGGGCGGCGTACAACGCGTTCCGGGACTGCGGGGAGCGGATGCGACGCTGGTCC
GTCGACGTGCCGGGCCTGGCCCTGTGGCGGGTCGACGCCGCCGAAGCGCTTCTGCTGCTCGGCCGCGGCCG
TGACGAGGGGCTGAGGCTCATCTCCGAGCAGCTGTCCCGGCCGATGGGGTCCCGGGCGCGGGTGATGACGC
TGCGGGTGCAGGCGGCCTACAGTCCGCCGGCCAAGCGGATCGAACTGCTCGACGAGGCCGCCGATCTGCTC
ATCATGTGCCGCGACCAGTACGAGCTGGCCCGCGTCCTCGCCGACATGGGCGAAGCGTGCGGCATGCTCCG
GCGGCACAGCCGTGCGCGGGGACTGTTCCGCCGCGCACGGCACCTCGCGACCCAGTGCGGAGCCGTGCCGC
TCCTCCGGCGGCTCGGTGGGGAGTCCTCGGACGCGGACGGCACCCAGGACGTGACGCCGGCGCAGCGGATC
ACATCGCTGACCGAGGCGGAGCGGCGGGTGGCGTCGCACGCCGCGGTCGGGCGCACCAACAAGGAGATCGC
CAGCCAGCTGTTCGTCACCTCCAGCACGGTGGAACAGCACCTCACCAACGTGTTCCGCAAGCTGGGGGTGA
AGGGCCGTCAGCAACTGCCCAAGGAACTGTCCGACGCCGGCTGA

SEQ ID NO: 10
GTGGAGTTTTACGACCTGGTCGCCCGCGATGACGAGCTCAGAAGGTTGGACCAGGCCCTCGGCCGCGCCGC
CGGCGGACGGGGTGTCGTGGTCACCGTCACCGGACCGGTCGGCTGCGGCAAGACCGAACTGCTGGACGCGG
CCGCGGCCGAGGAGGAATTCATCACGTTGCGTGCGGTCTGCTCGGCCGAGGAGCGGGCCCTGCCGTACGCC
GTGATCGGCCAACTCCTCGACCATCCCGTACTCTCCGCACGCGCGCCCGACCTGGCCTGCGTGACGGCTCC
GGGCCGGACGCTGCCGGCCGACACCGAGAACCGCCTGCCGCGCGACCTCACCCGGGCCCTGCTGGCCCTGG
CCTCCGAACGACCGGTTCTGATCTGCATCGACGACGTGCACCAGGCCGACACCGCCTCGCTGAACTGCCTG
CTGCACCTGGCCCGGCGGGTCGCCTCGGCCCGGATCGCCATGATCCTCACCGAGTTGCGCCGGCTCACCCC
GGCTCACTCCCGGTTCGAGGCGGAACTGCTCAGCCTGCGGCACCGCCACGAGATCGCGCTGCGTCCCCTCG
GCCCGGCCGACACCGCCGAACTGGCCCGCGCCCGGCTCGGCGCCGGCGTCACCGCCGACGAGCTGGCCCAG
GTCCACGAGGCCACCAGCGGGAACCCCAACCTGGTCGGAGGCCTGGTCAACGACGTGCGAGAGGCCTGGGC
GGCCGGTGGCACGGGCATTGCGGCGGGGCGGGCGTACCGGCTGGCGTACCTCAGCTCCGTGTACCGCTGTG
GTCCGGTCCCGTTGCGGATCGCCCAGGCGGCGGCGGTGCTGGGTCCCAGCGCCACCGTCACGCTGGTGCGC
CGGATCAGCGGGCTCGACGCCGAGACGGTGGACGAGGCGACCGCGATCCTCACCGAGGGCGGCCTGCTCCG
GGACCACCGGTTCCCGCATCCGGCGGCCCGCTCGGTCGTACTCGACGACATGTCCGCGCAGGAACGCCGCC
GCCTGCACCGGTCCACGCTGGACGTGCTGGACGGCGTACCCGTCGACGTGCTCGCGCACCACCAGGCCGGC

-continued

```
GCCGGTCTGCTGCACGGCCCGCAGGCGGCCGAGATGTTCGCCCGGGCCAGCCAGGAGCTGCGGGTACGCGG

CGAGCTGGACGCCGCGACCGAGTACCTGCAACTGGCCTACCGGGCCTCCGACGACGCCGGCGCCCGGGCCG

CCCTGCAGGTGGAGACCGTGGCCGGCGAGCGCCGCCGCAACCCGCTGGCCGCCAGCCGGCACCTGGACGAG

CTGGCCGCCGCCCGGGCCGGCCTGCTGTCGGCCGAGCACGCCGCCCTGGTCGTGCACTGGCTGGCCGA

CGCCGGACGACCCGGCGAGGCCGCCGAGGTGCTGGCGCTGCAGCGGGCGCTGGCCGTCACCGACCACGACC

GGGCCCGCCTGCGGGCGGCCGAGGTGTCGCTCGCGCTGTTCCACCCCGGCGTCCCCGGTTCGGACCCGCGG

CCCCTCGCGCCGGAGGAGCTCGCGAGCCTGTCCCTGTCGGCCCGGCACGGTGTGACCGCCGACAACGCGGT

GCTGGCGGCGCTGCGCGGCCGTCCCGAGTCGGCCGCCGCCGAGGCGGAGAACGTGCTGCGCAACGCCGACG

CCGCCGCGTCCGGCCCGACCGCCCTGGCCGCGCTGACGGCCCTGCTCTACGCCGAGAACACCGACGCCGCC

CAGCTCTGGGCGGACAAGCTGGCCGCGGGCATCGGGGCGGGGAGGGGGAGGCCGGCTACGCGGGCCGCG

GACCGTGGCCGCCCTGCGTCGCGGCGACCTGACCACCGCGGTCCAGGCGGCCGGCGCGGTCCTGGACCGCG

GCCGGCCGTCGTCGCTCGGCATCACCGCCGTGTTGCCGTTGAGCGGCGCGGTCGCCGCCGCGATCCGGCTG

GGCGAGCTCGAGCGGGCCGAGAAGTGGCTGGCCGAGCCGCTGCCCGAAGCCGTCCACGACAGCCTGTTCGG

CCTGCACCTGCTGATGGCGCGGGGCCGCTACAGCCTCGCGGTGGGCCGGCACGAGGCGGCGTACGCCGCGT

TCCGGGACTGCGGTGAACGGATGCGCCGGTGGGACGTCGACGTGCCCGGGCTGGCCCTGTGGCGGGTGGAC

GCGGCCGAGGCGCTGCTGCCCGGCGATGACCGGGCGGAGGGCCGGCGGCTGATCGACGAGCAGCTCACCCG

GCCGATGGGGCCCCGGTCACGAGCCCTGACCCTGCGGGTACGAGCGGCCTACGCCCCGCCGGCGAAACGGA

TCGACCTGCTCGACGAAGCGGCCGACCTGCTGCTCTCCAGCAACGACCAGTACGAGCGGGCACGGGTGCTG

GCCGACCTGAGCGAGGCGTTCAGCGCGCTCCGGCAGAACGGCCGGGCGCGCGGCATCCTGCGGCAGGCCCG

GCACCTGGCCGCCCAGTGCGGGCGGTCCCCCTGCTGCGCCGGCTGGGCGTCAAGGCCGGCCGGTCCGGTC

GGCTCGGCCGGCCGCCGCAGGGAATCCGCTCCCTGACCGAGGCCGAGCGCCGGGTGGCCACGCTGGCCGCC

GCCGGGCAGACCAACCGGGAGATCGCCGACCAGCTCTTCGTCACCGCCAGCACGGTCGAGCAGCACCTCAC

CAACGTGTTCCGCAAGCTCGGCGTGAAGGGCCGCCAGCAATTGCCGGCCGAGCTGGCCGACCTGCGGCCGC

CGGGCTGA
```

SEQ ID NO: 11
```
ATGGAGTTTTACGACCTGGTCGCCCGCGATGACGAGCTCAGAAGGTTGGACCAGGCCCTCGGCCGCGCCGC

CGGCGGACGGGGTGTCGTGGTCACCGTCACCGGACCGGTCGGCTGCGGCAAGACCGAACTGCTGGACGCGG

CCGCGGCCGAGGAGGAATTCATCACGTTGCGTGCGGTCTGCTCGGCCGAGGAGCGGGCCCTGCCGTACGCC

GTGATCGGCCAACTCCTCGACCATCCCGTACTCTCCGCACGCGCGCCCGACCTGGCCTGCGTGACGGCTCC

GGGCCGGACGCTGCCGGCCGACACCGAGAACCGCCTGCGCCGCGACCTCACCCGGGCCCTGCTGGCCCTGG

CCTCCGAACGACCGGTTCTGATCTGCATCGACGACGTGCACCAGGCCGACACCGCCTCGCTGAACTGCCTG

CTGCACCTGGCCCGGCGGGTCGCCTCGGCCCGGATCGCCATGATCCTCACCGAGTTGCGCCGGCTCACCCC

GGCTCACTCCCGGTTCGAGGCGGAACTGCTCAGCCTGCGGCACCGCCACGAGATCGCGCTGCGTCCCCTCG

GCCCGGCCGACACCGCCGAACTGGCCCGCGCCCGGCTCGGCGCCGGCGTCACCGCCGACGAGCTGGCCCAG

GTCCACGAGGCCACCAGCGGGAACCCCAACCTGGTCGGAGGCCTGGTCAACGACGTGCGAGAGGCCTGGGC

GGCCGGTGGCACGGGCATTGCGGCGGGGCGGGCGTACCGGCTGGCGTACCTCAGCTCCGTGTACCGCTGTG

GTCCGGTCCCGTTGCGGATCGCCCAGGCGGCGGCGGTGCTGGGTCCAGCGCCACCGTCACGCTGGTGCGC

CGGATCAGCGGGCTCGACGCCGAGACGGTGGACGAGGCGACCGCGATCCTCACCGAGGGCGGCCTGCTCCG

GGACCACCGGTTCCCGCATCCGGCGGCCCGCTCGGTCGTACTCGACGACATGTCCGCGCAGGAACGCCGCC

GCCTGCACCGGTCCACGCTGGACGTGCTGGACGGCGTACCCGTCGACGTGCTCGCGCACCACCAGGCCGGC

GCCGGTCTGCTGCACGGCCCGCAGGCGGCCGAGATGTTCGCCCGGGCCAGCCAGGAGCTGCGGGTACGCGG
```

-continued

CGAGCTGGACGCCGCGACCGAGTACCTGCAACTGGCCTACCGGGCCTCCGACGACGCCGGCGCCCGGGCCG
CCCTGCAGGTGGAGACCGTGGCCGGCGAGCGCCGCCGCAACCCGCTGGCCGCCAGCCGGCACCTGGACGAG
CTGGCCGCCGCCGCCCGGGCCGGCCTGCTGTCGGCCGAGCACGCCGCCCTGGTCGTGCACTGGCTGGCCGA
CGCCGGACGACCCGGCGAGGCCGCCGAGGTGCTGGCGCTGCAGCGGGCGCTGGCCGTCACCGACCACGACC
GGGCCCGCCTGCGGGCGGCCGAGGTGTCGCTCGCGCTGTTCCACCCCGGCGTCCCCGGTTCGGACCCGCGG
CCCCTCGCGCCGGAGGAGCTCGCGAGCCTGTCCCTGTCGGCCCGGCACGGTGTGACCGCCGACAACGCGGT
GCTGGCGGCGCTGCGCGGCCGTCCCGAGTCGGCCGCCGCCGAGGCGGAGAACGTGCTGCGCAACGCCGACG
CCGCCGCGTCCGGCCCGACCGCCCTGGCCGCGCTGACGGCCCTGCTCTACGCCGAGAACACCGACGCCGCC
CAGCTCTGGGCGGACAAGCTGGCCGCGGGCATCGGGGCGGGGGAGGGGGAGGCCGGCTACGCGGGGCCGCG
GACCGTGGCCGCCCTGCGTCGCGGCGACCTGACCACCGCGGTCCAGGCGGCCGGCGCGGTCCTGGACCGCG
GCCGGCCGTCGTCGCTCGGCATCACCGCCGTGTTGCCGTTGAGCGGCGCGGTCGCCGCCGCGATCCGGCTG
GGCGAGCTCGAGCGGGCCGAGAAGTGGCTGGCCGAGCCGCTGCCCGAAGCCGTCCACGACAGCCTGTTCGG
CCTGCACCTGCTGATGGCGCGGGGCCGCTACAGCCTCGCGGTGGGCCGGCACGAGGCGGCGTACGCCGCGT
TCCGGGACTGCGGTGAACGGATGCGCCGGTGGGACGTCGACGTGCCCGGGCTGGCCCTGTGGCGGGTGGAC
GCGGCCGAGGCGCTGCTGCCCGGCGATGACCGGGCGGAGGGCCGGCGGCTGATCGACGAGCAGCTCACCCG
GCCGATGGGGCCCCGGTCACGAGCCCTGACCCTGCGGGTACGAGCGGCCTACGCCCCGCCGGCGAAACGGA
TCGACCTGCTCGACGAAGCGGCCGACCTGCTGCTCTCCAGCAACGACCAGTACGAGCGGGCACGGGTGCTG
GCCGACCTGAGCGAGGCGTTCAGCGCGCTCCGGCAGAACGGCCGGGCGCGCGGCATCCTGCGGCAGGCCCG
GCACCTGGCCGCCCAGTGCGGGGCGGTCCCCCTGCTGCGCCGGCTGGGCGTCAAGGCCGGCCGGTCCGGTC
GGCTCGGCCGGCCGCCGCAGGGAATCCGCTCCCTGACCGAGGCCGAGCGCCGGGTGGCCACGCTGGCCGCC
GCCGGGCAGACCAACCGGGAGATCGCCGACCAGCTCTTCGTCACCGCCAGCACGGTCGAGCAGCACCTCAC
CAACGTGTTCCGCAAGCTCGGCGTGAAGGGCCGCCAGCAATTGCCGGCCGAGCTGGCCGACCTGCGGCCGC
CGGGCTGA

SEQ ID NO: 12
GTGGTCACCGTCACCGGCCCAATCGCCTGCGGCAAGACAGAACTGCTTGACGCGGCTGCCGCGAAGGCTGA
GGCCATCATTCTGCGCGCGGTCTGCGCGCCAGAAGAGCGGGCTATGCCGTACGCCATGATCGGGCAGCTCA
TCGACGACCCGGCGCTCGCGCATCGGGCGCCGGGGCTGGCTGATCGGATAGCCCAGGGCGGGCAGCTGTCG
CTGAGGGCCGAGAACCGACTGCGCAGGGATCTCACCCGTGCCCTGCTGGCGCTTGCCGTCGACCGGCCTGT
GCTGATCGGCGTCGACGATGTGCATCACGCCGACACCGCCTCTTTGAACTGTCTGCTGCATTTGGCGCGCC
GGGTCCGTCCGGCCCGGATATCCATGATCTTCACCGAGTTGCGCAGCCTCACCCCTACTCAGTCACGGTTC
AAGGCGGAGCTGCTCAGCCTGCCGTACCACCACGAGATCGCGCTGCGTCCGTTCGGACCGGAGCAATCGGC
GGAGCTGGCCCGCGCCGCCTTCGGCCCGGGCCTCGCCGAGGATGTGCTCGTGGGGTTGTATAAAACGACCA
GGGGCAATCTGAGTCTCAGCCGTGGACTGATCAGCGATGTGCGGGAGGCCCTGGCCAACGGAGAGAGCGCC
TTCGAGGCGGGCCGCGCGTTCCGGCTGGCGTACCTCGGCTCGCTCTACCGCTGTGGCCCGGTCGCGCTGCG
GGTCGCCCGAGTGGCTGCCGTGCTGGGCCCGAGCGCCACCACCACGCTGGTGCGCCGTCTAAGCGGGCTCA
GCGCGGAGACGATAGACCGGGCAACCAAGATCCTCACCGAGGGCGGGCTGCTGCTCGACCAGCAGTTCCCG
CACCCGGCCGCCCGCTCGGTGGTGCTTGATGACATGTCCGCCCAGGAACGACGCGGCCTGCACACTCTCGC
CCTGGAACTGCTGGACGAGGCGCCGGTTGAAGTGCTCGCGCACCACCAGGTCGGCGCCGGTCTCATACACG
GGCCCAAGGCTGCGGAGATGTTCGCCAAGGCCGGCAAGGCTCTGGTCGTACGCAACGAGTTGGGCGACGCG
GCAGAATACCTGCAACTGGCTCACCGGGCCTCCGACGATGTCTCCACCCGGGCCGCCTTACGGGTCGAGGC
CGTGGCGATCGAGCGCCGCCGCAATCCGCTGGCCTCCAGTCGGCACATGGACGAGCTGAGCGCCGCCGGCC

-continued

GCGCCGGTCTGCTTTCCCCCAAGCATGCGGCGCTGGCCGTCTTCTGGCTGGCCGACGGCGGGCGATCCGGC

GAGGCAGCCGAGGTGCTGGCGTCGGAACGCCCGCTAGCGACCACCGATCAGAACCGGGCCCACTTGCGATT

TGTCGAGGTGACTCTCGCGCTGTTCTCTCCCGGCGCCTTCGGATCGGACCGGCGCCCACCTCCGCTGACGC

CGGACGAACTCGCCAGCCTGCCGAAGGCGGCCTGGCAATGCGCGGTCGCCGACAACGCGGCCATGACCGCC

TTGCACGGTCATCCAGAACTTGCCACCGCTCAGGCGGAAACAGTTCTGCGGCAGGCTGATTCGGCAGCCGA

CGCGATCCCCGCCGCGCTGATCGCCCTGTTGTACGCGGAGAACACCGAGTCCGCTCATATCTGGGCCGACA

AGCTGGGCAGCACGAATGGCGGGGTATCGAACGAGGCGGAAGCGGGCTACGCCGGCCCGTGCGCCGAGATC

GCCCTGCGGCGCGGCGACCTGGCCACGGCGTTCGAGGCTGGTAGCACCGTCCTGGACACCGGTCGCTGCC

GTCGCTCGGCATCACCGCCGCATTGCTGTTGAGCAGCAAGACGGCCGCCGCTGTCCGGCTGGGCGAACTCG

AGCGTGCGGAGAAGCTGCTCGCCGAGCCGCTTCCGAACGGCGTCCAGGACAGCCTTTTCGGTCTGCACCTG

CTCTCGGCATACGGCCAGTACAGCCTCGCGATGGGCCGATATGAATCGGCTCTCCGGGCGTTTCACACCTG

CGGAGAACGTATGCGCAGCTGGGATGTTGACGTGCCTGGTCTGGCCCTGTGGCGTGTCGACGCCGCCGAGG

CGCTGCTCAGCCTCGACCGGAACGAGGGCCAGCGGCTCATCGACGAACAACTCACCCGTCCGATGGGCCT

CGTTCCCGCGCGTTAACGCTGCGGATCAAGGCGGCATACCTCCCGCGGACGAAGCGGATCCCCCTGCTCCA

TGAGGCGGCCGAGCTGCTGCTCCCCTGCCCCGACCCGTACGAGCAAGCGCGGGTGCTCGCCGATCTGGGCG

ACACGCTCAGCGCGCTCAGACGCTATAGCCGGGCGCGGGGAGTTCTCCGGCAGGCTCGTCACCTGGCCGCC

CAGTGCGGTGCTGTCCCGCTGCTGCGCAGGCTCGGGGGCGAGCCCGGCCGGATCGACGACGCCGGCCTGCC

GCAGCGGAGCACATCGTTGACCGATGCGGAGCGGCGGGTGGCGGCGCTGGCCGCGGCCGACAGACCAACC

GGGAGATCGCCAAACAGCTGTTCGTCACGGCCAGCACAGTGGAACAGCACCTCACAAGCGTCTTCCGCAAA

CTGGGGGTCAAGGGTCGCAAGCAGCTGCCGACCGCGCTGGCCGACGTGGAACAGACCTGA

SEQ ID NO: 13
ATGTATAGCGGTACCTGCCGTGAAGGATACGAACTCGTCGCACGCGAGGACGAACTCGGCATTCTACAGAG

GTCTCTGGAACAAGCGAGCAGCGGCCAGGGCGTCGTGGTCACCGTCACCGGCCCAATCGCCTGCGGCAAGA

CAGAACTGCTTGACGCGGCTGCCGCGAAGGCTGAGGCCATCATTCTGCGCGCGGTCTGCGCGCCAGAAGAG

CGGGCTATGCCGTACGCCATGATCGGGCAGCTCATCGACGACCCGGCGCTCGCGCATCGGGCGCGGGGCT

GGCTGATCGGATAGCCCAGGGCGGGCAGCTGTCGCTGAGGGCCGAGAACCGACTGCGCAGGGATCTCACCC

GTGCCCTGCTGGCGCTTGCCGTCGACCGGCCTGTGCTGATCGGCGTCGACGATGTGCATCACGCCGACACC

GCCTCTTTGAACTGTCTGCTGCATTTGGCGCGCCGGGTCCGTCCGGCCCGGATATCCATGATCTTCACCGA

GTTGCGCAGCCTCACCCCTACTCAGTCACGGTTCAAGGCGGAGCTGCTCAGCCTGCCGTACCACCACGAGA

TCGCGCTGCGTCCGTTCGGACCGGAGCAATCGGCGGAGCTGGCCCGCGCCGCCTTCGGCCCGGGCCTCGCC

GAGGATGTGCTCGTGGGGTTGTATAAAACGACCAGGGGCAATCTGAGTCTCAGCCGTGGACTGATCAGCGA

TGTGCGGGAGGCCCTGGCCAACGGAGAGAGCGCCTTCGAGGCGGGCCGCGCGTTCCGGCTGGCGTACCTCG

GCTCGCTCTACCGCTGTGGCCCGGTCGCGCTGCGGGTCGCCCGAGTGGCTGCCGTGCTGGGCCCGAGCGCC

ACCACCACGCTGGTGCGCCGTCTAAGCGGGCTCAGCGCGGAGACGATAGACCGGGCAACCAAGATCCTCAC

CGAGGGCGGGCTGCTGCTCGACCAGCAGTTCCCGCACCCGGCCGCCCGCTCGGTGGTGCTTGATGACATGT

CCGCCCAGGAACGACGCGGCCTGCACACTCTCGCCCTGGAACTGCTGGACGAGGCGCCGGTTGAAGTGCTC

GCGCACCACCAGGTCGGCGCCGGTCTCATACACGGGCCCAAGGCTGCGGAGATGTTCGCCAAGGCCGGCAA

GGCTCTGGTCGTACGCAACGAGTTGGGCGACGCGCAGAATACCTGCAACTGGCTCACCGGGCCTCCGACG

ATGTCTCCACCCGGGCCGCCCTGCGGGTCGAGGCCGTGGCGATCGAGCGCCGCCGCAATCCGCTGGCCTCC

AGTCGGCACATGGACGAGCTGAGCGCCGCCGGCCGCGCCGGTCTGCTTTCCCCCAAGCATGCGGCGCTGGC

CGTCTTCTGGCTGGCCGACGGCGGGCGATCCGGCGAGGCAGCCGAGGTGCTGGCGTCGGAACGCCCGCTAG

-continued

```
CGACCACCGATCAGAACCGGGCCCACTTGCGATTTGTCGAGGTGACTCTCGCGCTGTTCTCTCCCGGCGCC

TTCGGATCGGACCGGCGCCCACCTCCGCTGACGCCGGACGAACTCGCCAGCCTGCCGAAGGCGGCCTGGCA

ATGCGCGGTCGCCGACAACGCGGCCATGACCGCCTTGCACGGTCATCCAGAACTTGCCACCGCTCAGGCGG

AAACAGTTCTGCGGCAGGCTGATTCGGCAGCCGACGCGATCCCCGCCGCGCTGATCGCCCTGTTGTACGCG

GAGAACACCGAGTCCGCTCATATCTGGGCCGACAAGCTGGGCAGCACGAATGGCGGGGTATCGAACGAGGC

GGAAGCGGGCTACGCCGGCCCGTGCGCCGAGATCGCCCTGCGGCGCGGCGACCTGGCCACGGCGTTCGAGG

CTGGTAGCACCGTCCTGGACGACCGGTCGCTGCCGTCGCTCGGCATCACCGCCGCATTGCTGTTGAGCAGC

AAGACGGCCGCCGCTGTCCGGCTGGGCGAACTCGAGCGTGCGGAGAAGCTGCTCGCCGAGCCGCTTCCGAA

CGGCGTCCAGGACAGCCTTTTCGGTCTGCACCTGCTCTCGGCATACGGCCAGTACAGCCTCGCGATGGGCC

GATATGAATCGGCTCTCCGGGCGTTTCACACCTGCGGAGAACGTATGCGCAGCTGGGATGTTGACGTGCCT

GGTCTGGCCCTGTGGCGTGTCGACGCCGCCGAGGCGCTGCTCAGCCTCGACCGGAACGAGGGCCAGCGGCT

CATCGACAACAACTCACCCGTCCGATGGGGCCTCGTTCCCGCGCGCTGACGCTGCGGATCAAGGCGGCAT

ACCTCCCGCGGACGAAGCGGATCCCCCTGCTCCATGAGGCGGCCGAGCTGCTGCTCCCCTGCCCCGACCCG

TACGAGCAAGCGCGGGTGCTCGCCGATCTGGGCGACACGCTCAGCGCGCTCAGACGCTATAGCCGGGCGCG

GGGAGTTCTCCGGCAGGCTCGTCACCTGGCCGCCCAGTGCGGTGCTGTCCCGCTGCTGCGCAGGCTCGGGG

GCGAGCCCGGCCGGATCGACGACGCCGGCCTGCCGCAGCGGAGCACATCGTTGACCGATGCGGAGCGGCGG

GTGGCGGCGCTGGCCGCGGCCGGACAGACCAACCGGGAGATCGCCAAACAGCTGTTCGTCACGGCCAGCAC

AGTGGAACAGCACCTCACAAGCGTCTTCCGCAAACTGGGGGTCAAGGGTCGCAAGCAGCTGCCGACCGCGC

TGGCCGACGTGGAACAGACCTGA

SEQ ID NO: 14
ATGCCTGCCGTGGAGAGCTATGAACTGGACGCCCGCGATGACGAGCTCAGAAGACTGGAGGAGGCGGTAGG

CCAGGCGGGCAACGGCCGGGGTGTGGTGGTCACCATCACCGGGCCGATCGCCTGCGGCAAGACCGAACTGC

TCGACGCGGCCGCCGCGAAGAGCGACGCCATCACATTACGTGCGGTCTGCTCCGAGGAGGAACGGGCCCTC

CCGTACGCCCTGATCGGGCAGCTCATCGACAACCCGGCGGTCGCCTCCCAGCTGCCGGATCCGGTCTCCAT

GGCCCTCCCGGGCGAGCACCTGTCGCCGGAGGCCGAGAACCGGCTGCGCGGCGACCTCACCCGTACCCTGC

TGGCGCTCGCCGCCGAACGGCCGGTGCTGATCGGCATCGACGACATGCACCACGCCGACACCGCCTCTTTG

AACTGCCTGCTCCACCTGGCCCGGAGGGTCGGCCCGGCCCGGATCGCCATGGTCCTCACCGAGCTGCGCCG

GCTCACCCCGGCCCACTCCCAGTTCCACGCCGAGCTGCTCAGCCTGGGGCACCACCGCGAGATCGCGCTGC

GCCCGCTCGGCCCGAAGCACATCGCCGAGCTGGCCCGCGCCGGCCTCGGTCCCGATGTCGACGAGGACGTG

CTCACGGGGTTGTACCGGGCGACCGGCGGCAACCTGAACCTCGGCCACGGACTGATCAAGGATGTGCGGGA

GGCCTGGGCGACGGGCGGGACGGGCATCAACGCGGGCCGCGCGTACCGGCTGGCGTACCTCGGTTCCCTCT

ACCGCTGCGGCCCGGTCCCGTTGCGGGTCGCACGGGTGGCCGCCGTGCTGGGCCAGAGCGCCAACACCACC

CTGGTGCGCTGGATCAGCGGGCTCAACGCGGACGCGGTGGGCGAGGCGACCGAGATCCTCACCGAGGGCGG

CCTGCTGCACGACCTGCGGTTCCCGCATCCGGCGGCCCGTTCGGTCGTACTCAACGACCTGTCCGCCCGGG

AACGCCGCCGACTGCACCGGTCCGCTCTGGAAGTGCTGGATGACGTACCCGTTGAAGTGGTCGCGCACCAC

CAGGCCGGTGCCGGTTTCATCCACGGTCCCAAGGCCGCCGAGATCTTCGCCAAGGCCGGCCAGGAGCTGCA

TGTGCGGCGAGCTGGACGCCGCGTCCGACTATCTGCAACTGGCCCACCACGCCTCCGACGACGCCGTCA

CCCGGGCCGCGCTGCGGGTCGAGGCCGTGGCGATCGAGCGCCGCCGCAACCCGCTGGCCTCCAGCCGCCAC

CTCGACGAGCTGACCGTCGCCGCCCGTGCCGGTCTGCTCTCCCTCGAGCACGCCGCGCTGATGATCCGCTG

GCTGGCTCTCGGCGGGCGGTCCGGCGAGGCGGCCGAGGTGCTGGCCGCGCAGCGCCCGCGTGCGGTCACCG

ACCAGGACAGGGCCCACCTGCGGGCCGCCGAGGTATCGCTGGCGCTGGTCAGCCCGGGCGCGTCCGGCGTC
```

-continued

```
AGCCCGGGTGCGTCCGGCCCGGATCGGCGGCCGCGTCCGCTCCCGCCGGATGAGCTCGCGAACCTGCCGAA
GGCGGCCCGGCTTTGTGCGATCGCCGACAACGCCGTCATATCGGCCCTGCACGGTCGTCCCGAGCTTGCCT
CGGCCCGAGGCGGAGAACGTCCTGAAGCAGGCTGACTCGGCGGCGGACGGCGCCACCGCCCTCTCCGCGCTG
ACGGCCTTGCTGTACGCGGAGAACACCGACACCGCTCAGCTCTGGGCCGACAAGCTCGTCTCCGAGACCGG
GGCGTCGAACGAGGAGGAAGGCGCGGGCTACGCGGGGCCGCGCGCCGAGACCGCGTTGCGCCGCGGCGACC
TGGCCGCGGCGGTCGAGGCGGGCAGCGCCATTCTGGACCACCGGCGGGGGTCGTTGCTCGGCATCACCGCC
GCGCTACCGCTGAGCAGCGCGGTAGCCGCCGCCATCCGGCTGGGCGAGACCGAGCGGGCGGAGAAGTGGCT
CGCCGAGCCGCTGCCGGAGGCCATTCGGGACAGCCTGTTCGGGCTGCACCTGCTCTCGGCGCGCGGCCAGT
ACTGCCTCGCGACGGGCCGGCACGAGTCGGCGTACACGGCGTTCCGCACCTGCGGGGAACGGATGCGGAAC
TGGGGCGTCGACGTGCCGGGTCTGTCCCTGTGGCGCGTCGACGCCGCCGAGGCGCTGCTGCACGGCCGCGA
CCGGGACGAGGGCCGACGGCTCATCGACGAGCAGCTCACCCATGCGATGGGACCCCGTTCCCGCGCTTTGA
CGCTGCGGGTGCAGGCGGCGTACAGCCCGCAGGCGCAGCGGGTCGACCTGCTCGAAGAGGCGGCCGACCTG
CTGCTCTCCTGCAACGACCAGTACGAGCGGGCGCGGGTGCTCGCCGATCTGAGCGAGGCGTTCAGCGCGCT
CAGGCACCACAGCCGGGCGCGGGGACTGCTCCGGCAGGCCCGGCACCTGGCCGCCCAGTGCGGCGCGACCC
CGCTGCTGCGCCGGCTCGGGGCCAAGCCCGGAGGCCCCGGCTGGCTGGAGGAATCCGGCCTGCCGCAGCGG
ATCAAGTCGCTGACCGACGCGGAGCGGCGGGTGGCGTCGCTGGCCGCCGGCGGCCAGACCAACCGCGTGAT
CGCCGACCAGCTCTTCGTCACGGCCAGCACGGTGGAGCAGCACCTCACGAACGTCTTCCGCAAGCTGGGCG
TCAAGGGCCGCCAGCACCTGCCGGCCGAACTCGCCAACGCGGAATAG
```

SEQ ID NO: 15
```
ATGCCTGCCGTGGAGAGCTATGAACTGGACGCCCGCGATGACGAGCTCAGAAGACTGGAGGAGGCGGTAGG
CCAGGCGGGCAACGGCCGGGGTGTGGTGGTCACCATCACCGGGCCGATCGCCTGCGGCAAGACCGAACTGC
TCGACGCGGCCGCCGCGAAGAGCGACGCCATCACACTGCGTGCGGTCTGCTCCGAGGAGGAACGGGCCCTC
CCGTACGCCCTGATCGGGCAGCTCATCGACAACCCGGCGGTCGCCTCCCAGCTGCCGGATCCGGTCTCCAT
GGCCCTCCCGGGCGAGCACCTGTCGCCGGAGGCCGAGAACCGGCTGCGCGGCGACCTCACCCGTACCCTGC
TGGCGCTCGCCGCCGAACGGCCGGTGCTGATCGGCATCGACGACATGCACCACGCCGACACCGCCTCTTTG
AACTGCCTGCTCCACCTGGCCCGGAGGGTCGGCCCGGCCCGGATCGCCATGGTCCTCACCGAGCTGCGCCG
GCTCACCCCGGCCCACTCCCAGTTCCACGCCGAGCTGCTCAGCCTGGGGCACCACCGCGAGATCGCGCTGC
GCCCGCTCGGCCCGAAGCACATCGCCGAGCTGGCCCGCGCCGGCCTCGGTCCCGATGTCGACGAGGACGTG
CTCACGGGGTTGTACCGGGCGACCGGCGGCAACCTGAACCTCGGCCACGGACTGATCAAGGATGTGCGGGA
GGCCTGGGCGACGGGCGGGACGGGCATCAACGCGGGCCGCGCGTACCGGCTGGCGTACCTCGGTTCCCTCT
ACCGCTGCGGCCCGGTCCCGTTGCGGGTCGCACGGGTGGCCGCCGTGCTGGGCCAGAGCGCCAACACCACC
CTGGTGCGCTGGATCAGCGGGCTCAACGCGGACGCGGTGGGCGAGGCGACCGAGATCCTCACCGAGGGCGG
CCTGCTGCACGACCTGCGGTTCCCGCATCCGGCGGCCCGTTCGGTCGTACTCAACGACCTGTCCGCCCGGG
AACGCCGCCGACTGCACCGGTCCGCTCTGGAAGTGCTGGATGACGTACCCGTTGAAGTGGTCGCGCACCAC
CAGGCCGGTGCCGGTTTCATCCACGGTCCCAAGGCCGCCGAGATCTTCGCCAAGGCCGGCCAGGAGCTGCA
TGTGCGCGGCGAGCTGGACGCCGCGTCCGACTATCTGCAACTGGCCCACCACGCCTCCGACGACGCCGTCA
CCCGGGCCGCGCTGCGGGTCGAGGCCGTGGCGATCGAGCGCCGCCGCAACCCGCTGGCCTCCAGCCGCCAC
CTCGACGAGCTGACCGTCGCCGCCCGTGCCGGTCTGCTCTCCCTCGAGCACGCCGCGCTGATGATCCGCTG
GCTGGCTCTCGGCGGGCGGTCCGGCGAGGCGGCCGAGGTGCTGGCCGCGCAGCGCCCGCGTGCGGTCACCG
ACCAGGACAGGGCCCACCTGCGGGCCGCCGAGGTATCGCTGGCGCTGGTCAGCCCGGGCGCGTCCGGCGTC
AGCCCGGGTGCGTCCGGCCCGGATCGGCGGCCGCGTCCGCTCCCGCCGGATGAGCTCGCGAACCTGCCGAA
```

-continued

GGCGGCCCGGCTTTGTGCGATCGCCGACAACGCCGTCATATCGGCCCTGCACGGTCGTCCCGAGCTTGCCT

CGGCCGAGGCGGAGAACGTCCTGAAGCAGGCTGACTCGGCGGCGGACGGCGCCACCGCCCTCTCCGCGCTG

ACGGCCTTGCTGTACGCGGAGAACACCGACACCGCTCAGCTCTGGGCCGACAAGCTCGTCTCCGAGACCGG

GGCGTCGAACGAGGAGGAAGGCGCGGGCTACGCGGGCCGCGCGCCGAGACCGCGTTGCGCCGCGGCGACC

TGGCCGCGGCGGTCGAGGCGGGCAGCGCCATTCTGGACCACCGGCGGGGTCGTTGCTCGGCATCACCGCC

GCGCTACCGCTGAGCAGCGCGGTAGCCGCCGCCATCCGGCTGGGCGAGACCGAGCGGGCGGAGAAGTGGCT

CGCCGAGCCGCTGCCGGAGGCCATTCGGGACAGCCTGTTCGGGCTGCACCTGCTCTCGGCGCGCGGCCAGT

ACTGCCTCGCGACGGGCCGGCACGAGTCGGCGTACACGGCGTTCCGCACCTGCGGGGAACGGATGCGGAAC

TGGGGCGTCGACGTGCCGGGTCTGTCCCTGTGGCGCGTCGACGCCGCCGAGGCGCTGCTGCACGGCCGCGA

CCGGGACGAGGGCCGACGGCTCATCGACGAGCAGCTCACCCATGCGATGGGACCCCGTTCCCGCGCTTTGA

CGCTGCGGGTGCAGGCGGCGTACAGCCCGCAGGCGCAGCGGGTCGACCTGCTCGAAGAGGCGGCCGACCTG

CTGCTCTCCTGCAACGACCAGTACGAGCGGGCGCGGGTGCTCGCCGATCTGAGCGAGGCGTTCAGCGCGCT

CAGGCACCACAGCCGGGCGCGGGGACTGCTCCGGCAGGCCCGGCACCTGGCCGCCCAGTGCGGCGCGACCC

CGCTGCTGCGCCGGCTCGGGGCCAAGCCCGGAGGCCCCGGCTGGCTGGAGGAATCCGGCCTGCCGCAGCGG

ATCAAGTCGCTGACCGACGCGGAGCGGCGGGTGGCGTCGCTGGCCGCCGGCGGCCAGACCAACCGCGTGAT

CGCCGACCAGCTCTTCGTCACGGCCAGCACGGTGGAGCAGCACCTCACGAACGTCTTCCGCAAGCTGGGCG

TCAAGGGCCGCCAGCACCTGCCGGCCGAACTCGCCAACGCGGAATAG

SEQ ID NO: 16
GTGAAGCGCAACGATCTGGTTGCCCGCGATGGCGAGCTCAGGTGGATGCAAGAGATTCTCAGTCAGGCGAG

CGAGGGCCGGGGGCCGTGGTCACCATCACGGGGGCGATCGCCTGTGGCAAGACGGTGCTGCTGGACGCCG

CGGCAGCCAGTCAAGACGTGATCCAACTGCGTGCGGTCTGCTCGGCGGAGGAGCAGGAGCTGCCGTACGCG

ATGGTCGGACAACTACTCGACAATCCGGTGCTCGCCGCGCGAGTGCCGGCCCTGGGCAACCTGGCTGCGGC

GGGCGAGCGGCTGCTGCCGGGCACCGAGAACAGGATCCGGCGGGAGCTCACCCGCACCCTGCTGGCTCTCG

CCGACGAACGACCGGTGCTGATCGGCGTCGACGACATGCACCATGCGGACCCCGCCTCGCTGGACTGCCTG

CTGCACCTGGCCCGGCGGGTCGGCCCGGCCCGCATCGCGATCGTTCTGACCGAGTTGCGCCGGCTCACCCC

GGCTCACTCGCGCTTCCAGTCCGAGCTGCTCAGCCTGCGGTACCACCACGAGATCGGGTTGCAGCCGCTCA

CCGCGGAGCACACCGCCGACCTGGCCCGCGTCGGCCTCGGTGCCGAGGTCGACGACGACGTGCTCACCGAG

CTCTACGAGGCGACCGGCGGCAACCCGAGTCTGTGCTGCGGCCTGATCAGGGACGTGCGGCAGGACTGGGA

GGCCGGGGTCACCGGTATCCACGTCGGCCGGGCGTACCGGCTGGCCTATCTCAGTTCGCTCTACCGCTGCG

GCCCGGCGGCGCTGCGGACCGCCCGCGCGGCCGCGGTGCTGGGCGACAGCGCCGACGCCTGCCTGATCCGC

CGGGTCAGCGGCCTCGGTACGGAGGCCGTGGGCCAGGCGATCCAGCAGCTCACCGAGGGCGGCCTGCTGCG

TGACCAGCAGTTCCCGCACCCGGCGGCCCGCTCGGTCGTGCTCGACGACATGTCCGCGCAGGAACGCCACG

CGATGTATCGCAGCGCCCGGGAGGCAGCCGCCGAAGGTCAGGCCGACCCCGGCACCCCGGGCGAGCCGCGG

GCGGCTACGGCGTACGCCGGGTGTGGTGAGCAAGCCGGTGACTACCCGGAGCCGGCCGGCCGGGCCTGCGT

GGACGGTGCCGGTCCGGCCGAGTACTGCGGCGACCCGCACGGCGCCGACGACGACCCGGACGAGCTGGTCG

CCGCGCTGGGCGGGCTGCTGCCGAGCCGGCTCGTGGCGATGAAGATCCGGCGCCTGGCGGTGGCCGGGCGC

CCCGGGGCGGCTGCCGAGCTGCTGACCTCGCAGCGGTTGCACGCGGTGACCAGCGAGGACCGGGCCAGCCT

GCGGGCCGCCGAGGTGGCGCTCGCCACGCTGTGGCCGGGTGCGACCGGCCCGGACCGGCATCCGCTCACGG

AGCAGGAGGCGGCGAGCCTGCCGGAGGGTCCGCGCCTGCTCGCTGCCGCCGACGATGCCGTCGGGGCCGCC

CTGCGCGGTCGCGCCGAGTACGCCGCGGCCGAGGCGGAGAACGTCCTGCGGCACGCCGATCCGGCAGCCGG

TGGTGACGCCTACGCCGCCATGATCGCCCTGCTGTACACGGAGCACCCCGAGAACGTGCTGTTCTGGGCCG

```
ACAAGCTCGACGCGGGCCGCCCCGACGAGGAGACCAGTTATCCCGGGCTGCGGGCCGAGACCGCGGTGCGG
CTCGGTGACCTGGAAACGGCGATGGAGCTGGGCCGCACGGTGCTGGACCAGCGGCGGCTGCCGTCCCTGGG
TGTCGCCGCGGGCCTGCTCCTGGGCGGCGCGGTGACGGCCGCCATCCGGCTCGGCGACCTCGACCGGGCGG
AGAAGTGGCTCGCCGAGCCGATCCCCGACGCCATCCGTACCAGCCTCTACGGCCTGCACGTGCTGGCCGCG
CGGGGCCGGCTCGACCTGGCCGCGGGCCGCTACGAGGCGGCGTACACGGCGTTCCGGCTGTGTGGCGAGCG
GATGGCAGGCTGGGATGCCGATGTCTCCGGGCTGGCGCTGTGGCGCGTCGACGCCGCCGAGGCCCTGCTGT
CCGCGGGCATCCGCCCGGACGAGGGCCGCAAGCTCATCGACGACCAGCTCACCCGTGAGATGGGGGCCCGC
TCCCGGGCGCTGACGCTGCGGGCGCAAGCGGCGTACAGCCTGCCGGTGCACCGGGTGGGCCTGCTCGACGA
GGCGGCCGGCCTGCTGCTCGCCTGCCATGACGGGTACGAGCGGGCGCGGGTGCTCGCGGACCTGGGGGAGA
CCCTGCGCACGCTGCGGCACACCGACGCGGCCCAGCGGGTGCTCCGGCAGGCCGAGCAGGCGGCCGCGCGG
TGCGGGTCGGTCCCGCTGCTGCGGCGGCTCGGGGCCGAACCCGTACGCATCGGCACCCGGCGTGGTGAACC
CGGCCTGCCGCAGCGGATCAGGCTGCTGACCGATGCCGAGCGGCGGGTTGCCGCGATGGCCGCCGCCGGGC
AGACCAACCGGGAGATCGCCGGTCGGCTCTTCGTCACGGCCAGCACGGTGGAGCAGCACCTGACCAGCGTC
TTCCGCAAGCTGGGCGTCAAGGGCCGCCGGTTCCTGCCGACCGAGCTCGCCCAAGCCGTCTGA
                                                                SEQ ID NO: 17
ATGCCTGCCGTGAAGCGCAACGATCTGGTTGCCCGCGATGGCGAGCTCAGGTGGATGCAAGAGATTCTCAG
TCAGGCGAGCGAGGGCCGGGGGCCGTGGTCACCATCACGGGGGCGATCGCCTGTGGCAAGACGGTGCTGC
TGGACGCCGCGGCAGCCAGTCAAGACGTGATCCAACTGCGTGCGGTCTGCTCGGCGGAGGAGCAGGAGCTG
CCGTACGCGATGGTCGGACAACTACTCGACAATCCGGTGCTCGCCGCGCGAGTGCCGGCCCTGGGCAACCT
GGCTGCGGCGGGCGAGCGGCTGCTGCCGGGCACCGAGAACAGGATCCGGCGGGAGCTCACCCGCACCCTGC
TGGCTCTCGCCGACGAACGACCGGTGCTGATCGGCGTCGACGACATGCACCATGCGGACCCCGCCTCGCTG
GACTGCCTGCTGCACCTGGCCCGGCGGGTCGGCCCGGCCCGCATCGCGATCGTTCTGACCGAGTTGCGCCG
GCTCACCCCGGCTCACTCGCGCTTCCAGTCCGAGCTGCTCAGCCTGCGGTACCACCACGAGATCGGGTTGC
AGCCGCTCACCGCGGAGCACACCGCCGACCTGGCCCGCGTCGGCCTCGGTGCCGAGGTCGACGACGACGTG
CTCACCGAGCTCTACGAGGCGACCGGCGGCAACCCGAGTCTGTGCTGCGGCCTGATCAGGGACGTGCGGCA
GGACTGGGAGGCCGGGGTCACCGGTATCCACGTCGGCCGGGCGTACCGGCTGGCCTATCTCAGTTCGCTCT
ACCGCTGCGGCCCGGCGGCGCTGCGGACCGCCCGCGCGGCCCGCGGTGCTGGGCGACAGCGCCGACGCCTGC
CTGATCCGCCGGGTCAGCGGCCTCGGTACGGAGGCCGTGGGCCAGGCGATCCAGCAGCTCACCGAGGGCGG
CCTGCTGCGTGACCAGCAGTTCCCGCACCCGGCGGCCCGCTCGGTCGTGCTCGACGACATGTCCGCGCAGG
AACGCCACGCGATGTATCGCAGCGCCCGGGAGGCAGCCGCCGAAGGTCAGGCCGACCCCGGCACCCCGGGC
GAGCCGCGGCGGCTACGGCGTACGCCGGGTGTGGTGAGCAAGCCGGTGACTACCCGGAGCCGGCCGGCCG
GGCCTGCGTGGACGGTGCCGGTCCGGCCGAGTACTGCGGCGACCCGCACGGCGCCGACGACGACCCGGACG
AGCTGGTCGCCGCGCTGGGCGGCTGCTGCCGAGCCGGCTCGTGGCGATGAAGATCCGGCGCCTGGCGGTG
GCCGGGCGCCCCGGGGCGGCTGCCGAGCTGCTGACCTCGCAGCGGTTGCACGCGGTGACCAGCGAGGACCG
GGCCAGCCTGCGGGCCGCCGAGGTGGCGCTCGCCACGCTGTGGCCGGGTGCGACCGGCCCGGACCGGCATC
CGCTCACGGAGCAGGAGGCGGCGAGCCTGCCGGAGGGTCCGCGCCTGCTCGCTGCCGCCGACGATGCCGTC
GGGGCCGCCCTGCGCGGTCGCGCCGAGTACGCCGCGCCGAGGCGGAGAACGTCCTGCGGCACGCCGATCC
GGCAGCCGGTGGTGACGCCTACGCCGCCATGATCGCCCTGCTGTACACGGAGCACCCCGAGAACGTGCTGT
TCTGGGCCGACAAGCTCGACGCGGGCCGCCCCGACGAGGAGACCAGTTATCCCGGGCTGCGGGCCGAGACC
GCGGTGCGGCTCGGTGACCTGGAAACGGCGATGGAGCTGGGCCGCACGGTGCTGGACCAGCGGCGGCTGCC
GTCCCTGGGTGTCGCCGCGGGCCTGCTCCTGGGCGGCGCGGTGACGGCCGCCATCCGGCTCGGCGACCTCG
```

-continued

ACCGGGCGGAGAAGTGGCTCGCCGAGCCGATCCCCGACGCCATCCGTACCAGCCTCTACGGCCTGCACGTG
CTGGCCGCGCGGGGCCGGCTCGACCTGGCCGCGGGCCGCTACGAGGCGGCGTACACGGCGTTCCGGCTGTG
TGGCGAGCGGATGGCAGGCTGGGATGCCGATGTCTCCGGGCTGGCGCTGTGGCGCGTCGACGCCGCCGAGG
CCCTGCTGTCCGCGGGCATCCGCCCGGACGAGGGCCGCAAGCTCATCGACGACCAGCTCACCCGTGAGATG
GGGGCCCGCTCCCGGGCGCTGACGCTGCGGGCGCAAGCGGCGTACAGCCTGCCGGTGCACCGGGTGGGCCT
GCTCGACGAGGCGGCCGGCCTGCTGCTCGCCTGCCATGACGGGTACGAGCGGGCGCGGGTGCTCGCGGACC
TGGGGGAGACCCTGCGCACGCTGCGGCACACCGACGCGGCCCAGCGGGTGCTCCGGCAGGCCGAGCAGGCG
GCCGCGCGGTGCGGGTCGGTCCCGCTGCTGCGGCGGCTCGGGGCCGAACCCGTACGCATCGGCACCCGGCG
TGGTGAACCCGGCCTGCCGCAGCGGATCAGGCTGCTGACCGATGCCGAGCGGCGGGTTGCCGCGATGGCCG
CCGCCGGGCAGACCAACCGGGAGATCGCCGGTCGGCTCTTCGTCACGGCCAGCACGGTGGAGCAGCACCTG
ACCAGCGTCTTCCGCAAGCTGGGCGTCAAGGGCCGCCGGTTCCTGCCGACCGAGCTCGCCCAAGCCGTCTG
A

SEQ ID NO: 18
GTGGTCACCGTCACCGGCCCAATCGCCTGCGGCAAGACAGAACTGCTTGACGCGGCTGCCGCGAAGGCTGA
GGCCATCATTCTGCGCGCGGTCTGCGCGCCAGAAGAGCGGGCTATGCCGTACGCCATGATCGGGCAGCTCA
TCGACGACCCGGCGCTCGCGCATCGGGCGCCGGGGCTGGCTGATCGGATAGCCCAGGGCGGGCAGCTGTCG
CTGAGGGCCGAGAACCGACTGCGCAGGGATCTCACCCGTGCCCTGCTGGCGCTTGCCGTGGACCGGCCTGT
GCTGATCGGCGTCGACGATGTGCATCACGCCGACACCGCCTCTTTGAACTGTCTGCTGCATTTGGCCCGCC
GGGTCCGTCCGGCCCGGATATCCATGATCTTCACCGAGTTGCGCAGCCTCACCCCTACTCAGTCACGGTTC
AAGGCGGAGCTGCTCAGCCTGCCATACCACCACGAGATCGCGCTGCGTCCATTCGGACCGGAGCAATCGGC
GGAGCTGGCTCGCGCCGCCTTCGGCCCGGGCCTCGCCGAGGATGTGCTCGCGGGGTTGTATAAAACGACCA
GGGGCAATCTGAGTCTCAGCCGTGGACTGATCAGCGATGTGCGGGAGGCCCTGGCCAACGGAGAGAGCGCT
TTCGAGGCGGGCCGCGCGTTCCGGCTGGCGTACCTCAGCTCGCTCTACCGCTGTGGCCCGGTCGCGCTGCG
GGTCGCCCGAGTGGCTGCCGTGCTGGGCCCAAGCGCCACCACCACGCTGGTGCGCCGGCTAAGCGGGCTCA
GCGCGGAGACGATAGACCGGGCAACCAAGATCCTCACTGAGGGCGGGCTGCTGCTCGACCAGCAGTTCCCG
CACCCGGCCGCCCGCTCGGTGGTGCTCGATGACATGTCCGCCCAGGAACGACGCAGCCTGCACACTCTCGC
CCTGGAACTGCTGGACGAGGCGCCGGTTGAAGTGCTCGCGCACCACCAGGTCGGCGCCGGTCTCATACACG
GGCCCAAGGCTGCGGAGATGTTCGCCAAGGCCGGCAAGGCTCTGGTCGTACGCAACGAGTTGGGCGACGCG
GCCGAATACCTGCAACTGGCTCACCGGGCCTCCGACGATGTCTCCACCCGGGCCGCCTTACGGGTCGAGGC
CGTGGCCATCGAGCGCCGCCGCAATCCGCTGGCCTCCAGTCGGCACATGGACGAACTGAGCGCCGCCGGCC
GCGCCGGTCTGCTTTCCCCCAAGCATGCGGCGCTGGCCGTCTTCTGGCTAGCCGACGGCGGGCGATCCGGC
GAGGCAGCCGAAGTGCTGGCGTCGGAACGCCCGCTCGCGACCACCGATCAGAACCGGGCCCACCTGCGATT
TGTCGAGGTGACTCTCGCGCTGTTCTCTCCCGGCGCCTTCGGATCGGACCGGCGCCCACCTCCGCTGACGC
CGGACGAACTCGCCAGCCTGCCGAAGGCGGCCTGGCAATGCGCGGTCGCCGACAACGCGGCCATGACCGCC
TTGCACGGCCATCCAGAACTTGCCACCGCTCAGGCGGAAACAGTTCTGCGGCAGGCTGATTCGGCAGCCGA
CGCGATCCCCGCCGCGCTGATCGCCCTGTTGTACGCGGAGAACACCGAGTCCGCTCATATCTGGGCCGACA
AGCTGGGCAGCACGAATGCCGGGGTATCGAACGAGGCGGAAGCGGGCTACGCCGGCCCGTGCGCCGAGATC
GCCCTGCGGCGCGGCGACCTGGCCACGGCGTTCGAGGCTGGTAGCGCCGTCCTGGACGACCGGTCGCTGCC
GTCGCTCGGCATCACCGCCGCATTGCTGTTGAGCAGCAAGACGGCCGCCGCTGTCCGGCTGGGCGAACTCG
AGCGTGCGGAGAAGCTGCTCGCCGAGCCGCTTCCGAACGGCGTCCAGGACAGCCTTTTCGGTCTGCACCTG
CTCTCGGCGTACGGCCAGTACAGCCTCGCGATGGGCCGATATGAATCAGCTCACCGGGCGTTTCGCACCTG

```
CGGAGAACGTATGCGCAGCTGGGATGTTGACGTGCCTGGTCTGGCCCTGTGGCGTGTCGACGCCGCCGAGG

CGCTGCTCAGCCTCGACCGGAACGAGGGCCAGCGGCTCATCGACGAACAACTCACCCGTCCGATGGGGCCT

CGTTCCCACGCGTTAACGCTGCGGATCAAGGCGGCATACCTCCCGCGGACGAAGCGGATCCCCCTGCTCCA

TGAGGCGGCCGAGCTGCTGCTCCCCTGCCCCGACCCGTACGAGCAAGCGCGGGTGCTCGCCGATCTGGGCG

ACACGCTCAGCGCGCTCAGACGCTATAGCCGGGCGCGGGGAGTTCTCCGGCAGGCTCGTCACCTGGCCACC

CAGTGCGGTGCTGTCCCGCTGCTGCGCAGGCTCGGGGGCGAGCCCGGCCGGATCGACGACGCCGGCCTGCC

GCAGCGGAGCACATCGTTGACCGATGCGGAGCGGCGGGTGGCGGCGCTGGCCGCGGCCGGACAGACCAACC

GGGAGATCGCCGAACAGCTGTTCGTCACGGCCAGCACAGTGGAACAGCACCTCACAAGCGTCTTCCGCAAG

CTGGGCGTCAAGGGCCGCAAGCAGCTGCCGACCGCGCTGGCCGACGTGGAACAGACCTGA
```

SEQ ID NO: 19
```
ATGTATAGCGGTACCTGCCGTGAAGGATACGAACTCGTCGCACGCGAGGACGAACTCGGTATTCTACAGAG

GTCTCTGGAACAAGCGAGCAGCGGCCAGGGCGTCGTGGTCACCGTCACCGGCCCAATCGCCTGCGGCAAGA

CAGAACTGCTTGACGCGGCTGCCGCGAAGGCTGAGGCCATCATTCTGCGCGCGGTCTGCGCGCCAGAAGAG

CGGGCTATGCCGTACGCCATGATCGGGCAGCTCATCGACGACCCGGCGCTCGCGCATCGGGCGCCGGGGCT

GGCTGATCGGATAGCCCAGGGCGGGCAGCTGTCGCTGAGGGCCGAGAACGACTGCGCAGGGATCTCACCC

GTGCCCTGCTGGCGCTTGCCGTGGACCGGCCTGTGCTGATCGGCGTCGACGATGTGCATCACGCCGACACC

GCCTCTTTGAACTGTCTGCTGCATTTGGCCCGCCGGGTCCGTCCGGCCCGGATATCCATGATCTTCACCGA

GTTGCGCAGCCTCACCCCTACTCAGTCACGGTTCAAGGCGGAGCTGCTCAGCCTGCCATACCACCACGAGA

TCGCGCTGCGTCCATTCGGACCGGAGCAATCGGCGGAGCTGGCTCGCGCCGCCTTCGGCCCGGGCCTCGCC

GAGGATGTGCTCGCGGGGTTGTATAAAACGACCAGGGGCAATCTGAGTCTCAGCCGTGGACTGATCAGCGA

TGTGCGGGAGGCCCTGGCCAACGGAGAGAGCGCTTTCGAGGCGGCCGCGCGTTCCGGCTGGCGTACCTCA

GCTCGCTCTACCGCTGTGGCCCGGTCGCGCTGCGGGTCGCCCGAGTGGCTGCCGTGCTGGGCCCAAGCGCC

ACCACCACGCTGGTGCGCCGGCTAAGCGGGCTCAGCGCGGAGACGATAGACCGGGCAACCAAGATCCTCAC

TGAGGGCGGGCTGCTGCTCGACCAGCAGTTCCCGCACCCGGCCGCCCGCTCGGTGGTGCTCGATGACATGT

CCGCCCAGGAACGACGCAGCCTGCACACTCTCGCCCTGGAACTGCTGGACGAGGCGCCGGTTGAAGTGCTC

GCGCACCACCAGGTCGGCGCCGGTCTCATACACGGGCCCAAGGCTGCGGAGATGTTCGCCAAGGCCGGCAA

GGCTCTGGTCGTACGCAACGAGTTGGGCGACGCGGCCGAATACCTGCAACTGGCTCACCGGGCCTCCGACG

ATGTCTCCACCCGGGCCGCCCTGCGGGTCGAGGCCGTGGCCATCGAGCGCCGCCGCAATCCGCTGGCCTCC

AGTCGGCACATGGACGAACTGAGCGCCGCCGCCGCGCCGGTCTGCTTTCCCCCAAGCATGCGGCGCTGGC

CGTCTTCTGGCTAGCCGACGGCGGGCGATCCGGCGAGGCAGCCGAAGTGCTGGCGTCGGAACGCCCGCTCG

CGACCACCGATCAGAACCGGGCCCACCTGCGATTTGTCGAGGTGACTCTCGCGCTGTTCTCTCCCGGCGCC

TTCGGATCGGACCGGCGCCCACCTCCGCTGACGCCGGACGAACTCGCCAGCCTGCCGAAGGCGGCCTGGCA

ATGCGCGGTCGCCGACAACGCGGCCATGACCGCCTTGCACGGCCATCCAGAACTTGCCACCGCTCAGGCGG

AAACAGTTCTGCGGCAGGCTGATTCGGCAGCCGACGCGATCCCCGCCGCGCTGATCGCCCTGTTGTACGCG

GAGAACACCGAGTCCGCTCATATCTGGGCCGACAAGCTGGGCAGCACGAATGCCGGGGTATCGAACGAGGC

GGAAGCGGGCTACGCCGGCCCGTGCGCCGAGATCGCCCTGCGGCGCGGCGACCTGGCCACGGCGTTCGAGG

CTGGTAGCGCCGTCCTGGACGACCGGTCGCTGCCGTCGCTCGGCATCACCGCCGCATTGCTGTTGAGCAGC

AAGACGGCCGCCGCTGTCCGGCTGGGCGAACTCGAGCGTGCGGAGAAGCTGCTCGCCGAGCCGCTTCCGAA

CGGCGTCCAGGACAGCCTTTTCGGTCTGCACCTGCTCTCGGCGTACGGCCAGTACAGCCTCGCGATGGGCC

GATATGAATCAGCTCACCGGGCGTTTCGCACCTGCGGAGAACGTATGCGCAGCTGGGATGTTGACGTGCCT

GGTCTGGCCCTGTGGCGTGTCGACGCCGCCGAGGCGCTGCTCAGCCTCGACCGGAACGAGGGCCAGCGGCT
```

-continued

CATCGACGAACAACTCACCCGTCCGATGGGGCCTCGTTCCCACGCGCTGACGCTGCGGATCAAGGCGGCAT

ACCTCCCGCGGACGAAGCGGATCCCCCTGCTCCATGAGGCGGCCGAGCTGCTGCTCCCCTGCCCCGACCCG

TACGAGCAAGCGCGGGTGCTCGCCGATCTGGGCGACACGCTCAGCGCGCTCAGACGCTATAGCCGGGCGCG

GGGAGTTCTCCGGCAGGCTCGTCACCTGGCCACCCAGTGCGGTGCTGTCCCGCTGCTGCGCAGGCTCGGGG

GCGAGCCCGGCCGGATCGACGACGCCGGCCTGCCGCAGCGGAGCACATCGTTGACCGATGCGGAGCGGCGG

GTGGCGGCGCTGGCCGCGGCCGGACAGACCAACCGGGAGATCGCCGAACAGCTGTTCGTCACGGCCAGCAC

AGTGGAACAGCACCTCACAAGCGTCTTCCGCAAGCTGGGCGTCAAGGGCCGCAAGCAGCTGCCGACCGCGC

TGGCCGACGTGGAACAGACCTGA

SEQ ID NO: 20
GTGTATAGCGGTACCTGCCGTGAAGGATACGAACTCGTCGCCCGCGAGGACGAACTCGGCATTCTGCAGAG

GTCTCTGGAAGAAGCAGGCAGCGGCCAGGGCGCCGTGGTCACCGTCACCGGCCCGATCGCCTGCGGCAAGA

CAGAACTGCTTGACGCGGCTGCCGCGAAGGCTGACGCCATCATTCTGCGCGCGGTCTGCGCGCCCGAAGAG

CGCGCTATGCCGTACGCCATGATCGGGCAGCTCATCGACGACCCGGCGCTCGCGCATCGGGCGCGGAGCT

GGCTGATCGGATAGCCCAGGGCGGGCATCTGTCGCTGAGGGCCGAGAACCGACTGCGCAGGGATCTCACCC

GTGCCCTGCTGGCGCTTGCCGTCGACCGGCCTGTGCTGATCGGCGTCGACGATGTGCATCACGCCGACACC

GCCTCTTTGAACTGTCTGCTGCATTTAGCCCGCCGGGTCCGTCCGGCCCGGATATCCATGATCTTCACCGA

GTTGCGCAGCCTCACCCCTACTCAGTCACGATTCAAGGCGGAGCTGCTCAGCCTGCCGTACCACCACGAGA

TCGCGCTGCGTCCACTCGGACCGGAGCAATCGGCGGAGCTGGCCCACGCCGCCTTCGGCCCGGGCCTCGCC

GAGGATGTGCTCGCGGGGTTGTATGGGATGACCAGGGGCAACCTGAGTCTCAGCCGTGGACTGATCAGCGA

TGTGCGGGAGGCCCAGGCCAACGGAGAGAGCGCTTTCGAGGTGGGCCGCGCGTTCCGGCTGGCGTACCTCA

GCTCGCTCTACCGCTGTGGCCCGATCGCGCTGCGGGTCGCCCGAGTGGCTGCCGTGCTGGGCCCAAGCGCC

ACCACCACGCTGGTGCGCCGTCTAAGCGGGCTCAGCGCGGAGACGATAGACCGGGCAACCAAGATCCTCAC

TGAGGGCGGGCTGCTGCTCGACCACCAGTTCCCGCACCCGGCCGCCCGCTCGGTGGTGCTCGATGACATGT

CCGCCCAGGAACGACGCAGCCTGCACACTCTCGCCCTGGAACTGCTGGACGAGGCGCCGGTTGAAGTGCTC

GCGCACCACCAGGTCGGCGCCGGTCTCATACACGGGCCCAAGGCTGCGGAGATATTCGCCAGGGCTGGCCA

GGCTCTGGTTGTACGCAACGAGTTGGGCGACGCGGCCGAATACCTGCAACTGGCTCACCGAGCCTCCGACG

ATGTCTCCACCCGGGCCGCCTTACGGGTCGAGGCCGTGGCAATCGAGCGCCGCCGCAATCCGCTGGCCTCC

AGTCGTCACATGGACGAGCTGAGCGCCGCCGGCCGCGCCGGTCTGCTTTCCCCCAAGCATGCAGCGCTGGC

TGTCTTCTGGCTGGCCGACGGCGGGCGATCCGGCGAGGCAGCCGAGGTGCTGGCGTCGGAACACCCGCTCG

CGACCACCGATCAGAACCGAGCACACCTGCGATTTGCCGAGGTGACTCTCGCGCTGTTCTGTCCCGGCGCC

TTCGGGTCGGACCGGCGCCCACCTCCGCTGGCGCCGGACGAGCTCGCCAGCTTGCCGAAGGCGGCCTGGCA

ATGCGCGGTCGCCGACAACGCGGTCATGACAGCGTTGCATGCTCATCCAGAACTTGCCACCGCTCAGGCGG

AAACAGTTCTGCGGCAGGCTGATTCGGCAGCCGACGCAATCCCCGCCGCACTGATCGCCCTGTTGTACGCA

GAGAACACCGAGTCCGCTCAGATCTGGGCCGACAAGCTGGGCAGCACCAATGCCGGGGTATCGAACGAGGC

GGAAGCGGGCTACGCCGGCCCGTGCGCCGAGATCGCCCTGCGGCGCGGCGACCTGGCCACGGCGTTCGAGG

CTGGTGGCACCGTCCTGGACGACCGGCCGCTGCCGTCGCTCGGCATCACCGCCGCATTGCTGTTGAGCAGC

AAGACGGCAGCCGCTGTCCGCCTGGGCGAACTCGAGCGTGCGGAGAAGCTGCTCGCTGAGCCGCTTCCGAA

CGGTGTCCAGGACAGCCTTTTCGGTCTGCACCTGCTCTCGGCGCACGGCCAGTACAGCCTCGCGATGGGCC

GATATGAATCGGCTCACCGGGCGTTTCACACCTGCGGAGAACGTATGCGCAGCTGGGGTGTTGACGTGCCT

GGTCTAGCCCTGTGGCGTGTCGACGCCGCCGAGGCACTGCTCAGCCTCGACCGGAACGAGGGCCAGCGGCT

CATCGACGAACAACTCGCCCGTCCGATGGGACCTCGTTCCCGCGCATTAACGCTGCGGATCAAGGCGGCAT

-continued

ACCTCCCGCGGACGAAGCGGATCCCCCTGCTCCATGAGGCAGCTGAGCTGCTGCTCTCCTGCCCCGACCCG

TACGAGCAAGCGCGGGTGCTCGCCGATCTGGGCGACACGCTCAGCGCGCTCAGACGCTATAGCCGGGCGCG

GGGAGTTCTCCGGCAGGCTCGTCACCTGGCCACCCAGTGCGGTGCTGTCCCGCTGCTGCGCCGACTCGGGG

GCGAGCCCGGCCGGATCGACGACGCCGGCCTGCCGCAGCGGAGCACATCGTTGACCGATGCGGAGCGGCGG

GTGTCGGCCCTGGCCGCGGCCGGACAGACCAACCGGGAGATCGCCAAACAGCTATTCGTCACGGCCAGCAC

CGTGGAACAGCACCTCACAAGCGTCTTCCGCAAGCTGGGCGTTAAGGGCCGCAGGCAGCTACCGACCGCGC

TGGCCGACGTGGAATAG

SEQ ID NO: 21
ATGTATAGCGGTACCTGCCGTGAAGGATACGAACTCGTCGCCCGCGAGGACGAACTCGGCATTCTGCAGAG

GTCTCTGGAAGAAGCAGGCAGCGGCCAGGGCGCCGTGGTCACCGTCACCGGCCCGATCGCCTGCGGCAAGA

CAGAACTGCTTGACGCGGCTGCCGCGAAGGCTGACGCCATCATTCTGCGCGCGGTCTGCGCGCCCGAAGAG

CGCGCTATGCCGTACGCCATGATCGGGCAGCTCATCGACGACCCGGCGCTCGCGCATCGGGCGCCGGAGCT

GGCTGATCGGATAGCCCAGGGCGGGCATCTGTCGCTGAGGGCCGAGAACCGACTGCGCAGGGATCTCACCC

GTGCCCTGCTGGCGCTTGCCGTCGACCGGCCTGTGCTGATCGGCGTCGACGATGTGCATCACGCCGACACC

GCCTCTTTGAACTGTCTGCTGCATCTGGCCCGCCGGGTCCGTCCGGCCCGGATATCCATGATCTTCACCGA

GTTGCGCAGCCTCACCCCTACTCAGTCACGATTCAAGGCGGAGCTGCTCAGCCTGCCGTACCACCACGAGA

TCGCGCTGCGTCCACTCGGACCGGAGCAATCGGCGGAGCTGGCCCACGCCGCCTTCGGCCCGGGCCTCGCC

GAGGATGTGCTCGCGGGGTTGTATGGGATGACCAGGGGCAACCTGAGTCTCAGCCGTGGACTGATCAGCGA

TGTGCGGGAGGCCCAGGCCAACGGAGAGAGCGCTTTCGAGGTGGCCGCGCGTTCCGGCTGGCGTACCTCA

GCTCGCTCTACCGCTGTGGCCCGATCGCGCTGCGGGTCGCCCGAGTGGCTGCCGTGCTGGGCCCAAGCGCC

ACCACCACGCTGGTGCGCCGTCTAAGCGGGCTCAGCGCGGAGACGATAGACCGGGCAACCAAGATCCTCAC

TGAGGGCGGGCTGCTGCTCGACCACCAGTTCCCGCACCCGGCCGCCCGCTCGGTGGTGCTCGATGACATGT

CCGCCCAGGAACGACGCAGCCTGCACACTCTCGCCCTGGAACTGCTGGACGAGGCGCCGGTTGAAGTGCTC

GCGCACCACCAGGTCGGCGCCGGTCTCATACACGGGCCCAAGGCTGCGGAGATATTCGCCAGGGCTGGCCA

GGCTCTGGTTGTACGCAACGAGTTGGGCGACGCGGCCGAATACCTGCAACTGGCTCACCGAGCCTCCGACG

ATGTCTCCACCCGGGCCGCCCTGCGGGTCGAGGCCGTGGCAATCGAGCGCCGCCGCAATCCGCTGGCCTCC

AGTCGTCACATGGACGAGCTGAGCGCCGCCGGCCGCGCCGGTCTGCTTTCCCCCAAGCATGCAGCGCTGGC

TGTCTTCTGGCTGGCCGACGGCGGGCGATCCGGCGAGGCAGCCGAGGTGCTGGCGTCGGAACACCCGCTCG

CGACCACCGATCAGAACCGAGCACACCTGCGATTTGCCGAGGTGACTCTCGCGCTGTTCTGTCCCGGCGCC

TTCGGGTCGGACCGGCGCCCACCTCCGCTGGCGCCGGACGAGCTCGCCAGCTTGCCGAAGGCGGCCTGGCA

ATGCGCGGTCGCCGACAACGCGGTCATGACAGCGTTGCATGCTCATCCAGAACTTGCCACCGCTCAGGCGG

AAACAGTTCTGCGGCAGGCTGATTCGGCAGCCGACGCAATCCCCGCCGCACTGATCGCCCTGTTGTACGCA

GAGAACACCGAGTCCGCTCAGATCTGGGCCGACAAGCTGGGCAGCACCAATGCCGGGGTATCGAACGAGGC

GGAAGCGGGCTACGCCGGCCCGTGCGCCGAGATCGCCCTGCGGCGCGGCGACCTGGCCACGGCGTTCGAGG

CTGGTGGCACCGTCCTGGACGACCGGCCGCTGCCGTCGCTCGGCATCACCGCCGCATTGCTGTTGAGCAGC

AAGACGGCAGCCGCTGTCCGCCTGGGCGAACTCGAGCGTGCGGAGAAGCTGCTCGCTGAGCCGCTTCCGAA

CGGTGTCCAGGACAGCCTTTTCGGTCTGCACCTGCTCTCGGCGCACGGCCAGTACGCCTCGCGATGGGCC

GATATGAATCGGCTCACCGGGCGTTTCACACCTGCGGAGAACGTATGCGCAGCTGGGGTGTTGACGTGCCT

GGTCTAGCCCTGTGGCGTGTCGACGCCGCCGAGGCACTGCTCAGCCTCGACCGGAACGAGGGCCAGCGGCT

CATCGACGAACAACTCGCCCGTCCGATGGGACCTCGTTCCCGCGCACTGACGCTGCGGATCAAGGCGGCAT

ACCTCCCGCGGACGAAGCGGATCCCCCTGCTCCATGAGGCAGCTGAGCTGCTGCTCTCCTGCCCCGACCCG

-continued

```
TACGAGCAAGCGCGGGTGCTCGCCGATCTGGGCGACACGCTCAGCGCGCTCAGACGCTATAGCCGGGCGCG
GGGAGTTCTCCGGCAGGCTCGTCACCTGGCCACCCAGTGCGGTGCTGTCCCGCTGCTGCGCCGACTCGGGG
GCGAGCCCGGCCGGATCGACGACGCCGGCCTGCCGCAGCGGAGCACATCGTTGACCGATGCGGAGCGGCGG
GTGTCGGCCCTGGCCGCGGCCGGACAGACCAACCGGGAGATCGCCAAACAGCTATTCGTCACGGCCAGCAC
CGTGGAACAGCACCTCACAAGCGTCTTCCGCAAGCTGGGCGTTAAGGGCCGCAGGCAGCTACCGACCGCGC
TGGCCGACGTGGAATAG
```

SEQ ID NO: 22
```
GTGTATAGCGGTACCTGCCGTGAAGGATACGAACTCGTCGCACGCGAGGACGAACTCGGCATTCTACAGAG
GTCTCTGGAACAAGCGAGCAGCGGCCAGGGCGTCGTGGTCACCGTCACCGGCCCAATCGCCTGCGGCAAGA
CAGAACTGCTTGACGCGGCTGCCGCGAAGGCTGAGGCCATCATTCTGCGCGCGGTCTGCGCGCCCGAAGAG
CGGGCTATGCCGTACGCCATGATCGGGCAGCTCATCGACGACCCGGCGCTCGCGCATCGGGCGCGGGGCT
GGCTGATCGGATAGCCCAGGGCGGGCAGCTGTCGCTGAGGGCCGAGAACCGACTGCGCAGGGATCTCACCC
GTGCCCTGCTGGCGCTTGCCGTGCACCGGCCTGTGCTGATCGGCGTCGATGATGTGCATCACGCCGACACC
GCCTCTTTGAACTGTCTGCTGCATTTGGCGCGCCGGGTCCGTCCGGCCCGGATATCCATGATCTTCACCGA
GTTGCGCAGCCTCACCCCTACTCAGTCACGATTCAAGGCGGAGCTGCTCAGCCTGCCGTACCACCACGAGA
TCGCGCTGCGTCCATTCGGACCGGAGCAATCGGCGGAGCTGGCTCGCGCCGCCTTCGGCCCGGGCCTCGCC
GAGGATGTGCTCGCGGGGTTGTATAAAACGACCAGGGGCAATCTGAGTCTCAGCCGTGGACTGATCAGCGA
TGTGCGGGAGGCCCTGGCCAACGGAGAGAGCGCTTTCGAGGCGGGCCGCGCGTTCCGGCTGGCGTACCTCA
GCTCGCTCTACCGCTGTGGCCCGGTCGCGCTGCGGGTCGCCCGAGTGGCTGCCGTGCTGGGCCCAAGCGCC
ACCACCACGCTGGTGCGCCGGCTAAGCGGGCTCAGCGCGGAGACGATAGACCGGGCAACCAAGATCCTCAC
CGAGGGCGGGCTGCTGCTCGACCAGCAGTTTCCGCACCCGGCCGCCCGCTCGGTGGTGCTCGATGACATGT
CCGCCCAGGAACGACGCGGCCTGCACACTCTCGCCCTGGAACTGCTGGACGAGGCGCCGGTTGAAGTGCTC
GCGCACCACCAGGTCGGCGCCGGTCTCATACACGGGCCCAAGGCTGCGGAGATGTTCGCCAAGGCCGGCAA
GGCTCTGGTCGTACGCAACGAGTTGGGCGACGCGGCCGAATACCTGCAACTGGCTCACCGGGCCTCCGACG
ATGTCTCCACCCGGGCCGCCTTACGGGTCGAGGCCGTGGCGATCGAGCGCCGCCGCAATCCGCTGGCCTCC
AGTCGGCACATGGACGAGCTGAGCGCCGCCGGCCGCGCCGGTCTGCTTTCCCCCAAGCATGCGGCGCTGGC
CGTCTTCTGGCTGGCCGACGGCGGGCGATCCGGCGAGGCAGCCCAGGTGCTGGCGTCGGAACGCCCGCTCG
CGACCACCGATCAGAACCGGGCCCACCTGCGATTTGTCGAGGTGACTCTCGCGCTGTTCTCTCCCGGCGCC
TTCGGATCGGACCGGCGCCCACCTCCGCTGACGCCGGACGAACTCGCCAGCCTGCCGAAGGCGGCCTGGCA
ATGCGCGGTCGCCGACAACGCGGCCATGACCGCCTTGCACGGCCATCCAGAACTTGCCACCGCTCAGGCGG
AAACAGTTCTGCGGCAGGCTGATTCGGCAGCCGACGCGATCCCCGCCGCGCTGATCGCCCTGTTGTACGCG
GAGAACACCGAGTCCGCTCATATCTGGGCCGACAAGCTGGGCAGCATGAATGCCGGGGTATCGAACGAGGC
GGAAGCGGGCTACGCCGGCCCGTGCGCCGAGATCGCCCTGCGGCGCGGCGACCTGGCCACGGCGTTCGAGG
CTGGTAGCACCGTCCTGGACGACCGGTCACTGCCGTCGCTCGGCATCACCGCCGCATTGCTGTTGAGCAGC
AAGACGGCCGCCGCTGTCCGGCTGGGCGAACTCGAGCGTGCGGAGAAGCTGCTCGCCGAGCCGCTTCCGAA
CGGCGTCCAGGACAGCCTTTTCGGTCTGCACCTGCTCTCGGCGTACGGCCAGTACAGCCTCGCGATGGGCC
GATATGAATCGGCTCACCGGGCGTTTCGCACCTGCGGAGAACGTATGCGCAGCTGGGATGTTGACGTGCCT
GGTCTGGCCCTGTGGCGTGTCGACGCCGCCGAGGCGCTGCTCAGCCTCGACCGGAACGAGGGCCAGCGGCT
CATCGACGAACAACTCACCCGTCCGATGGGACCTCGTTCCCGCGCGTTAACGCTGCGGATCAAGGCGGCAT
ACCTCCCGCGGACGAAGCGGATCCCCCTGCTCCATGAGGCGGCCGAGCTGCTGCTCCCCTGCCCCGACCCG
TACGAGCAAGCGCGGGTGCTCGCCGATCTGGGCGACACGCTCAGCGCGCTCAGACGCTATAGCCGGGCGCG
```

-continued

GGGAGTTCTCCGGCAGGCTCGTCACCTGGCCACCCAGTGCGGTGCTGTCCCGCTGCTGCGCCGACTCGGGG

GCGAGCCCGGCCGGATCGACGACGCCGGCCTGCCGCAGCGGAGCACATCGTTGACCGATGCGGAGCGGCGG

GTGGCGGCGCTGGCCGCGGCCGGACAGACCAACCGGGAGATCGCCGAACAGCTGTTCGTCACGGCCAGCAC

AGTGGAACAGCACCTCACAAGCGTCTTCCGCAAGCTGGGCGTCAAGGGCCGCAAGCAGCTGCCGACCGCGC

TGGCCGACGTGGAACAGACCTGA

SEQ ID NO: 23

ATGTATAGCGGTACCTGCCGTGAAGGATACGAACTCGTCGCACGCGAGGACGAACTCGGCATTCTACAGAG

GTCTCTGGAACAAGCGAGCAGCGGCCAGGGCGTCGTGGTCACCGTCACCGGCCCAATCGCCTGCGGCAAGA

CAGAACTGCTTGACGCGGCTGCCGCGAAGGCTGAGGCCATCATTCTGCGCGCGGTCTGCGCGCCCGAAGAG

CGGGCTATGCCGTACGCCATGATCGGGCAGCTCATCGACGACCCGGCGCTCGCGCATCGGGCGCGGGGCT

GGCTGATCGGATAGCCCAGGGCGGGCAGCTGTCGCTGAGGGCCGAGAACCGACTGCGCAGGGATCTCACCC

GTGCCCTGCTGGCGCTTGCCGTGCACCGGCCTGTGCTGATCGGCGTCGATGATGTGCATCACGCCGACACC

GCCTCTTTGAACTGTCTGCTGCATTTGGCGCGCCGGGTCCGTCCGGCCCGGATATCCATGATCTTCACCGA

GTTGCGCAGCCTCACCCCTACTCAGTCACGATTCAAGGCGGAGCTGCTCAGCCTGCCGTACCACCACGAGA

TCGCGCTGCGTCCATTCGGACCGGAGCAATCGGCGGAGCTGGCTCGCGCCGCCTTCGGCCCGGGCCTCGCC

GAGGATGTGCTCGCGGGGTTGTATAAAACGACCAGGGGCAATCTGAGTCTCAGCCGTGGACTGATCAGCGA

TGTGCGGGAGGCCCTGGCCAACGGAGAGAGCGCTTTCGAGGCGGGCCGCGCGTTCCGGCTGGCGTACCTCA

GCTCGCTCTACCGCTGTGGCCCGGTCGCGCTGCGGGTCGCCCGAGTGGCTGCCGTGCTGGGCCCAAGCGCC

ACCACCACGCTGGTGCGCCGGCTAAGCGGGCTCAGCGCGGAGACGATAGACCGGGCAACCAAGATCCTCAC

CGAGGGCGGGCTGCTGCTCGACCAGCAGTTTCCGCACCCGGCCGCCCGCTCGGTGGTGCTCGATGACATGT

CCGCCCAGGAACGACGCGGCCTGCACACTCTCGCCCTGGAACTGCTGGACGAGGCGCCGGTTGAAGTGCTC

GCGCACCACCAGGTCGGCGCCGGTCTCATACACGGGCCCAAGGCTGCGGAGATGTTCGCCAAGGCCGGCAA

GGCTCTGGTCGTACGCAACGAGTTGGGCGACGCGGCCGAATACCTGCAACTGGCTCACCGGGCCTCCGACG

ATGTCTCCACCCGGGCCGCCCTGCGGGTCGAGGCCGTGGCGATCGAGCGCCGCCGCAATCCGCTGGCCTCC

AGTCGGCACATGGACGAGCTGAGCGCCGCCGGCCGCGCCGGTCTGCTTTCCCCCAAGCATGCGGCGCTGGC

CGTCTTCTGGCTGGCCGACGGCGGGCGATCCGGCGAGGCAGCCCAGGTGCTGGCGTCGGAACGCCCGCTCG

CGACCACCGATCAGAACCGGGCCCACCTGCGATTTGTCGAGGTGACTCTCGCGCTGTTCTCTCCCGGCGCC

TTCGGATCGGACCGGCGCCCACCTCCGCTGACGCCGGACGAACTCGCCAGCCTGCCGAAGGCGGCCTGGCA

ATGCGCGGTCGCCGACAACGCGGCCATGACCGCCTTGCACGGCCATCCAGAACTTGCCACCGCTCAGGCGG

AAACAGTTCTGCGGCAGGCTGATTCGGCAGCCGACGCGATCCCCGCCGCGCTGATCGCCCTGTTGTACGCG

GAGAACACCGAGTCCGCTCATATCTGGGCCGACAAGCTGGGCAGCATGAATGCCGGGGTATCGAACGAGGC

GGAAGCGGGCTACGCCGGCCCGTGCGCCGAGATCGCCCTGCGGCGCGGCGACCTGGCCACGGCGTTCGAGG

CTGGTAGCACCGTCCTGGACGACCGGTCACTGCCGTCGCTCGGCATCACCGCCGCATTGCTGTTGAGCAGC

AAGACGGCCGCCGCTGTCCGGCTGGGCGAACTCGAGCGTGCGGAGAAGCTGCTCGCCGAGCCGCTTCCGAA

CGGCGTCCAGGACAGCCTTTTCGGTCTGCACCTGCTCTCGGCGTACGGCCAGTACGCCTCGCGATGGGCC

GATATGAATCGGCTCACCGGGCGTTTCGCACCTGCGGAGAACGTATGCGCAGCTGGGATGTTGACGTGCCT

GGTCTGGCCCTGTGGCGTGTCGACGCCGCCGAGGCGCTGCTCAGCCTCGACCGGAACGAGGGCCAGCGGCT

CATCGACGAACAACTCACCCGTCCGATGGGACCTCGTTCCCGCGCGCTGACGCTGCGGATCAAGGCGGCAT

ACCTCCGCGGACGAAGCGGATCCCCCTGCTCCATGAGGCGGCCGAGCTGCTGCTCCCCTGCCCGACCCG

TACGAGCAAGCGCGGGTGCTCGCCGATCTGGGCGACACGCTCAGCGCGCTCAGACGCTATAGCGGGCGCG

GGGAGTTCTCCGGCAGGCTCGTCACCTGGCCACCCAGTGCGGTGCTGTCCCGCTGCTGCGCCGACTCGGGG

-continued

GCGAGCCCGGCCGGATCGACGACGCCGGCCTGCCGCAGCGGAGCACATCGTTGACCGATGCGGAGCGGCGG

GTGGCGGCGCTGGCCGCGGCCGGACAGACCAACCGGGAGATCGCCGAACAGCTGTTCGTCACGGCCAGCAC

AGTGGAACAGCACCTCACAAGCGTCTTCCGCAAGCTGGGCGTCAAGGGCCGCAAGCAGCTGCCGACCGCGC

TGGCCGACGTGGAACAGACCTGA

SEQ ID NO: 24
GTGCGAGCTATTAATGCGTCCGACACCGGTCCTGAACTGGTCGCCCGCGAAGACGAACTGGGACGTGTACG

AAGTGCCCTGAACCGAGCGAACGGCGGCCAAGGTGTCCTGATCTCCATTACCGGTCCGATCGCCTGCGGCA

AGACCGAACTGCTTGAGGCTGCCGCCTCGGAAGTTGACGCCATCACTCTGCGCGCGGTCTGTGCCGCCGAG

GAACGGGCGATACCTTATGCCCTGATCGGGCAGCTTATCGACAACCCCGCGCTCGGCATTCCGGTTCCGGA

TCCGGCCGGCCTGACCGCCCAGGGCGGACGACTGTCATCGAGCGCCGAGAACCGACTGCGTCGCGACCTCA

CCCGTGCCCTGCTGACGCTCGCCACCGACCGGCTGGTGCTGATCTGTGTCGATGACGTGCAGCACGCCGAC

AACGCCTCGTTGAGCTGCCTTCTGTATCTGGCCCGACGGCTTGTCCCGGCTCGAATCGCTCTGGTATTCAC

CGAGTTGCGAGTCCTCACCTCGTCTCAGTTACGGTTCAACGCGGAGCTGCTCAGCTTGCGGAACCACTGCG

AGATCGCGCTGCGCCCACTCGGCCCGGGGCATGCGGCCGAGCTGGCCCGCGCCACCCTCGGCCCCGGCCTC

TCCGACGAAACACTCACGGAGCTGTACCGGGTGACCGGAGGCAACCTGAGTCTCAGCCGCGGGCTGATCGA

CGATGTGCGGGACGCCTGGGCACGAGGGGAAACGGGCGTCCAGGTGGGCCGGGCGTTCCGGCTGGCCTACC

TCGGTTCCCTCCACCGCTGTGGTCCGCTGGCGTTGCGGGTCGCCCGCGTAGCCGCCGTACTGGGCCCGAGC

GCCACCAGCGTCCTGGTGCGCCGGATCAGTGGGCTCAGCGCGGAGGCCATGGCCCAGGCGACCGATATCCT

CGCTGACGGCGCCTCCTGCGCGACCAGCGGTTCACACATCCAGCGGCCCGCTCGGTGGTGCTCGACGACA

TGTCCGCCGAGGAACGACGCAGCGTGCACAGCCTCGCCCTGGAACTGCTGGACGAGGCACCGGCCGAGATG

CTCGCGCACCACCGGGTCGGCGCCGGTCTCGTGCACGGGCCGAAGGCCGCGGAGACATTCACCGGGGCCGG

CCGGGCACTGGCCGTTCGCGGCATGCTGGGCGAGGCAGCCGACTACCTGCAACTGGCGTACCGGGCCTCCG

GCGACGCCGCTACCAAGGCCGCGATACGCGTCGAGTCCGTGGCGGTCGAGCGCCGACGCAATCCGCTGGTC

GTCAGTCGCCATTGGGACGAGCTGAGCGTCGCGGCCCGCGCCGGTCTGCTCTCCTGCGAGCACGTGTCCAG

GACGGCCCGCTGGCTGACCGTCGGTGGGCGGCCCGGCGAGGCGGCCAGGGTGCTGGCGTCGCAACACCGAC

GGGTCGTCACCGATCAGGACCGGGCCCACCTGCGGGTCGCCGAGTTCTCGCTCGCGCTGCTGTACCCCGGT

ACGTCCGGCTCGGACCGGCGCCCGCACCCGCTCACGTCGGACGAACTCGCGGCCCTACCGACTGCGACCAG

ACACTGCGCGATCGCCGATAACGCTGTCATGGCTGCCTTGCGTGGTCATCCGGAGCTTGCCACCGCCGAGG

CAGAAGCCGTTCTGCAGCAAGCCGACGCGGCGGACGGCGCTGCTCTCACCGCGCTGATGGCCCTGCTGTAC

GCGGAGAGCATCGAGGTCGCTGAAGTCTGGGCGGACAAGCTGGCGGCAGAGGCCGGAGCATCGAACGGGCA

GGACGCGGAGTACGCCGGTATACGCGCCGAAATCGCCCTGCGGCGCGGCGATCTGACCGCGGCCGTCGAGA

CCGCCGGCATGGTCCTGGACGGCCGGCCGCTGCCGTCGCTCGACATCACCGCCACGTTGCTGTTGGCCGGC

AGGGCGTCCGTCGCCGTCCGGCTGGGCGAACTCGACCACGCGGAGGAGCTGTTCGCCGCGCCGCGGAGGA

CGCCTTCCAGGACAGCCTCTTCGGTCTGCATCTGCTCTCGGCGCACGGCCAGTACAGCCTCGCGACAGGCC

GGCCCGAGTCGGCATACCGGGCCTTTCGTGCCTGCGGCGAACGTATGCGCGATTGGGCTTCGACGCGCCC

GGTGTGGCCCTGTGGCGCGTCGGCGCCGCCGAGGCGCTGCTCGGCCTCGACCGGAACGAGGGCCGACGGCT

CATCGACGAACAGCTGAGCCGGACGATGGCCCCCCGGTCCCACGCGTTGACGCTGCGGATAAAAGCGGCGT

ACATGCCGGAGCCGAAGCGGGTCGACCTGCTCTACGAAGCGGCTGAGCTGCTGCTCTCCTGCCGGGACCAG

TATGAGCGAGCGCGGGTGCTCGCCGATCTGGGCGAGGCGCTCAGCGCGCTCGGGAACTACCGGCAGGCGCG

AGGTGTGCTCCGGCAGGCTCGGCATCTGGCCATGCGAACCGGCGCGGACCCGCTGCTGCGCCGGCTCGGAA

TCAGGCCCGGCCGGCAGGACGACCCCGACCCGCAGCCGCGGGAGCAGATCGCTGACCAACGCTGAGCGGCGT

-continued

GCGGCGTCGCTGGCCGCGACCGGACTGACCAACCGGGAGATCGCCGACCGGCTCTTCGTCACCGCCAGCAC

CGTGGAGCAGCACCTCACCAACGTCTTCCGCAAGCTGGGCGTCAAGGGCCGCAAGCAGCTGCCGGCCGAGT

TGGACGACATGGAATAG

SEQ ID NO: 25

ATGCGAGCTATTAATGCGTCCGACACCGGTCCTGAACTGGTCGCCCGCGAAGACGAACTGGGACGTGTACG

AAGTGCCCTGAACCGAGCGAACGGCGGCCAAGGTGTCCTGATCTCCATTACCGGTCCGATCGCCTGCGGCA

AGACCGAACTGCTTGAGGCTGCCGCCTCGGAAGTTGACGCCATCACTCTGCGCGCGGTCTGTGCCGCCGAG

GAACGGGCGATACCTTATGCCCTGATCGGGCAGCTTATCGACAACCCCGCGCTCGGCATTCCGGTTCCGGA

TCCGGCCGGCCTGACCGCCCAGGGCGGACGACTGTCATCGAGCGCCGAGAACCGACTGCGTCGCGACCTCA

CCCGTGCCCTGCTGACGCTCGCCACCGACCGGCTGGTGCTGATCTGTGTCGATGACGTGCAGCACGCCGAC

AACGCCTCGTTGAGCTGCCTTCTGTATCTGGCCCGACGGCTTGTCCCGGCTCGAATCGCTCTGGTATTCAC

CGAGTTGCGAGTCCTCACCTCGTCTCAGCTGCGGTTCAACGCGGAGCTGCTCAGCTTGCGGAACCACTGCG

AGATCGCGCTGCGCCCACTCGGCCCGGGGCATGCGGCCGAGCTGGCCCGCGCCACCCTCGGCCCCGGCCTC

TCCGACGAAACACTCACGGAGCTGTACCGGGTGACCGGAGGCAACCTGAGTCTCAGCCGCGGGCTGATCGA

CGATGTGCGGGACGCCTGGGCACGAGGGGAAACGGGCGTCCAGGTGGGCCGGGCGTTCCGGCTGGCCTACC

TCGGTTCCCTCCACCGCTGTGGTCCGCTGGCGTTGCGGGTCGCCCGCGTAGCCGCCGTACTGGGCCCGAGC

GCCACCAGCGTCCTGGTGCGCCGGATCAGTGGGCTCAGCGCGGAGGCCATGCCCAGGCGACCGATATCCT

CGCTGACGGCGGCCTCCTGCGCGACCAGCGGTTCACACATCCAGCGGCCCGCTCGGTGGTGCTCGACGACA

TGTCCGCCGAGGAACGACGCAGCGTGCACAGCCTCGCCCTGGAACTGCTGGACGAGGCACCGGCCGAGATG

CTCGCGCACCACCGGGTCGGCGCCGGTCTCGTGCACGGGCCGAAGGCCGCGGAGACATTCACCGGGGCCGG

CCGGGCACTGGCCGTTCGCGGCATGCTGGGCGAGGCAGCCGACTACCTGCAACTGGCGTACCGGGCCTCCG

GCGACGCCGCTACCAAGGCCGCGATACGCGTCGAGTCCGTGGCGGTCGAGCGCCGACGCAATCCGCTGGTC

GTCAGTCGCCATTGGGACGAGCTGAGCGTCGCGGCCCGCGCCGGTCTGCTCTCCTGCGAGCACGTGTCCAG

GACGGCCCGCTGGCTGACCGTCGGTGGGCGGCCCGGCGAGGCGGCCAGGGTGCTGGCGTCGCAACACCGAC

GGGTCGTCACCGATCAGGACCGGGCCCACCTGCGGGTCGCCGAGTTCTCGCTCGCGCTGCTGTACCCCGGT

ACGTCCGGCTCGGACCGGCGCCCGCACCCGCTCACGTCGGACGAACTCGCGGCCCTACCGACTGCGACCAG

ACACTGCGCGATCGCCGATAACGCTGTCATGGCTGCCTTGCGTGGTCATCCGGAGCTTGCCACCGCCGAGG

CAGAAGCCGTTCTGCAGCAAGCCGACGCGGCGGACGGCGCTGCTCTCACCGCGCTGATGGCCCTGCTGTAC

GCGGAGAGCATCGAGGTCGCTGAAGTCTGGGCGGACAAGCTGGCGGCAGAGGCCGGAGCATCGAACGGGCA

GGACGCGGAGTACGCCGGTATACGCGCCGAAATCGCCCTGCGGCGCGGCGATCTGACCGCGGCCGTCGAGA

CCGCCGGCATGGTCCTGGACGGCCGGCCGCTGCCGTCGCTCGACATCACCGCCACGTTGCTGTTGGCCGGC

AGGGCGTCCGTCGCCGTCCGGCTGGGCGAACTCGACCACGCGGAGGAGCTGTTCGCCGCGCCGCCGGAGGA

CGCCTTCCAGGACAGCCTCTTCGGTCTGCATCTGCTCTCGGCGCACGGCCAGTACAGCCTCGCGACAGGCC

GGCCCGAGTCGGCATACCGGGCCTTTCGTGCCTGCGGCGAACGTATGCGCGATTGGGGCTTCGACGCGCCC

GGTGTGGCCCTGTGGCGCGTCGGCGCCGCCGAGGCGCTGCTCGGCCTCGACCGGAACGAGGGCCGACGGCT

CATCGACGAACAGCTGAGCCGGACGATGGCCCCCGGTCCCACGCGTTGACGCTGCGGATAAAAGCGGCGT

ACATGCCGGAGCCGAAGCGGGTCGACCTGCTCTACGAAGCGGCTGAGCTGCTGCTCTCCTGCCGGGACCAG

TATGAGCGAGCGCGGGTGCTCGCCGATCTGGGCGAGGCGCTCAGCGCGCTCGGGAACTACCGGCAGGCGCG

AGGTGTGCTCCGGCAGGCTCGGCATCTGGCCATGCGAACCGGCGCGGACCCGCTGCTGCGCCGGCTCGGAA

TCAGGCCCGGCCGGCAGGACGACCCCGACCCGCAGCCGCGGAGCAGATCGCTGACCAACGCTGAGCGGCGT

GCGGCGTCGCTGGCCGCGACCGGACTGACCAACCGGGAGATCGCCGACCGGCTCTTCGTCACCGCCAGCAC

-continued

CGTGGAGCAGCACCTCACCAACGTCTTCCGCAAGCTGGGCGTCAAGGGCCGCAAGCAGCTGCCGGCCGAGT

TGGACGACATGGAATAG

SEQ ID NO: 26
MPAVECYELDARDDELRKLEEVVTGRANGRGVVVTITGPIACGKTELLDAAAAKADAITLRAVCSAEEQAL

PYALIGQLIDNPALASHALEPACPTLPGEHLSPEAENRLRSDLTRTLLALAAERPVLIGIDESHANALCLL

HLARRVGSARIAMVLTELRRLTPAHSQFQAELLSLGHHREIALRPLSPKHTAELVRAGLGPDVDEDVLTGL

YRATGGNLNLTRGLINDVREAWETGGTGISAGRAYRLAYLGSLYRCGPVPLRVARVAAVLGQSANTTLVRW

ISGLNADAVGEATEILTEGGLLHDLRFPHPAARSVVLNDMSAQERRRLHRSALEVLDDVPVEVVAHHQVGA

GLLHGPKAAEIFAKAGQELHVRGELDTASDYLQLAHQASDDAVTGMRAEAVAIERRRNPLASSRHLDELTV

VARAGLLFPEHTALMIRWLGVGGRSGEAAGLLASQRPRAVTDQDRAHMRAAEVSLALVSPGTSGPDRRPRP

LTPDELANLPKAARLCAIADNAVMSALRGRPELAAAEAENVLQHADSAAAGTTALAALTALLYAENTDTAQ

LWADKLVSETGASNEEEAGYAGPRAEAALRRGDLAAAVEAGSTVLDHRRLSTLGITAALPLSSAVAAAIRL

GETERAEKWLAQPLPQAIQDGLFGLHLLSARGQYSLATGQHESAYTAFRTCGERMRNWGVDVPGLSLWRVD

AAEALLHGRDRDEGRRLVDEQLTRAMGPRSRALTLRVQAAYSPPAKRVDLLLDEAADLLLSCNDQYERARVL

ADLSETFSALRHHSRARGLLRQARHLAAQRGAIPLLRRLGAKPGGPGWLEESGLPQRIKSLTDAERRVASL

AAGGQTNRVIADQLFVTASTVEQHLTDVSTGSRPPAPAAELV

SEQ ID NO: 27
MVPEVRAAPDELIARDDELSRLQRALTRAGSGRGGVVAITGPIASGKTALLDAGAAKSGFVALRAVCSWEE

RTLPYGMLGQLFDHPELAAQAPDLAHFTASCESPQAGTDNRLRAEFTRTLLALAADWPVLIGIDDVHHADA

ESLRCLLHLARRIGPARIAVVLTELRRPTPADSRFQAELLSLRSYQEIALRPLTEAQTGELVRRHLGAETH

EDVSADTFRATGGNLLLGHGLINDIREARTAGRPGVVAGRAYRLAYLSSLYRCGPSALRVARASAVLGASA

EAVLVQRMTGLNKDAVEQVYEQLNEGRLLQGERFPHPAARSIVLDDLSALERRNLHESALELLRDHGVAGN

VLARHQIGAGRVHGEEAVELFTGAAREHHLRGELDDAAGYLELAHRASDDPVTRAALRVGAAAIERLCNPV

RAGRHLPELLTASRAGLLSSEHAVSLADWLAMGGRPGEAAEVLATQRPAADSEQHRALLRSGELSLALVHP

GAWDPLRRTDRFAAGGLGSLPGPARHRAVADQAVIAALRGRLDRADANAESVLQHTDATADRTTAIMALLA

LLYAENTDAVQFWVDKLAGDEGTRTPADEAVHAGFNAEIALRRGDLMRAVEYGEAALGHRHLPTWGMAAAL

PLSSTVVAAIRLGDLDRAERWLAEPLPQQTPESLFGLHLLWARGQHHLATGRHGAAYTAFRECGERMRRWA

VDVPGLALWRVDAAESLLLLGRDRAEGLRLVSEQLSRPMRPRARVQTLRVQAAYSPPPQRIDLLEEAADLL

VTCNDQYELANVLSDLAEASSMVRQHSRARGLLRRARHLATQCGAVPLLRRLGAEPSDIGGAWDATLGQRI

ASLTESERRVAALAAVGRTNREIAEQLFVTASTVEQHLTNVFRKLAVKGRQQLPKELADVGEPADRDRRCG

SEQ ID NO: 28
MIARLSPPDLIARDDEFGSLHRALTRAGGGRGVVAAVTGPIACGKTELLDAAAAKAGFVTLRAVCSMEERA

LPYGMLGQLLDQPELAARTPELVRLTASCENLPADVDNRLGTELTRTVLTLAAERPVLIGIDDVHHADAPS

LRCLLHLARRISRARVAIVLTELLRPTPAHSQFRAALLSLRHYQEIALRPLTEAQTTELVRRHLGQDAHDD

VVAQAFRATGGNLLLGHGLIDDIREARTRTSGCLEVVAGRAYRLAYLGSLYRCGPAALSVARASAVLGESV

ELTLVQRMTGLDTEAVEQAHEQLVEGRLLREGRFPHPAARSVVLDDLSAAERRGLHELALELLRDRGVASK

VLARHQMGTGRVHGAEVAGLFTDAAREHHLRGELDEAVTYLEFAYRASDDPAVHAALRVDTAAIERLCDPA

RSGRHVPELLTASRERLLSSEHAVSLACWLAMDGRPGEAAEVLAAQRSAAPSEQGRAHLRVADLSLALIYP

GAADPPRPADPPAEDEVASFSGAVRHRAVADKALSNALRGWSEQAEAKAEYVLQHSRVTTDRTTTMMALLA

LLYAEDTDAVQSWVDKLAGDDNMRTPADEAVHAGFRAEAALRRGDLTAAVECGEAALAPRVVPSWGMAAAL

PLSSTVAAAIRLGDLDRAERWLAEPLPEETSDSLFGLHMVWARGQHHLAAGRYRAAYNAFRDCGERMRRWS

VDVPGLALWRVDAAEALLLLGRGRDEGLRLISEQLSRPMGSRARVMTLRVQAAYSPPAKRIELLDEAADLL

-continued

IMCRDQYELARVLADMGEACGMLRRHSRARGLFRRARHLATQCGAVPLLRRLGGESSDADGTQDVTPAQRI
TSLTEAERRVASHAAVGRTNKEIASQLFVTSSTVEQHLTNVFRKLGVKGRQQLPKELSDAG

SEQ ID NO: 29
MEFYDLVARDDELRRLDQALGRAAGGRGVVVTVTGPVGCGKTELLDAAAAEEEFITLRAVCSAEERALPYA
VIGQLLDHPVLSARAPDLACVTAPGRTLPADTENRLRRDLTRALLALASERPVLICIDDVHQADTASLNCL
LHLARRVASARIAMILTELRRLTPAHSRFEAELLSLRHRHEIALRPLGPADTAELARARLGAGVTADELAQ
VHEATSGNPNLVGGLVNDVREAWAAGGTGIAAGRAYRLAYLSSVYRCGPVPLRIAQAAAVLGPSATVTLVR
RISGLDAETVDEATAILTEGGLLRDHRFPHPAARSVVLDDMSAQERRRLHRSTLDVLDGVPVDVLAHHQAG
AGLLHGPQAAEMFARASQELRVRGELDAATEYLQLAYRASDDAGARAALQVETVAGERRRNPLAASRHLDE
LAAAARAGLLSAEHAALVVHWLADAGRPGEAAEVLALQRALAVTDHDRARLRAAEVSLALFHPGVPGSDPR
PLAPEELASLSLSARHGVTADNAVLAALRGRPESAAAEAENVLRNADAAASGPTALAALTALLYAENTDAA
QLWADKLAAGIGAGEGEAGYAGPRTVAALRRGDLTTAVQAAGAVLDRGRPSSLGITAVLPLSGAVAAAIRL
GELERAEKWLAEPLPEAVHDSLFGLHLLMARGRYSLAVGRHEAAYAAFRDCGERMRRWDVDVPGLALWRVD
AAEALLPGDDRAEGRRLIDEQLTRPMGPRSRALTLRVRAAYAPPAKRIDLLDEAADLLLSSNDQYERARVL
ADLSEAFSALRQNGRARGILRQARHLAAQCGAVPLLRRLGVKAGRSGRLGRPPQGIRSLTEAERRVATLAA
AGQTNREIADQLFVTASTVEQHLTNVFRKLGVKGRQQLPAELADLRPPG

SEQ ID NO: 30
MYSGTCREGYELVAREDELGILQRSLEQASSGQGVVVTVTGPIACGKTELLDAAAAKAEAIILRAVCAPEE
RAMPYAMIGQLIDDPALAHRAPGLADRIAQGGQLSLRAENRLRRDLTRALLALAVDRPVLIGVDDVHHADT
ASLNCLLHLARRVRPARISMIFTELRSLTPTQSRFKAELLSLPYHHEIALRPFGPEQSAELARAAFGPGLA
EDVLVGLYKTTRGNLSLSRGLISDVREALANGESAFEAGRAFRLAYLGSLYRCGPVALRVARVAAVLGPSA
TTTLVRRLSGLSAETIDRATKILTEGGLLLDQQFPHPAARSVVLDDMSAQERRGLHTLALELLDEAPVEVL
AHHQVGAGLIHGPKAAEMFAKAGKALVVRNELGDAAEYLQLAHRASDDVSTRAALRVEAVAIERRRNPLAS
SRHMDELSAAGRAGLLSPKHAALAVFWLADGGRSGEAAEVLASERPLATTDQNRAHLRFVEVTLALFSPGA
FGSDRRPPPLTPDELASLPKAAWQCAVADNAAMTALHGHPELATAQAETVLRQADSAADAIPAALIALLYA
ENTESAHIWADKLGSTNGGVSNEAEAGYAGPCAEIALRRGDLATAFEAGSTVLDDRSLPSLGITAALLLSS
KTAAAVRLGELERAEKLLAEPLPNGVQDSLFGLHLLSAYGQYSLAMGRYESALRAFHTCGERMRSWDVDVP
GLALWRVDAAEALLSLDRNEGQRLIDEQLTRPMGPRSRALTLRIKAAYLPRTKRIPLLHEAAELLLPCPDP
YEQARVLADLGDTLSALRRYSRARGVLRQARHLAAQCGAVPLLRRLGGEPGRIDDAGLPQRSTSLTDAERR
VAALAAAGQTNREIAKQLFVTASTVEQHLTSVFRKLGVKGRKQLPTALADVEQT

SEQ ID NO: 31
MPAVESYELDARDDELRRLEEAVGQAGNGRGVVVTITGPIACGKTELLDAAAAKSDAITLRAVCSEEERAL
PYALIGQLIDNPAVASQLPDPVSMALPGEHLSPEAENRLRGDLTRTLLALAAERPVLIGIDDMHHADTASL
NCLLHLARRVGPARIAMVLTELRRLTPAHSQFHAELLSLGHHREIALRPLGPKHIAELARAGLGPDVDEDV
LTGLYRATGGNLNLGHGLIKDVREAWATGGTGINAGRAYRLAYLGSLYRCGPVPLRVARVAAVLGQSANTT
LVRWISGLNADAVGEATEILTEGGLLHDLRFPHPAARSVVLNDLSARERRRLHRSALEVLDDVPVEVVAHH
QAGAGFIHGPKAAEIFAKAGQELHVRGELDAASDYLQLAHHASDDAVTRAALRVEAVAIERRRNPLASSRH
LDELTVAARAGLLSLEHAALMIRWLALGGRSGEAAEVLAAQRPRAVTDQDRAHLRAAEVSLALVSPGASGV
SPGASGPDRRPRPLPPDELANLPKAARLCAIADNAVISALHGRPELASAEAENVLKQADSAADGATALSAL
TALLYAENTDTAQLWADKLVSETGASNEEEGAGYAGPRAETALRRGDLAAAVEAGSAILDHRRGSLLGITA
ALPLSSAVAAAIRLGETERAEKWLAEPLPEAIRDSLFGLHLLSARGQYCLATGRHESAYTAFRTCGERMRN
WGVDVPGLSLWRVDAAEALLHGRDRDEGRRLIDEQLTHAMGPRSRALTLRVQAAYSPQAQRVDLLEEAADL

-continued

LLSCNDQYERARVLADLSEAFSALRHHSRARGLLRQARHLAAQCGATPLLRRLGAKPGGPGWLEESGLPQR
IKSLTDAERRVASLAAGGQTNRVIADQLFVTASTVEQHLTNVFRKLGVKGRQHLPAELANAE

SEQ ID NO: 32
MPAVKRNDLVARDGELRWMQEILSQASEGRGAVVTITGAIACGKTVLLDAAAASQDVIQLRAVCSAEEQEL
PYAMVGQLLDNPVLAARVPALGNLAAAGERLLPGTENRIRRELTRTLLALADERPVLIGVDDMHHADPASL
DCLLHLARRVGPARIAIVLTELRRLTPAHSRFQSELLSLRYHHEIGLQPLTAEHTADLARVGLGAEVDDDV
LTELYEATGGNPSLCCGLIRDVRQDWEAGVTGIHVGRAYRLAYLSSLYRCGPAALRTARAAAVLGDSADAC
LIRRVSGLGTEAVGQAIQQLTEGGLLRDQQFPHPAARSVVLDDMSAQERHAMYRSAREAAAEGQADPGTPG
EPRAATAYAGCGEQAGDYPEPAGRACVDGAGPAEYCGDPHGADDDPDELVAALGGLLPSRLVAMKIRRLAV
AGRPGAAAELLTSQRLHAVTSEDRASLRAAEVALATLWPGATGPDRHPLTEQEAASLPEGPRLLAAADDAV
GAALRGRAEYAAAEAENVLRHADPAAGGDAYAAMIALLYTEHPENVLFWADKLDAGRPDEETSYPGLRAET
AVRLGDLETAMELGRTVLDQRRLPSLGVAAGLLLGGAVTAAIRLGDLDRAEKWLAEPIPDAIRTSLYGLHV
LAARGRLDLAAGRYEAAYTAFRLCGERMAGWDADVSGLALWRVDAAEALLSAGIRPDEGRKLIDDQLTREM
GARSRALTLRAQAAYSLPVHRVGLLDEAAGLLLACHDGYERARVLADLGETLRTLRHTDAAQRVLRQAEQA
AARCGSVPLLRRLGAEPVRIGTRRGEPGLPQRIRLLTDAERRVAAMAAAGQTNREIAGRLFVTASTVEQHL
TSVFRKLGVKGRRFLPTELAQAV

SEQ ID NO: 33
MYSGTCREGYELVAREDELGILQRSLEQASSGQGVVVTVTGPIACGKTELLDAAAAKAEAIILRAVCAPEE
RAMPYAMIGQLIDDPALAHRAPGLADRIAQGGQLSLRAENRLRRDLTRALLALAVDRPVLIGVDDVHHADT
ASLNCLLHLARRVRPARISMIFTELRSLTPTQSRFKAELLSLPYHHEIALRPFGPEQSAELARAAFGPGLA
EDVLAGLYKTTRGNLSLSRGLISDVREALANGESAFEAGRAFRLAYLSSLYRCGPVALRVARVAAVLGPSA
TTTLVRRLSGLSAETIDRATKILTEGGLLLDQQFPHPAARSVVLDDMSAQERRSLHTLALELLDEAPVEVL
AHHQVGAGLIHGPKAAEMFAKAGKALVVRNELGDAAEYLQLAHRASDDVSTRAALRVEAVAIERRRNPLAS
SRHMDELSAAGRAGLLSPKHAALAVFWLADGGRSGEAAEVLASERPLATTDQNRAHLRFVEVTLALFSPGA
FGSDRRPPPLTPDELASLPKAAWQCAVADNAAMTALHGHPELATAQAETVLRQADSAADAIPAALIALLYA
ENTESAHIWADKLGSTNAGVSNEAEAGYAGPCAEIALRRGDLATAFEAGSAVLDDRSLPSLGITAALLLSS
KTAAAVRLGELERAEKLLAEPLPNGVQDSLFGLHLLSAYGQYSLAMGRYESAHRAFRTCGERMRSWDVDVP
GLALWRVDAAEALLSLDRNEGQRLIDEQLTRPMGPRSHALTLRIKAAYLPRTKRIPLLHEAAELLLPCPDP
YEQARVLADLGDTLSALRRYSRARGVLRQARHLATQCGAVPLLRRLGGEPGRIDDAGLPQRSTSLTDAERR
VAALAAAGQTNREIAEQLFVTASTVEQHLTSVFRKLGVKGRKQLPTALADVEQT

SEQ ID NO: 34
MYSGTCREGYELVAREDELGILQRSLEEAGSGQGAVVTVTGPIACGKTELLDAAAAKADAIILRAVCAPEE
RAMPYAMIGQLIDDPALAHRAPELADRIAQGGHLSLRAENRLRRDLTRALLALAVDRPVLIGVDDVHHADT
ASLNCLLHLARRVRPARISMIFTELRSLTPTQSRFKAELLSLPYHHEIALRPLGPEQSAELAHAAFGPGLA
EDVLAGLYGMTRGNLSLSRGLISDVREAQANGESAFEVGRAFRLAYLSSLYRCGPIALRVARVAAVLGPSA
TTTLVRRLSGLSAETIDRATKILTEGGLLLDHQFPHPAARSVVLDDMSAQERRSLHTLALELLDEAPVEVL
AHHQVGAGLIHGPKAAEIFARAGQALVVRNELGDAAEYLQLAHRASDDVSTRAALRVEAVAIERRRNPLAS
SRHMDELSAAGRAGLLSPKHAALAVFWLADGGRSGEAAEVLASEHPLATTDQNRAHLRFAEVTLALFCPGA
FGSDRRPPPLAPDELASLPKAAWQCAVADNAVMTALHAHPELATAQAETVLRQADSAADAIPAALIALLYA
ENTESAQIWADKLGSTNAGVSNEAEAGYAGPCAEIALRRGDLATAFEAGGTVLDDRPLPSLGITAALLLSS
KTAAAVRLGELERAEKLLAEPLPNGVQDSLFGLHLLSAHGQYSLAMGRYESAHRAFHTCGERMRSWGVDVP
GLALWRVDAAEALLSLDRNEGQRLIDEQLARPMGPRSRALTLRIKAAYLPRTKRIPLLHEAAELLLSCPDP

```
                                                                -continued
YEQARVLADLGDTLSALRRYSRARGVLRQARHLATQCGAVPLLRRLGGEPGRIDDAGLPQRSTSLTDAERR

VSALAAAGQTNREIAKQLFVTASTVEQHLTSVFRKLGVKGRRQLPTALADVE

SEQ ID NO: 35
MYSGTCREGYELVAREDELGILQRSLEQASSGQGVVVTVTGPIACGKTELLDAAAAKAEAIILRAVCAPEE

RAMPYAMIGQLIDDPALAHRAPGLADRIAQGGQLSLRAENRLRRDLTRALLALAVHRPVLIGVDDVHHADT

ASLNCLLHLARRVRPARISMIFTELRSLTPTQSRFKAELLSLPYHHEIALRPFGPEQSAELARAAFGPGLA

EDVLAGLYKTTRGNLSLSRGLISDVREALANGESAFEAGRAFRLAYLSSLYRCGPVALRVARVAAVLGPSA

TTTLVRRLSGLSAETIDRATKILTEGGLLLDQQFPHPAARSVVLDDMSAQERRGLHTLALELLDEAPVEVL

AHHQVGAGLIHGPKAAEMFAKAGKALVVRNELGDAAEYLQLAHRASDDVSTRAALRVEAVAIERRRNPLAS

SRHMDELSAAGRAGLLSPKHAALAVFWLADGGRSGEAAQVLASERPLATTDQNRAHLRFVEVTLALFSPGA

FGSDRRPPPLTPDELASLPKAAWQCAVADNAAMTALHGHPELATAQAETVLRQADSAADAIPAALIALLYA

ENTESAHIWADKLGSMNAGVSNEAEAGYAGPCAEIALRRGDLATAFEAGSTVLDDRSLPSLGITAALLLSS

KTAAAVRLGELERAEKLLAEPLPNGVQDSLFGLHLLSAYGQYSLAMGRYESAHRAFRTCGERMRSWDVDVP

GLALWRVDAAEALLSLDRNEGQRLIDEQLTRPMGPRSRALTLRIKAAYLPRTKRIPLLHEAAELLLPCPDP

YEQARVLADLGDTLSALRRYSRARGVLRQARHLATQCGAVPLLRRLGGEPGRIDDAGLPQRSTSLTDAERR

VAALAAAGQTNREIAEQLFVTASTVEQHLTSVFRKLGVKGRKQLPTALADVEQT

SEQ ID NO: 36
MRAINASDTGPELVAREDELGRVRSALNRANGGQGVLISITGPIACGKTELLEAAASEVDAITLRAVCAAE

ERAIPYALIGQLIDNPALGIPVPDPAGLTAQGGRLSSSAENRLRRDLTRALLTLATDRLVLICVDDVQHAD

NASLSCLLYLARRLVPARIALVFTELRVLTSSQLRFNAELLSLRNHCEIALRPLGPGHAAELARATLGPGL

SDETLTELYRVTGGNLSLSRGLIDDVRDAWARGETGVQVGRAFRLAYLGSLHRCGPLALRVARVAAVLGPS

ATSVLVRRISGLSAEAMAQATDILADGGLLRDQRFTHPAARSVVLDDMSAEERRSVHSLALELLDEAPAEM

LAHHRVGAGLVHGPKAAETFTGAGRALAVRGMLGEAADYLQLAYRASGDAATKAAIRVESVAVERRRNPLV

VSRHWDELSVAARAGLLSCEHVSRTARWLTVGGRPGEAARVLASQHRRVVTDQDRAHLRVAEFSLALLYPG

TSGSDRRPHPLTSDELAALPTATRHCAIADNAVMAALRGHPELATAEAEAVLQQADAADGAALTALMALLY

AESIEVAEVWADKLAAEAGASNGQDAEYAGIRAEIALRRGDLTAAVETAGMVLDGRPLPSLDITATLLLAG

RASVAVRLGELDHAEELFAAPPEDAFQDSLFGLHLLSAHGQYSLATGRPESAYRAFRACGERMRDWGFDAP

GVALWRVGAAEALLGLDRNEGRRLIDEQLSRTMAPRSHALTLRIKAAYMPEPKRVDLLYEAAELLLSCRDQ

YERARVLADLGEALSALGNYRQARGVLRQARHLAMRTGADPLLRRLGIRPGRQDDPDPQPRSRSLTNAERR

AASLAATGLTNREIADRLFVTASTVEQHLTNVFRKLGVKGRKQLPAELDDME
```

LAL Binding Sites

In some embodiments, a gene cluster (e.g., a PKS gene cluster or a β-lactam compound gene cluster) includes one or more promoters that include one or more LAL binding sites. The LAL binding sites may include a polynucleotide consensus LAL binding site sequence (e.g., as described herein). In some instances, the LAL binding site includes a core AGGGGG motif. In certain instances, the LAL binding site includes a sequence having at least 80% (e.g., 80%, 85%, 90%, 95%, 97%, 98%, 99%, or 100%) homology to SEQ ID NO: 2. The LAL binding site may include mutation sites that have been restored to match the sequence of a consensus or optimized LAL binding site. In some embodiments, the LAL binding site is a synthetic LAL binding site. In some embodiments, a synthetic LAL binding sites may be identified by (a) providing a plurality of synthetic nucleic acids including at least eight nucleotides; (b) contacting one or more of the plurality of nucleotides including at least eight nucleotides with one or more LALs; (c) determining the binding affinity between a nucleic acid of step (a) and an LAL of step (b), wherein a synthetic nucleic acid is identified as a synthetic LAL binding site if the affinity between the synthetic nucleic acid and an LAL is greater than X. The identified synthetic LAL binding sites may then be introduced into a host cell in a compound-producing cluster (e.g., a PKS cluster or a β-lactam compound producing protein gene cluster).

In some embodiments, a pair of LAL binding site and a heterologous LAL or a heterologous LAL binding site and an LAL that have increased expression compared a natural pair may be identified by (a) providing one or more LAL binding sites; (b) contacting one or more of the LAL binding sites with one or more LALs; (c) determining the binding affinity between a LAL binding site and an LAL, wherein a pair having increased expression is identified if the affinity between the LAL binding site and the LAL is greater than the affinity between the LAL binding site and its homologous LAL and/or the LAL at its homologous LAL binding site. In some embodiments, the binding affinity between the LAL binding site and the LAL is determined by determining the expression of a protein or compound by a cell which includes both the LAL and the LAL binding site.

Constitutively Active LALs

In some embodiments, the recombinant LAL is a constitutively active LAL. For example, the amino acid sequence of the LAL has been modified in such a way that it does not require the presence of an inducer compound for the altered LAL to engage its cognate binding site and activate transcription of a compound producing protein (e.g., polyketide synthase or a β-lactam compound producing protein). Introduction of a constitutively active LAL to a host cell would likely result in increased expression of the compound-producing protein (e.g., polyketide synthase or a β-lactam compound producing protein) and, in turn, increased production of the corresponding compound (e.g., polyketide or a β-lactam compound).

Engineering Unidirectional LALs

FkPhD gene clusters are arranged with a multicistronic architecture driven by multiple bidirectional promoter-operators that harbor conserved (in single or multiple, and inverted to each other and/or directly repeating) GGGGGT (SEQ ID NO: 3) motifs presumed to be LAL binding sites. Bidirectional LAL promoters may be converted to unidirectional ones (UniLALs) by strategically deleting one of the opposing promoters, but maintaining the tandem LAL binding sites (in case binding of LALs in the native promoter is cooperative, as was demonstrated for MalT). Functionally this is achieved by removal of all sequences 3' of the conserved GGGGGT (SEQ ID NO: 3) motif present on the antisense strand (likely containing the −35 and −10 promoter sequences), but leaving intact the entire sequence on the sense strand. As a consequence of this deletion, transcription would be activated in one direction only. The advantages of this feed-forward circuit architecture would be to tune and/or maximize LAL expression during the complex life cycle of *Streptomyces* vegetative and fermentation growth conditions.

Host Cells

In some embodiments, the host cell is a bacteria such as an Actiobacterium. For example, in some embodiments, the host cell is a *Streptomyces* strain. In some embodiments, the host cell is *Streptomyces anulatus, Streptomyces antibioticus, Streptomyces coelicolor, Streptomyces peucetius, Streptomyces* sp. ATCC 700974, *Streptomyces canus, Streptomyces nodosus, Streptomyces* (multiple sp.), *Streptoalloteicus hindustanus, Streptomyces hygroscopicus, Streptomyces avermitilis, Streptomyces viridochromogenes, Streptomyces verticillus, Streptomyces chartruensis, Streptomyces* (multiple sp.), *Saccharothrix mutabilis, Streptomyces halstedii, Streptomyces clavuligerus, Streptomyces venezuelae, Strteptomyces roseochromogenes, Amycolatopsis orientalis, Streptomyces clavuligerus, Streptomyces rishiriensis, Streptomyces lavendulae, Streptomyces roseosporus, Nonomuraea* sp., *Streptomyces peucetius, Saccharopolyspora erythraea, Streptomyces filipinensis, Streptomyces hygroscopicus, Micromonospora purpurea, Streptomyces hygroscopicus, Streptomyces narbonensis, Streptomyces kanamyceticus, Streptomyces collinus, Streptomyces lasaliensis, Streptomyces lincolnensis, Dactosporangium aurantiacum, Streptomyces toxitricini, Streptomyces hygroscopicus, Streptomyces plicatus, Streptomyces lavendulae, Streptomyces ghanaensis, Streptomyces cinnamonensis, Streptomyces aureofaciens, Streptomyces natalensis, Streptomyces chattanoogensis L10, Streptomyces lydicus A02, Streptomyces fradiae, Streptomyces ambofaciens, Streptomyces tendae, Streptomyces noursei, Streptomyces avermitilis, Streptomyces rimosus, Streptomyces wedmorensis, Streptomyces cacaoi, Streptomyces pristinaespiralis, Streptomyces pristinaespiralis, Actinoplanes* sp. ATCC 33076, *Streptomyces hygroscopicus, Lechevalieria aerocolonegenes, Amycolatopsis mediterranei, Amycolatopsis lurida, Streptomyces albus, Streptomyces griseolus, Streptomyces spectabilis, Saccharopolyspora spinosa, Streptomyces ambofaciens, Streptomyces staurosporeus, Streptomyces griseus, Streptomyces* (multiple species), *Streptomyces acromogenes, Streptomyces tsukubaensis, Actinoplanes teichomyceticus, Streptomyces glaucescens, Streptomyces rimosus, Streptomyces cattleya, Streptomyces azureus, Streptoalloteicus hindustanus, Streptomyces chartreusis, Streptomyces fradiae, Streptomyces coelicolor, Streptomyces hygroscopicus, Streptomyces* sp. 11861, *Streptomyces virginiae, Amycolatopsis japonicum, Amycolatopsis balhimycini, Streptomyces albus J1074, Streptomyces coelicolor M1146, Streptomyces lividans, Streptomyces incarnates, Streptomyces violaceoruber,* or *Streptomyces griseofuscus*. In some embodiments, the host cell is an *Escherichia* strain such as *Escherichia coli*. In some embodiments, the host cell is a *Bacillus* strain such as *Bacillus subtilis*. In some embodiments, the host cell is a *Pseudomonas* strain such as *Pseudomonas putitda*. In some embodiments, the host cell is a *Myxococcus* strain such as *Myxococcus xanthus*.

Methods

The nucleic acids, vectors, and host cells of the invention may be used for increased and/or more efficient production of compounds (e.g., polyketides or β-lactam compounds). Introduction of recombinant and/or heterologous LALs to host cells or the introduction of heterologous binding sites to the gene clusters that produce a small molecule (e.g., PKS gene clusters or β-lactam compound producing protein gene clusters) allow for greater control of the regulations of the genes which encode the compound-producing proteins (e.g., polyketide synthases or β-lactam compound producing proteins) responsible for the production of compounds (e.g., polyketides or β-lactam compounds) of interest.

Introduction of Heterologous LAL

In some embodiments, compounds (e.g., polyketides or β-lactam compounds) are produced by introduction of a heterologous LAL to a host cell (e.g., the LAL may be introduced with an expression vector, such as an artificial chromosome, including a nucleic acid encoding the LAL). In some embodiments, the host cell naturally lacks an LAL. In some embodiments, the host cell naturally produces an LAL that is different from the introduced LAL. The introduced LAL may be any LAL with the conserved four helix bundle DNA binding region of the PKS regulating LALs. In some embodiments, the introduced LAL is a natural LAL. In some embodiments, the introduced LAL is a modified LAL, e.g., a constitutively active LAL. In some embodiments, the introduced LAL has at least 70% sequence identity to SEQ ID NO: 1. In some embodiments, the introduced LAL includes or consists of the sequence of SEQ ID NO: 1. In some embodiments in which the host cell naturally produces an LAL, the nucleic acid which expresses the natural LAL is deleted prior to introduction of the heterologous LAL. In certain embodiments, the introduced LAL is expressed from an expression vector in which the polynucleotide sequence encoding the LAL is codon optimized. For example, TTA codons, which are known to exert translational control of genes having such codons in a *Streptomyces* host cell, may be removed and/or replaced in the LAL coding sequence. In some embodiments, the host cell may be modified, for example, to remove a cytochrome P450 oxygenase.

Introduction of a Heterologous LAL Binding Site

In some embodiments, compounds (e.g., polyketides or β-lactam compounds) are produced by introduction of a heterologous LAL binding site to a host cell (e.g., the LAL binding site may be introduced with an expression vector, such as an artificial chromosome, including a nucleic acid having the LAL binding site or insertion via homologous recombination). In some embodiments, the host cell naturally lacks an LAL binding site. In some embodiments, the host cell naturally includes an LAL binding site that is different from the introduced LAL binding site. In some embodiments, the introduced LAL binding site has at least 80% identity to SEQ ID NO: 2. In some embodiments, the introduced LAL binding site includes or consists of the sequence of SEQ ID NO: 2. In some embodiments, the introduced LAL binding site includes the sequence GGGGGT (SEQ ID NO: 3). In some embodiments, the introduced LAL binding site results in increased production of a compound (e.g., a polyketide or a β-lactam compound). In some embodiments, the open reading frame encoding the compound-producing protein (e.g., a polyketide synthase or a β-lactam compound producing protein) is positioned such that binding of an LAL to the LAL binding site promotes expression of the biosynthetic protein(s) (e.g., a polyketide synthase or a β-lactam compound producing protein) and thus the compound (e.g., a polyketide or a β-lactam compound). In some embodiments, the LAL binding site has the sequence of SEQ ID NO: 2 and the LAL has the sequence of SEQ ID NO: 1.

In some instances, a construct may include one or more promoters including a heterologous LAL binding site. For example, a construct may include a unidirectional promoter driving the expression of one or more genes (e.g., genes in a gene cluster that produces a small molecule, such as a PKS gene cluster or a β-lactam compound producing protein gene cluster). In some instances, a construct may include a bidirectional promoter located between two sets of genes to be expressed, with one portion of the bidirectional promoter including a first LAL binding site and driving expression of one set of genes, and a second portion of the bidirectional promoter including a second LAL binding site and driving expression of the second set of genes. The two sets of genes may be oriented antiparallel relative to each other. In certain instances, a host cell may include a gene cluster under the control of a unidirectional or bidirectional promoter, as well as at least one gene encoding a heterologous LAL that is under the control of a promoter containing an LAL binding site. The gene cluster and the heterologous LAL-encoding gene may be located on the same construct, or may be located on different constructs. Expression of an LAL (e.g., an endogenous LAL or a heterologous LAL) results in expression of the heterologous LAL as well as the genes in the gene cluster. The expressed heterologous LAL may in turn further drive expression of the genes in the gene cluster and the heterologous LAL in a positive feedback loop.

Introduction of a Heterologous PKS Gene Cluster

In some embodiments, polyketides are produced by introduction of a nucleic acid encoding a heterologous PKS gene cluster to a host cell (e.g., the nucleic acid may be introduced with an expression vector, such as an artificial chromosome). In some embodiments, the nucleic acid further includes an LAL binding site. In some embodiments, the LAL binding site is heterologous to the PKS gene cluster. In some embodiments, the LAL binding site is homologous to the PKS gene cluster. In some embodiments, a heterologous LAL is also introduced to the host cell (e.g., the LAL may be introduced with an expression vector, such as an artificial chromosome, including a nucleic acid encoding the LAL). In some embodiments, the LAL is encoded by the same nucleic acid which encodes the heterologous PKS gene cluster. In some embodiments, the LAL is heterologous to the LAL binding site and/or the PKS gene cluster. In some embodiments, the LAL is homologous to the LAL binding site and/or the PKS gene cluster. In some embodiments, the polyketide synthase is not expressed in the absence of either an LAL or an LAL binding site.

A host cell may be modified to optimize production from the heterologous PKS gene cluster. In some embodiments, one or more tailoring enzymes (e.g., the cytochrome P450 oxygenase, cypB) is deleted. In some embodiments, a host cell may be modified to include a particular allele that confers resistance to an antibiotic (e.g., resistance alleles against streptomycin (e.g., rpsL), rifampicin (e.g., rpoB), and gentamicin), which may result in the production of higher secondary metabolite titers.

Introduction of a Heterologous β-Lactam Compound Producing Protein Gene Cluster

In some embodiments, β-lactam compounds are produced by introduction of a nucleic acid encoding a heterologous β-lactam compound producing protein gene cluster to a host cell (e.g., the nucleic acid may be introduced with an expression vector, such as an artificial chromosome). In some embodiments, the nucleic acid further includes an LAL binding site. In some embodiments, the LAL binding site is heterologous to the β-lactam compound producing protein gene cluster. In some embodiments, the LAL binding site is homologous to the β-lactam compound producing protein gene cluster. In some embodiments, a heterologous LAL is also introduced to the host cell (e.g., the LAL may be introduced with an expression vector, such as an artificial chromosome, including a nucleic acid encoding the LAL). In some embodiments, the LAL is encoded by the same nucleic acid which encodes the heterologous β-lactam compound producing protein gene cluster. In some embodiments, the LAL is heterologous to the LAL binding site and/or the β-lactam compound producing protein gene cluster. In some embodiments, the LAL is homologous to the LAL binding site and/or the β-lactam compound producing protein gene cluster. In some embodiments, the β-lactam compound is not expressed in the absence of either an LAL or an LAL binding site.

A host cell may be modified to optimize production from the heterologous β-lactam compound producing protein gene cluster. In some embodiments, one or more tailoring enzymes is deleted. In some embodiments, a host cell may be modified to include a particular allele that confers resistance to an antibiotic (e.g., resistance alleles against streptomycin (e.g., rpsL), rifampicin (e.g., rpoB), and gentamicin), which may result in the production of higher secondary metabolite titers.

Quantification of mRNA Transcripts by NanoString Analysis

In some embodiments, gene expression (e.g., expression of one or more genes regulated by a heterologous LAL binding site) may be quantified using the NanoString nCounter Analysis System® (Nanostring). The NanoString nCounter assay involves direct digital detection of mRNA molecules using target-specific, color-coded probe pairs. It does not require the conversion of mRNA to cDNA by reverse transcription or the amplification of the resulting cDNA by PCR. Each target gene of interest is detected using a pair of reporter and capture probes carrying 35- to 50-base target-specific sequences. In addition, each reporter probe carries a unique color code at the 5' end that enables the molecular barcoding of the genes of interest, while the capture probes all carry a biotin label at the 3' end that provides a molecular handle for attachment of target genes to facilitate downstream digital detection. After solution-phase hybridization between target mRNA and reporter-capture probe pairs, excess probes are removed and the probe/target complexes are aligned and immobilized in the nCounter cartridge, which is then placed in a digital analyzer for image acquisition and data processing. Hundreds of thousands of color codes designating mRNA targets of interest are directly imaged on the surface of the cartridge. The expression level of a gene is measured by counting the number of times the color-coded barcode for that gene is detected, and the barcode counts are then tabulated. The methodology and uses of NanoString are further described in Kulkarni, M. Curr. Protoc. Mol. Biol. 94:256.10.1-256.10.17 (2011).

In some embodiments, Nanostring analysis is used to determine if the expression of a locus of a gene cluster (e.g., a PKS gene cluster or a β-lactam compound producing protein gene cluster), which is located in proximity to a heterologous LAL binding site, is upregulated relative to the same locus when the locus is not located in proximity to a heterologous LAL binding site.

EXAMPLES

Methods
LAL Cloning:
LAL gene sequences from FKPHD gene clusters were obtained from the WarpDrive genome database or from public sources such as GenBank. LAL genes were modified from wild-type to remove single or multiple TTA codons, which are known to exert translational control of genes having these codons in *Streptomyces*. Synthetic EcoRI/XbaI bounded cassettes composed of the strong constitutive ermE* promoter, the TTA-less LALs, and the transcriptional terminator from phage fd were cloned into pSET152 having a PhiC31 integrase and attP site, an apramycin resistance gene, and an oriT for conjugal transfer from conjugation-proficient *Escherichia coli*. The TTA-less LAL genes were also inserted into other integrative vectors (example pWFE1), or functional equivalents, remaining under the transcriptional control of the strong constitutive promoter PermE*.

LAL gene panels cloned into pWFE1 were introduced into Actinomycete bacteria harboring genomic FKPHD gene clusters, and also having predicted LAL binding sites in the promoter-operator regions of their FKPHD biosynthetic loci, by intergeneric conjugation using donor strain JV36. Intergeneric conjugations were carried out as using standard methods on R2NSY media at 30° C. or 37° C., and conjugation plates were overlaid after 18-48 hours with 0.3-2.0 mg apramycin and 0.5-1.0 mg nalidixic acid. Actinomycete exconjugants harboring the pWFE1-LAL plasmids were streaked to fresh plates containing apramycin (30-50 mg/L) and nalidixic acid (25-30 mg/L) to remove residual *E. coli* donor and confirm stable apramycin resistance.

Recombinant Actinomycetes carrying integrated LAL plasmids were tested for FKPHD production as follows: Starter cultures of Actinomycetes were grown in 15 ml Maltose-Yeast extract-Glucose broth containing apramycin (25-50 mg/L). After 2-3 days at 29-30° C., the starter cultures plated for confluence to solid media suitable for production (e.g., Medium 2 or 8430 or others). After 6-7 days of growth at 30° C., two agar plates having confluent actinomycete growth were harvested for extraction. Briefly, agar with adherent actinomycete growth was removed from petri plates and extracted with 100% methanol. After soaking overnight in methanol, the agar was removed, and the methanol was diluted with water to 15-30% final concentration. FKPHD compounds were captured from the aqueous extract using Phenomenex C18-U SPE columns (0.5 g, 6 mL capacity). After washing columns with bound extract with 30% Methanol, remaining molecules including FKPHDs were eluted with 100% methanol.

Methanol was removed from eluates in vacuo, and resulting crudes were dissolved in DMSO. The dissolved samples were then diluted as necessary in methanol (generally 10 μl into 490 μl neat methanol), and analyzed by LC/MS. (Agilent HPLC with diode array in line with Agilent 6120 single quad mass spectrometer). Screens for improved strains were determined on a semi-quantitative using conventional analyses using Agilent MassHunter or Agilent ChemStation software, measuring area-under-curve (AUC) of ion-extracted mass chromatograms. Final assessment of strain improvement was done by scaled liquid growths, molecule purification, and measurement by weight and NMR using internal standards as compared to wild-type strains lacking pWFE1-LAL constructs.

Deletion of Biosynthetic Enzymes:
Deletion of biosynthetic enzymes to increase the titer of specific FKPHD compounds were made in the following way: First, ~1 kb regions of homology flanking the start and stop codons of genes selected for deletion were amplified by PCR. These homology arms were assembled into a single deletion cassette using overlap-extension PCR, and cloned to the *E. coli-Streptomyces* shuttle vector pJVD52.1. Deletions were carried out as known in the art, with vectors carrying deletion cassettes being delivered into target strains using conjugation, as detailed above. Of note, pJVD52.1—based deletion strategies can make use of streptomycin counterselection, and utilize parent strains with rpsL mutations. Bacteria spontaneously mutated in the rpsL allele are known to be isolable when strains are plated in the presence of streptomycin (10 to 100 μg/mL) on suitable media (e.g., ISP2, Becton Dickinson Co.). Putative mutant actinobacterial deletion hosts were confirmed to have desired lesions in rpsL by amplification by PCR and comparison to wild-type rpsL DNA sequences.

Resulting deletion strains in an rpsL background were then fermented as above, and fermentation extracts containing FKPHD compounds were analyzed against wild-type and rpsL parent strain extracts, confirming increased titers of specific FKPHDs are attributable to specific gene deletions (e.g., genes encoding predicted cytochrome P450 oxygenases) and not to rpsL mutations required for the gene deletion process.

Inducing rpoB/rpsL:
Actinobacteria harboring specific alleles conferring resistance to certain antibiotics can sometimes produce higher secondary metabolite titers than strains lacking these alleles. Spontaneous bacterial mutants harboring these alleles can be selected for using antibiotics including streptomycin (rpsL), rifampicin (rpoB), gentamicin, and others. These antibiotic resistance phenotypes can be useful singly, or in combination (double, triple mutants, or more). Isolation of improved FKPHD producers, in combination with LAL gene cluster activation, illustrates the utility and compatibility of combining both recombinant strategies for strain enhancement over wild-type. To isolate spontaneous rpoB mutants (rpsL described above), vegetative mycelia or spores of desired strains were spread to ISP2 plates containing rifampicin, and resulting individual colonies were cultivated in the presence of rifampicin to confirm resistance. Nucleotide lesions in rpoB leading to antibiotic resistance were confirmed by PCR amplification of the rpoB locus from resistant isolates in parallel with sensitive parent strains, and the DNA sequences of both were compared. Sequence-confirmed rpoB mutants were then compared in fermentation panels, screening for increased production against wild-type and LAL-enhanced recombinant strains without resistance alleles.

Promoter Swap and Promoter Repair:

A PAC library was prepared from the genomic DNA of the *Streptomyces* strain harboring the wild-type X15 gene cluster and cloned into the pESAC13 backbone by Bio-SandT (Montreal, Canada). Molecular clones with intact wild-type X15 gene clusters were identified from the library by colony PCR. The X1.1-S12 promoter was PCR amplified with the following primers (see below) from the S12 gene cluster and cloned into the X15 gene cluster.

```
X15_LAL_F
                                    SEQ ID NO: 37
5'-CAAAGCGATTCGGAGAGCGGCCGGATCAGATCCAGGCGTGACATTCA
TACCCTTCCGGCGAAGTGCAGTTCACCC-3'

X15_LAL_R
                                    SEQ ID NO: 38
5'-CGATCTTCTCGAAACTGCACTGAGGAGGTTCGTCGGAGACTGCCATT
CACCTCTCCCGGAAAGGTATTGCTCG-3'
```

To introduce the S18 LAL transcription factor, a Gateway acceptor vector (ThermoFisher, Grand Island, N.Y.) was first cloned into the pESAC13 backbone. The S18 LAL was transferred to the X15 PAC backbone using LR Clonase. The same approach was used to repair the non-canonical LAL promoter sequences in the X11.2 PAC. The X11.1 and X11.2 promoters with repaired LAL sites were generated by synthetic gene construction design with the DNAWorks webserver (mc11.ncifcrf.gov/dnaworks/).

```
>PAC_HA_X11.1_promoter_G
                                    SEQ ID NO: 39
5'-GCGTTCGGCATTGACGCGAAGCAAGTCATGAATCGGCTGAATCAAT

TCCGCGCGCGACATTCGCACCCTTCCGGTGAAGTGCGGTATTGCTCAGA

CATAACCCGGATCGCAATCCAACGACCAGCCATGCACTACCGATAATCG

AATCGGAACAATAGCAAGCTCGTTGAGCATATTTTCCATGCGGCACCAC

CTCGGCGCCACCCCCTAGTTTTGCCGACCCCCTATGTGTATTTCGGCAG

GCAGACTAGGGGGTTGCGTGGGCCGCACCCGAGGCATTCGATTGGCGCA

CGGCGCACTCGGGCCATGTCACCGACCGTGAATGTTTCATCGCTACGGG

TAGCAATAGTCCTTTCTCGGGAGAAGTGAATGGCTTCCAAAAGTCCCCG

CCCAGGGTCCGAGAGAGCGGGTTCTGCGATTTCCCGGGCA-3'

>PAC_HA_X11.1_promoter_G_4bp
                                    SEQ ID NO: 40
5'-GCGTTCGGCATTGACGCGAAGCAAGTCATGAATCGGCTGAATCAAT

TCCGCGCGCGACATTCGCACCCTTCCGGTGAAGTGCGGTATTGCTCAGA

CATAACCCGGATCGCAATCCAACGACCAGCCATGCACTACCGATAATCG

AATCGGAACAATAGCAAGCTCGTTGAGCATATTTTCCATGCGGCACCAC
```

```
-continued
CTCGGCGCCACCCCCTAGTTTTGCCGACCCCCTATGTGTATTTCGGCAG

GCAGAACACCTAGGGGGTTGCGTGGGCCGCACCCGAGGCATTCGATTGG

CGCACGGCGCACTCGGGCCATGTCACCGACCGTGAATGTTTCATCGCTA

CGGGTAGCAATAGTCCTTTCTCGGGAGAAGTGAATGGCTTCCAAAAGTC

CCCGCCCAGGGTCCGAGAGAGCGGGTTCTGCGATTTCCCGGGCA-3'

>PAC_HA_X11.2_promoter_A
                                    SEQ ID NO: 41
5'-GCGTTCGGCATTGACGCGAAGCAAGTCATGAATCGGCTGAATCAAT

TCCGCGCGCGACATTCGCATCCTTCTGGTGAGGTGCAGTATTGCTGAGA

CATAATCCGGGCCGTAATCCAACGACCAGCCATGCGCCGCCGATAGTCG

AATCCGATAGTCGAATCTGAACGCTAGCAGCTCGTCGCAGGGGCTCCGG

GGAGCCCAACCCCCTAATTTTTCCGCCCCCCTATACATATCCACTGCAG

GCAGAACACCTAGGGGGTTGCGCGAACCGGGCGCGCGGTATCGGATTTA

CCGCACGGCACACTCGGGCGACGTCACCGACCGTGAATCCTTCATCGCT

ACGGGTAGCACAGTCCTTTCCGGGAGAAGTGAATGGCTTCCAAAAGTCC

CCGCCCAGGGTCCGAGAGAGCGGGTTCTGCGATTTCCCGGGCA-3'

>PAC_HA_X11.2_S12_promoter SEQ ID NO: 42:
5'-GCGTTCGGCATTGACGCGAAGCAAGTCATGAATCGGCTGAATCAAT

TCCGCGCGCGACATTCATACCCTTCCGGCGAAGTGCAGTTCACCCGGTA

ATGCATTCCGGACCGTAGCAGTCCGATACAGACGTCCGCCATGCCGTGC

CACCCTTGTTTTTCACCCCCCTACGCCCGTTTCGCCTGGCCGGAAACCT

AGGGGGTTGCGTGGAAAGCACCGGCGGGTGTTCGCTTGCACAGCGCCAC

CTCGGGCATTTTCTGGATGCGCGAGCAATACCTTTCCGGGAGAGGTGAA

TGGCTTCCAAAAGTCCCCGCCCAGGGTCCGAGAGAGCGGGTTCTGCGAT

TTCCCGGGCA-3'
```

The wild-type X2 gene cluster was prepared from *Streptomyces* genomic DNA and cloned into the modified pCC1 backbone by Intact Genomics, Inc. (St. Louis, Mo.). The UniLAL promoter was PCR amplified from the UniLAL-S18-LAL expression vector and cloned into the X2 gene cluster.

Example 1. Use of LAL Transcriptional Regulators as General Induction and Overexpression Strategy Gene clusters under the control of one or more bidirectional promoters were constructed. In particular, a set of FkPhD gene clusters was generated (FIG. 1A), each including two bidirectional promoters, shown as Promoter Region 1 and Promoter Region 2. Each promoter contained one or more LAL binding domains selected from those shown in FIG. 1B. Alignment of a set of such putative LAL binding domains extracted from FK gene cluster promoter regions revealed conserved regions. As shown in FIG. 1C, the general experimental approach involved subcloning of a codon-optimized LAL panel into an integrating vector driven by, e.g., a strong ermE* promoter.

LALs were selected for these experiments by clading all LALs in a high pass genomic database including publication-quality assembled genomes (FIG. 2). These LALs were cladded using the helix-turn-helix motif of the rapamycin LAL (S9), yielding a design query. FkPhD LALs were shown to clade together and were dissimilar on a sequence level from other Type I PKS-associated LALs, such as pikD (FIG. 3).

Figure 4:
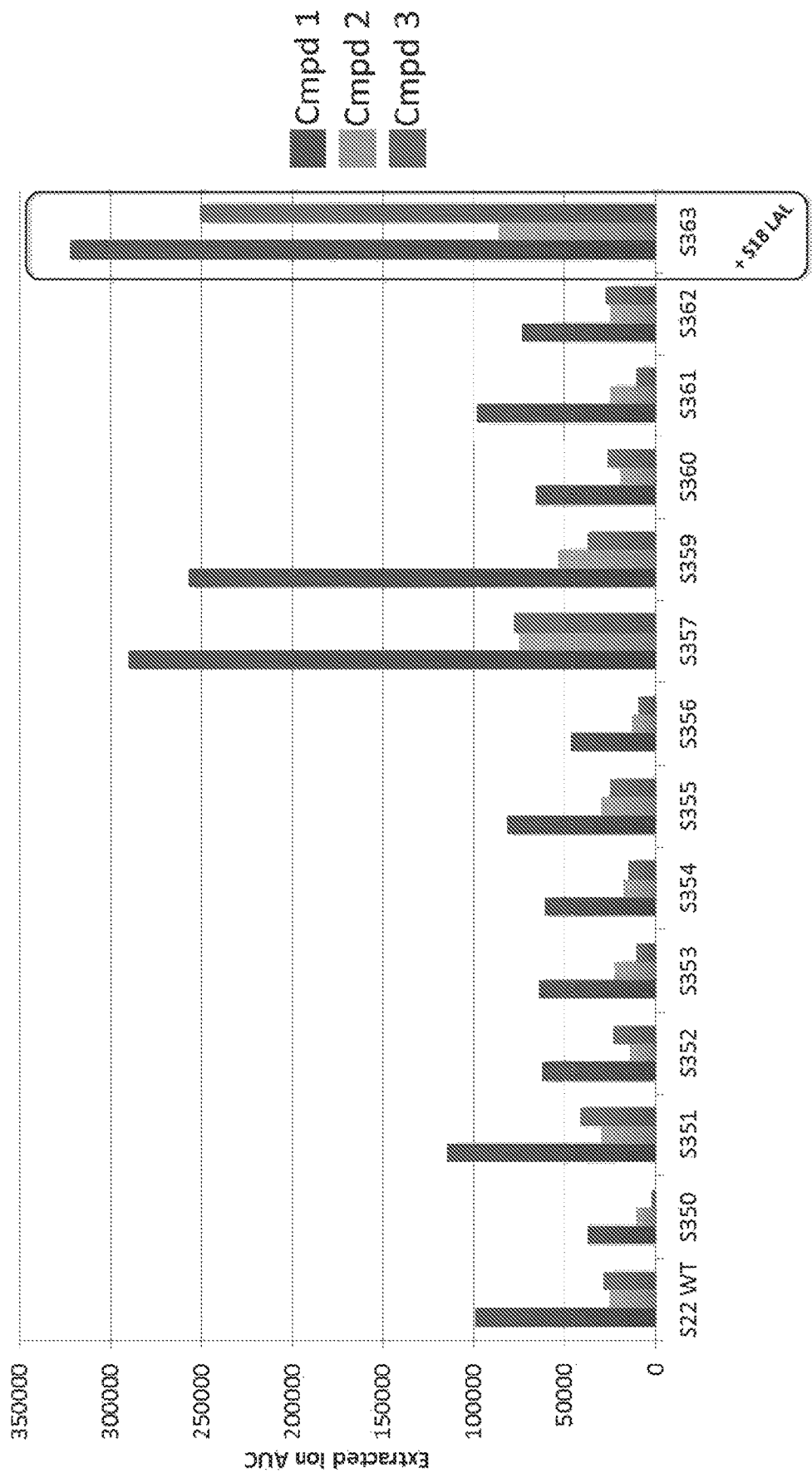
FIG. 4 is a graph showing S22/LAL exconjugants assayed for increased Compound 1, Compound 2, and Compound 3 production by LC/MS.
Figure 5:
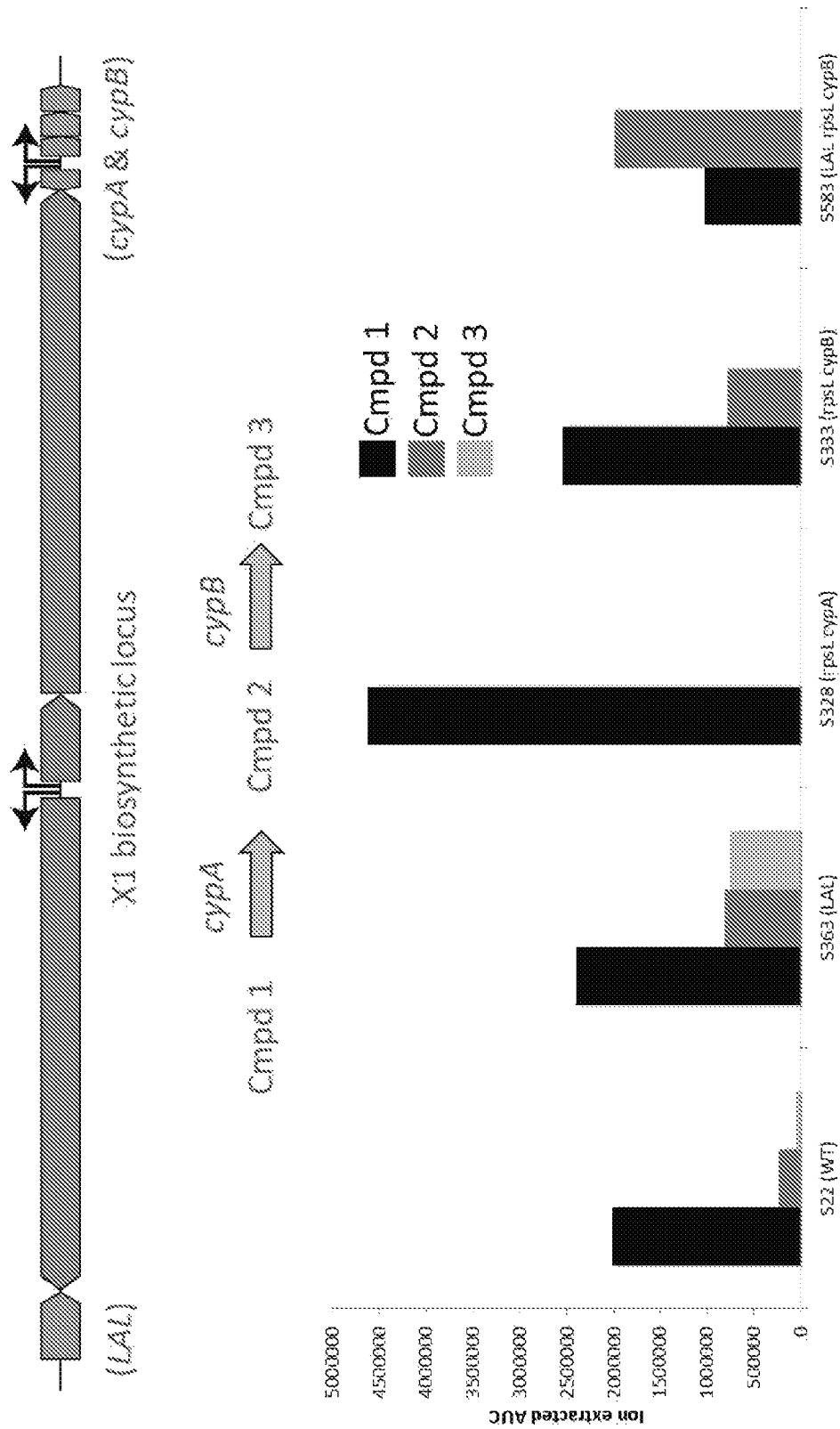
FIG. 5 is a series of diagrams showing combined LAL and cyp manipulations for increased production of Compound 1 and Compound 2 in S22.

Example 2. Expression of LALs Drives Polyketide Production from Biosynthetic Gene Clusters As presented in FIG. 4, a large panel of LALs was expressed in a native *Streptomyces* producer of the X1 family of molecules (Compound 1, Compound 2, and Compound 3). Specifically, the X1 FkPhD gene cluster was observed in the S22 native strain, and a panel of LALs were then conjugated into the S22. The resulting strains were assayed for enhanced expression of polyketides. Production of the X1 gene cluster family of products (i.e., Compound 1, Compound 2, and Compound 3) was assessed by LC/MS. The results indicated that some LALs acted as repressors and suppressed polyketide expression compared to wild-type (i.e., in the absence of LAL). In some cases, the LAL significantly increased the expression of the polyketide compared to wild-type. These results, therefore, indicated that certain LALs are constitutively active in this context. S363, the exconjugate with the integrated vector constitutively expressing the S18 LAL, produced the highest levels of Compound 1, Compound 2, and Compound 3. The production of the desired product, Compound 2, was further optimized by combining S18 overexpression with other modifications to the biosynthetic locus, including ribosomal protein rpsL mutations (e.g., induced by *streptomycin*) and P450 deletion (FIG. 5). The resultant strain, S583, yielded increased production of Compound 2.

Figure 6:
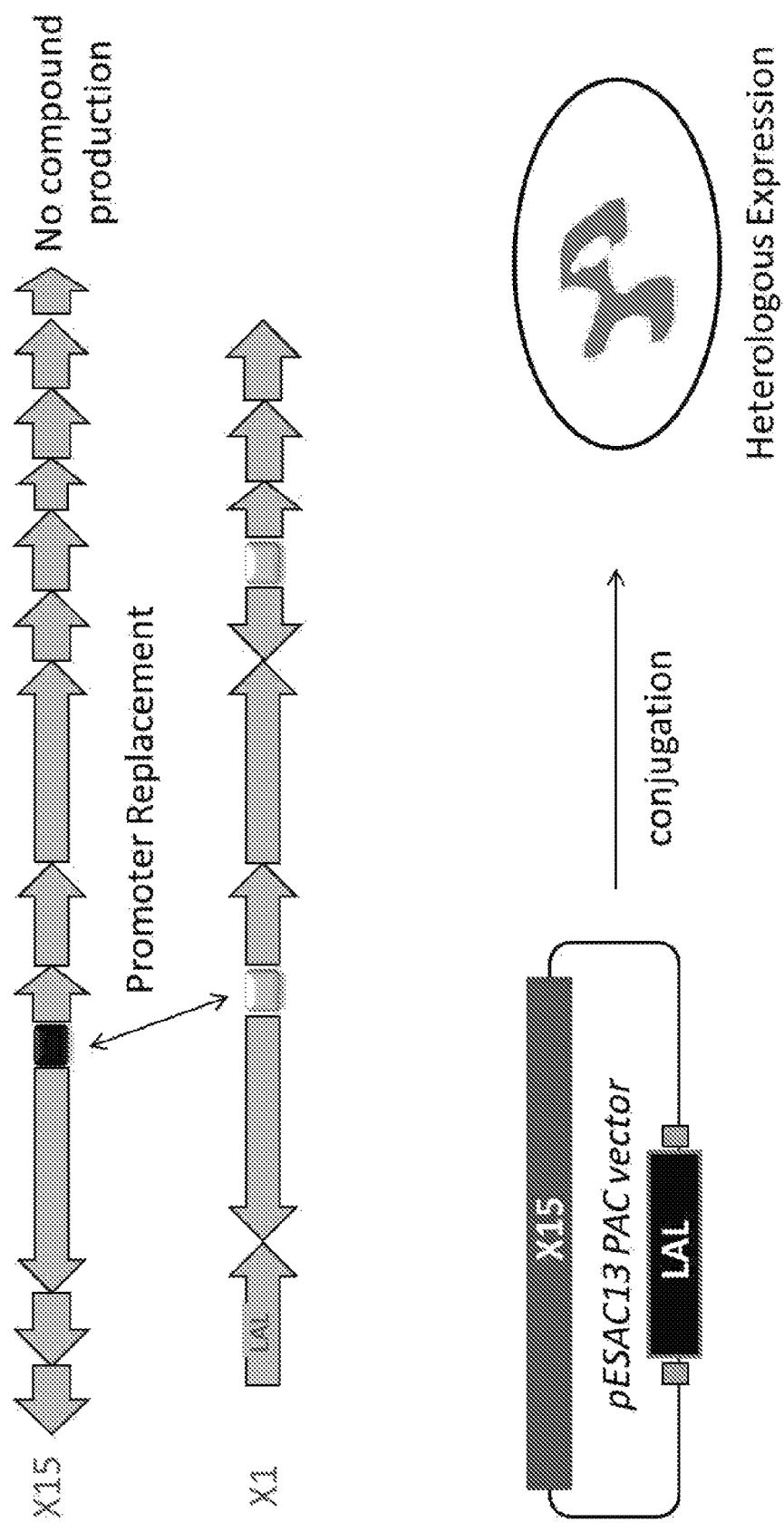
FIG. 6 is a diagram showing a strategy for replacement of the X15 promoter with an X1 promoter and introduction of a heterologous LAL-encoding locus.

Example 3. Promoter Engineering to Replace a Silent LAL Promoter in a Biosynthetic Gene Cluster The X15 gene cluster includes a silent promoter containing no canonical LAL binding sites. This promoter was replaced with the X1 promoter, which includes LAL binding sites to produce a refactored X15 gene cluster under the control of the X1 promoter (FIG. 6). A pESAC13 expression vector including the refactored X15 gene cluster was then modified by Gateway cloning to introduce a cassette where expression of the S18 LAL is under the control of the ermE* promoter. The resultant expression vector was then conjugated into S942 cells (a derivative of *Streptomyces ambofaciens*) for heterologous expression of the S18 LAL and biosynthetic genes in the X15 gene cluster.

Figure 7:
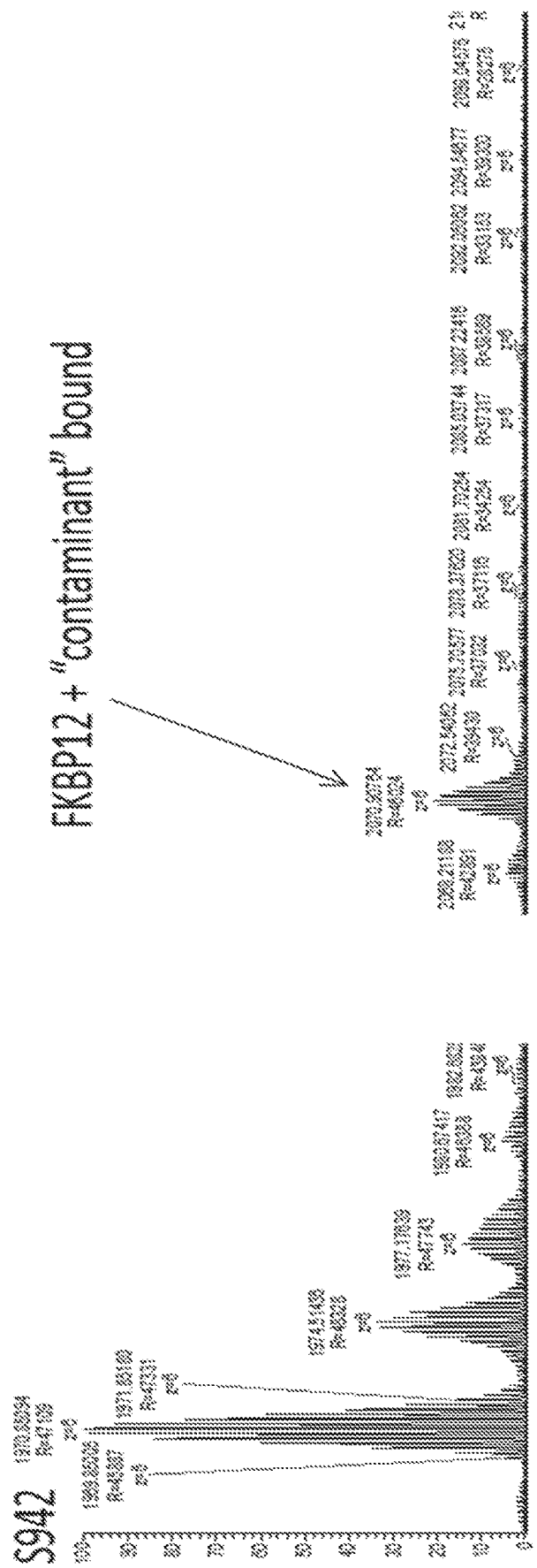
FIG. 7 is a series of graphs showing that replacement of the X15 promoter with an X1 promoter and heterologous LAL expression leads to biosynthetic production from the silent X15 cluster.
Figure 7:
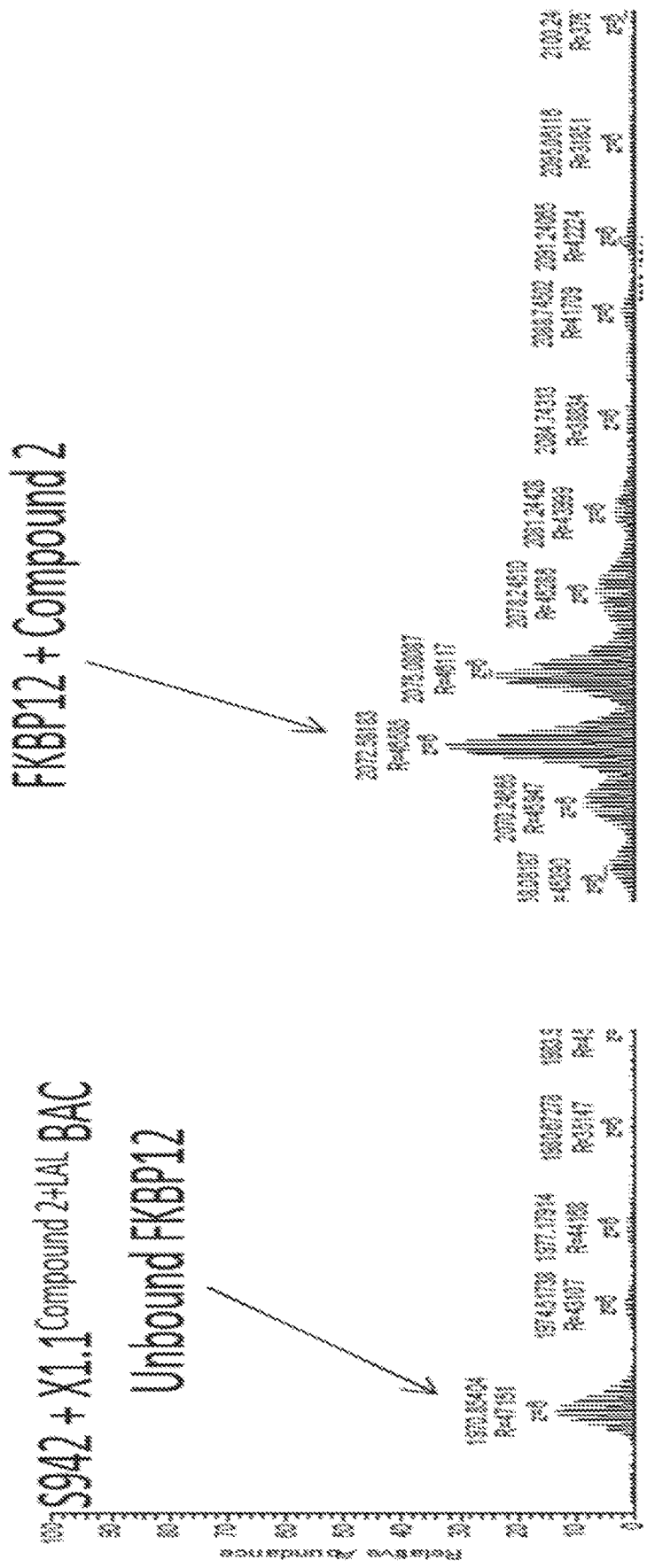
Figure 7:
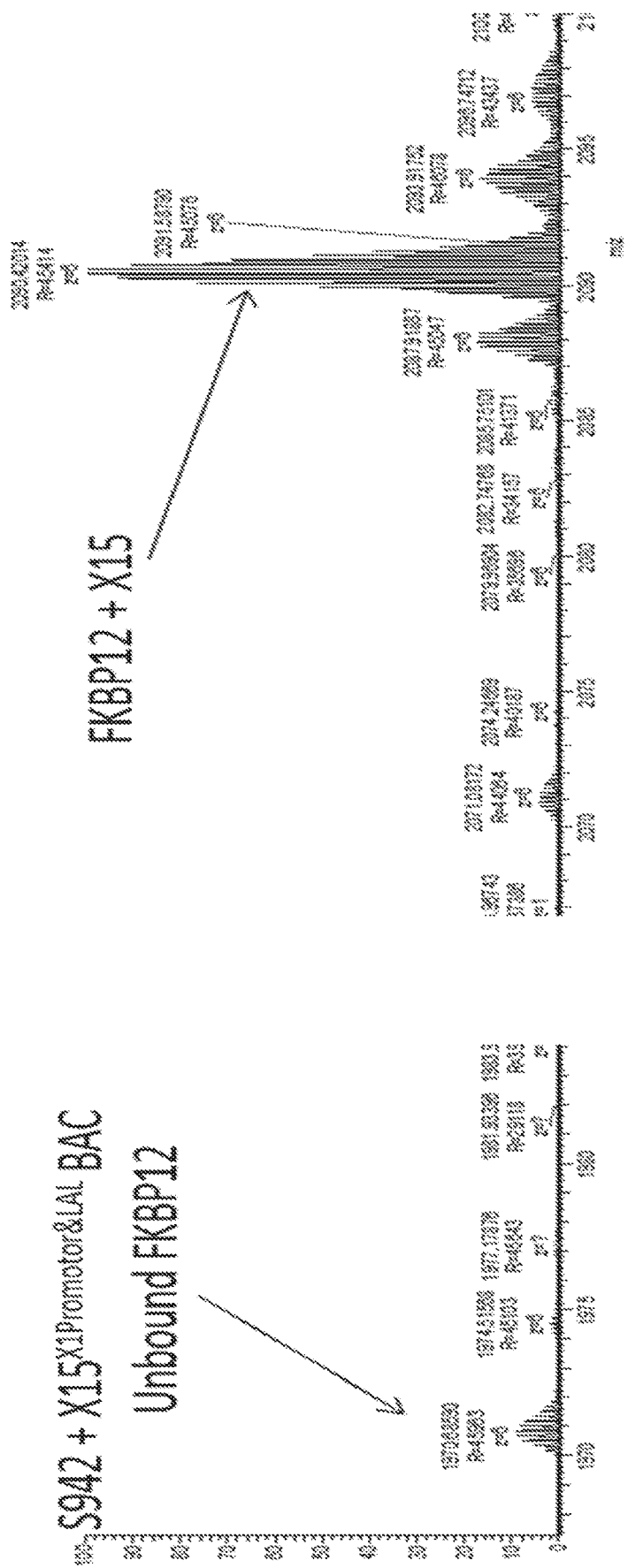

As shown in FIG. 7, re-engineering of the X15 gene cluster to replace the X15 promoter with the X1 promoter resulted in expression of X15 gene cluster genes and downstream production of X15 biosynthesis products at high levels. The top row of panels shows S942 alone as a control. The middle panel shows a strain generated by conjugating S942 to the X1 gene cluster (encoding Compound 1 and Compound 2) with the S18 LAL expressed from the vector backbone. Compound 2 expression is observed by Top-Down proteomics analysis. This data confirms that LAL expression can induce PKS expression of a strain with an intact promoter, as defined the by presence of functional LAL binding sites, in a heterologous producer strain. The bottom panels show the above-described strain generated by conjugating S942 to the X15 gene cluster with the endogenous promoter swapped with the X1 promoter and with the S18 LAL expressed from the vector backbone. These data showed that X15 production matched or exceeded that of S942 cells engineered to produce Compound 2 from an X1.1 locus. Thus, the data confirms that promoter replacement and LAL expression can induce PKS expression from a silent gene cluster in a heterologous producer.

Example 4. FK Bi-Directional Promoters

Figure 8:
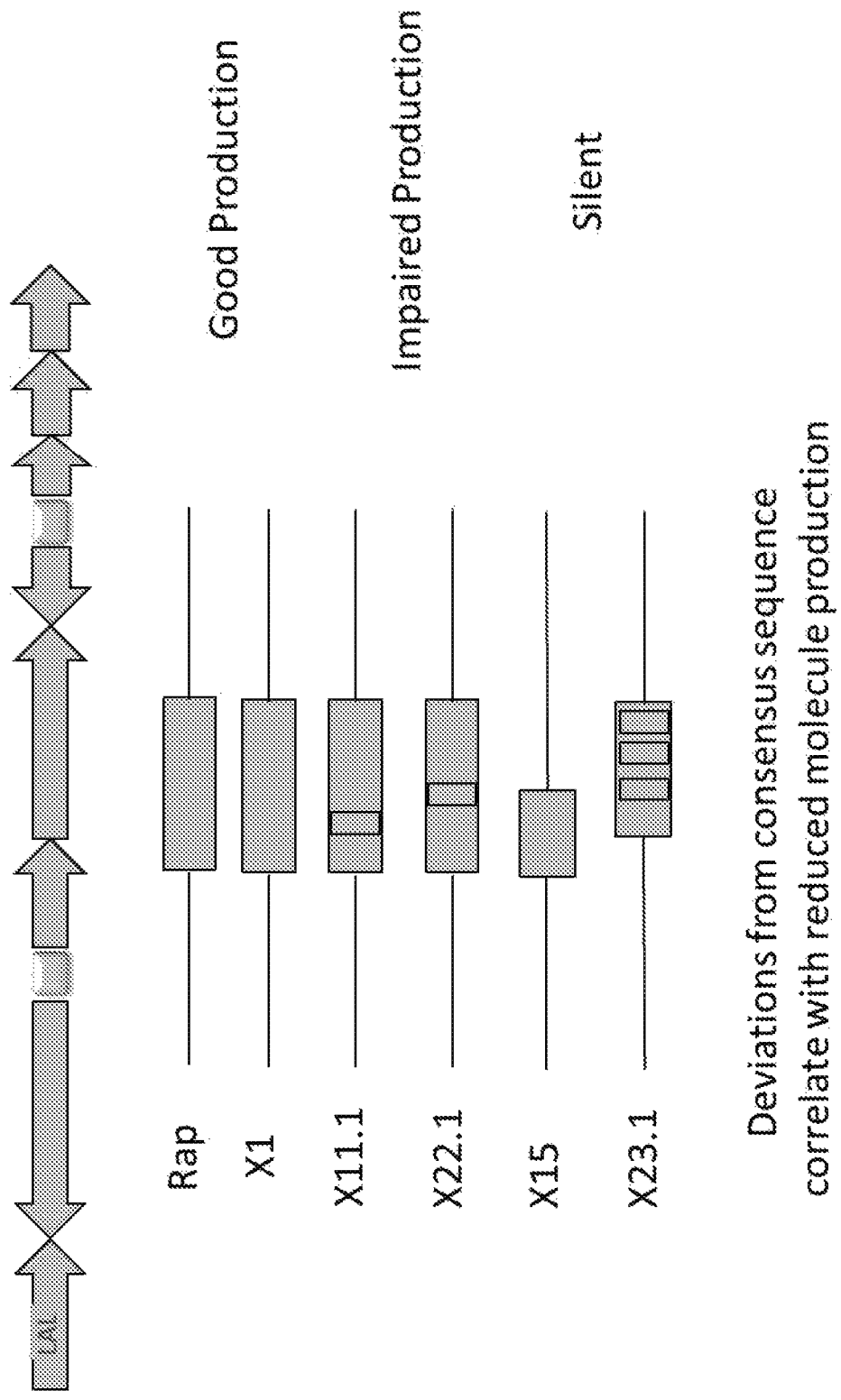
FIG. 8 is a diagram showing sequence analysis of various FK bidirectional promoters. Rap and X1 promoters were associated with good production. X11.1 and X22.1 promoters were associated with impaired production. X15 and X23.1 promoters were silent. Deviations from the consensus sequence correlated with reduced molecule production.

The sequences of the promoters from rapamycin, X1, X11.1, X22.1, X15, and X23.1 biosynthetic gene clusters were analyzed to correlate conserved sequence elements to native and/or heterologous production (FIG. 8). Three general classes of bidirectional FkPhD promoters were identified: (1) highly active promoters with intact promoter sequences including the functional LAL binding sites (e.g., rapamycin and X1), (2) less active promoters with impaired production in which mutations are observed in the core LAL binding sites (e.g., X11.1 and X22.1), and (3) silent promoters with severe deviations from the consensus sequence (e.g., X15 and X23.1). Generally, deviations from the consensus promoter sequence correlated with reduced compound production.

Figure 9:
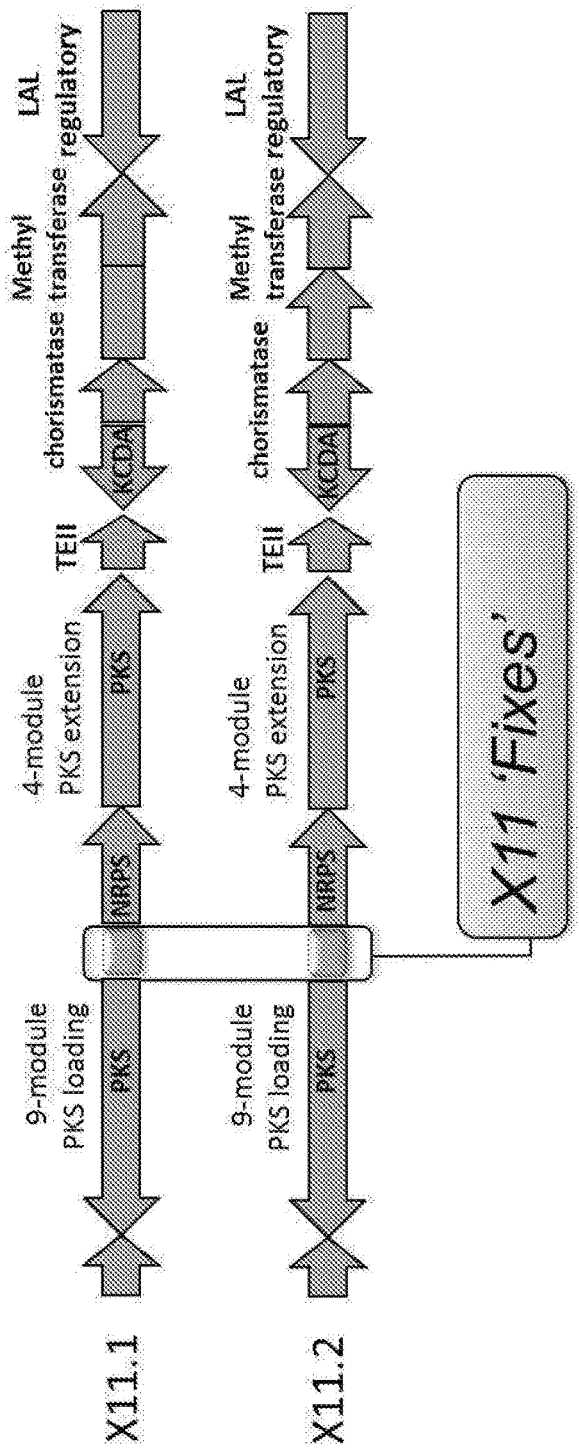
FIG. 9 is a diagram showing X11.1 and X11.2 bidirectional promoter engineering and sequence alignment of wild-type (i.e., X11.1 and X11.2) and restored (i.e., Seq1, Seq2, and Seq3) LAL binding sequences.

Sequence alignments of the LAL binding sites within the primary bi-directional promoters of two novel and related FkPhD gene clusters, X11.1 and X11.2, showed several mutations (deviations from the consensus LAL binding site) that appeared to modulate promoter strength and resultant production. For example, mutations were identified that reduced promoter strength and led to poor FkPhD expression (FIG. 9). In the case of X11.1, the wild-type promoter lacked the conserved ACAC motif and a G from a core LAL operator sequence (AGGGGG). In the case of X11.2, the wild-type promoter lacked an A from the core LAL operator sequence. We restored the X11.1 and X11.2 sequences to the consensus sequence to generate the sequences shown as Seq1, Seq2, and Seq3, and examined whether repairing these mutations impacted expression in the X11.2 gene cluster.

Figure 10:
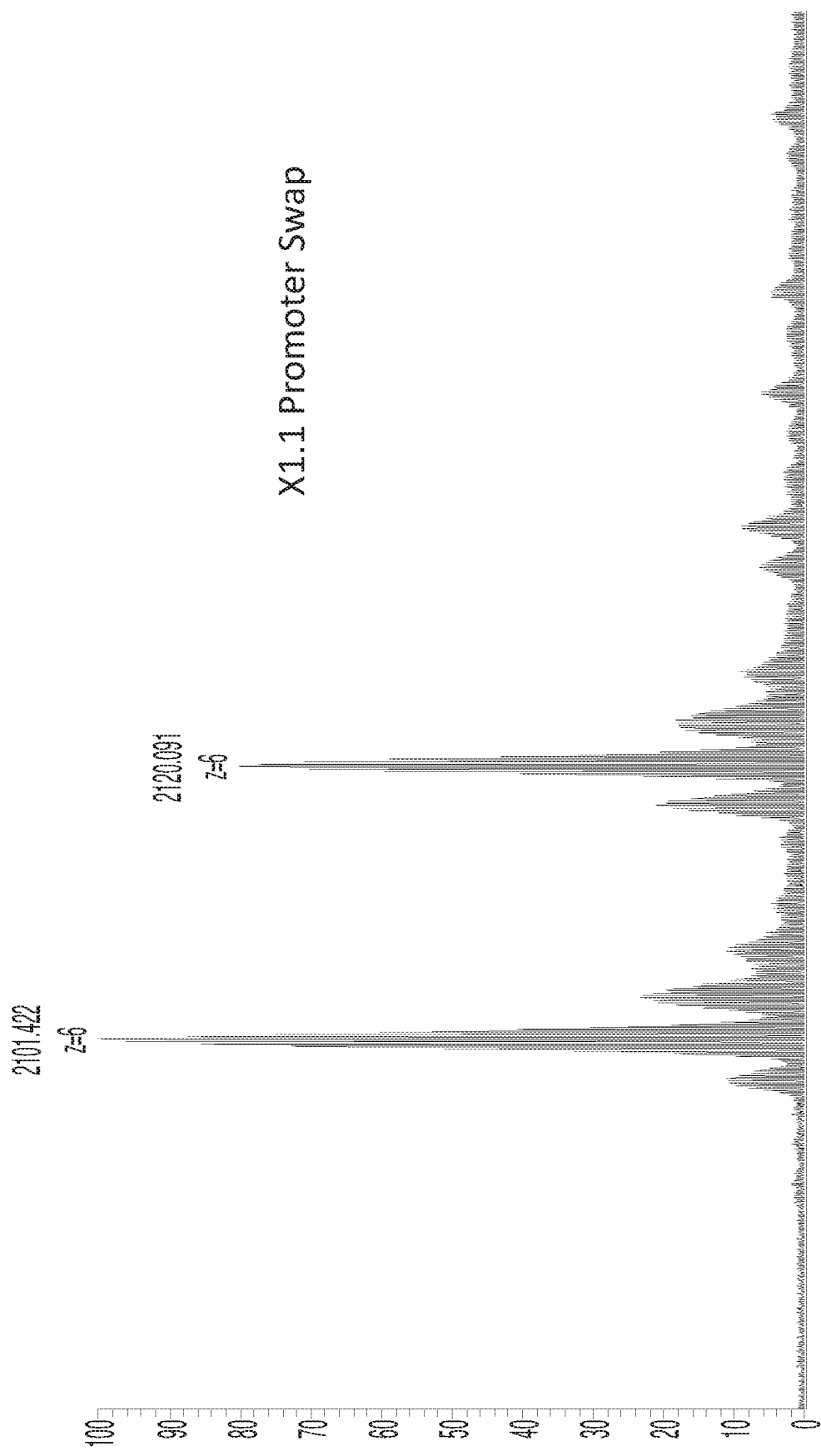
FIG. 10 is a series of graphs showing that restoration of sequence lesions in the LAL sequences yields increased PKS production.
Figure 10:
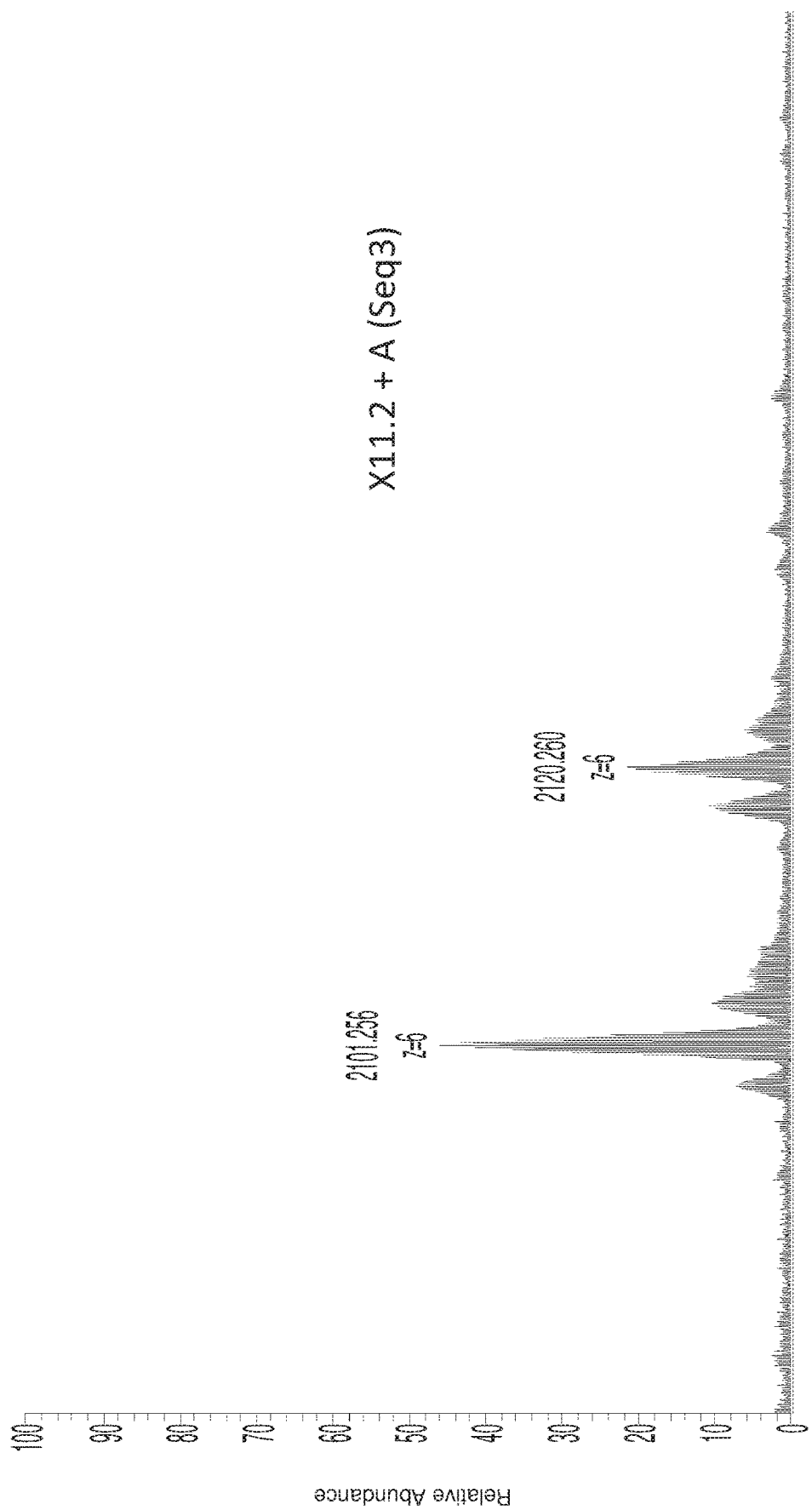
Figure 10:
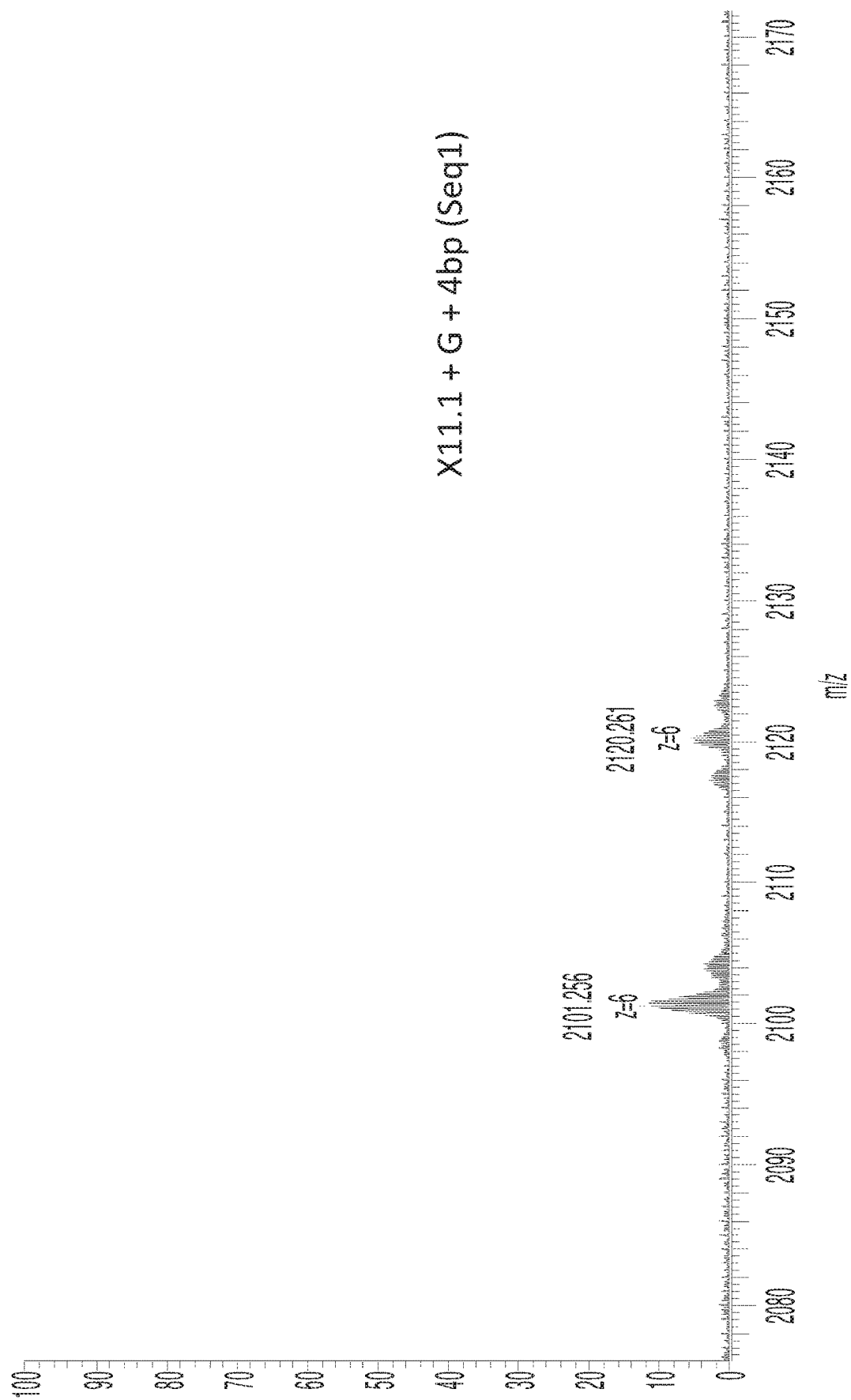

The restored sequence lesions in the LAL binding sequence yielded increased polyketide synthase production. FIG. 10 shows a comparison of X11.2 FkPhD expression with the X1.1 promoter swap, the X11.1 promoter with the core G and ACAC motif restored (Seq2), and the X11.2 promoter with the A from the core LAL binding sequence restored (Seq3). In contrast to the wild-type (WT) 11.2, the Seq2 promoter yielded a significant increase in FkPhD production. Restoration of the A from the core LAL binding sequence (Seq3) increased FkPhD production more than the Seq2 promoter. The total X1 promoter swap yielded the greatest FkPhD production. These data show that restoring mutated conserved promoter sequences is a reliable approach for increasing FkPhD production. These data also provide support experiment support for our definition of the core LAL binding site sequence.

Example 5. UniLAL Variants

Figure 11A:
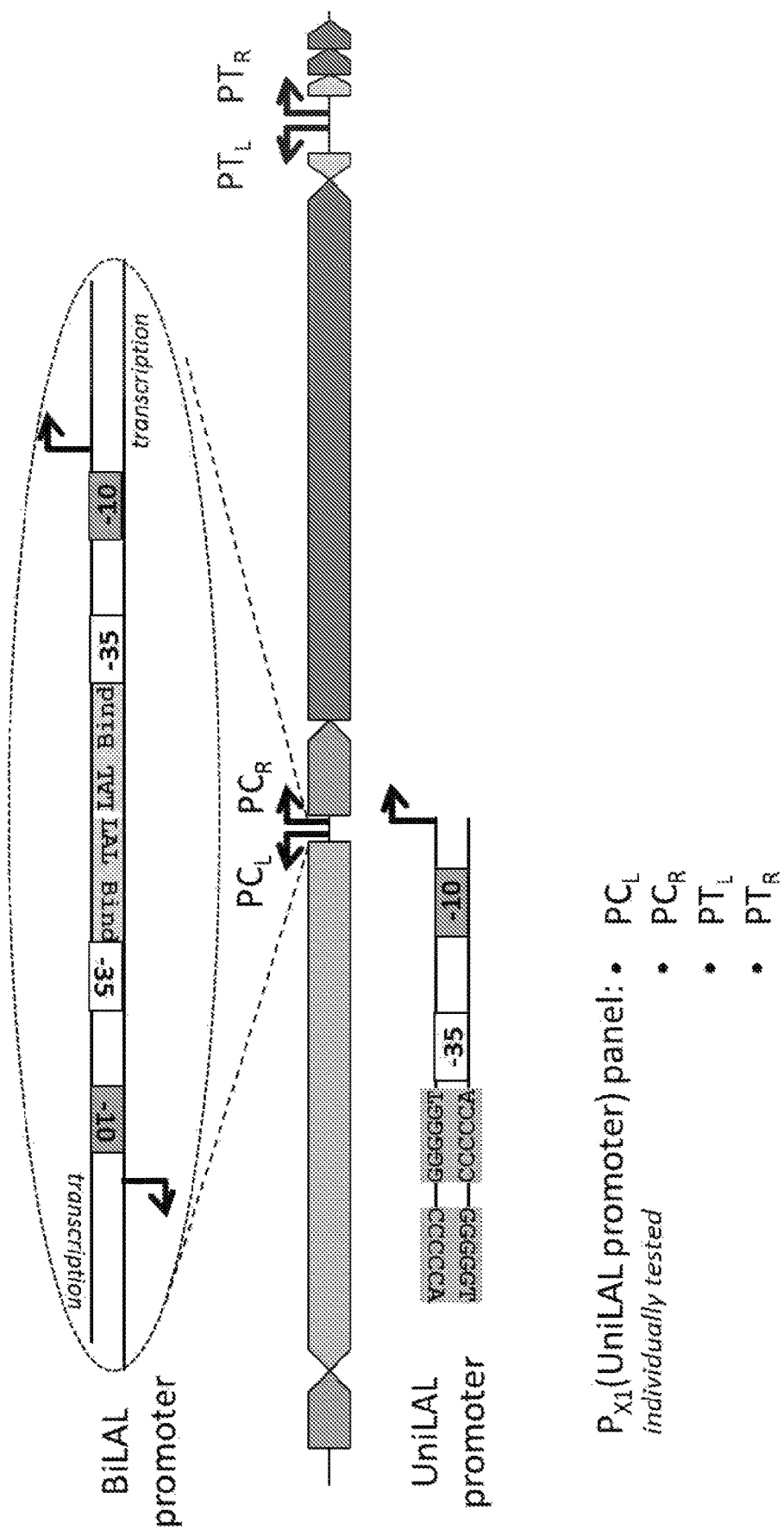
FIG. 11A is a diagram showing the dissection of the two promoter regions in a biosynthetic locus used to create the four UniLAL variants ($PC_L$, $PC_R$, $PT_L$, and $PT_R$).
Figure 11B:
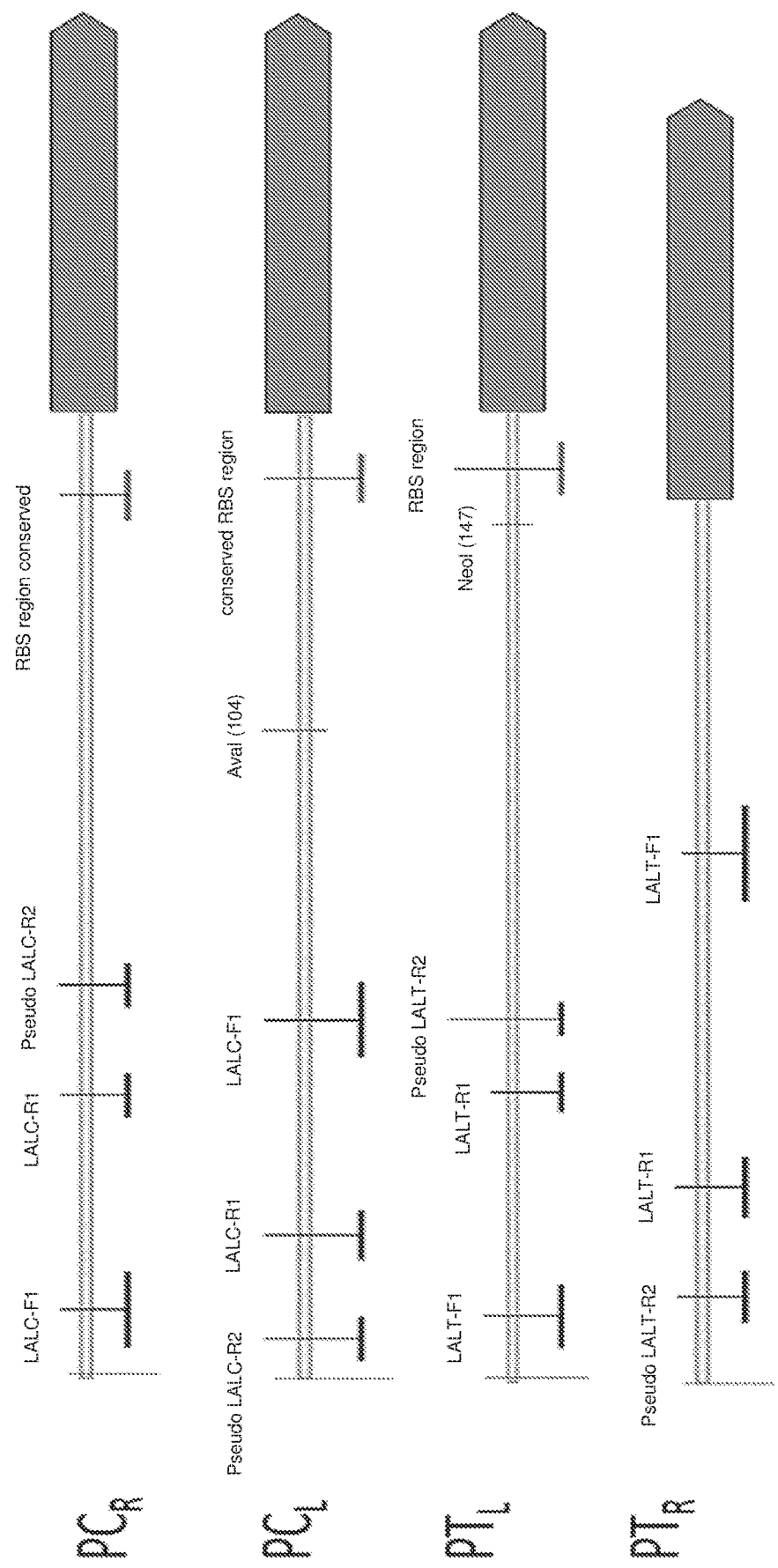
FIG. 11B is a diagram showing the nucleic acid sequence engineering strategy applied to generate the four UniLAL variants.

Promoter Region 1 and Region 2 bidirectional promoters were strategically dissected to yield four promoter designs (i.e., $PC_L$, $PC_R$, $PT_L$, $PT_R$) for subsequent functional testing (FIG. 11A) Each UniLAL variant included a −10 and −35 site as well as an LAL binding site. FIG. 11B captures the logic of UniLAL dissection. The UniLAL promoter was defined as the ribosome binding site (RBS), LAL binding sites and/or key prokaryotic promoter elements such as −10 and −35 sites. In some instances, the LAL binding site overlapped or replaced the −10 or −35 sites. In addition to the composition and sequence of these key elements, the spacing and orientation (sense/antisense) may be essential to the function of a particular design.

Figure 12:
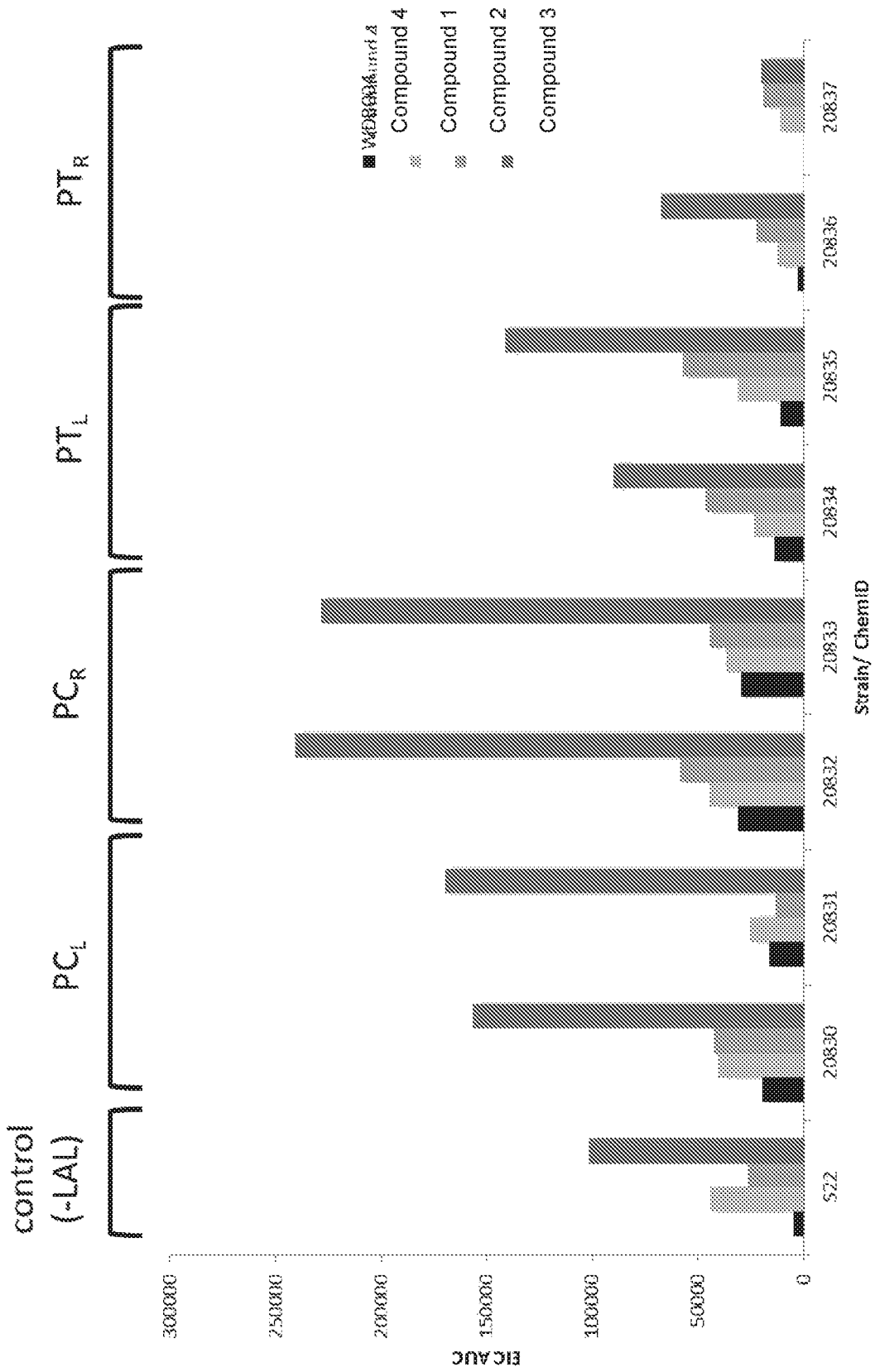
FIG. 12 is a graph showing the level of Compound 1, Compound 2, Compound 3, and Compound 4 produced in an LAL-negative S22 control and when one of each of the four UniLAL variants was subcloned in front of the S18 LAL and used to drive PKS expression in S22.

The promoter strength of each of the UniLAL variants was assessed. In order to rank order the 4 UniLAL designs ($PC_L$, $PC_R$, $PT_L$, $PT_R$), each UniLAL promoter was subcloned in front of the S18 LAL. The resulting integrative expression plasmid was conjugated to S22, which produces the Compound 2 family of compounds. As such, the UniLAL promoter in a particular conjugant was expected to be activated by the S18 LAL to create a feed-forward circuit to maximize LAL expression, gene cluster activation and produce an increase in Compound 2 production. Production of Compound 4, Compound 1, Compound 2, and Compound 3 induced by each of the UniLAL promoters is shown in FIG. 12. These data show that the Promoter Region 1 designs (i.e., PCL, PCR) are most effective for driving LAL expression and gene cluster production.

Figure 13:
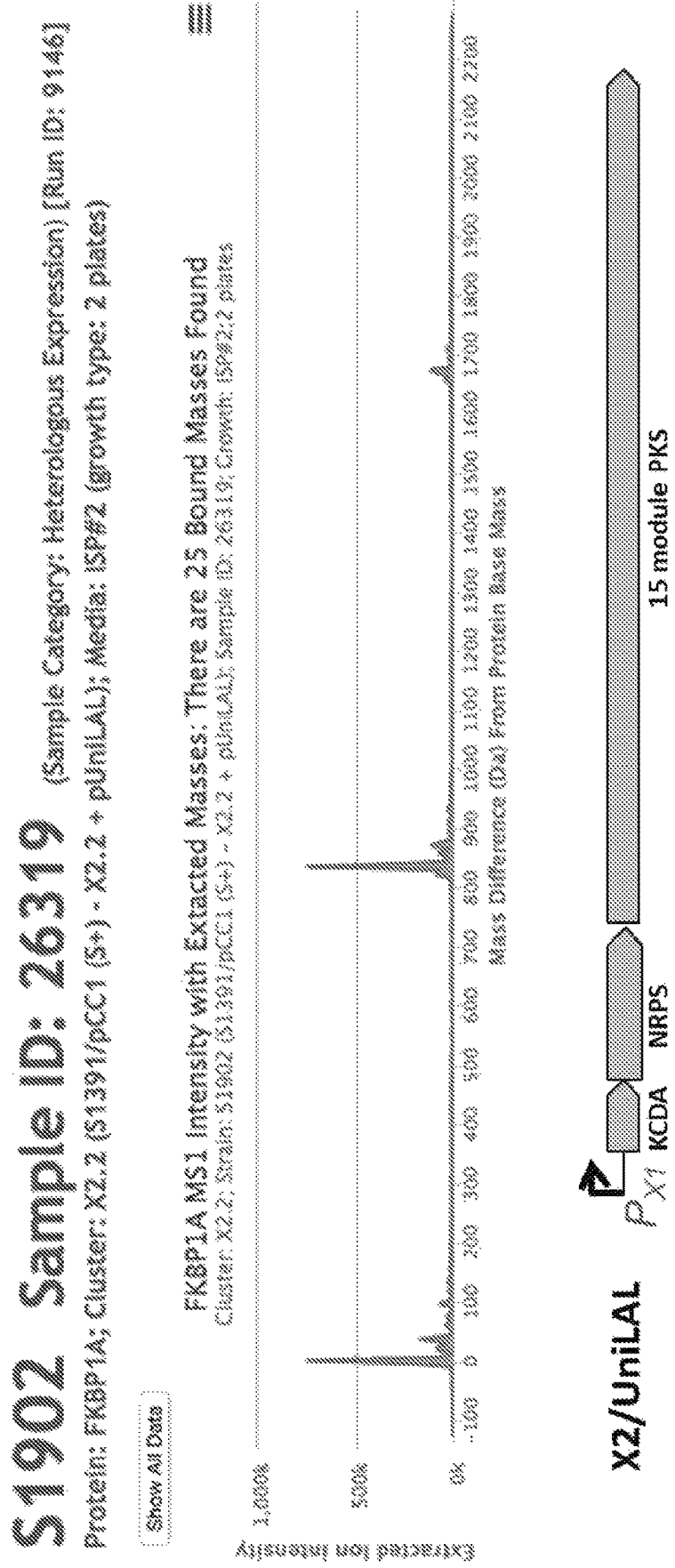
FIG. 13 is a graph showing activation of polyketide production from a trancsriptionally silent biosynthetic cluster that does not naturally include an LAL regulator using a UniLAL.

This approach was also tested for ability to drive polyketide production in an ordinarily silent biosynthetic gene cluster that does not naturally include an LAL regulator (FIG. 13). When the modified X2 gene cluster was expressed in the presence of the S18 LAL, robust expression of X2 was observed by the Top-Down assay.

Example 6. Positive Feedback Overexpression Strategy

Figure 14:
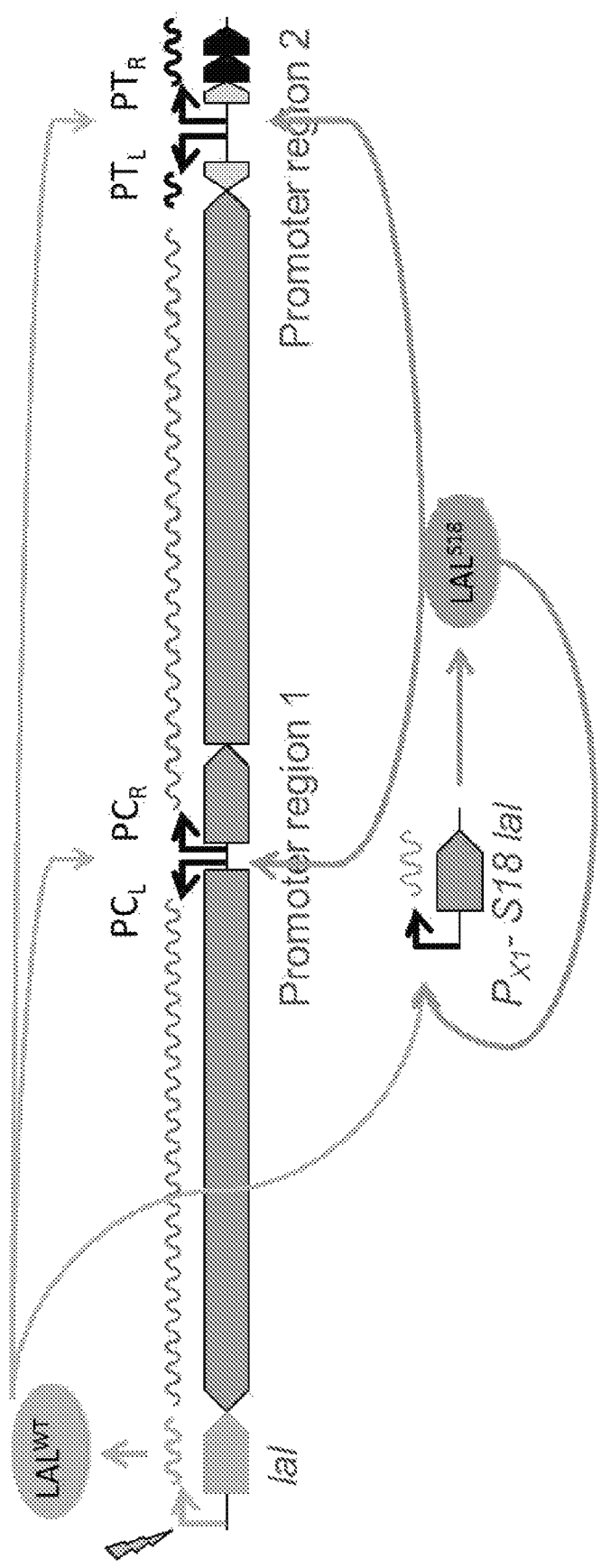
FIG. 14 is a diagram showing the use of an LAL regulon to create a positive feedback loop for overexpression from a biosynthetic cluster.
Figure 15:
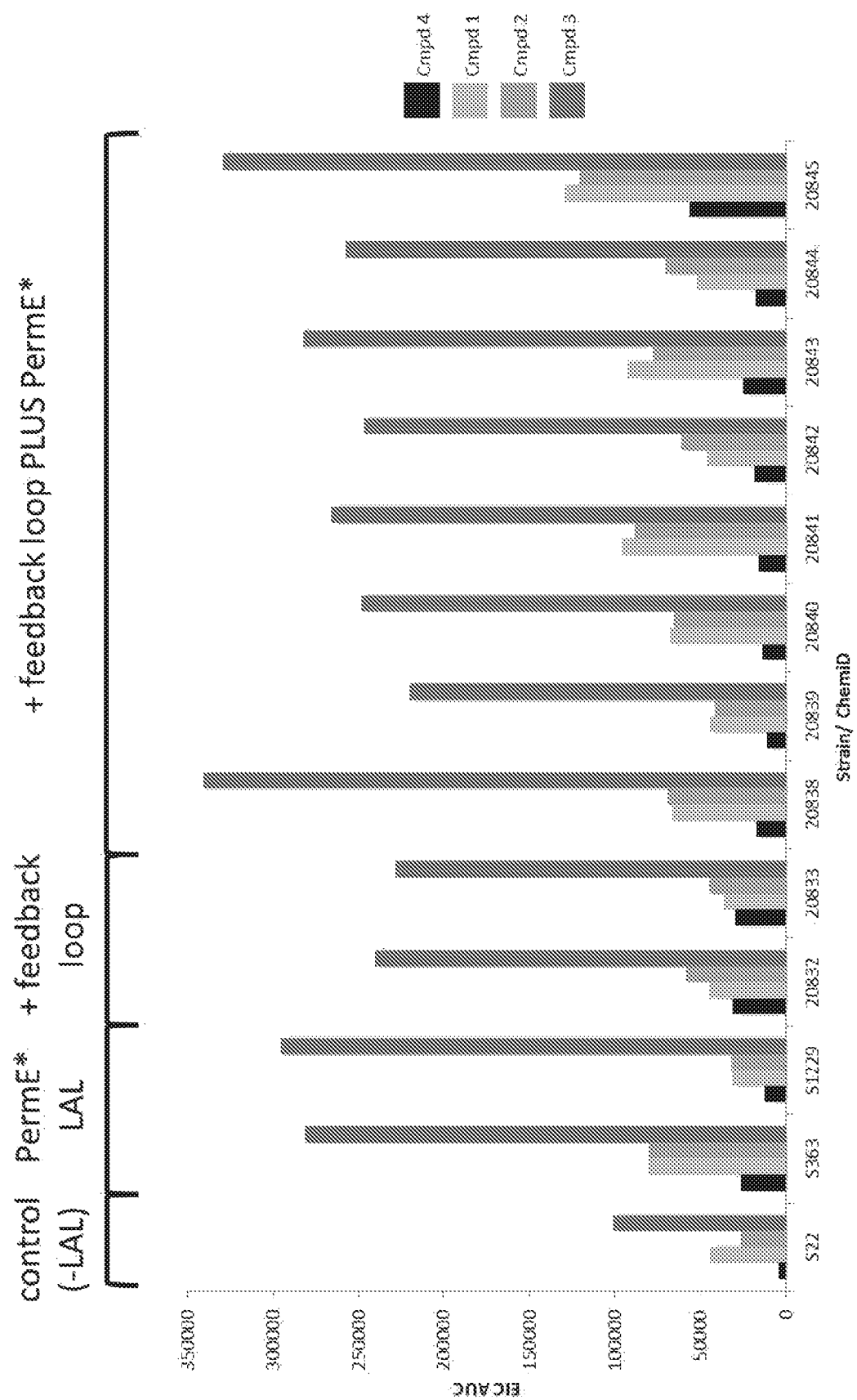
FIG. 15 is a graph showing the coupled use of a positive feedback loop and a constitutive S18 LAL.

The LAL regulon was designed to create a positive feedback loop (FIG. 14). This approach involved placement of LAL binding sites in the bi-directional promoters as well as upstream of a gene encoding an S18 LAL. As such, expression of an LAL (e.g., a wild-type LAL) could induce expression from each of the LAL binding sites: in the PKS biosynthetic gene cluster as well as those in the promoter of the S18 LAL, which can in turn further activate expression from the LAL binding sites, thereby resulting in a positive feedback loop. This may result in strong overexpression (e.g., stronger than expression driven by a PermE* promoter). Further, this strategy may permit idiophase timing according to precursor flux and/or post-translational modifications. FIG. 15 shows that the feedback loop can be used to enhance polyketide production. These data indicate that the feedback loop and/or constitutive LAL expression via the ErmE* promoter can induce PKS expression more than the native strain alone (S22). Constitutive and forward-feedback expression may yield additional PKS expression.

In one example, transcription of the single mega-cistron of the X2 biosynthetic gene cluster and the S18 LAL were placed under the control of the X1 UniLAL promoter, the latter effectively establishing an auto-regulatory operon. Transcription of the LAL would be further augmented by expression of the LAL itself. The UniLAL promoter regulated S18 LAL and X2 PKS constructs were sequentially conjugated into S1496 along with the native X2 gene cluster, to serve as a control.

Example 7. Knock-In of the X1 Promoter into a FKPHD Gene Cluster

Figure 16:
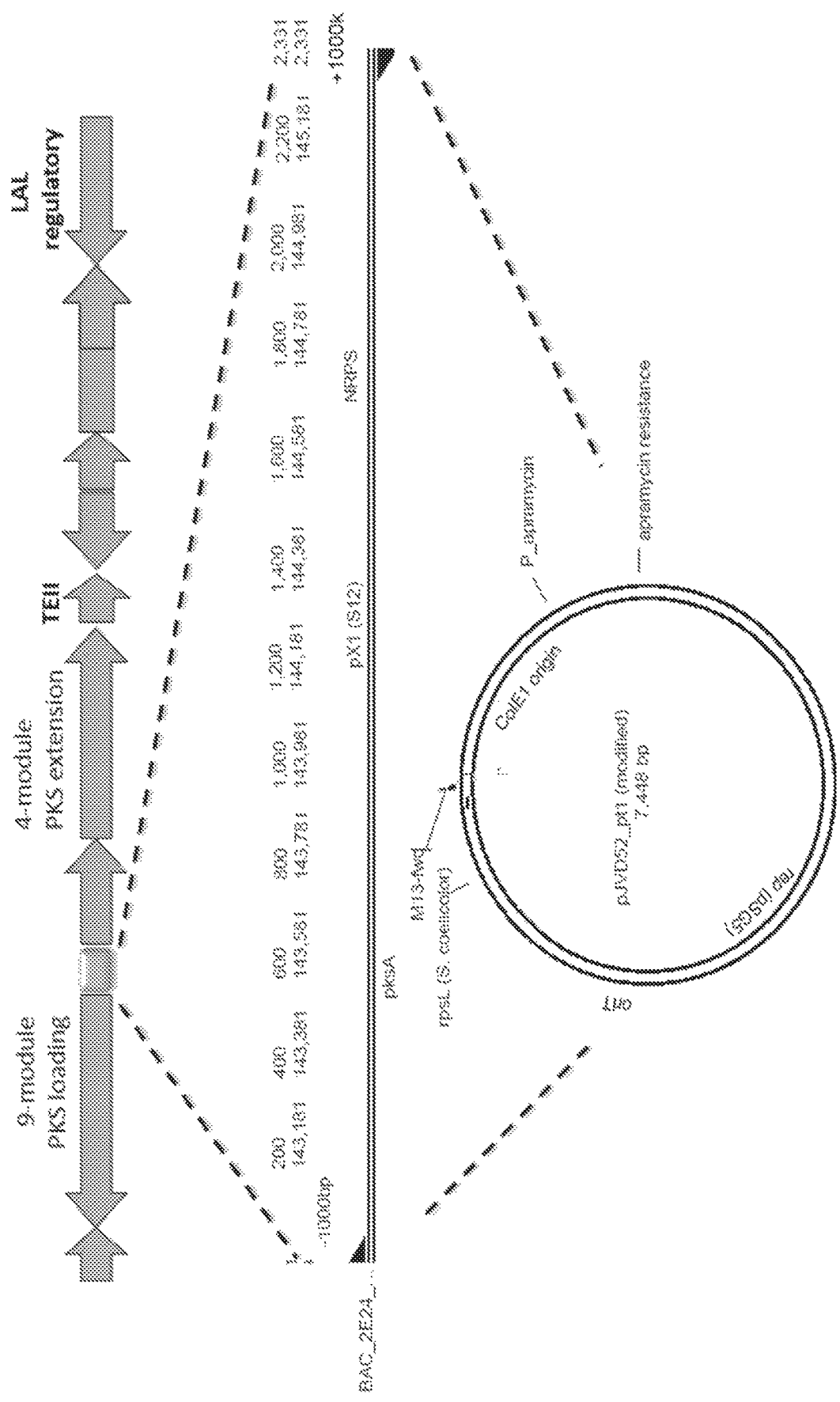
FIG. 16 is a diagram showing knock in of the X1 promoter into a FKPHD cluster in the endogenous locus for native strain expression.

Instead of inserting the X1 promoter to replace the wild-type promoter on a BAC or PAC harboring the FkPhD gene cluster for heterologous expression (e.g., as described in Example 4 above), the X1 promoter was knocked into the endogenous locus of the native strain (S61), which encodes the novel FkPhD gene cluster X11 (FIG. 16). pJVD possesses a temperature-sensitive origin of replication, an apramycin selection marker and a rpsLrplS counter-selection gene. The X1 promoter appended with 1000 bp of DNA sequence flanking the start codons of the opposing PKS mega orfs of X11 was cloned into pJVD52.1pJVD, and this vector was conjugated into S61 and selected for apramycin resistance at the permissive temperature of 30° C. Chromosomal integration was forced by growth at 39° C. and the maintenance of the apramycin selection. Cells were then passaged in the absence of apramycin, then challenged with streptomycin to bias for clones with selection for the desired resolution double crossover event, resulting in the scarless insertion of the X1 promoter precisely into the host chromosome to replace the WT X11 promoter. Colonies were confirmed as genuine pX1 knock-ins by replica plating to confirm susceptibility to apramycin and by junction PCR checking for the 5' and 3' amplicons of the expected sizes.

Example 8. Feed-Forward/UniLAL (Unidirectional LAL Sensitive) Promoter Methods Feed-Forward Configuration of the S18 LAL Initially the (TTA minus, synthetic) S18-derived LAL gene was put under the transcriptional control of the S12-derived "core" UniLAL-left and right promoters. The S18 LAL was substituted at the initiation codons for the left and right PKS transcripts of the S12 biosynthetic gene cluster via a two-step subcloning procedure. First, a BamHI to SpeI fragment containing all but the 5' 269 bases of the S18 LAL gene was subcloned into BamHI/XbaI digested pWFE1 cTR expression vector (which possesses the following features for conjugal delivery into Actinobacteria: the phage TG1 integrase gene and attP, an E. coli origin of transfer [oriT], and a gene that confers resistance to thiostrepton). Then the intermediate plasmid was digested with AarI and BamHI restriction endonucleases, and PCR amplicons composing either the left or right UniLAL promoter plus the missing ~269 bases of the S18 LAL from the initiation codon to the BamHI site in the gene were stitched together via a 3-part isothermal Gibson assembly using 2× Master Mix from New England Biolabs according to their instructions. To obtain the first amplicon, the UniLAL left promoter was PCR amplified and appended with the 5' end of the S18 LAL gene using the pWarp Factor 1×1 genomic TAR clone as template with the following primer pair:

```
FFcoreL_Aar_F
                                        SEQ ID NO: 43
gcgcccaccttaatcgcaggtgTCCACGCAACCCCCTAGGTTTCC
GGCCAGG C-L_S18_R
                                        SEQ ID NO: 44
gttcatagctctccacggcaggcatTCATACCCTTCCGGCGAAGTG
CAGTTCACCCGGT
```

Similarly, the UniLAL right promoter was amplified and appended with the 5' end of the S18 LAL gene with the following primer pair:

```
FFcoreR_Aar_F
                                        SEQ ID NO: 45
gcgcccaccttaatcgcagGTGCCACCCTTGTTTTTCACCCCCCT
ACGCCCGT
```

-continued

C-R_S18_R
SEQ ID NO: 46
gttcatagctctccacggcaggcatTCACCTCTCCCGGAAAGGTATT
GCTCGTGCATCCA For the second amplicon, 5' end of the S18 LAL gene was amplified and appended at the 5' end with either UniLAL-left or UniLAL-right sequence using pSET152 S18 LAL (TTA minus) as template with the following primer pairs:

C-L_Bam_F
SEQ ID NO: 47
actgcacttcgccggaagggtatgaATGCCTGCCGTGGAGAGCTAT
GAACTGGACGC S18LAL_Bam_R
SEQ ID NO: 48
CCGGGAGGGCCATGGAGACCGGA C-R_Bam_F
SEQ ID NO: 49
agcaataccttccgggagaggtgaATGCCTGCCGTGGAGAGCTAT
GAACTGGACGC S18LAL_Bam_R
SEQ ID NO: 50
CCGGGAGGGCCATGGAGACCGGA or All PCR amplifications were carried out using Q5 Hot Start DNA polymerase from New England Biolabs according to their specifications (with inclusion of the GC Enhancer supplement). Aarl/BamHI digested vector as well as amplicons were isolated by standard agarose electrophoresis and purified from the agarose using the Zymoclean™ Gel DNA Recovery Kit. One tenth of the Gibson assembly reaction was transformed into chemically competent NEB 10β E. coli and spread onto chloramphenicol (25 µg/mL) LB plates. After overnight incubation at 37° C., the chloramphenicol resistant colonies were picked into 5 mL cultures of Luria Bertani broth supplemented with 25 µg/mL chloramphenicol and shaken overnight at 37° C. Plasmid was isolated using the QIAprep Spin Miniprep Kit and then sent off for Sanger sequence verification at GeneWiz, Inc.

Example 9. Swapping of the "Core-Left" UniLAL Promoter for Native Promoter of the X2.1 Biosynthetic Gene Cluster Next generation sequencing (NGS) of genomic DNA from the actinomycete S17 had revealed a biosynthetic gene cluster with a polyketide synthase similar to but distinct from that of the biosynthetic gene cluster known to encode the information for the natural product meridamycin. This gene cluster was designated X2 (and later X2.1 when a second, near identical gene cluster (X2.2) was identified by NGS of S55). To obtain a molecular clone of the X2.1 biosynthetic gene cluster, S17 was liquid cultured in the presence of 0.5% w/v glycine. The mycelial biomass was frozen and sent to Lucigen Corporation who extracted and randomly sheared the genomic DNA, then used it to construct a BAC library in their shuttle vector pSMART BAC-S (which is a conventional BAC vector enabled for conjugation and integration into Streptomyces by the addition of the integrase gene and attP of phage ϕC31, an E. coli oriT, and a gene that confers resistance to apramycin) in their host E. coli strain Replicator v2.0 (whose genotype is rpsL). The library was supplied as glycerol stocks of E. coli arrayed in 384-well plates. Clones harboring the intact X2.1 locus were identified by dual color TaqMan assays using probes designed from proximal 5'- or 3'-flanking regions of the X2.1 gene cluster that were labeled with HEX and FAM fluors respectively. Primers and probes were designed using IDT's software and then ordered from them. To identify double positive clones, 1 µL of glycerol stock was used as template in conjunction with the primer pairs and probes and TaqMan® Fast Advanced Master Mix. Cycling and real-time fluorescence monitoring took place in a Bio Rad CFX384 Touch™ Real-Time PCR Detection System. BAC DNA prepped from double positive clones was confirmed to be correct by Sanger end sequencing at Tacgen, and ultimately exhaustively checked by Illumina and PacBio NGS at the Yale YOGA.

The X1.1 UniLAL left promoter was PCR amplified (using Q5 DNA polymerase and the pWF1 X1.1 plasmid as template) and appended at the 5' and 3' ends with 60 bp of sequence upstream of and precisely downstream of the initiation codon, respectively, of the X2.1 KCDA gene. The primer pair (flanking sequences denoted as capital letters/lower case letters denote regions that anneal to the X1 Core-Left UniLAL promoter; start anticodon in bold) used was:

X2.1_ULL-Run_F
SEQ ID NO: 51
CTACCCGAATACATCGCCTTCTGGGGCCCAGCCCAAACCAGC
GCCCTCATCCACACtccacgcaaccccctaggtttccggc X2.1_ULL-Run_R
SEQ ID NO: 52
gCGGCCCACAACGTGCACGAGCGTGGCGATATCGGACGCG
GAAAGAACCAGCGTGCTCATtcataccctttccggcgaagtgcagttcaccc Confirmation of insertion of the X1 Core-Left promoter precisely at the X2.1 KCDA initiation codon was obtained by performing 10 µL PCR amplifications using 0.5 µL of culture as template in conjunction with the following primer pair flanking the expected insertion site:

X2.1_HandR_cPCR_2F
SEQ ID NO: 53
CGCCGTCTACCCAGCCCAAAGCCAGC

X2.1_HandR_cPCR_2R
SEQ ID NO: 54
CGGGTTCGTGGTGCGGCATCCATTCG

Amplicons of the expected 476 bp in length were treated with ExoSAP-IT to degrade excess primer and dNTPs according to the manufacturer's conditions and sent off for Sanger sequence verification (each primer used separately for two individual reads) at GeneWiz Inc. A 250 ml LB broth culture derived from one of the clones with the exact anticipated sequence (X1 Core-Left UniLAL promoter fused to X2.1 KCDA gene at the initiation codon) was fed into the BAC XTRA purification system (according to the manufacturer's conditions) to isolate intact X2.1/Core-Left UniLAL BAC DNA. This DNA prep was used to electrotransform S181 E. coli that were allowed to recover, then selected on choramphenicol (25 µg/mL) and apramycin (100 µg/mL) LB agar plates at 37° C. overnight. Colonies were picked into 5 ml of LB broth supplemented with chloramphenicol and apramycin, grown overnight, and then used for conjugation into various heterologous production strains.

Example 10. Promoter Replacement via dsDNA Recombineering

To replace the endogenous promoter of X15, the X15 PAC is first engineered using dsDNA recombineering to harbor a positive/negative selection cassette, thus enabling a second round of seamless DNA insertion. *E. coli* harboring the PAC with the complete X15 promoter are rendered electrocompetent, transformed with pKD46 as known in the art (e.g., as described in Wanner and Datsenko; Proc Natl Acad Sci USA. (2000) 97:6640-5) and co-selected on kanamycin (50 μg/mL) and carbenicillin (100 μg/mL) LB agar plates at 30° C. A positive/negative selection cassette is generated by PCR amplifying the plasmid template pKDCR (for the bicistronic expression of rpsL and a chloramphenicol resistance gene) using Phusion polymerase (NEB Biosystems, Beverly, Mass.) with DNA oligonucleotides containing 50 bp overhangs homologous to the X15 NRPS gene and PKS-A.

X15_rpSL_cm_F
SEQ ID NO: 55
CAAAGCGATTCGGAGAGCGGCCGGATCAGATCCAGGCGTGACATGGCCTG
GTGATGATGGCGGGATCGT

X15_rpSL_cm_R
SEQ ID NO: 56
CGATCTTCTCGAAACTGCACTGAGGAGGTTCGTCGGAGACTGCCATTCAT
CGCAGTACTGTTGTATTCATTAAG

The amplicon from the PCR reaction is agarose gel-purified and extracted. A saturated culture of *E. coli* harboring the X15 PAC and pKD46 is diluted 1:100 into LB Lenox broth supplemented with kanamycin and carbenicillin and 1% w/v L-arabinose. The culture is shaken at 250 rpm at 30° C. until OD600 reached 0.5, at which point the cells are made electrocompetent with cold distilled dH$_2$O washes as described by Datsenko et al. 100 ng of the purified selection cassette is electroporated into *E. coli* using a Bio RAD MicroPulser™ electroporator on the "EC" setting. *E. coli* are allowed to recover in 1 mL of SOC at 30° C. for 1 hour, spread onto chloramphenicol (25 μg/mL) and carbenicillin (100 μg/mL) LB agar plates and selected overnight at 30° C. Colonies are picked into 1 mL cultures of LB broth supplemented with kanamycin, chloramphenicol, and carbenicillin and grown at 30° C. overnight. Confirmation of insertion of the positive/conditional negative selection cassette at the X15 major promoter locus is confirmed by junction PCR.

Cultures that are double positive for the expected 5' junction and 3' junction amplicons (as judge by agarose electrophoresis) are grown as above in LB Lenox with kanamycin, carbenicillin and arabinose and made electrocompetent. The S12 promoter is PCR amplified (using Q5 DNA polymerase and the pWF1.1X1.1 plasmid as template) and appended at the 5' and 3' ends with 50 bp homology arms to the X15 NRPS gene and PKS-A.

X15_LAL_F
SEQ ID NO: 57
5'-CAAAGCGATTCGGAGAGCGGCCGGATCAGATCCAGGCGTGACATTCA
TACCCTTCCGGCGAAGTGCAGTTCACCC-3'

X15_LAL_R
SEQ ID NO: 58
5'-CGATCTTCTCGAAACTGCACTGAGGAGGTTCGTCGGAGACTGCCATT
CACCTCTCCCGGAAAGGTATTGCTCG-3'

Electroporated cells are allowed to recover in 1 mL of SOC for 1 hour at 37° C. with shaking and then selected on kanamycin (50 μg/mL)+streptomycin (250 μg/mL) LB agar plates overnight at 37° C. Colonies are picked into 1 mL cultures of LB broth supplemented with kanamycin (50 μg/mL) and apramycin (100 μg/mL) and grown at 37° C. overnight with shaking. Confirmation of insertion of the S12 promoter at the X15 major promoter locus is confirmed by junction PCR.

Example 11. Promoter Replacement Via ssDNA Recombineering and Gibson Cloning In another technique, to replace the endogenous promoter of X15, the X15 PAC is first engineered using ssDNA recombineering to introduce AT-rich PmeI restriction sites (5'-GTTTAAAC-3') flanking the endogenous X15 major promoter locus. *E. coli* harboring the PAC with the complete X15 promoter are rendered electrocompetent, transformed with pKD466, a variant of pKD46 (Wanner and Datsenko; Proc Natl Acad Sci USA. (2000) 97:6640-5) in which the exo and gamma genes had been deleted, and co-selected on kanamycin (50 μg/mL) and carbenicillin (10 μg/mL) LB agar plates at 30° C. A saturated culture of *E. coli* harboring the X15 PAC and pKD466 is diluted 1:100 into LB Lenox broth supplemented with kanamycin and carbenicillin and 1% w/v L-arabinose. The culture is shaken at 250 rpm at 30° C. until OD600 reached 0.5, at which point the cells were made electrocompetent with cold distilled dH$_2$O washes as described by Datsenko et al. Cells are resuspended in 50 μL of a 1 μM ssDNA oligonucleotide solution and electroporated into *E. coli* using a Bio RAD MicroPulser™ electroporator on the "EC" setting. *E. coli* are allowed to recover in 1 mL of SOC at 30° C. for 1 hour, spread onto kanamycin (25 μg/mL) LB Lennox overnight to saturation. Confirmation of insertion of the PmeI site at the X15 major promoter locus is confirmed by allele-specific PCR combined with two serial rounds of a limited dilution cloning protocol that allowed the clonal selection of a successfully modified X15 PAC with a single PmeI site. This protocol is then repeated to introduce a second flanking PmeI site. Both "sense" and "antisense" oligonucleotides, which are synthesized with 5' phosphothiorate caps, are tested to define the lagging strand of the PAC.

ssDNA Oligonucleotides (PmeI Site underlined)

5'_X15_PmeI_sense
SEQ ID NO: 59
GCAAAGCGATTCGGAGAGCGGCCGGATCAGATCCAGGCGTGACAT<u>GTTTA
AAC</u>ACAACGTACCTTTCGGACAAGAGTGCCGCGGTGCACAGCCTGACC 5'_X15_PmeI_antisense
SEQ ID NO: 60
GGTCAGGCTGTGCACCGCGGCACTCTTGTCCGAAAGGTACGTT<u>GTGTTTA
AAC</u>ATGTCACGCCTGGATCTGATCCGGCCGCTCTCCGAATCGCTTTGC 3'_X15_PmeI_sense
SEQ ID NO: 61
TCCACACCTCTCGGTTCACAAACGTCCGAGCATAAGGGAGGTAAA<u>GTTTA
AAC</u>ATGGCAGTCTCCGACGAACCTCCTCAGTGCAGTTTCGAGAAGATC 3'_X15_PmeI_antisense
SEQ ID NO: 62
GATCTTCTCGAAACTGCACTGAGGAGGTTCGTCGGAGACTGCCAT<u>GTTTA
AAC</u>TTTACCTCCCTTATGCTCGGACGTTTGTGAACCGAGAGGTGTGGA The X15 PAC, now modified with PmeI sites, is linearized with PmeI. The S12 promoter is PCR amplified (using PQ5 DNA polymerase and the pWF1.1x1.1 plasmid as template; primers listed below) and appended at the 5' and 3' ends with 50 bp homology arms to the X15 NRPS gene and PKS-A.

X15_LAL_F

SEQ ID NO: 63

5'-CAAAGCGATTCGGAGAGCGGCCGGATCAGATCCAGGCGTGACATTCA
TACCCTTCCGGCGAAGTGCAGTTCACCC-3'

X15_LAL_R

SEQ ID NO: 64

5'-CGATCTTCTCGAAACTGCACTGAGGAGGTTCGTCGGAGACTGCCATT
CACCTCTCCCGGAAAGGTATTGCTCG-3'

S12 promoter and the PmeI linearized X15 PAC is seamlessly cloned by Gibson cloning using the Gibson Assembly Ultra Kit (SGI-DNA, Inc.) using the recommended protocol. After electroporation, correct clones are identified as above.

Figure 17:
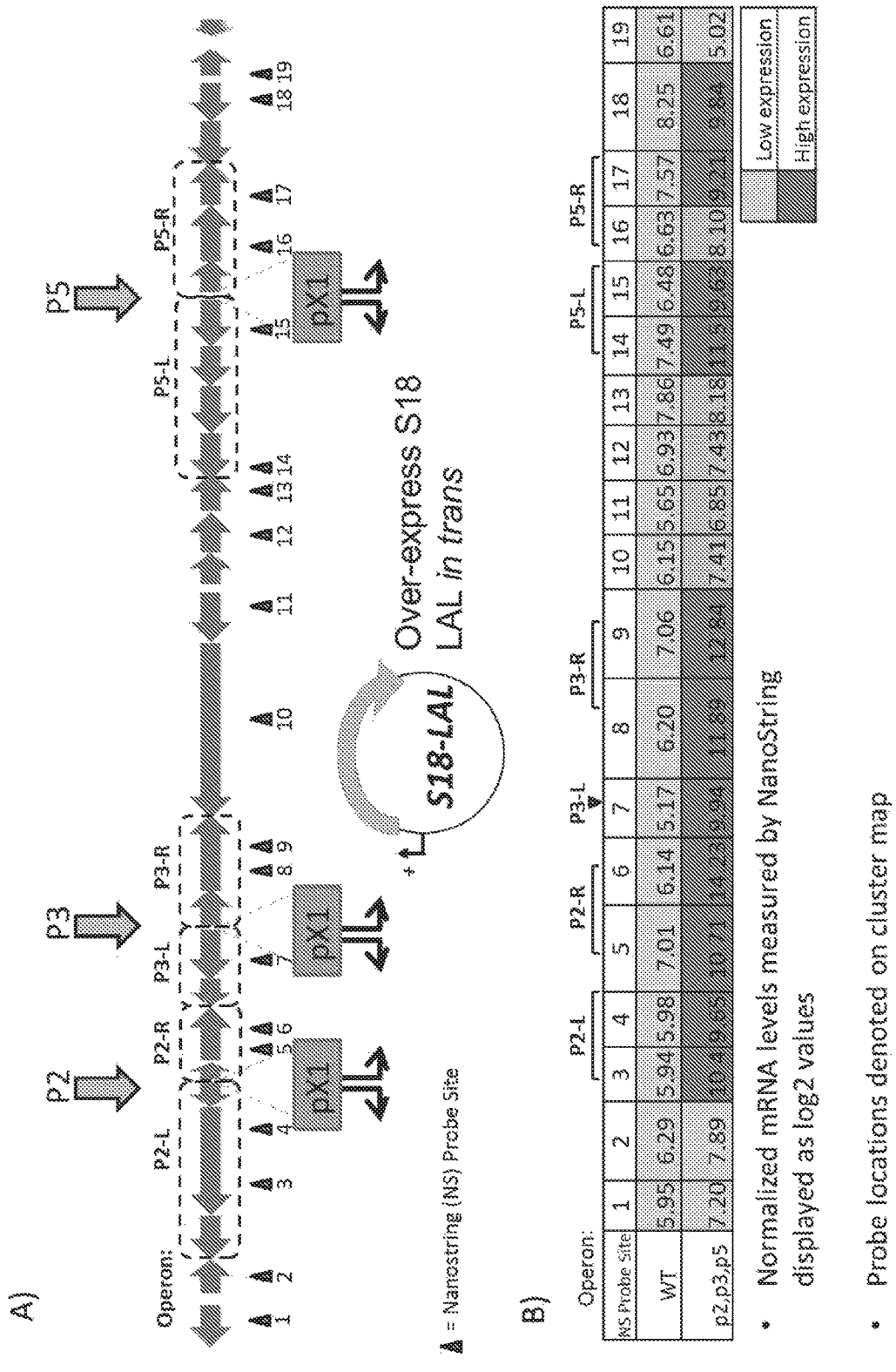
FIGS. 17A-B is a diagram showing the use of the pX1-S18 LAL system to drive the overexpression of a novel β-lactam gene cluster, WAC292.

Example 12. Expression of LALs Drives β-Lactam Compound Production from a β-Lactam Gene Cluster The previously described pX1-S18 LAL system was used to drive the overexpression of a novel beta-lactam gene cluster, WAC292 (FIG. 17A). Three copies of the pX1 promoter were subcloned into WAC292 to drive the predicted core biosynthetic operons at 3 of the 5 promoter sites to generate WAC292-p2p3p5. The S18 LAL was cloned onto the backbone of WAC292-p2p3p5, and the resulting engineered BAC was conjugated to S5627, a known beta-lactam producing strain with the endogenous beta-lactam cluster deleted, thus removing any endogenous beta-lactam activity. After fermentation, WT and WAC292-p2p3p5 S5627 strains were compared to Nanostring analysis mRNA using a custom probe set designed against 19 sites of the cluster. Transcripts linked to the P2, P3, and P5 promoters were significantly upregulated in WAC292-p2p3p5 as compared to WAC292-WT (FIG. 17B).

Cloning Protocol to Generate WAC292-p2p3p5

The YAC/BAC conjugative vector pWF10 harboring the β-lactam gene cluster was linearized at the unique PacI and SwaI (NEB) sites. The S18LAL expression cassette (ermE* promoter/synthetic TTA codon minus S18 LAL gene/phage fd transcriptional terminator) was PCR amplified using pWFE1 S18LAL as template and appended at each end with ~40 bp of vector sequence 5' proximal to the PacI site and 3' proximal to the SwaI site using Q5 HotStart DNA polymerase.

LAL_N2_292_F

SEQ ID NO: 65

5'-CCCGAACCACGATGAGCACTTGCCTATGCGGTGTAGGGATAACAGGG
TAATTAATTAATGACCTGCGCCCACCTTAATCGCAGGTGC-3'

LAL_N2_292_F

SEQ ID NO: 66

5'-TACTTTCTATTTTTAATTTATATATTTATATTAAAAAATTTAAAATA
TAATTATTTTTATAGCACGTGATGGAGCCTATGGAAAAACGCCAGCAACG
C-3'

The restriction digested BAC and the PCR amplicon were mixed in a total of 5 µl and an equal volume of NEBuilder HiFi DNA Assembly 2× Master Mix added, after which the reaction proceeded for one hour at 50° C. 1.5 µl of the completed reaction was added to 70 µl of electrocompetent NEB 10-beta *E. coli*, mixed, the contents deposited in a Bulldog Bio 0.1 cm gap electrocuvette and transformed using a BioRad Micropulser electroporator set to the "EC1" parameters. 930 µl of SOC media was used to resuspend the electroporated cells and the entire volume pipetted into a 50 ml Falcon tube. The tube was placed in a shaking incubator set at 37° C. and the electroporated *E. coli* allowed to recover for 1 hour. 200 µls of recovered bacteria were spread onto five LB agar-100 µg/ml apramycin Petri dishes. The dishes were inverted and incubated overnight @ 37° C. Colonies were picked into 1 ml cultures of LB broth supplemented with 100 µg/ml apramycin and incubated with shaking @ 37° C. overnight. 1 µl of saturated bacterial culture was used as template in PCR reactions to amplify the entire S18 LAL expression cassette.

pWF10_Swa_cPCR_R

SEQ ID NO: 67

5'-GGTAGTATTTGTTGGCGATCCCCCTAGAGTCTTTTACATCTTCG
G-3' pWF10_Swa_cPCR_F

SEQ ID NO: 68

5'-AGCCTGCCCCTCATCTGTCAAC-3'

The resulting amplicons were diluted and 1:144 with dH$_2$O, 14.5 µls of the diluted amplicons were added to 0.5 µl of a series of 100 µM sequencing primers and sent off for Sanger verification to ensure no errors had been introduced into the S18 LAL expression cassette during the cloning process. A sequence perfect clone was grown at scale (300 ml culture prep) and the YAC/BAC purified using a Macherey Nagel Nucleobond Xtra BAC kit.

The purified YAC/BAC was concomitantly digested with three Alt-R guide crRNAs complexed with Alt-R CRISPR-Cas9 tracRNA and recombinant *S. pyogenes* Cas9 protein (all from Integrated DNA Technologies) for one hour @ 37° C. The guide cRNAs were designed to cut within bidirectional promoters 2, 3, & 5 of the βlactam biosynthetic gene cluster. The triply Cas9 digested BAC vector was ethanol precipitated and resuspended in 20 µl of 10 mM Tris pH 8.0. Meanwhile, three PCR amplicons, two yeast auxotrophic markers and a single X1 bidirectional core promoter, were generated for "gap repair" insertion at the three sites of cas9 digestion upon cotransformation into *S. cerevisiae*.

292_bi2_TRP-BstZ_F

SEQ ID NO: 69

5'-GTTGATCGTGTGGGGCGGCCTGCCGAGCAGCTGGTGGACCCCTGGGG
CGAGCTGGCGCATTCACCTGTATACTGAGAGTGCACCATAAACGACATTA
CT-3'

292_bi2_TRP-BstZ_R

SEQ ID NO: 70

5'-GACGACCGCGGTCCCCACGAGGACAGCGGCCGACGCAACAGCTTTGC
GAAGACGAGTCATTCATACGTATACAGGCAAGTGCACAAACAATACT-3'

292_bi3_LEU-Hpa_F

SEQ ID NO: 71

5'-CGCCGGTGAGGCCAGACCCATGAGGGTCAGTGCTGCGACCACCGCGT
ACCTGATCCGCATTCACCTGTTAACTCCTGATGCGGTATTTTCTCCTTAC
GCA-3

292_bi3_LEU-Hpa_R

SEQ ID NO: 72

5'-CTCGGCCGGCAGCAAGGTCTGCTCGATCGCGATGATCCGGCCGTTCC
CCCAGTCGATCGTGTTAACCGACTACGTCGTAAGGCCGTTTCT-3'

292_bi5_F

SEQ ID NO: 73

5'-GACGAACGCGAAGTCGTCGCCGCCCTCCTTCATGCCCAGTCCGGTGG
TCCAGCCGCGGAAGCCGTGCGGATGCATTCACCTCTCCCGGAAAGGTATT
GCTCG-3'

292_bi5_R

SEQ ID NO: 74

5'-TCGCCACGGGCGGTCGAGGAACTCGTCGCGGACCGCCGCGACCCGTG
TTCGCGCGCCGTCACCGCCGACGCGCATTCATACCCTTCCGGCGAAGTGC
AGTTC-3'

Using the above primer pairs, Q5 HotStart DNA polymerase and pRS414, pRS415, and pWF1 X1 as template, the amplicons were obtained and gel purified (using the Zymo Research Gel DNA Recovery Kit).

The three amplicons added in >10× molar excess to the triple digested βlactam YAC/BAC and transformed into BY4727 S. cerevisiae (ATCC 200889) using the lithium acetate/PEG method from the Geitz lab. Following heat shock, the transformed yeast out of the lithium/PEG/DNA mix, the yeast were pelleted @ 10,000× g for 30 seconds and resuspended in 1 ml of SD TRP, LEU minus broth. The yeast were then spread onto four SD TRP, LEU minus agar plates (Teknova), the plates inverted, and incubated at 30° C. until colonies were visible (~four days). The YAC/BAC residing in the cells of the yeast colonies were rescued and transformed into E. coli as follows: colonies were picked into a microcentrifuge tube with 20 μl of 200 mM lithium acetate/1% SDS, five or six 100 μm diameter acid washed ceramic beads (OPS Diagnostics) added and the contents vortexed for 5 minutes at maximum rpm. 1 μl of the lysate was electroporated into electrocompetent NEB10-beta E. coli and selected on LB agar 100 μg/ml apramycin Petri dishes. Colonies were used to inoculate 1 ml cultures in LB broth supplemented with 100 μg/ml apramycin, and 1 μl from these cultures used as template in PCR (Bioline MyTaq Hotstart Red 2× master mix) to verify the presence of the expected 5' & 3' junctions for the X1 bidirectional core (P5) and TRP (P2) and LEU (P3) marker insertions.

292_Bi2_Hit_5'F

SEQ ID NO: 75

5'-GGCGTGGCTGGAGCCGAAGTGGTC-3'

TRP_5'jPCR_R

SEQ ID NO: 76

5'-TCTTCCACTACTGCCATCTGGCGTCATAACTGC-3'

TRP_3'jPCR_F

SEQ ID NO: 77

5'-AGGTTATTACTGAGTAGTATTTATTTAAGTATTGTTTGTGCACTTGC
CT-3

292_Bi2_Hit_3'R

SEQ ID NO: 78

5'-ACTCGGCGGCGTTGGCGTGGC-3'

292_Bi3_Hit_5'F

SEQ ID NO: 79

5'-ACCGTCGCCCCGCCGCAGC-3'

LEU_5'jPCR_R

SEQ ID NO: 80

5'-CGCACAGATTCGTAAGGAGAAAATACCGCATCAGGA-3'

LEU_3'jPCR_F

SEQ ID NO: 81

5'-ACTCTGTCAGAAACGGCCTTACGACGTAGTCG-3'

292_Bi3_Hit_3'R

SEQ ID NO: 82

5'-CGGGCGGCACGCAACCGAAGTG-3'

292_Bi5_Hit_5'F

SEQ ID NO: 83

5'-GTGAAGACCGCCGATACCGCCGC-3'

X1_pro_cPCR_3'

SEQ ID NO: 84

5'-GGGTGAAAAACAAGGGTGGCACGGCA-3'

X1_pro_cPCR_5'

SEQ ID NO: 85

5'-TGCCGTGCCACCCTTGTTTTTCACCC-3'

292_Bi5_Hit_3'R

SEQ ID NO: 86

5'-ACGCCAGGCCCGTTCACGACGACCGC-3'

One clone positive for the six junctions was grown at scale (300 ml culture prep) and the YAC/BAC purified, digested with an excess of BstZ171 and Hpal restriction enzymes (NEB), ethanol precipitated, and resuspended in 50 μl of 10 mM Tris pH 8.0. For multiplex insertion of X1 bidirectional core promoters, in two separate reactions the promoter was amplified and appended with ~30 bp 5' & 3' sequence proximal to the sites of BstZ171 and Hpal digestion, and gel purified.

292_bi2_Run_F

SEQ ID NO: 87

5'-GCTGGTGGACCCCTGGGGCGAGCTGGCGCATTCACCTCTCCCGGAAA

GGTATTGCTCGC-3'

292_bi2_Run_R

SEQ ID NO: 88

5'-AACAGCTTTGCGAAGACGAGTCATTCATACCATTCATACCCTTCCGG

CGAAGTGCAGTTCACCCG-3'

292_bi3_Run_F

SEQ ID NO: 89

5'-TCAGTGCTGCGACCACCGCGTACCTGATCCGCATTCACCTCTCCCGG

AAAGGTATTGCTCGC-3'

292_bi3_Run_R

SEQ ID NO: 90

5'ATCGCGATGATCCGGCCGTTCCCCCAGTCGATCGTCCGCATTCATACC

CTTCCGGCGAAGTGCAGTTCACCCG-3'

The X1 bidirectional promoter amplicons were added in tenfold molar excess to the BstZ171/Hpal digested BAC, the mixture ethanol precipitated and resuspended in 5 μl 10 mM Tris pH 8.0. 5 μl of SGI Gibson Assembly Ultra Kit "A mix" was added, mixed, and incubated @ 37° C. for 5 minutes, heat killed @ 75° C. for 20 minutes, stepped down to 60° C. and the temperature dropped at a rate of 0.1° C./second to 4° C. 10 μl of "B mix" was then added and the reaction allowed to proceed @ 45° C. for 15 minutes. 1.5 μl of the completed reaction was electroporated into 70 μl of electrocompetent NEB10-beta E. coli and selected on 100 μg/ml apramycin LB agar Petri dishes. Colonies were used to inoculate 1 ml cultures in LB broth supplemented with 100 μg/ml apramycin and 1 μl used as template in PCR to confirm the presence of four new junctions indicative of insertion of the X1 bidirectional promoter in place of the native βlactam's bidirectional promoters 2 & 3.

The loci surrounding the X1 bidirectional core promoters inserted at P2, P3, and P5 were PCR amplified and used as template for Sanger sequence QC to ensure no errors had been introduced during the cloning process.

Strain Construction and Nanostring Methods

The construct WAC292-p2p3p5 was mobilized by conjugation from an E. coli donor into Streptomyces sp. S5627, a carbapenem-producing strain in which the endogenous carbapenem cluster had been deleted by homologous recombination. The resulting ex-conjugants were selected on medium containing 50 µg/ml apramycin. The resulting strain WAC292-p2p3p5-S5627 was grown in seed culture in 25 ml WDSM1 medium in a baffled 125 ml flask for 48 h before being sub-cultured (5% inoculum) into 25 ml fermentation medium FMKN1 in an unbaffled 125 ml flask for a further 48 h. A 1 ml sample was removed on ice and centrifuged to pellet the mycelium (wet weight approx. 150 mg). The pellet was resuspended in lysis buffer RA1 (Macherey-Nagal 740955.50) and transferred to a FastPrep lysing matrix B tube (MP Biomedical 116911050). The mycelium was disrupted by bead beating in a Qiagen TissueLyser II at speed 30 for 5 min. The cell debris was pelleted by centrifugation and 1 µl of the cell lysate utilized for hybridization for Nanostring analysis (following manufacturer's instructions). Nanostring probe pools were prepared and used as per manufacturer's instructions.

Nanostring Data Analysis and Normalization

RCC files were imported into nSolver 3.0 (Nanostring Inc). Raw count data was then exported to Excel. One of the following genes or the median of a set of these genes were used as the normalization factor: GAPDH, HrdB, phiC31 int, AprR. Normalization was performed by dividing the measurement of interest by the normalization factor, taking the base two log of that value and adding a scaling constant of 10.

Other Embodiments

It is to be understood that while the present disclosure has been described in conjunction with the detailed description thereof, the foregoing description is intended to illustrate and not limit the scope of the present disclosure, which is defined by the scope of the appended claims. Other aspects, advantages, and alterations are within the scope of the following claims.

Those skilled in the art will recognize, or be able to ascertain using no more than routine experimentation, many equivalents to the specific embodiments in accordance with the invention described herein. The scope of the present invention is not intended to be limited to the above Description, but rather is as set forth in the appended claims.

In the claims, articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

It is also noted that the term "comprising" is intended to be open and permits but does not require the inclusion of additional elements or steps. When the term "comprising" is used herein, the term "consisting of" is thus also encompassed and disclosed.

Where ranges are given, endpoints are included. Furthermore, it is to be understood that unless otherwise indicated or otherwise evident from the context and understanding of one of ordinary skill in the art, values that are expressed as ranges can assume any specific value or subrange within the stated ranges in different embodiments of the invention, to the tenth of the unit of the lower limit of the range, unless the context clearly dictates otherwise.

In addition, it is to be understood that any particular embodiment of the present invention that falls within the prior art may be explicitly excluded from any one or more of the claims. Since such embodiments are deemed to be known to one of ordinary skill in the art, they may be excluded even if the exclusion is not set forth explicitly herein. Any particular embodiment of the compositions of the invention (e.g., any polynucleotide or protein encoded thereby; any method of production; any method of use) can be excluded from any one or more claims, for any reason, whether or not related to the existence of prior art.

What is claims is:

1. A genetically modified host cell comprising:
(i) a nucleic acid encoding a recombinant Large ATP-binding regulator of the LuxR family (LAL) that is heterologous to the host cell; and
(ii) a nucleic acid comprising an LAL binding site that is heterologous to the host cell.

2. The host cell of claim 1, wherein the host cell naturally lacks an LAL or the host cell naturally lacks an LAL binding site.

3. The host cell of claim 1, wherein the LAL binding site is operably linked to an open reading frame.

4. The host cell of claim 3, wherein the open reading frame encodes a compound-producing protein.

5. The host cell of claim 1, wherein:
the recombinant LAL comprises a portion having at least 90% sequence identity to the amino acid sequence of SEQ ID NO: 1;
the recombinant LAL comprises a portion having the amino acid sequence of SEQ ID NO: 1; or
the recombinant LAL has the amino acid sequence of SEQ ID NO: 1.

6. The host cell of claim 4, wherein the host cell has been modified to enhance expression of the compound-producing protein by (i) deletion of an endogenous gene cluster which expresses an endogenous compound-producing protein; (ii) insertion of a heterologous gene cluster which expresses a heterologous compound-producing protein; (iii) exposure of the host cell to an antibiotic challenge; and/or (iv) introduction of a heterologous promoter that results in an at least 2-fold increase in expression of a compound produced by the compound-producing protein compared to the expression of the compound when the homologous promoter has not been replaced.

7. The host cell of claim 1, wherein:
the nucleic acid further comprises one or more additional LAL binding sites;
at least one of the LAL binding sites is in a promoter; or
the nucleic acid further comprises a gene encoding an LAL.

8. The host cell of claim 7, wherein:
the gene encoding an LAL is under the control of a promoter comprising an LAL binding site; or
at least one of the LAL binding sites is in a promoter.

9. The host cell of claim 8, wherein at least one of the LAL binding sites is in a promoter and the promoter is a bidirectional promoter.

10. A nucleic acid comprising an LAL binding site and a sequence encoding an LAL, wherein the LAL binding site comprises a sequence having no more than one insertion, deletion, or substitution with respect to the nucleic acid sequence of SEQ ID NO:2 and/or comprises the nucleic acid sequence of SEQ ID NO: 3, and wherein
the LAL comprises a portion having at least 90% sequence identity to the amino acid sequence of SEQ ID NO: 1;
the LAL comprises a portion having the amino acid sequence of SEQ ID NO: 1; or
the LAL has the amino acid sequence of SEQ ID NO: 1.

11. The nucleic acid of claim 10, wherein the nucleic acid lacks a TTA inhibitory codon in at least one open reading frame.

12. The nucleic acid of claim 10, wherein the LAL binding site comprises the nucleic acid sequence of SEQ ID NO:2.

13. The nucleic acid of claim 10, wherein the nucleic acid further comprises an open reading frame.

14. The nucleic acid of claim 13, wherein the open reading frame encodes a compound-producing protein.

15. The nucleic acid of claim 14, wherein the compound-producing protein is a polyketide synthase, a β-lactam compound-producing protein, or a non-ribosomal peptide synthase.

16. The nucleic acid of claim 10, wherein:
the nucleic acid further comprises one or more additional LAL binding sites; or
the gene encoding the LAL is under the control of a promoter comprising an LAL binding site.

17. The nucleic acid of claim 16, wherein at least one of the LAL binding sites is in a promoter.

18. The nucleic acid of claim 17, wherein the promoter is a bidirectional promoter.

19. An expression vector comprising a nucleic acid of claim 10.

20. A host cell comprising the nucleic acid of claim 10.

* * * * *